US012622910B2

(12) United States Patent
Balasubramanian et al.

(10) Patent No.: US 12,622,910 B2
(45) Date of Patent: May 12, 2026

(54) INHIBITORS OF BRUTON'S TYROSINE KINASE AND METHODS OF THEIR USE

(71) Applicant: Janssen Pharmaceutica NV, Beerse (BE)

(72) Inventors: Sriram Balasubramanian, San Diego, CA (US); Ivo Cornelissen, Turnhout (BE); Yue Guo, North Wales, PA (US); Jocelyn H. Leu, Lower Gwynedd, PA (US); Kathryn E. Packman, Newton, MA (US); James Alexander Palmer, San Diego, CA (US); Ulrike Philippar, Antwerp (BE); Navin Rao, Maple Glen, PA (US); Mark S. Tichenor, San Diego, CA (US); Jennifer D. Venable, Solana Beach, CA (US); John J. M. Wiener, La Jolla, CA (US); Xin Miao, Blue Bell, PA (US)

(73) Assignee: Janssen Pharmaceutica NV, Beerse (BE)

( * ) Notice: Subject to any disclaimer, the term of this patent is extended or adjusted under 35 U.S.C. 154(b) by 289 days.

(21) Appl. No.: 17/830,714

(22) Filed: Jun. 2, 2022

(65) Prior Publication Data

US 2023/0013755 A1 Jan. 19, 2023

Related U.S. Application Data

(60) Provisional application No. 63/196,843, filed on Jun. 4, 2021.

(51) Int. Cl.
*A61K 31/519* (2006.01)
*A61P 35/00* (2006.01)

(52) U.S. Cl.
CPC ............ *A61K 31/519* (2013.01); *A61P 35/00* (2018.01)

(58) Field of Classification Search
CPC .. A61K 31/519; A61K 31/522; A61K 31/704; A61P 35/00
See application file for complete search history.

(56) References Cited

U.S. PATENT DOCUMENTS

| | | | |
|---|---|---|---|
| 4,886,646 | A | 12/1989 | Carter et al. |
| 5,096,676 | A | 3/1992 | Mcpherson et al. |
| 5,130,105 | A | 7/1992 | Carter et al. |
| 5,221,410 | A | 6/1993 | Kushner et al. |
| 5,300,478 | A | 4/1994 | Michaely et al. |
| 5,400,741 | A | 3/1995 | Detitta et al. |
| 7,579,356 | B2 | 8/2009 | Battista et al. |
| 8,486,965 | B2 | 7/2013 | Ohashi et al. |
| 10,717,745 | B2 | 7/2020 | Arora et al. |
| 10,934,310 | B2 | 3/2021 | Arora et al. |
| 11,319,329 | B2 * | 5/2022 | Arora ...................... A61P 29/00 |
| 12,065,446 | B2 * | 8/2024 | Arora .................. C07D 519/00 |
| 2006/0058341 | A1 | 3/2006 | Connolly et al. |
| 2007/0128709 | A1 | 6/2007 | Wilks et al. |
| 2008/0076921 | A1 | 3/2008 | Honigberg et al. |
| 2014/0249105 | A1 | 9/2014 | Brayer et al. |
| 2015/0238490 | A1 | 8/2015 | Burger |
| 2016/0032404 | A1 | 2/2016 | Schweighofer et al. |
| 2017/0283430 | A1 * | 10/2017 | Arora ...................... A61P 17/00 |
| 2017/0283431 | A1 | 10/2017 | Arora et al. |
| 2019/0276471 | A1 | 9/2019 | Arora et al. |
| 2019/0284203 | A1 | 9/2019 | Arora et al. |
| 2019/0284204 | A1 | 9/2019 | Arora et al. |
| 2021/0101910 | A1 | 4/2021 | Arora et al. |
| 2023/0097422 | A1 * | 3/2023 | Arora .................. C07D 519/00 514/252.02 |
| 2025/0163076 | A1 | 5/2025 | Tran et al. |

FOREIGN PATENT DOCUMENTS

| | | | |
|---|---|---|---|
| EP | 0061588 | A1 | 10/1982 |
| EP | 0602306 | A1 | 6/1994 |
| EP | 2471789 | A1 | 7/2012 |
| WO | 03016338 | A1 | 2/2003 |
| WO | 2006031929 | A2 | 3/2006 |
| WO | 2006118749 | A1 | 11/2006 |

(Continued)

OTHER PUBLICATIONS

Barf T, Covey T, Izumi R, van de Kar B, et al A Covalent Bruton Tyrosine Kinase Inhibitor with a Differentiated Selectivity and In Vivo Potency Profile. J Pharmacol Exp Ther. Nov. 2017;363(2):240-252. doi: 10.1124/jpet.117.242909. (Year: 2017).*

Tam CS, Trotman J, Opat S, et al., Phase 1 study of the selective BTK inhibitor zanubrutinib in B-cell malignancies and safety and efficacy evaluation in CLL. Blood. Sep. 12, 2019;134(11):851-859. doi: 10.1182/blood.2019001160 (Year: 2019).*

Deng J, Isik E, Fernandes SM, Brown JR, Letai A, Davids MS. Bruton's tyrosine kinase inhibition increases BCL-2 dependence and enhances sensitivity to venetoclax in chronic lymphocytic leukemia. Leukemia. Oct. 2017;31(10):2075-2084. doi: 10.1038/leu.2017.32. Epub Jan. 23, 2017. PMID: 28111464; (Year: 2017).*

NCI Dictionary, https://web.archive.org/web/20180222162444/https://www.cancer.gov/publications/dictionaries/cancer-terms/def/malignancy): (Year: 2018).*

(Continued)

*Primary Examiner* — Brenda L Coleman
*Assistant Examiner* — Madeline E Braun

(57) ABSTRACT

The present disclosure is directed to the use of a compound of Formula (III) in the treatment of malignancies.

(III)

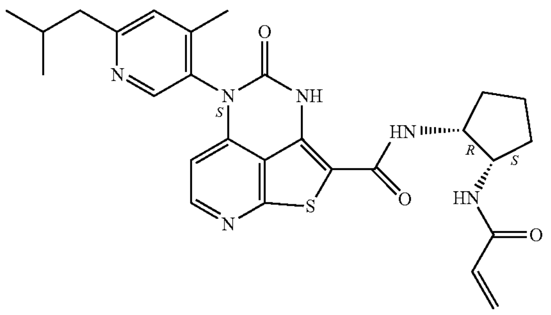

6 Claims, 27 Drawing Sheets

(56) References Cited

FOREIGN PATENT DOCUMENTS

| | | | | |
|---|---|---|---|---|
| WO | 2007019191 | A2 | | 2/2007 |
| WO | 2007092879 | A2 | | 8/2007 |
| WO | 2010056875 | A1 | | 5/2010 |
| WO | 2011133609 | A3 | | 3/2014 |
| WO | WO 2014/059368 | A1 | | 4/2014 |
| WO | 2014139970 | A1 | | 9/2014 |
| WO | 2015089337 | A1 | | 6/2015 |
| WO | WO 2016/024230 | A1 | | 2/2016 |
| WO | 2017100668 | A1 | | 6/2017 |
| WO | WO 2017/100662 | A1 | | 6/2017 |
| WO | 2018103058 | A1 | | 6/2018 |
| WO | WO-2018103060 | A1 | * | 6/2018 |
| WO | 2021216786 | A1 | | 10/2021 |

OTHER PUBLICATIONS

PubChem Compound Summary for CID 49846579, Venetoclax, (from National Center for Biotechnology Information, https://web.archive.org/web/20200421014747/https://pubchem.ncbi.nlm.nih.gov/compound/Venetoclax) (Year: 2020).*

Corneth, O.B.J., et al. "BTK Signaling in B Cell Differentiation and Autoimmunity", (2016), Current Topics in Microbiology and Immunology, vol. 393, pp. 67-105.

Lucas, F., et al., "Inhibiting Bruton's Tyrosine Kinase in CLL and Other B-Cell Malignancies", (2019), vol. 14, No. 2, pp. 125-138.

Saidu, N.E.B., et al., "New Approaches for the Treatment of Chronic Graft-Versus-Host Disease: Current Status and Future Directions", (2020), Frontiers in Immunology, vol. 11, No. 9, pp. 1-19.

International Search Report from PCT/IB2022/055154 mailed Sep. 9, 2022.

"Pemphigus and Pemphigoid", Retrieved from: https://rarediseases.org/rare-diseases/pemphigus/, 3 Pages, Jun. 4, 2019.

International Search Report and Written Opinion, Received for PCT Application No. PCT/CN2016/109134, 13 Pages, Aug. 2, 2017.

International Search Report and Written Opinion, Received for PCT Application No. PCT/CN2016/109143, 13 Pages, Sep. 14, 2017.

International Search Report and Written Opinion, Received for PCT Application No. PCT/EP2022/067957, 12 Pages, Oct. 21, 2022.

International Search Report and Written Opinion, Received for PCT Application No. PCT/EP2022/084855, 21 Pages, Feb. 28, 2023.

International Search Report and Written Opinion, Received for PCT Application No. PCT/US2016/065954, 11 Pages, Feb. 9, 2017.

International Search Report and Written Opinion, Received for PCT Application No. PCT/US2016/065964, 8 Pages, Mar. 1, 2017.

"Venetoclax (Venclexta) Tablets", Retrieved from: https://www.fda.gov/drugs/resources-information-approved-drugs/venetoclax-venclexta-tablets, 2016.

Balbes et al., "A Perspective of Modern Methods in Computer-Aided Drug Design", Reviews in Computational Chemistry, vol. 5, pp. 337-379, Jan. 1, 1994.

Bartlett et al., "Caveat a Program to Facilitate the Structure Derived Design of Biologically Active Molecules", Chemistry, Computer Science, Biology, vol. 78, pp. 182-196, Jul. 25, 1989.

Bender et al., "Ability of Bruton's Tyrosine Kinase Inhibitors to Sequester Y551 and Prevent Phosphorylation Determines Potency for Inhibition of Fc Receptor but Not B-cell Receptor Signaling", Molecular Pharmacology, vol. 91, No. 3, pp. 208-219, Mar. 30, 2017.

Bohm H. J., "The Computer Program LUDI: A New Method for the De Novo Design of Enzyme Inhibitors", Journal of Computer-Aided Molecular Design, vol. 6, pp. 61-78, Feb. 1992.

Bradshaw et al., "Prolonged and Tunable Residence Time Using Reversible Covalent Kinase Inhibitors", Nature Chemical Biology, vol. 11, No. 7, pp. 525-531, May 25, 2015.

Carson, M., "Ribbons 2.0", Journal of Applied Crystallography, vol. 24, No. 5, pp. 958-961, Oct. 1991.

Chayen, N. E., "A Novel Technique to Control the Rate of Vapour Diffusion, Giving Larger Protein Crystals", Journal of Applied Crystallography, vol. 30, No. 2, pp. 198-202, Apr. 1997., International Union of Crystallography.

Chen et al., "A Pilot Study of Lower Doses of Ibrutinib in Patients With Chronic Lymphocytic Leukemia", Blood, vol. 132, No. 21, pp. 2249-2259, Nov. 22, 2018.

Cohen et al., "Molecular Modeling Software and Methods for Medicinal Chemistry", Journal of Medicinal Chemistry, vol. 33, No. 3, pp. 883-894, Mar. 1, 1990.

Copeland, Robert A., "Evaluation of Enzyme Inhibitors in Drug Discovery. A Guide for Medicinal Chemists and Pharmacologists", Second Edition, John Wiley & Sons, Inc, 26 Pages., Mar. 8, 2013.

D'Arcy et al., "A Novel Approach to Crystallising Proteins Under Oil", Journal of Crystal Growth, vol. 168, No. 1-4, pp. 175-180, Oct. 2, 1996.

Davids et al., "Ibrutinib Plus Fludarabine, Cyclophosphamide, and Rituximab as Initial Treatment for Younger Patients With Chronic Lymphocytic Leukaemia: A Single-arm, Multicentre, Phase 2 Trial", Lancet Haematol, vol. 6, No. 8, pp. e419-e428, Aug. 2019.

Di Paolo et al., "Specific BTK Inhibition Suppresses B-Cell and Myeloid Cell-Mediated Arthritis", Nature Chemical Biology, vol. 7, pp. 41-50, Jan. 2011.

Eisen et al., "Hook: A Program for Finding Novel Molecular Architectures That Satisfy the Chemical and Steric Requirements of a Macromolecule Binding Site", Proteins: Structure, Function, Bioinformatics, vol. 19, No. 3, pp. 199-221, Jul. 1994.

Emsley et al., "Features and Development of Coot", Acta Crystallographica Section D: Structural Biology, vol. 66, No. 4, pp. 486-501, Apr. 2010.

Evan et al., "Inhibition of BTK with CC-292 Provides Early Pharmacodynamic Assessment of Activity in Mice and Humans", The Journal of Pharmacology and Experimental Therapeutics, vol. 346, pp. 219-228, Aug. 2013.

Gillet et al., "Sprout: A Program for Structure Generation", Journal of Computer-Aided Molecular Design, vol. 7, pp. 127-153, Apr. 1993.

Goodford, P. J., "A Computational Procedure for Determining Energetically Favorable Binding Sites on Biologically Important Macromolecules", Journal of Medicinal Chemistry, vol. 28, No. 7, pp. 849-857, Jul. 1, 1985.

Goodsell et al., "Automated Docking of Substrates to Proteins by Simulated Annealing", Proteins: Structure. Function, and Genetics, vol. 8, No. 3, pp. 195-202, 1990.

Gualco et al., "Bcl6, Mum1, and Cd10 Expression in Mantle Cell Lymphoma", Applied Immunohistochemistry and Molecular Morphology, vol. 18, No. 2, pp. 103-108, Mar. 2010.

Guex et al., "Swiss-model and the Swiss-pdbviewer: an Environment for Comparative Protein Modeling", Electrophoresis, vol. 18, No. 15, pp. 2714-2723, Dec. 1997.

Guida, Wayne C., "Software for Structure Based Drug Design", Current Opinion in Structural Biology, vol. 4, No. 5, pp. 777-781, Oct. 1994.

Hanks et al., "Protein Kinase Catalytic Domain Sequence Database: Identification of Conserved Features of Primary Structure and Classification of Family Members", Methods in Enzymology, vol. 200, pp. 38-62, 1991.

Hanks et al., "The Protein Kinase Family: Conserved Features and Deduced Phylogeny of the Catalytic Domains", Science, vol. 241, No. 4861, pp. 42-52, Jul. 1, 1988.

Hans et al., "Confirmation of the Molecular Classification of Diffuse Large B-cell Lymphoma by Immunohistochemistry Using a Tissue Microarray", Neoplasia, vol. 3, No. 1, pp. 275-282, 2004.

Hendriks et al., "Targeting Bruton's Tyrosine Kinase in B Cell Malignancies", Nature Reviews Cancer, vol. 14, No. 4, pp. 219-232, Apr. 2014.

Honigberg et al., "The Bruton Tyrosine Kinase Inhibitor PCI-32765 Blocks B-Cell Activation and is Efficacious in Models of Autoimmune Disease and B-cell Malignancy", PNAS, vol. 107, No. 29, pp. 13075-13080, Jul. 20, 2010.

(56) References Cited

OTHER PUBLICATIONS

Jones et al., "Improved Methods for Building Protein Models in Electron Density Maps and the Location of Errors in These Models", Acta Crystallographica Section A, vol. 47, No. 2, pp. 110-119, Mar. 1991.
Kametani et al., "Syntheses of Heterocyclic Compounds", S. Lxxvi. Synthesis of 4-methylpyridine Derivatives, vol. 34, pp. 117-124, 1962.
Kenny et al., "Bruton's Tyrosine Kinase Mediates the Syngergistic Signalling between TLR9 and the B Cell Receptor by Regulating Calcium and Calmodulin", PLOS One, vol. 8, No. 8, pp. 1-14, Aug. 2013.
Kershaw et al., "X-ray Crystallography and Computational Docking for the Detection and Development of Protein-Ligand Interactions", Current Medicinal Chemistry, vol. 20, No. 4, pp. 569-575, Feb. 2013.
Kong et al., "Increased Expression of Bruton Tyrosine Kinase in Patients with Lupus Nephritis and Its Clinic Significance", 2015 ACR/ARHP Annual Meeting, vol. 63, No. S10, 4053 pages, Sep. 29, 2015.
Kuntz et al., "A Geometric Approach to Macromolecule-ligand Interactions", Journal of Molecular Biology, vol. 161, No. 2, pp. 269-288, Oct. 25, 1982.
Lauri et al., "Caveat: A Program to Facilitate the Design of Organic Molecules", Journal of Computer-Aided Molecular Design, vol. 8, No. 1, pp. 51-66, Feb. 1994.
Liebschner et al., "Macromolecular Structure Determination Using X-rays, Neutrons and Electrons: Recent Developments in Phenix", Structural Biology, vol. 75, No. 10, pp. 861-877, Oct. 2019.
Liu et al., "Antiarthritis Effect of a Novel Bruton's Tyrosine Kinase (BTK) Inhibitor in Rat Collagen-Induced Arthritis and Mechanism-Based Pharmacokinetic/Pharmacodynamic Modeling: Relationships between Inhibition of BTK Phosphorylation and Efficacy", The Journal of Pharmacology and Experimental Therapeutics, vol. 388, No. 1, pp. 154-163, Jul. 1, 2011.
Lodhi et al., "Biomarkers and Novel Therapeutic Approaches for Diffuse Large B-cell Lymphoma in the Era of Precision Medicine", Oncotarget, vol. 11, No. 44, pp. 4045-4073, Nov. 3, 2020.
Lu et al., "The Distinct Clinical Features and Prognosis of the CD10+MUM1+ and CD10-Bcl6-MUM1-Diffuse Large B-Cell Lymphoma", Non-Hodgkin Lymphoma: Biology, excluding Therapy: Poster III, Blood, vol. 126, No. 23, 10 Pages, Dec. 3, 2015.
Magidson et al., "lodization of A-aminopyridine", Trudy Nauchnogo Khimiko-Farmatsevticheskogo Instituta, vol. 16, pp. 23-31, 1926.
Martin, Y. C., "3D Database Searching in Drug Design", Journal of Medicinal Chemistry, vol. 35, No. 12, pp. 2145-2154, Jun. 12, 1992.
Meng et al., "Automated Docking with Grid-Based Energy Evaluation", Journal of Computational Chemistry, vol. 13, No. 4, pp. 505-524, 1992.
Miranker et al., "Functionality Maps of Binding Sites: A Multiple Copy Simultaneous Search Method", Proteins: Structure, Function and Genetics, vol. 11, No. 1, pp. 29-34, Sep. 1991.
Navia et al., "Use of Structural Information in Drug Design", Current Opinion in Structural Biology, vol. 2, No. 2, pp. 202-210, Apr. 1992.
NCT04210219, "A Study of JNJ-64264681 in Participants With Non-Hodgkin Lymphoma and Chronic Lymphocytic Leukemia", Case Medical Research, Dec. 24, 2019, Kernel Networks Inc.
Nishibata et al., "Automatic Creation of Drug Candidate Structures Based on Receptor Structure. Starting Point for Artificial Lead Generation.", Tetrahedron, vol. 47, No. 43, pp. 8985-8990, Nov. 4, 1991.
Otwinowski et al., "Processing of X-ray Diffraction Data Collected in Oscillation Mode", Methods in Enzymology, vol. 276, pp. 307-326, 1997.
Pan et al., "Discovery of Selective Irreversible Inhibitors for Bruton's Tyrosine Kinase", Chem Med Chem, vol. 2, pp. 58-61, 2007.
Pav et al., "Microtube Batch Protein Crystallization: Applications to Human Immunodeficiency Virus Type 2 (Hiv-2) Protease and Human Renin", Proteins: Structure, Function, and Genetics, vol. 20, pp. 98-102, 1994.
Ponzoni et al., "Prognostic Value of Bcl-6, Cd10 and Cd38 Immunoreactivity in Stage I-ii Gastric Lymphomas: Identification of a Subset of Cd10+ Large B-cell Lymphomas with a Favorable Outcome", International Journal of Cancer, vol. 106, No. 2, pp. 288-291, Aug. 20, 2003.
Rocca et al., "First Metalation of Aryl Iodides: Directed Ortho-Lithiation of Iodopyridines, Halogen-Dance, and Application to Synthesis", The Journal of Organic Chemistry, vol. 58, No. 27, pp. 7832-7838, Jun. 2, 1993.
Schnute et al., "Aminopyrazole Carboxamide Bruton's Tyrosine Kinase Inhibitors. Irreversible to Reversible Covalent Reactive Group Tuning", ACS Medicinal Chemistry Letters, vol. 10, No. 1, pp. 80-85, Dec. 3, 2018.
Selby, Thomas P., "Synthesis of a Novel Thiadiazacyclazine", Journal of Organic Chemistry, vol. 53, No. 8, pp. 2386-2388, 1988.
Shanafelt et al., "Ibrutinib-Rituximab or Chemoimmunotherapy for Chronic Lymphocytic Leukemia", The New England Journal of Medicine, vol. 381, No. 5, pp. 432-443, 2019.
Smith et al., "Comparision of Biosequences", Advances in Applied Mathematics, vol. 02, No. 04, pp. 482-489, Dec. 1981.
Svensson et al., "B Cell-deficient Mice Do Not Develop Type Ii Collagen-induced Arthritis (Cia)", Clinical and Experimental Immunology, vol. 111, No. 3, pp. 521-526, Mar. 1998.
Tichenor et al., "Discovery of a Potent and Selective Covalent Inhibitor of Bruton's Tyrosine Kinase with Oral Anti-Inflammatory Activity", ACS Medicinal Chemistry Letters, vol. 12, No. 5, pp. 782-790, Apr. 5, 2021.
West et al., "Solid State Chemistry and Its Applications", Solid Solutions, Chapter 10, pp. 358-365, 1988., Wiley, New York.
Whang et al., "Bruton's Tyrosine Kinase Inhibitors for the Treatment of Rheumatoid Arthritis", Drug Discovery Today, vol. 19, No. 8, pp. 1200-1204, Aug. 2014.
Woyach et al., "Bruton's Tyrosine Kinase (Btk) Function Is Important to the Development and Expansion of Chronic Lymphocytic Leukemia (CII)", Blood, vol. 123, No. 8, pp. 1207-1213, Feb. 20, 2014.
Wu et al., "Second-generation Inhibitors of Bruton Tyrosine Kinase", Journal of Hematology & Oncology, vol. 9, No. 1, 7 pages, Sep. 2, 2016.
Younes et al., "Combination of Ibrutinib with Rituximab, Cyclophosphamide, Doxorubicin, Vincristine, and Prednisone (R-chop) for Treatment-naive Patients With Cd20-postive B-cell Non-hodgkin Lymphoma: a Non-randomised, Phase 1b Study", Lancet Oncology, vol. 15, pp. 1019-1026, 2014.
NCT04657224, "A Study of JNJ-64264681 and JNJ-67856633 in Participants With Non-Hodgkin Lymphoma and Chronic Lymphocytic Leukemia", Clinical Trial NCT04657224, 3 Pages, Feb. 25, 2021.

* cited by examiner $$\% \text{ occupancy} = 100 \times \frac{\text{Baseline Free BTK (BTKb) + Free BTK (BTKi)}}{\text{BTK + BTKb + BTKi}}$$

1, ibrutinib 2, acalabrutinib 3, zanubrutinib

| | |
|---|---|
| IC50 | 2.088e-008 |
| 95% CI | 1.816e-008 to 2.401e-008 |
| R square | 0.9547 |

A

B

A

B

INHIBITORS OF BRUTON'S TYROSINE KINASE AND METHODS OF THEIR USE

CROSS REFERENCE TO OTHER APPLICATIONS

This application claims priority to U.S. Provisional Application No. 63/196,843 filed on Jun. 4, 2021 titled "Inhibitors Of Bruton's Tyrosine Kinase And Methods Of Their Use" which is incorporated herein by reference in its entiriety.

TECHNICAL FIELD

The present disclosure is directed to the use of small molecule tyrosine kinase inhibitors for the treatment of malignancies.

BACKGROUND

Malignancies, in particular diffuse large B-cell lymphoma (DLBCL), mantle cell lymphoma (MCL), follicular lymphoma (FL), marginal zone lymphoma (MZL), chronic lymphocytic leukemia (CLL), small lymphocytic lymphoma (SLL), Waldenstrom macroglobulinemia, and other conditions such as chronic graft versus hos disease, continues to afflict patients. Alternative, effective treatments of cancer are still needed.

Human Bruton's tyrosine kinase ("BTK") is a ~76 kDa protein belonging to the Tec family of non-receptor tyrosine kinases. Tec kinases form the second largest family of cytoplasmic tyrosine kinases in mammalian cells, which consists of four other members in addition to BTK: the eponymous kinase TEC, ITK, TXK/RLK and BMX. Tec kinases are evolutionarily conserved throughout vertebrates. They are related to, but structurally distinct from, the larger Src and Syk kinase families. Tec family proteins are abundantly expressed in hematopoietic tissues and play important roles in the growth and differentiation of blood and endothelial cells in mammals.

Based upon BTK expression from IHC studies described in the art, Btk inhibition has the potential to modulate biology associated with B cells, macrophages, mast cells, osteoclasts, and platelet microparticles. Corneth, O. B., et al. Curr. Top. Microbiol. Immunol. *BTK Signaling in B Cell Differentiation and Autoimmunity.* 2015 Sept. 5.

SUMMARY

Compositions comprising the compound of Formula (III) are described. Methods of using the compound of Formula (III) are also within the scope of the disclosure. Also described are methods of treating a malignancy in an individual in need thereof, comprising administering a therapeutically effective amount of a compound of Formula (III):

(III)

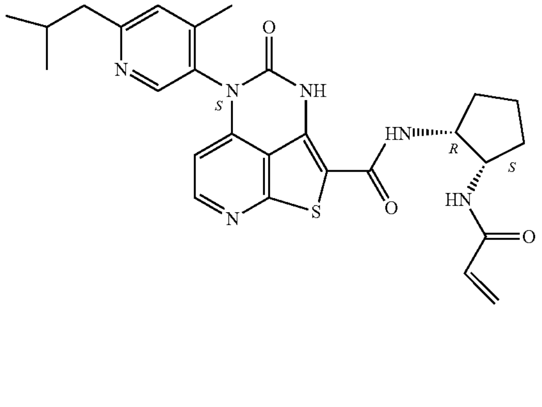

or a pharmaceutically acceptable salt, hydrate, polymorph or solvate thereof. In some aspects, the malignancy is selected from the group consisting of a diffuse large B-cell lymphoma (DLBCL), mantle cell lymphoma (MCL), follicular lymphoma (FL), marginal zone lymphoma (MZL), chronic lymphocytic leukemia (CLL), small lymphocytic lymphoma (SLL), and Waldenstrom macroglobulinemia, Chronic graft versus host disease.

Some aspects are directed to methods of treating chronic graft versus host disease in an individual in need thereof, comprising administering a therapeutically effective amount of a compound of Formula (III):

(III)

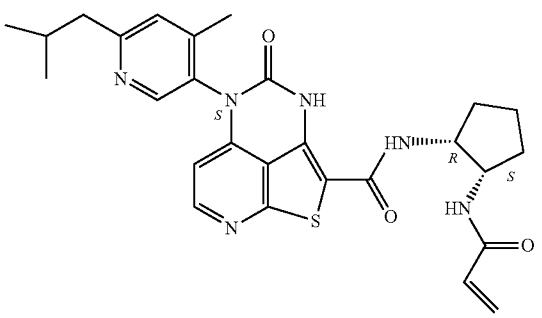

or a pharmaceutically acceptable salt, hydrate, polymorph or solvate thereof.

In some aspects the therapeutically effective amount of the compound of Formula (III) is from about 140 mg to about 560 mg. In some aspects, the therapeutically effective amount of the compound of Formula (III) is administered once a day. In some aspects, the therapeutically effective amount of the compound of Formula (III) is administered twice daily. In some aspects, the therapeutically effective amount of the compound of Formula (III)is about 140 mg. In some aspects, the therapeutically effective amount of the compound of Formula (III) is about 280 mg. In some aspects, the therapeutically effective amount of the compound of Formula (III) is about 560 mg.

In some aspects the therapeutically effective amount of the compound of Formula (III) is an amount that results in a $C_{(max,day1)}$ of about 59.992 ng/ml to about 2,377.2 ng/ml. In some aspects, the therapeutically effective amount of the compound of Formula (III) is an amount that results in a $C_{(max,day1)}$ of about 239.97 ng/ml to about 9,509 ng/ml. In some aspects, the therapeutically effective amount of the compound of Formula (III) is an amount that results in a $C_{(max,ss)}$ of about 66.855 ng/ml to about 2,395.4 ng/ml. In some aspects, the therapeutically effective amount of the compound of Formula (III) is an amount that results in a $C_{(max,ss)}$ of about 267.42 ng/ml to about 9,581.5 ng/ml. In some aspects, the therapeutically effective amount of the compound of Formula (III) is an amount that results in a $AUC_{(day\ 1)}$ of about 312.1 ng·hr/ml to about 11,517 ng·hr/ml. In some aspects, the therapeutically effective amount of the compound of Formula (III) is an amount that results in a $AUC_{(day\ 1)}$ of about 1,248.4 ng·hr/ml to about 46,068 ng·hr/ml. In some aspects, the therapeutically effective amount of the compound of Formula (III) is an amount that results in a $AUC_{(ss)}$ of about 312.27 ng·hr/ml to about 13,015 ng·hr/ml. In some aspects, the therapeutically effective amount of the compound of Formula (III) is an amount that results in a $AUC_{(ss)}$ of about 1,249.1 ng·hr/ml to about 52,061 ng·hr/ ml. In some aspects, the therapeutically effective amount of the compound of Formula (III) is an amount that results in a $BTKO_{(max/day1)}$ of about 30.9% occupancy to about 99.8% occupancy. In some aspects, the therapeutically effective amount of the compound of Formula (III) is an amount that results in a $BTKO_{(max/day1)}$ of about 87.1% occupancy to about 100% occupancy. In some aspects, the therapeutically effective amount of the compound of Formula (III) is an amount that results in a $BTKO_{(max/ss)}$ of about 59.4% occupancy to about 99.9% occupancy. In some aspects, the therapeutically effective amount of the compound of Formula (III) is an amount that results in a $BTKO_{(max/ss)}$ of about 90.2% occupancy to about 100% occupancy. In some aspects, the therapeutically effective amount of the compound of Formula (III) is an amount that results in a $BTKO_{(trough/day1)}$ of about 23.3% occupancy to about 91.3% occupancy. In some aspects, the therapeutically effective amount of the compound of Formula (III) is an amount that results in a $BTKO_{(trough/day1)}$ of about 63.9% occupancy to about 97.3% occupancy. In some aspects, the therapeutically effective amount of the compound of Formula (III) is an amount that results in a $BTKO_{(trough/ss)}$ of about 50.2% occupancy to about 95.4% occupancy. In some aspects, the therapeutically effective amount of the compound of Formula (III) is an amount that results in a $BTKO_{(trough/ss)}$ of about 75.5% occupancy to about 99.3% occupancy.

In some aspects, the therapeutically effective amount of the compound of Formula (III) is administered once a day. In some aspects, the therapeutically effective amount of the compound of Formula (III) is administered twice a day. In some aspects, the therapeutically effective amount of the compound of Formula (III) is administered three times a day. In some aspects the compound of Formula (III) is administered orally.

In some aspects, the methods described herein further comprise administering 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin5-yloxy)benzamide). In some aspects, the methods described herein further comprise administering cyclophosphamide, doxorubicin, vincristine, prednisone and rituximab.

FIGURES

FIG. 1 depicts a schematic overview of the design for NCT03607513 (MAD=multiple ascending dose; PBO= placebo; SAD=single ascending dose).

FIG. 2 depicts a mechanistic PK/BTKO Model. Aα=Amount of compound of Formula (III) in the depot compartment of the PK model; Ka=absorption rate constant; Q=intercompartmental clearance between compartments 1 and 2; CL=apparent clearance; Syn=synthesis rate constant for free BTK; Kdegf=degradation rate constant of free BTK; Kon=association rate constant; Koff=dissociation rate constant; Kdegi=degradation rate of bound BTK; Kinact= covalent binding rate; BTK=free BTK; BTKb=bound BTK; BTKi=inactivated BTK.

Figure 7:
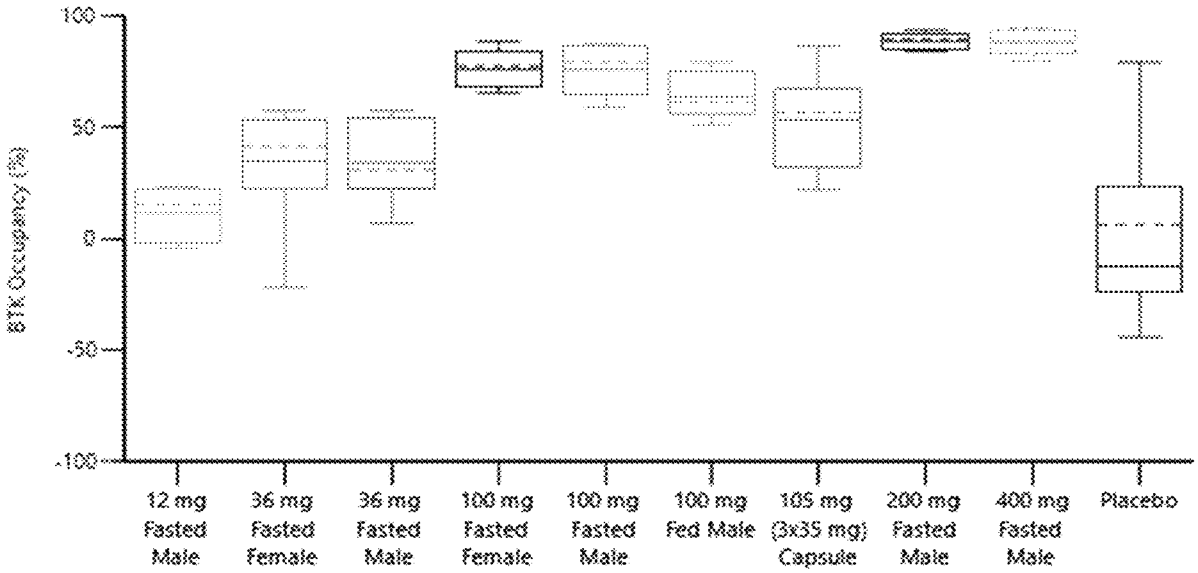

FIG. 7 depitcs observed % BTK Occupancy at 24 hours post-dose.

Figure 8:
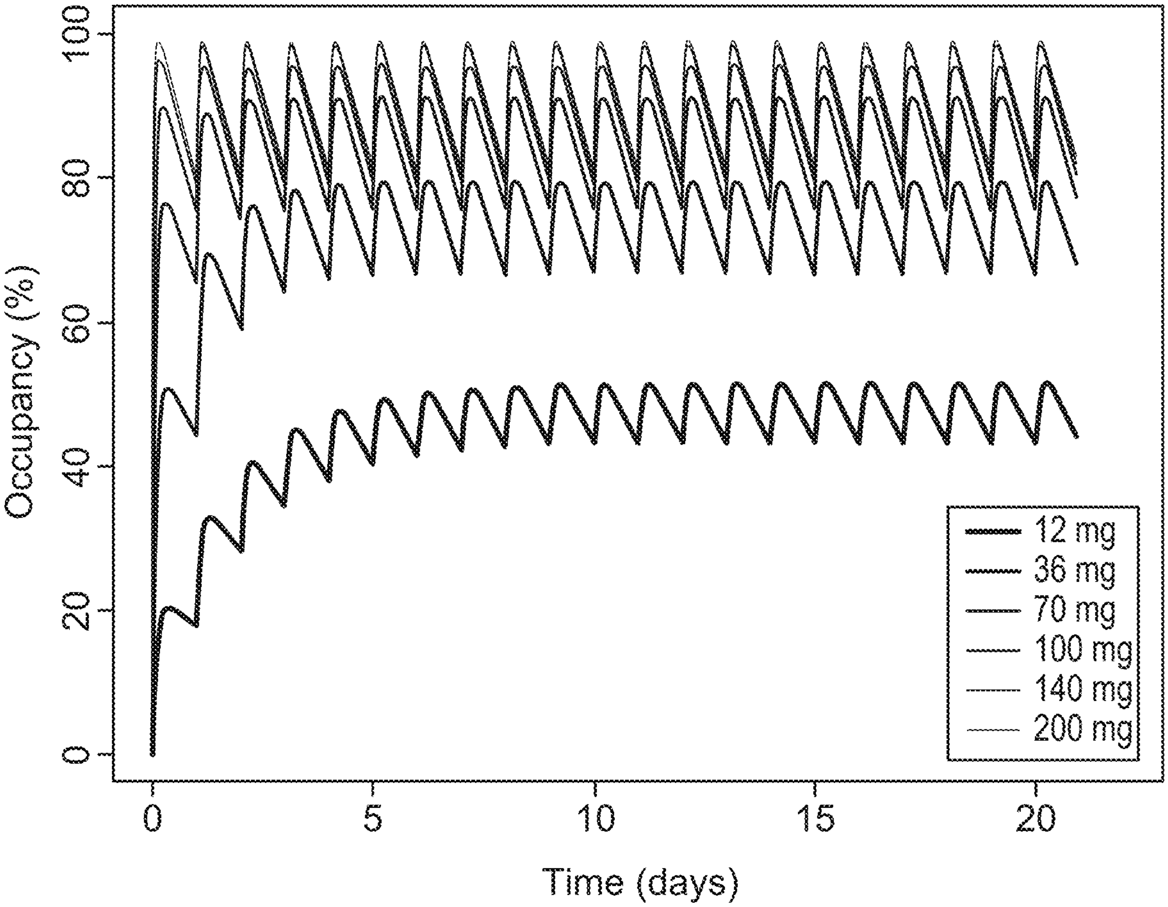

FIG. 8 depicts predicted % BTKO for multiple dosing based on PK/BTKO Simulations Based on Oral Solution Data from SAD Cohorts 1-5.

Figure 9A:
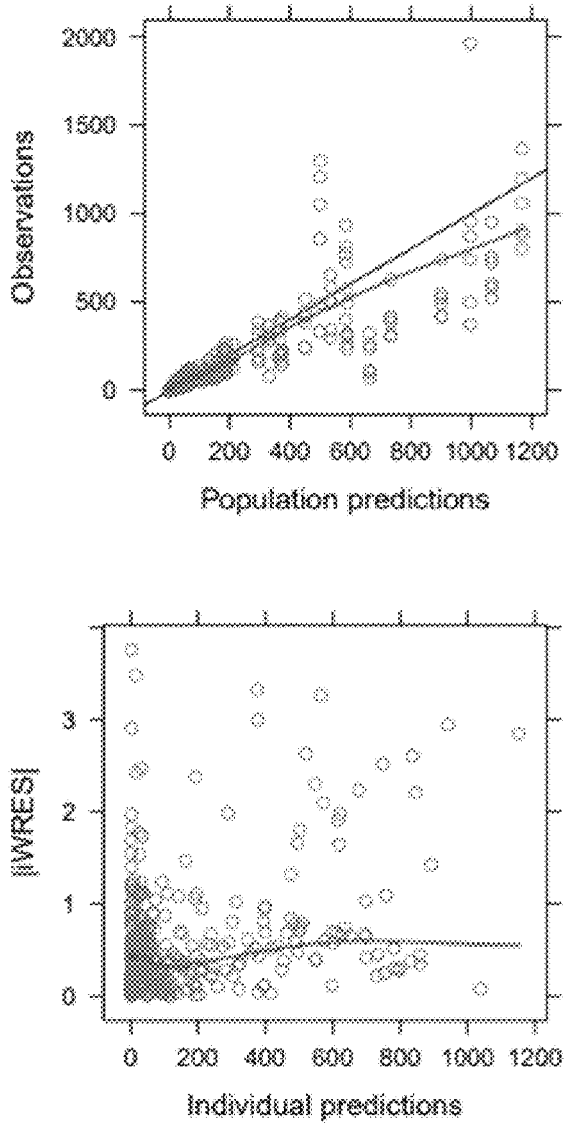
Figure 9B:
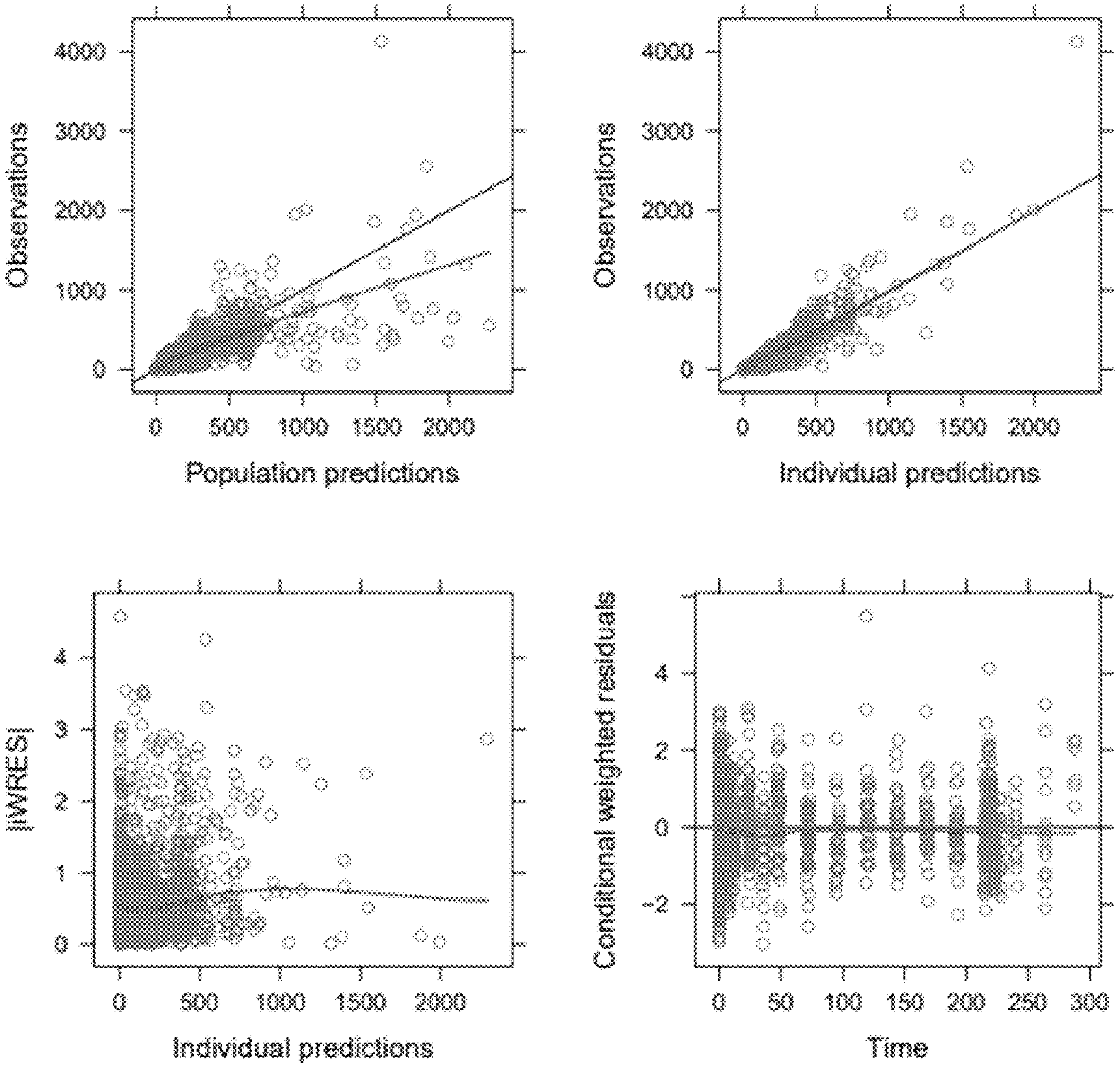

FIG. 9A-B depict Goodness-of-Fit Plots for the Population PK Model Using (A) First 5 SAD Cohorts Data (B) All SAD and MAD Data. iWRES|=absolute individual weighted residuals. Units: Observations or predictions=ng/mL; Time=hour.

Figure 10A:
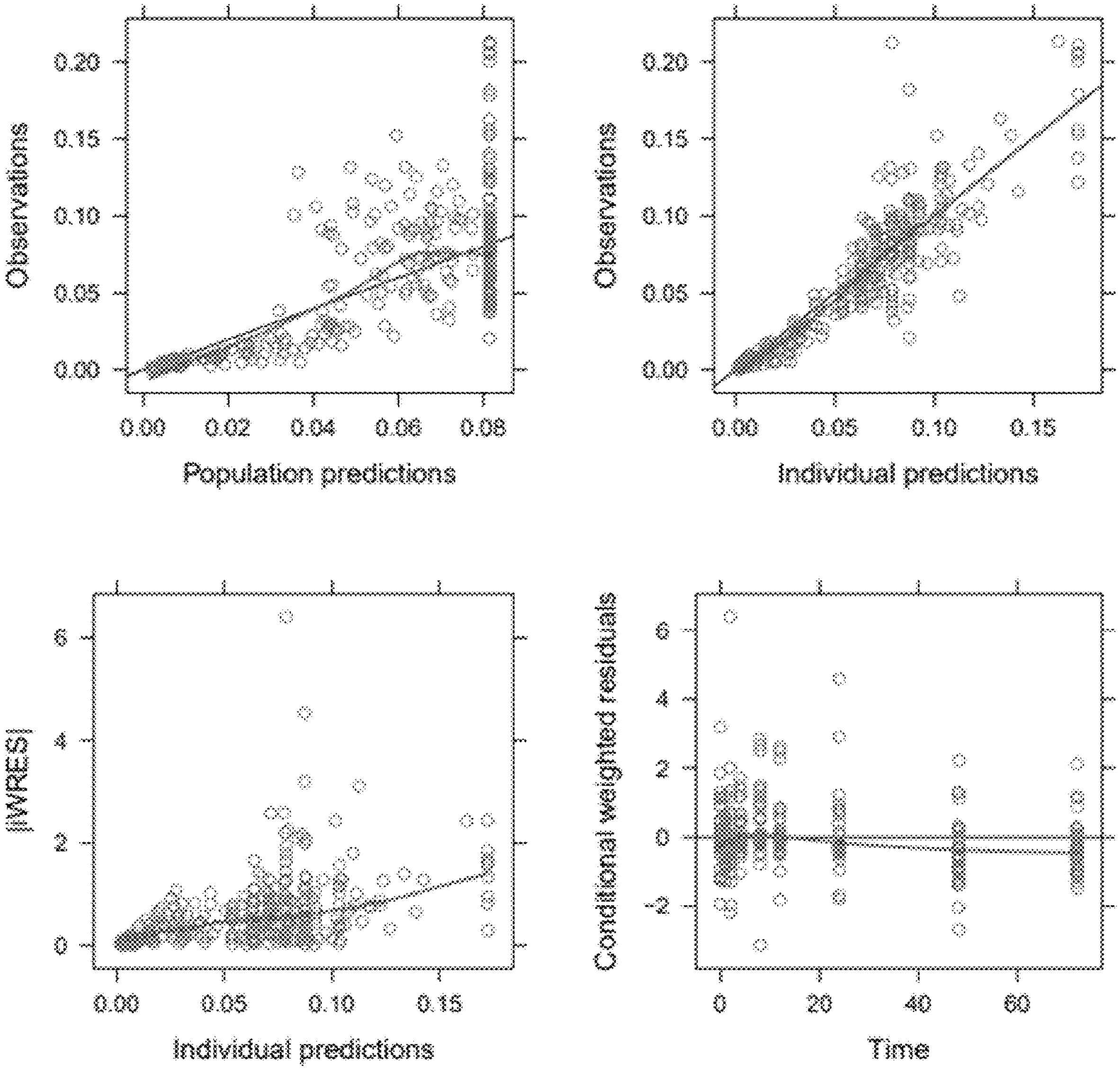
Figure 10B:
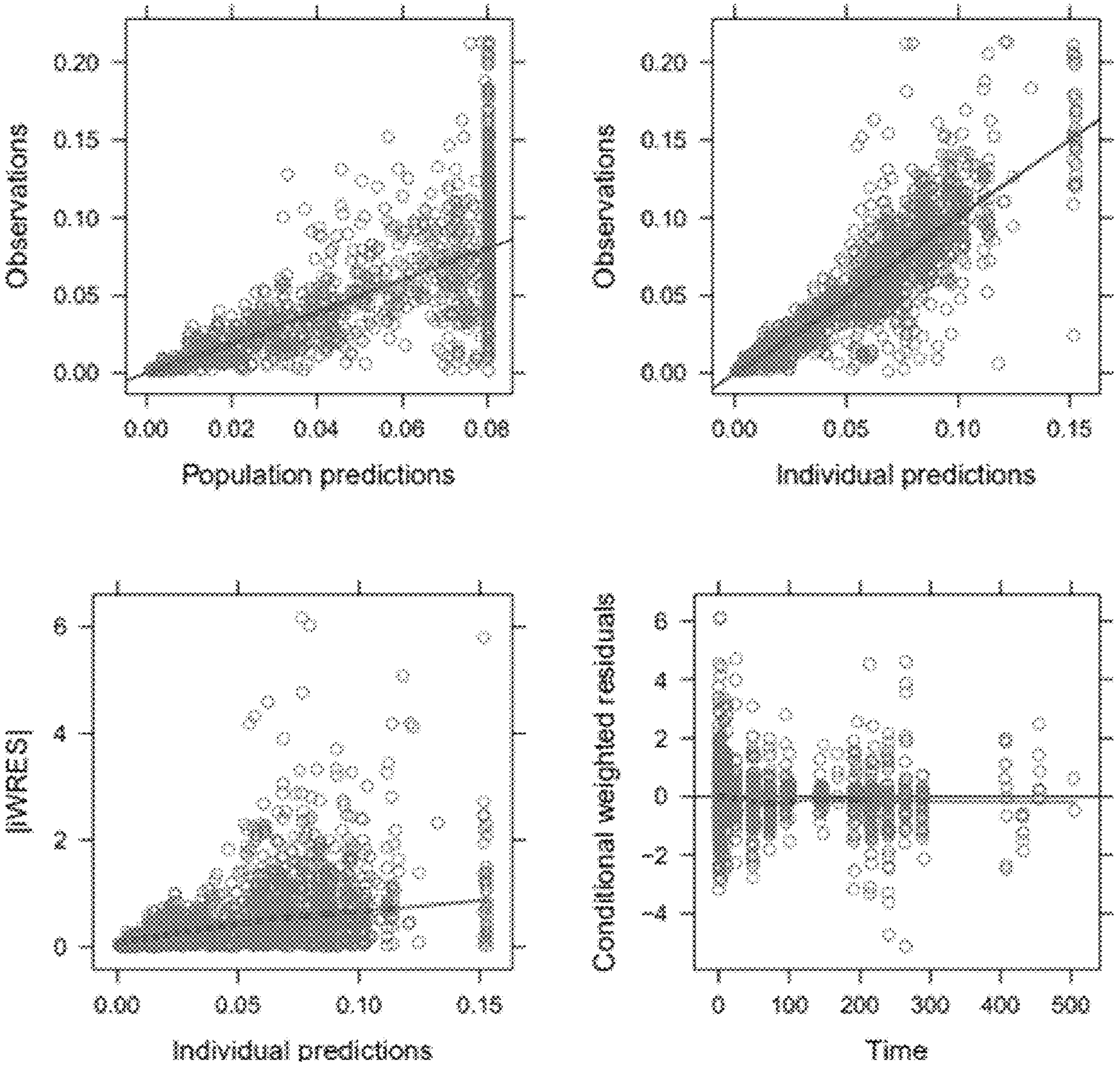

FIG. 10A-B depict Goodness-of-Fit Plots for the PD Model Using (A) Cohort 2-5 Data (B) All SAD and MAD Data. iWRES|=absolute individual weighted residuals. Units: Observations or predictions=ng/mL; Time=hour.

Figure 11:
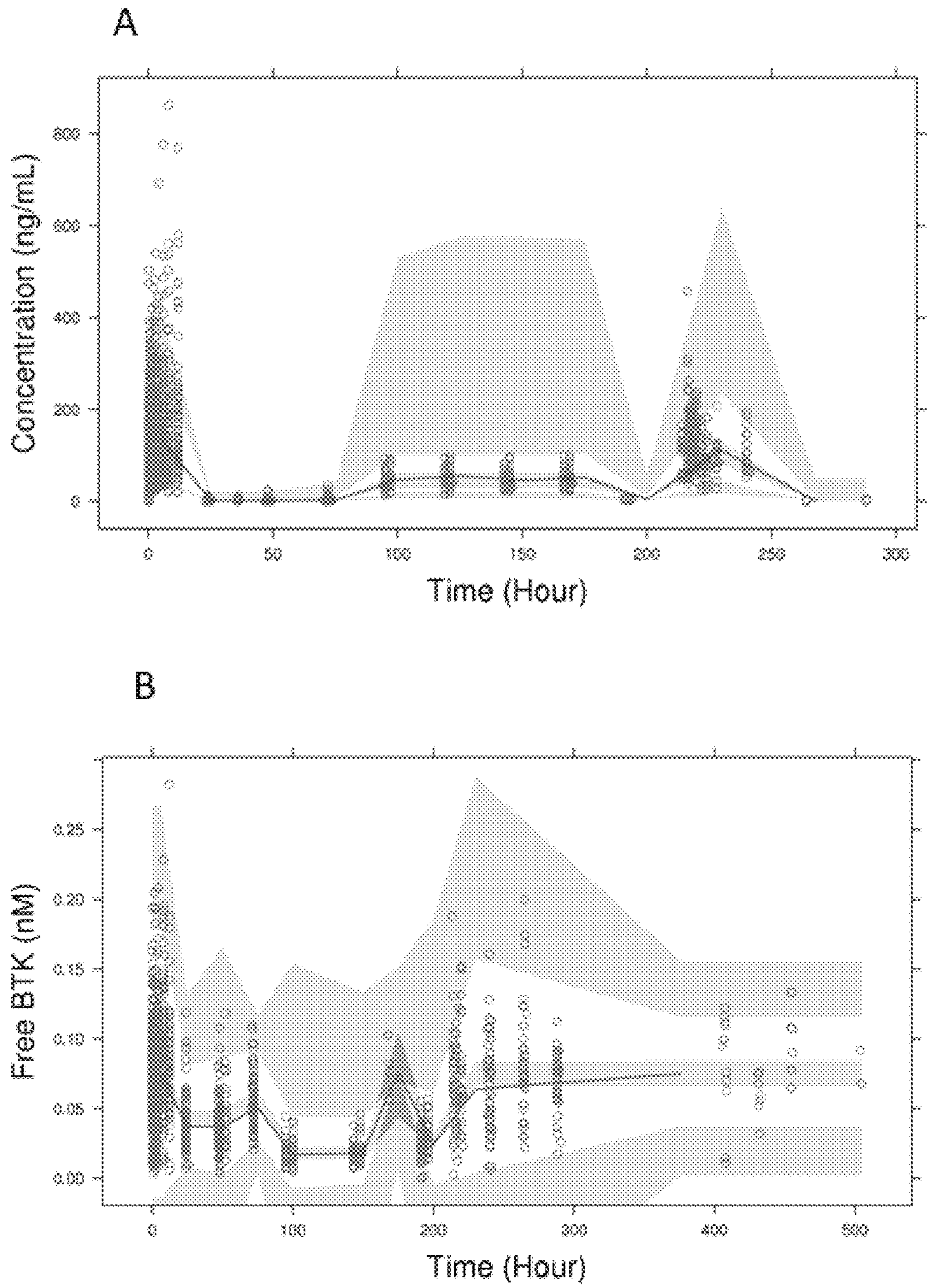

FIG. 11. depicts Prediction-Corrected Visual Predictive Check for (A) Population PK (B) PD.

Figure 12:
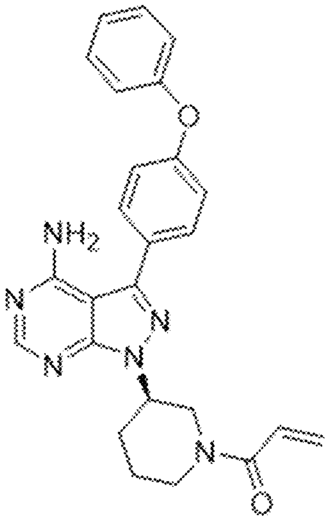
Figure 12:
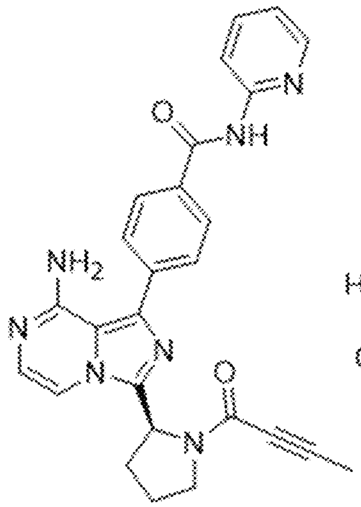
Figure 12:
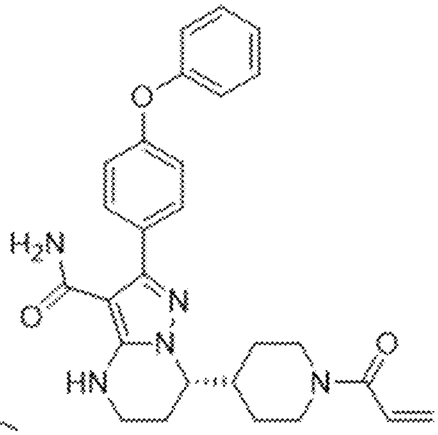

FIG. 12 depicts exemplary covalent BTK inhibitors.

Figure 13:
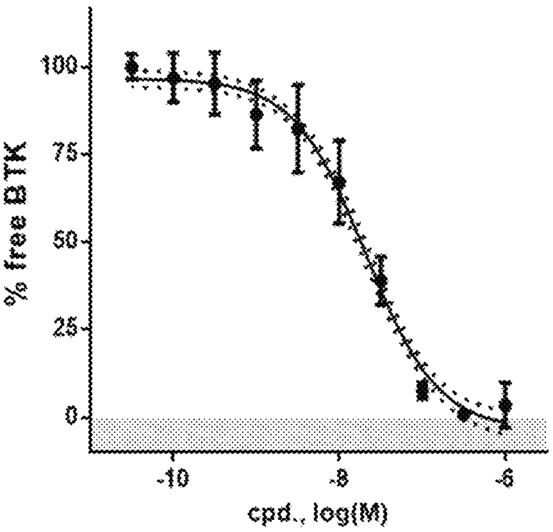

FIG. 13 depicts concentration-dependent occupancy of Bruton's tyrosine kinase by the compound of Formula (III) in Ramos human B cells (mean±SD; n=11).

Figure 14:
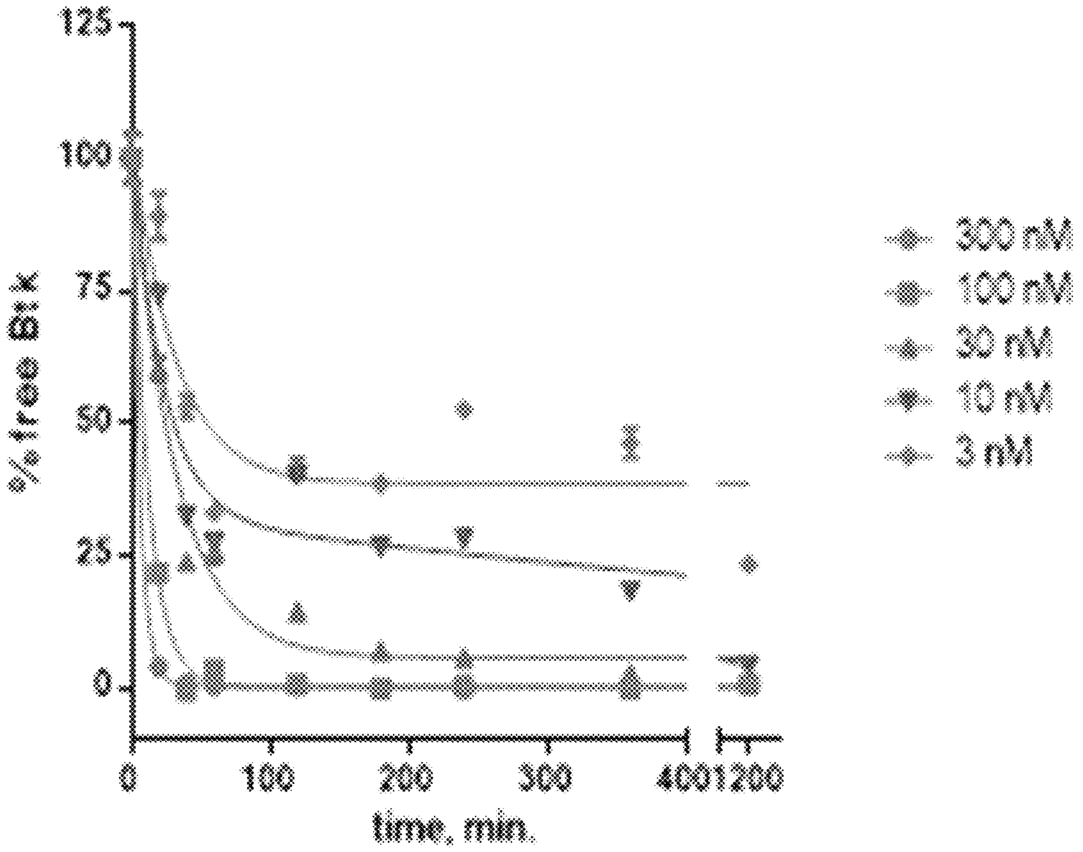

FIG. 14 depicts time-dependent occupancy of Bruton's tyrosine kinase in Ramos B cells by the compound of Formula (III).

Figure 15:
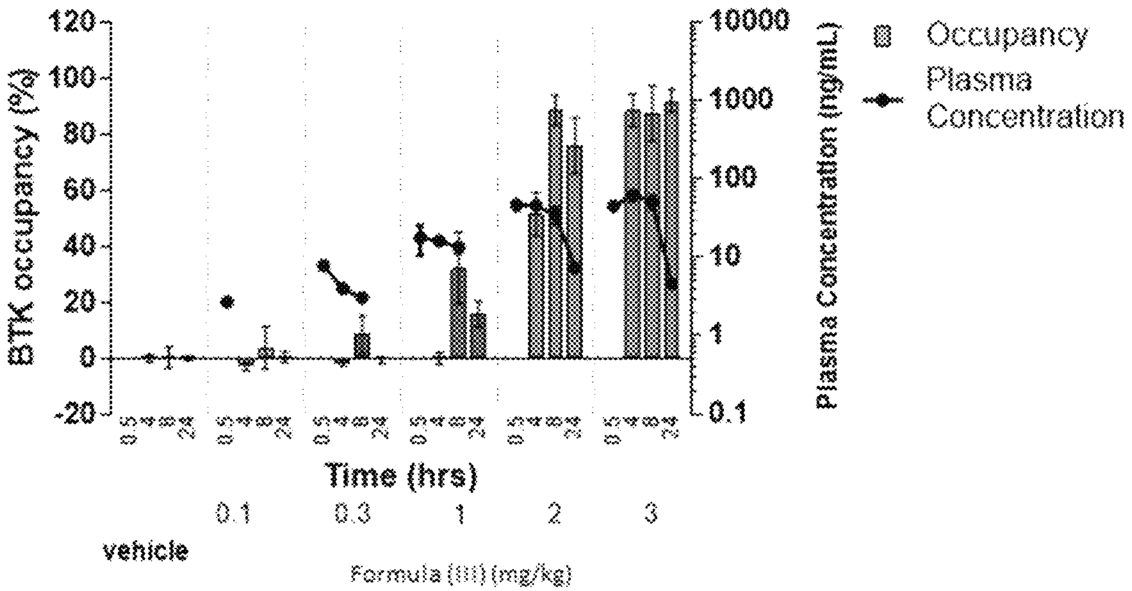
Figure 15:
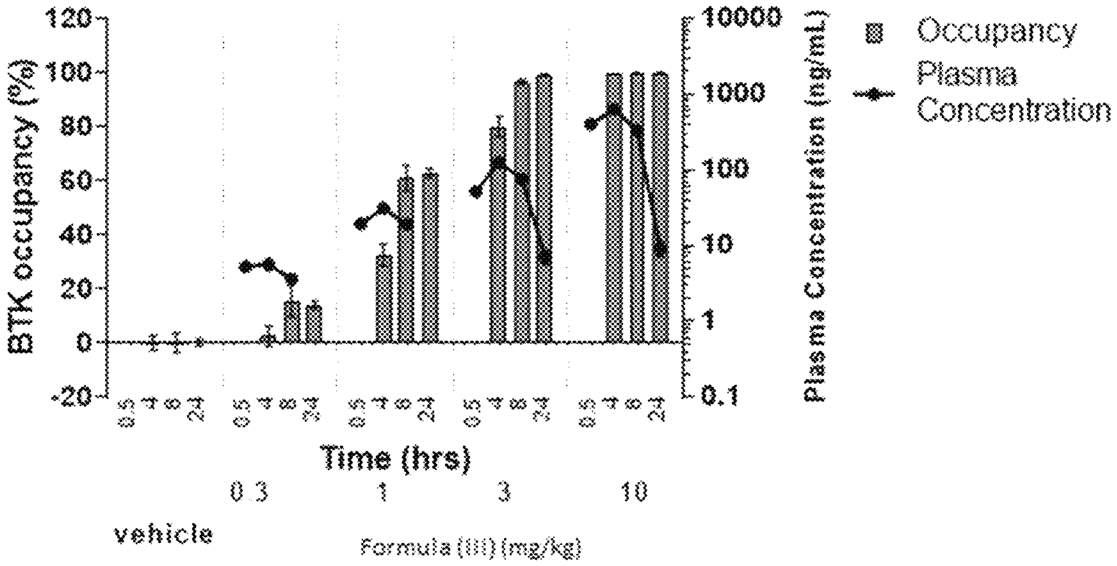

FIG. 15 depicts plasma concentration and receptor occupancy of Bruton's tyrosine kinase by the compound of Formula (III) from two independent studies (A-B). Target-site occupancy was measured using enzyme-linked immunosorbent assay, and plasma concentration was measured using liquid chromatography-mass spectrometry. Data represent mean±SEM (n=4/group).

Figure 16:
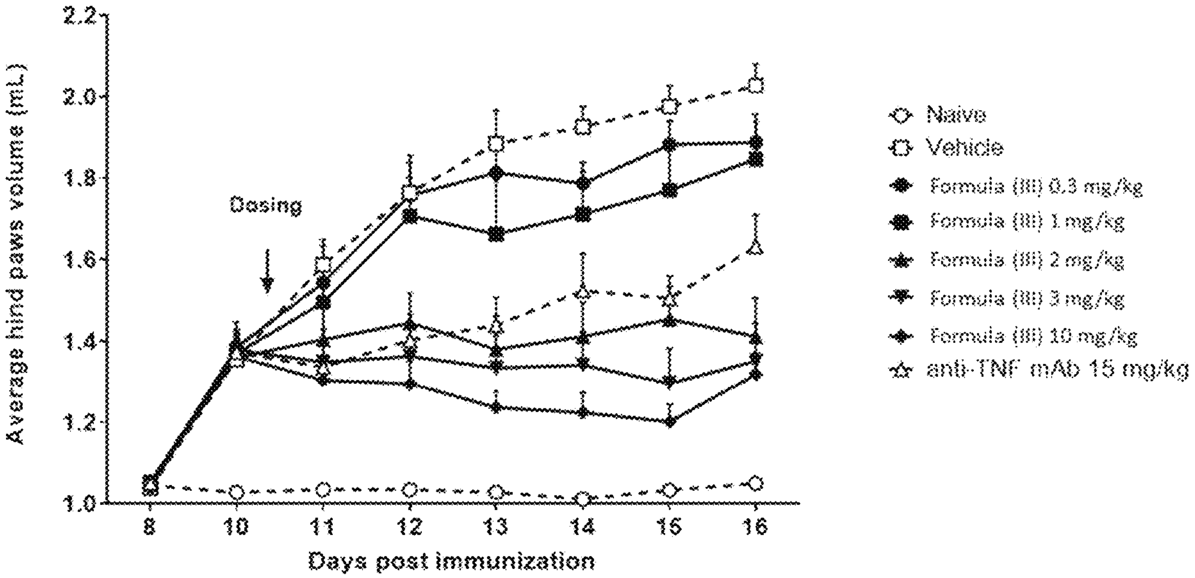

FIG. 16 depicts the effect of the compound of Formula (III) on hind paw inflammation in the rat effect of the compound of Formula (III) (0.3, 1, 2, 3, 10 mg/kg/day, PO, QD, for all 7 days (day 10-16) of dosing) on hind paw inflammation in rats. Data represent mean and error bars indicate standard error of the mean (SEM) (n=6 for the naïve group, n=8 for treatment groups).

Figure 17:
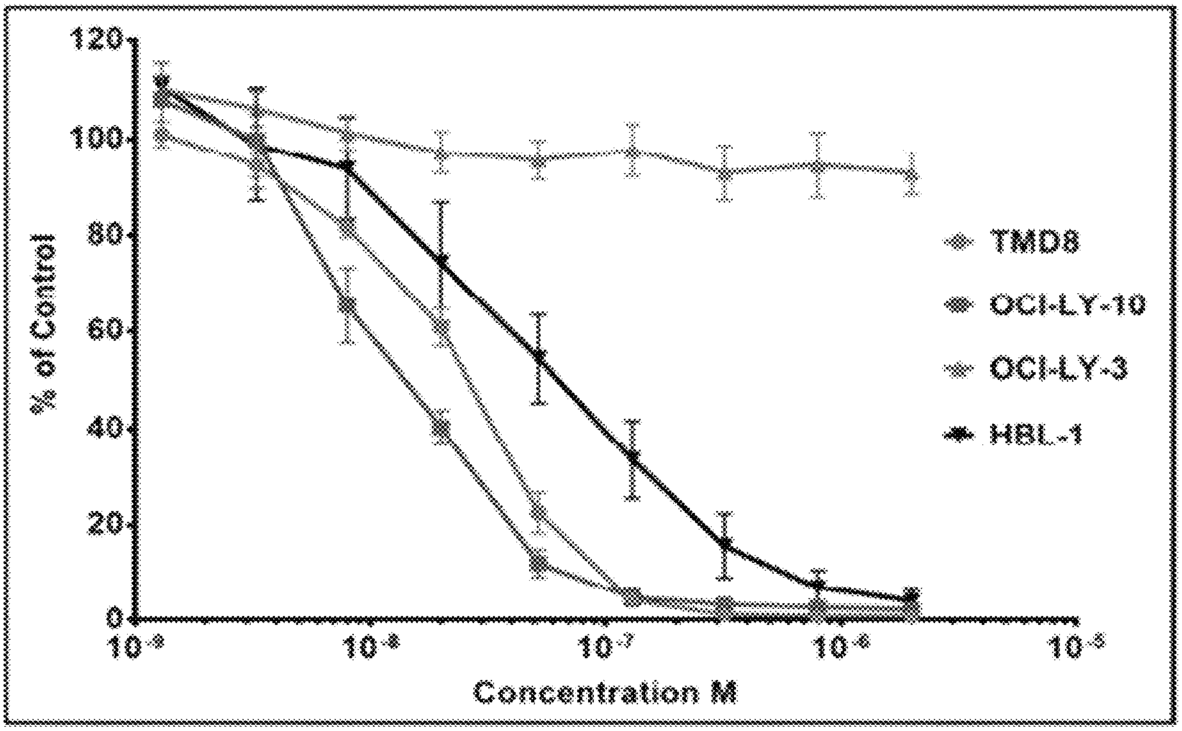

FIG. 17 depicts antiproliferative activity of the compound of Formula (III) in ABC-DLBCL cell lines (8 days) (n=4).

Figure 18:
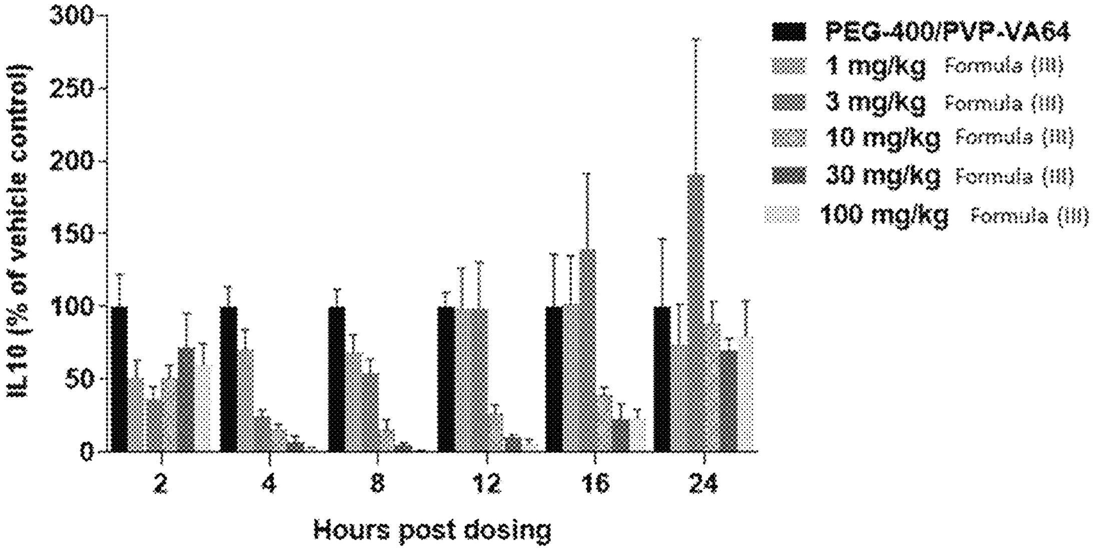

FIG. 18 depicts circulating human IL-10 cytokine serum levels of mice treated with the compound of Formula (III). IL-10 cytokine levels are graphed as % normalized to vehicle control IL-10 levels ±SEM. Female NSG mice were implanted SC with OCI-LY10 cells on the right flank on Day 0. After tumors were established 39 days post implantation, mice were randomized into experimental groups and dosed orally with a single dose (n=5/dose level/time point). Serum samples were collected 2, 4, 8, 12, 16 and 24 hours after compound administration.

Figure 19:
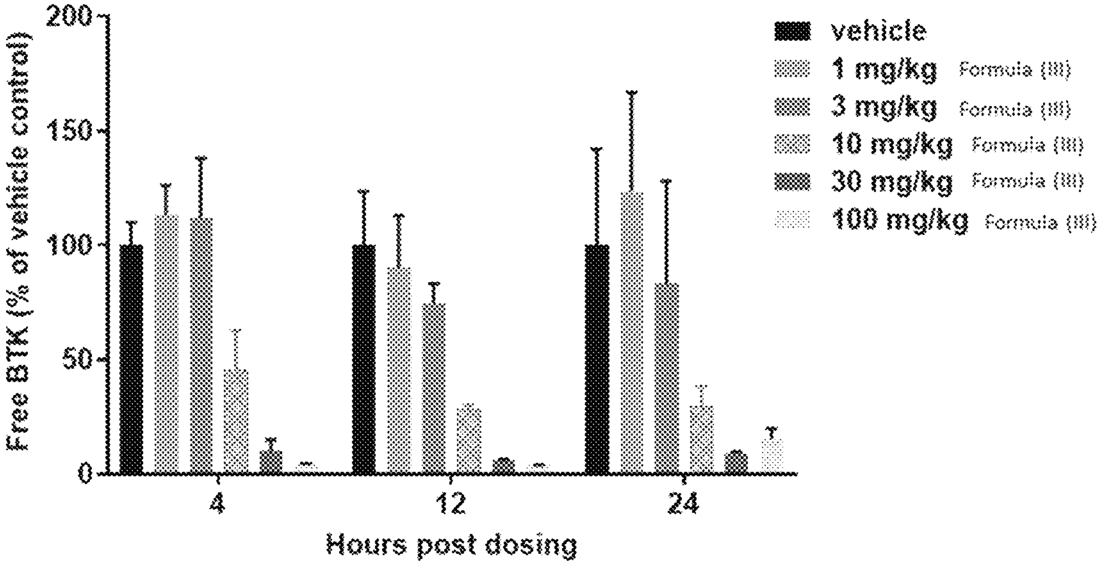

FIG. 19 depicts BTK protein occupancy in OCI-LY10 ABC-DLBCL tumor lysates of NSG mice treated with the compound of Formula (III). Unoccupied BTK protein levels are graphed as % normalized to vehicle control BTK levels ±SEM. Female mice were implanted SC on the right flank on day 0. Tumors were established 39 days post implantation, randomized into experimental groups and dosed orally with a single dose (n=5/dose level/time point). Tumor samples were harvested 4, 12 and 24 hours after compound administration.

Figure 20:
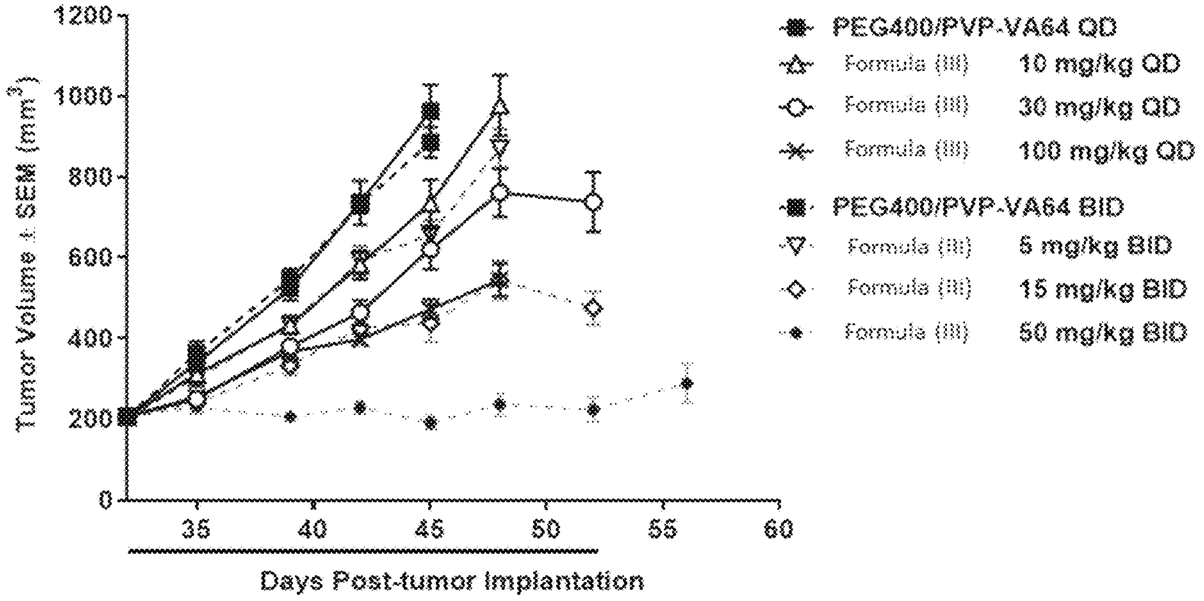

FIG. 20 depicts the effect of the compound of Formula (III) on growth of established OCI-LY10 human ABC-DLBCL xenografts in mice PEG400/PVP-VA64, Polyethylene glycol 400/N-vinylpyrrolidone and vinyl acetate 64; SEM, standard error of the mean. Group tumor volumes are graphed as the mean±SEM. Bar below x-axis indicates the treatment period. Groups are plotted while at least ⅔ of the animals remained on the study. Mice were implanted SC on the right flank on Day 0. Tumors were established 33 days post implantation, mice were randomized into experimental groups and dosed orally twice or once daily for 3 weeks (n=10/group).

Figure 21:
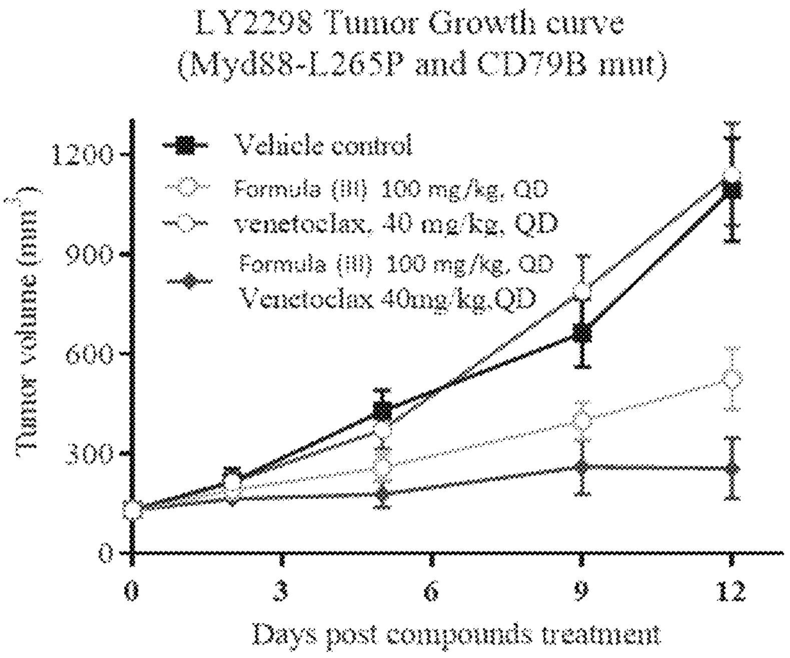
Figure 21:
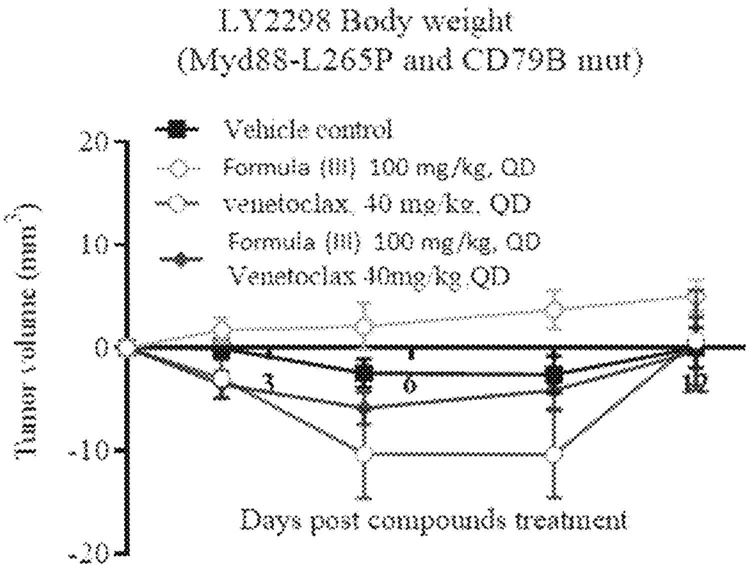

FIG. 21 depicts a LY2298 tumor xenograft study with the compound of Formula (III) and venetoclax as single agents and in combination. Tumor Growth inhibition of the compound of Formula (III)-100 mpk QD, venetoclax-40 mpk QD, the compound of Formula (III)-100 mpk+ venetoclax−40 mpk in LY2298 were 59.2%, −4.8% and 87.0% respectively.

Figure 22:
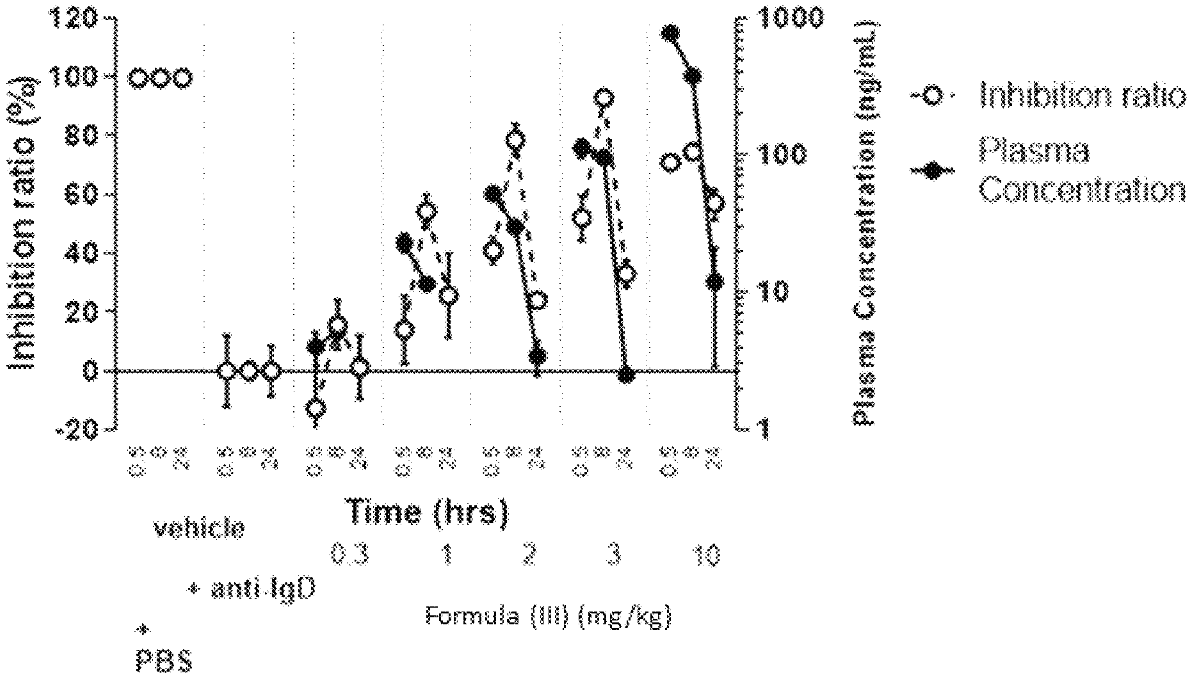

FIG. 22 depicts plasma concentration and inhibition of B-cell activation by the compound of Formula (III) at 2, 3, and 10 mg/kg achieved prolonged inhibition of B-cell activation compared with plasma concentration, with an inhibition ratio of 78% or greater at 8 hours. Data represent mean±SEM (n=3/group).

Figure 23:
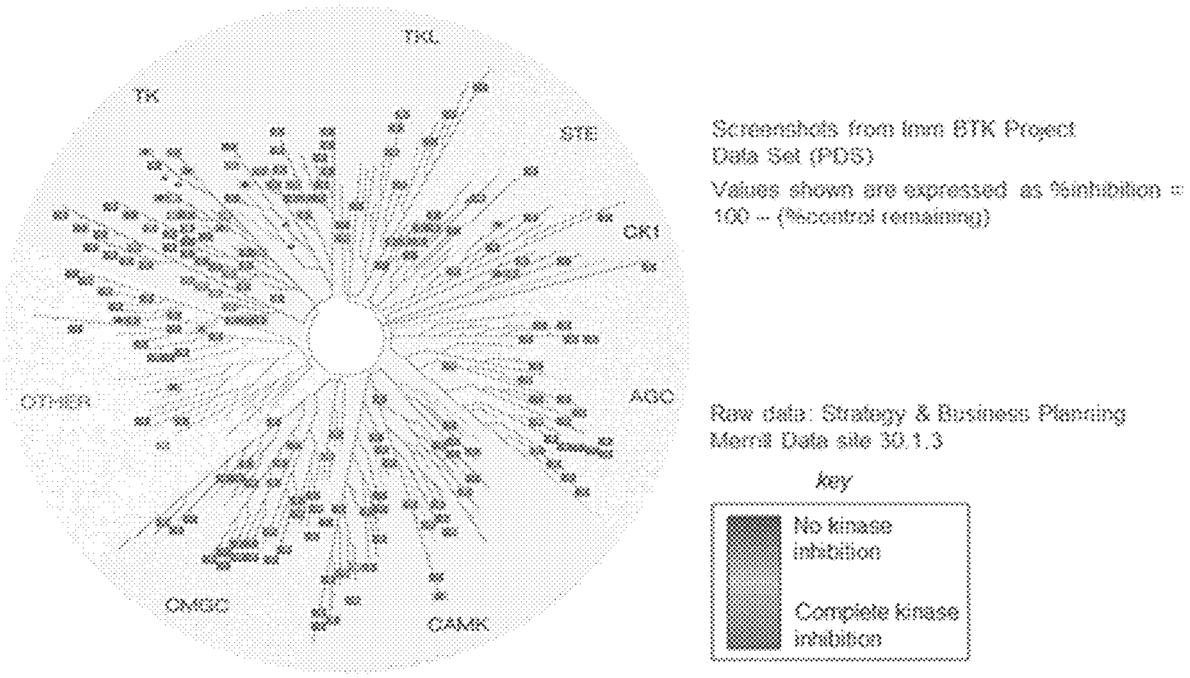

FIG. 23 depicts kinase percent inhibition by the compound of Formula (III) grouped by kinase family.

Figure 24:
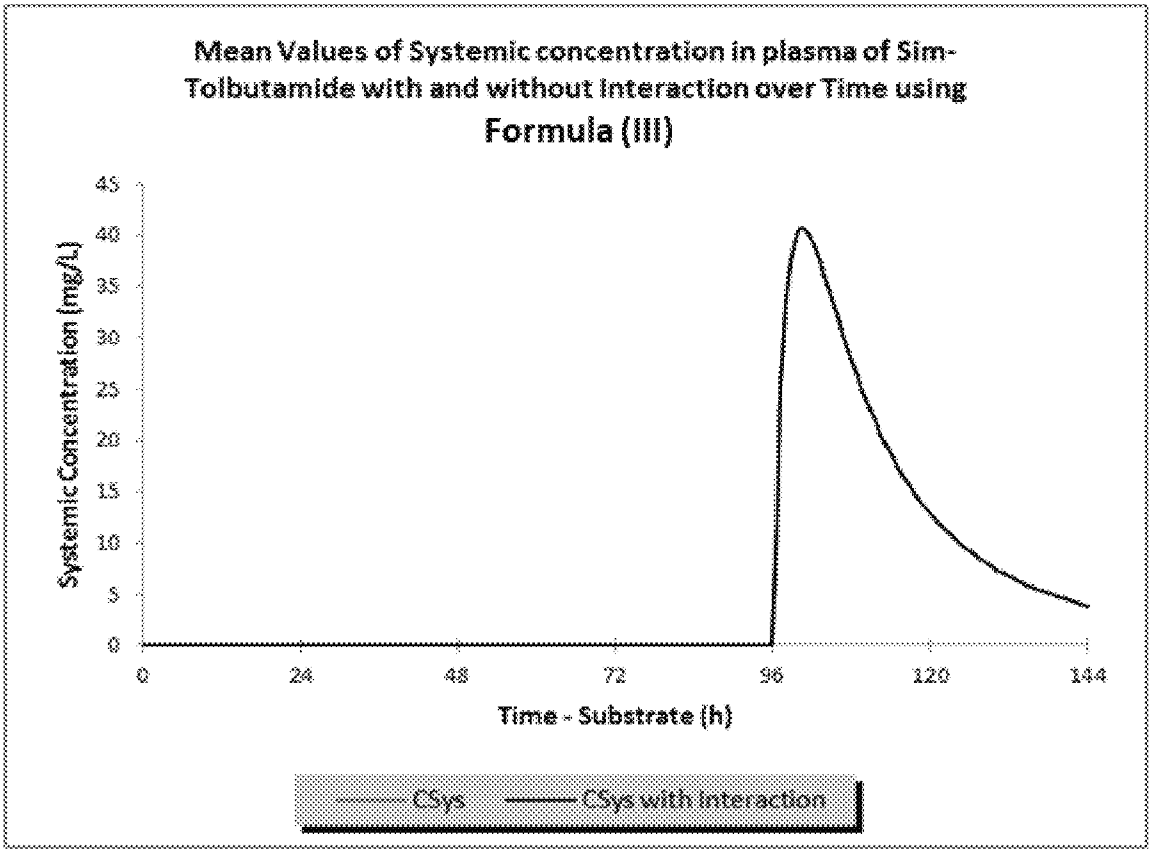

FIG. 24 depicts simulation of tolbutamide (500 mg on day 5) plasma concentrations upon coadministration with the compound of Formula (III) (10 mg once daily for 5 days).

Figure 25:
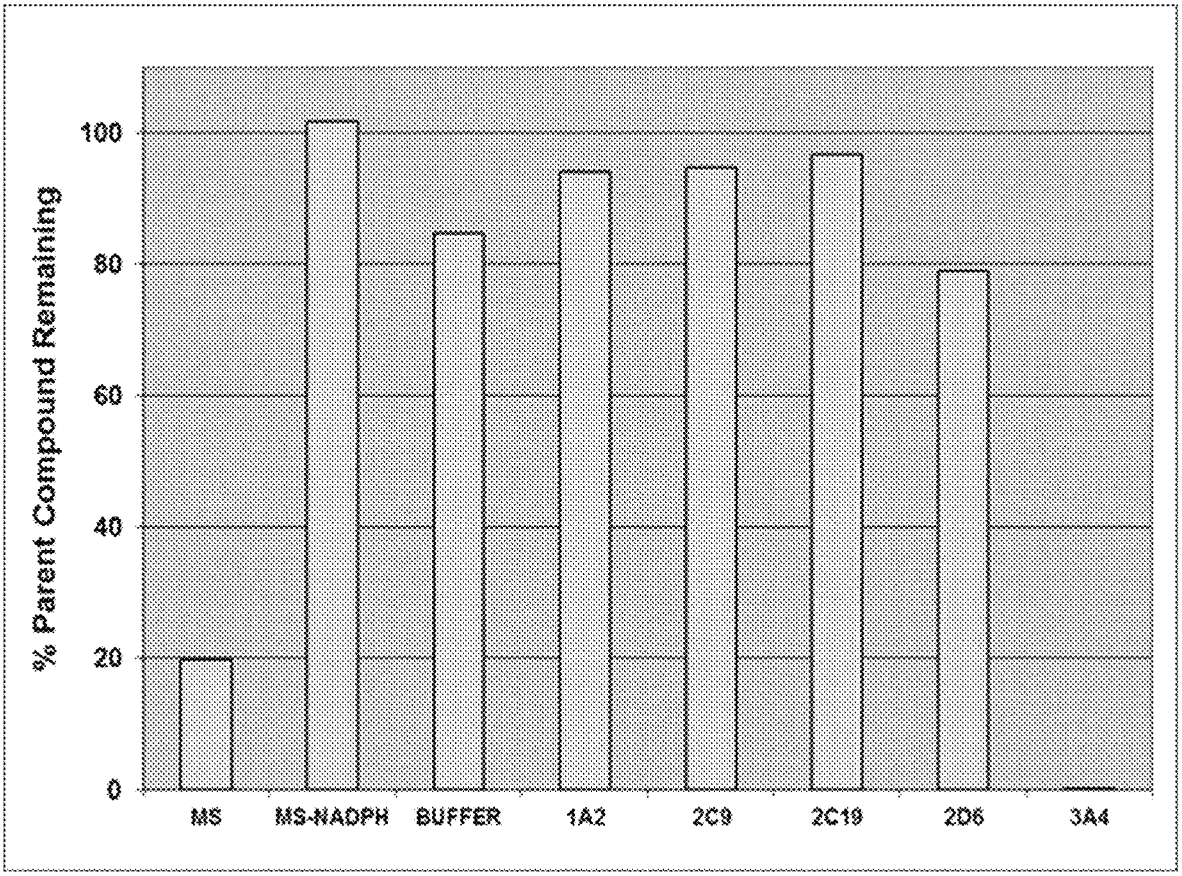

FIG. 25 depicts metabolism of the compound of Formula (III) by human rCYPs.

DETAILED DESCRIPTION

The disclosure may be more fully appreciated by reference to the following description, including the following glossary of terms and the concluding examples. It is to be appreciated that certain features of the disclosed compositions and methods which are, for clarity, described herein in the context of separate aspects, may also be provided in combination in a single aspect. Conversely, various features of the disclosed compositions and methods that are, for brevity, described in the context of a single aspect, may also be provided separately or in any subcombination. It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to aspects containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed aspect.

The term "about" as used herein when immediately preceding a numerical value means a range of plus or minus 10% of that value, for example, "about 50" means 45 to 55, "about 25,000" means 22,500 to 27,500, etc., unless the context of the disclosure indicates otherwise, or is inconsistent with such an interpretation.

The term "alkyl," when used alone or as part of a substituent group, refers to a straight- or branched-chain alkyl group having from 1 to 12 carbon atoms ("$C_{1-12}$"), preferably 1 to 6 carbons atoms ("$C_{1-6}$"), in the chain. Examples of alkyl groups include methyl (Me, $C_1$alkyl) ethyl (Et, $C_2$alkyl), n-propyl ($C_3$alkyl), isopropyl ($C_3$alkyl), butyl ($C_4$alkyl), isobutyl ($C_4$alkyl), sec-butyl ($C_4$alkyl), tert-butyl ($C_4$alkyl), pentyl ($C_5$alkyl), isopentyl ($C_5$alkyl), tert-pentyl ($C_5$alkyl), hexyl ($C_6$alkyl), isohexyl ($C_6$alkyl), and groups that in light of the ordinary skill in the art and the teachings provided herein would be considered equivalent to any one of the foregoing examples.

When a range of carbon atoms is used herein, for example, $C_{1-6}$, all ranges, as well as individual numbers of carbon atoms are encompassed. For example, "$C_{1-3}$" includes $C_{1-3}$, $C_{1-2}$, $C_{2-3}$, $C_1$, $C_2$, and $C_3$.

The term "$C_{1-6}$alk" refers to an aliphatic linker having 1, 2, 3, 4, 5, or 6 carbon atoms and includes, for example, $CH_2$, $CH(CH_3)$, $CH(CH_3)—CH_2$, and $C(CH_3)_2—$. The term "—$C_0$alk-" refers to a bond. In some aspects, the $C_{1-6}$alk can be substituted with an oxo group or an OH group.

The term "alkenyl," when used alone or as part of a substituent group, refers to straight and branched carbon chains having from 2 to 12 carbon atoms ("$C_{2-12}$"), preferably 2 to 6 carbon atoms ("$C_{2-6}$"), wherein the carbon chain contains at least one, preferably one to two, more preferably one double bond. For example, alkenyl moieties include, but are not limited to allyl, 1-propen-3-yl, 1-buten-4-yl, propa-1,2-dien-3-yl, and the like.

The term "alkynyl," when used alone or as part of a substituent group, refers to straight and branched carbon chains having from 2 to 12 carbon atoms ("$C_{2-12}$"), preferably 2 to 6 carbon atoms ("$C_{2-6}$"), wherein the carbon chain contains at least one, preferably one to two, more preferably one triple bond. For example, alkynyl moieties include, but are not limited to vinyl, 1-propyn-3-yl, 2-butyn-4-yl, and the like.

The term "aryl" refers to carbocylic aromatic groups having from 6 to 10 carbon atoms ("$C_{6-10}$") such as phenyl, naphthyl, and the like.

The term "cycloalkyl" refers to monocyclic, non-aromatic hydrocarbon groups having from 3 to 10 carbon atoms ("$C_{3-10}$"), preferably from 3 to 6 carbon atoms ("$C_{3-6}$"). Examples of cycloalkyl groups include, for example, cyclopropyl ($C_3$), cyclobutyl ($C_4$), cyclopentyl ($C_5$), cyclohexyl ($C_6$), 1-methylcyclopropyl ($C_4$), 2-methylcyclopentyl ($C_4$), adamantanyl ($C_{10}$) and the like.

The term "heterocycloalkyl" refers to any five to ten membered monocyclic or bicyclic, saturated ring structure containing at least one heteroatom selected from the group consisting of O, N and S. The heterocycloalkyl group may be attached at any heteroatom or carbon atom of the ring such that the result is a stable structure. Examples of suitable heterocycloalkyl groups include, but are not limited to, azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, quinuclidinyl, tetrahyofuranyl, tetrahydropyranyl, piperazinyl, hexahydro-5H-[1,4]dioxino[2,3-c]pyrrolyl, benzo[d][1,3]dioxolyl, and the like.

The term "heteroaryl" refers to a mono-or bicyclic aromatic ring structure including carbon atoms as well as up to four heteroatoms selected from nitrogen, oxygen, and sulfur. Heteroaryl rings can include a total of 5, 6, 9, or 10 ring atoms ("$C_{5-10}$"). Examples of heteroaryl groups include but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

The term "halogen" represents chlorine, fluorine, bromine, or iodine. The term "halo" represents chloro, fluoro, bromo, or iodo.

The term "haloalkyl" refers to an alkyl moiety wherein one or more of the hydrogen atoms has been replaced with one or more halogen atoms. One exemplary substitutent is fluoro. Preferred haloalkyl groups of the disclosure include trihalogenated alkyl groups such as trifluoromethyl groups.

The term "oxo" refers to a ═O moiety, wherein two hydrogens from the same carbon atom have be replaced with a carbonyl. For example, an oxo-substituted pyrrolidinyl moiety could be a pyrrolidin-2-one moiety or a pyrrolidin-3-one moiety.

The term "benzofuranyl" represents the following moiety:

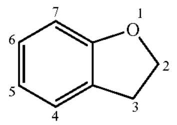

The benzofuranyl moiety can be attached through any one of the 2-, 3-, 4-, 5-, 6-, or 7-carbon atoms.

The term "benzo[d][1,3]dioxolyl" represents the following moiety:

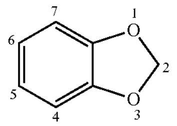

The benzo[d][1,3]dioxolyl moiety can be attached through any one of the 2-, 4-, 5-, 6-, or 7-carbon atoms. In those aspects wherein the" benzo[d][1,3]dioxolyl moiety is substituted with halogen," the following moieties are preferred:

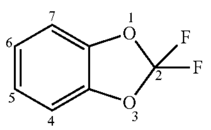

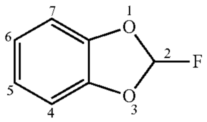

The term "benzothiophenyl" represents the following moiety:

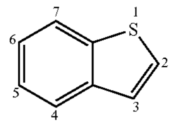

The benzothiophenyl moiety can be attached through any one of the 2-, 3-, 4-, 5-, 6-, or 7-carbon atoms.

The term "phenyl" represents the following moiety:

The phenyl moiety can be attached through any of the carbon atoms.

The term "napthalenyl" (i.e., naphthyl) represents the following moiety:

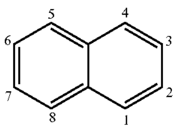

The naphthalenyl moiety can be attached through any one of the 1-, 2-, 3-, 4-, 5-, 6-, 7-, or 8-position carbon atoms.

The term "pyridyl" represents the following moiety:

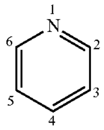

The pyridyl moiety can be attached through any one of the 2-, 3-, 4-, 5-, or 6-position carbon atoms.

The term "pyrimidinyl" represents the following moiety:

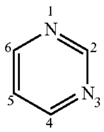

The pyrimidinyl moiety can be attached through any one of the 2-, 4-, 5-, or 6-position carbon atoms.

The term "pyrazinyl" represents the following moiety:

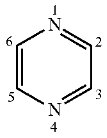

The pyrazinyl moiety can be attached through any one of the 2-, 3-, 5-, or 6-position carbon atoms.

The term "pyridazinyl" represents the following moiety:

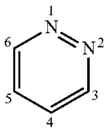

The pyridazinyl moiety can be attached through any one of the 3-, 4-, 5-, or 6-position carbon atoms.

The term "pyrazolyl" represents the following moiety:

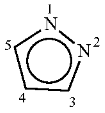

The pyrazolyl moiety can be attached through any one of the 1-, 2-, 3-, 4-, or 5-position carbon atoms.

The term "thiophenyl" represents the following moiety:

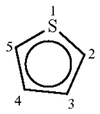

The thiophenyl moiety can be attached through any one of the 2-, 3-, 4-, or 5-position carbon atoms.

The term "linker-PEG-Biotin" refers to a moiety comprising -linker-PEG-$CH_2$—NH-biotinyl. Compounds of the disclosure that include a linker-PEG-Biotin moiety can be used according to any of the methods described herein. Alternatively, compounds of the disclosure that include a linker-PEG-Biotin moiety can be used as diagnostic probes according to methods known in the art. Preferred linkers are known in the art, with the linker —$CH_2$—NHC(O)-$(CH_2)_3$—C(O)—NH—$CH_2$— being particularly preferred. Preferred PEG moieties include at least two or three repeating —$CH_2$—$CH_2$—O— moieties. A preferred linker-PEG-Biotin moiety is

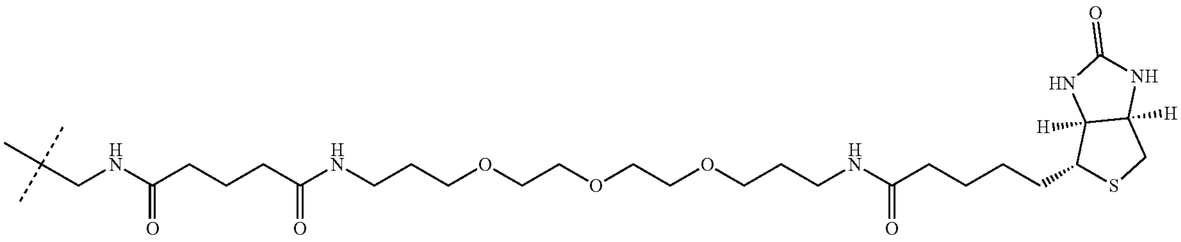

The term "piperidinyl" represents the following moiety:

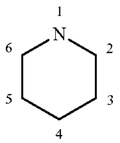

When the piperidinyl moiety is a substituent, it can be attached through any one of the 1-, 2-, 3-, 4-, 5-, or 6-position atoms, as permitted.

The term "pyrrolidinyl" represents the following moiety:

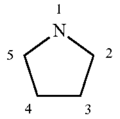

When the piperidinyl moiety is a substituent, it can be attached through any one of the 1-, 2-, 3-, 4-, or 5-position atoms, as permitted.

The term "oxazepanyl" refers to a 7-membered heterocycloalkyl moiety having one ring nitrogen atom and one ring oxygen atom. Examples include 1,3-oxazepanyl and 1,4-oxazepanyl moieties

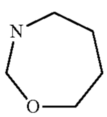

1,3-oxazepanyl

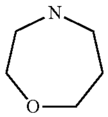

1,4-oxazepanyl

When the oxazepanyl moiety is a substituent, it can be attached through any ring carbon atom or through the nitrogen atom, as permitted.

The term "aziridinyl" represents a 3-membered heterocycloalkyl moiety having one ring nitrogen. When the aziridinyl moiety is a substituent, it can be attached through any ring carbon atom or through the nitrogen atom, as permitted.

The term "azetidinyl" represents a 4-membered heterocycloalkyl moiety having one ring nitrogen. When the azetidinyl moiety is a substituent, it can be attached through any carbon atom or through the nitrogen atom, as permitted.

The term "azepanyl" represents a 7-membered heterocycloalkyl moiety having one ring nitrogen. When the azepanyl moiety is a substitutent, it can be attached through any carbon atom or through the nitrogen atom, as permitted The term "quinuclidinyl" represents the following moiety:

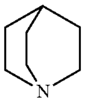

Within the disclosure, when the quinuclidinyl moiety is a substituent, it can be attached to the compound of Formula (I) through any one of the ring carbon atoms.

The term "imidazolidinyl" represents the following moiety:

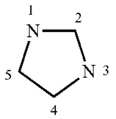

When the imidazolidinyl moiety is a substituent, it can be attached through any one of the 1-, 2-, 3-, 4-, or 5-position atoms., as permitted The term "piperazinyl" represents the following moiety:

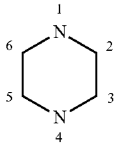

When the piperazinyl moiety is a substituent, it can be attached through any one of the 1-, 2-, 3-, 4-, 5-, or 6-position atoms, as permitted The term "morpholinyl" represents the following moiety:

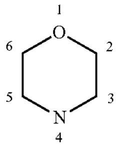

When the morpholinyl moiety is a substituent, it can be attached through any one of the 2-, 3-, 4-, 5-, or 6-position atoms, as permitted.

The term "tetrahydropyranyl" represents a 6-membered heterocycloalkyl moiety having one ring oxygen. The tetrahydropyranyl moiety can be attached through any carbon atom on the ring.

The term "tetrahydrofuranyl" represents a 5-membered heterocycloalkyl moiety having one ring oxygen. The tetrahydrofuranyl moiety can be attached through any carbon atom on the ring.

As used herein, the term "compound(s) of Formula (I)" includes those compounds of "Formula (I)," as well as compounds of any of the Formula (I) subgenera.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the disclosure that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like.

"Pharmaceutically acceptable vehicle" refers to a diluent, adjuvant, excipient or carrier with which a compound of the disclosure is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

"Subject" includes humans. The terms "human," "patient," and "subject" are used interchangeably herein.

"Treating" or "treatment" of any disease or disorder refers, in one aspect, to ameliorating the disease or disorder (i.e., arresting or reducing the development of the disease or at least one of the clinical symptoms thereof). In another aspect "treating" or "treatment" refers to ameliorating at least one physical parameter, which may not be discernible by the subject. In yet another aspect, "treating" or "treatment" refers to modulating the disease or disorder, either physically, (e.g., stabilization of a discernible symptom), physiologically, (e.g., stabilization of a physical parameter), or both. In yet another aspect, "treating" or "treatment" refers to delaying the onset of the disease or disorder.

The term "administer" or "administered" or "administering" refers to the administration of compound(s) of Formula (I) and their respective solvates or pharmaceutically acceptable salt forms thereof, or a pharmaceutical compositions thereof to a subject by any method known to those skilled in the art in view of the present disclosure, such as by intramuscular, subcutaneous, oral, intravenous, cutaneous, intramucosal (e.g., gut), intranasal or intraperitoneal route of administration. In particular embodiments, a pharmaceutical composition of the invention is administered to a subject orally.

The terms "therapeutically effective amount" or "therapeutically effective dose" are used interchangeably and means an amount or dose sufficient to generally bring about the desired therapeutic benefit in patients in need of such treatment for the designated disease, disorder, or condition.

As used herein, the term "condition" refers to any disease, syndrome, or disorder detected or diagnosed by a researcher, veterinarian, medical doctor, or other clinician, wherein said researcher, veterinarian, medical doctor, or other clinician determines that it desirable to seek a biological or medicinal response in an animal tissue system, particularly a mammalian or human tissue system.

"Compounds of the present disclosure," and equivalent expressions, are meant to embrace compounds of the Formula (I) as described herein, and in particular the compound of Formula (III), which expression includes the pharmaceutically acceptable salts, and the solvates, e.g., hydrates, and polymorphs thereof, where the context so permits. Similarly, reference to intermediates, whether or not they themselves are claimed, is meant to embrace their salts, and solvates, where the context so permits.

As used herein, the term "isotopic variant" refers to a compound that contains unnatural proportions of isotopes at one or more of the atoms that constitute such compound. For example, an "isotopic variant" of a compound can be radiolabeled, that is, contain one or more non-radioactive isotopes, such as for example, deuterium ($^{2}H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^{2}H$/D, any carbon may be $^{13}C$, or any nitrogen may be $^{15}N$, and that the presence and placement of such atoms may be determined within the skill of the art. Likewise, the disclosure may include the preparation of isotopic variants with radioisotopes, in the instance for example, where the resulting compounds may be used for drug and/or substrate tissue distribution studies. Radiolabeled compounds of the disclosure can be used in diagnostic methods such as Single-photon emission computed tomography (SPECT). The radioactive isotopes tritium, i.e. $^{3}H$, and carbon-14, i.e. $^{14}C$, are particularly useful for their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy.

All isotopic variants of the compounds of the disclosure, radioactive or not, are intended to be encompassed within the scope of the disclosure.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers.

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

"Atropisomers" refer to stereoisomers that arise because of hindered rotation around a single bond.

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci-and nitro-forms of phenyl nitromethane, that are likewise formed by treatment with acid or base.

Tautomeric forms may be relevant to the attainment of the optimal chemical reactivity and biological activity of a compound of interest.

The compounds of this disclosure may possess one or more asymmetric centers; such compounds can therefore be produced as individual (R)-or (S)-stereoisomers or as mixtures thereof.

Unless indicated otherwise, the description or naming of a particular compound in the specification and claims is intended to include both individual enantiomers and mixtures, racemic or otherwise, thereof. Within the present disclosure, any open valency appearing on a carbon, oxygen, or nitrogen atom in any structure described herein indicates the presence of a hydrogen atom. Where a chiral center exists in a structure, but no specific stereochemistry is shown for that center, both enantiomers, separately or as a mixture, are encompassed by that structure. The methods for the determination of stereochemistry and the separation of stereoisomers are well-known in the art.

The present disclosure is directed to the use of a compound of Formula (III):

(III)

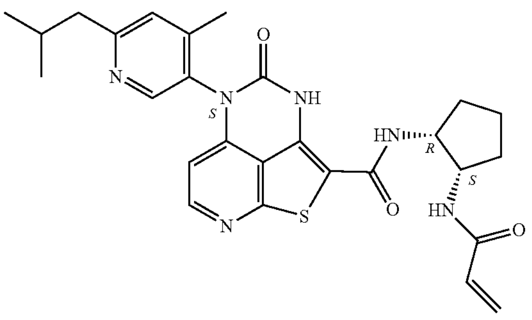

or a pharmaceutically acceptable salt, hydrate, polymorph or solvate thereof. The compound of Formula (III) is also known as N-((1R,2S)-2-Acrylamidocyclopentyl)-5-(S)-(6-isobutyl-4-methylpyridin-3-yl)-4-oxo-4,5-dihydro-3H-1-thia-3,5,8-triazaacenaphthylene-2-carboxamide or compound of Formula (III).

The present disclosure is also directed to the use of compounds of Formula (I):

(I)

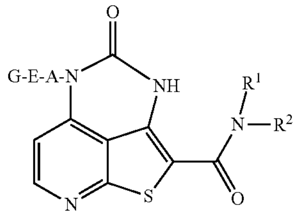

or a pharmaceutically acceptable salt, hydrate, polymorph or solvate thereof;

wherein $R^1$ is H or $C_{1-6}$alkyl;

$R^2$ is selected from the group consisting of: $C_{0-6}$alk-cycloalkyl optionally substituted with 1, 2, or 3 substituents each independently selected from the group consisting of: $NR^8$—C(O)—C($R^3$)═$CR^4$($R^5$); $NR^6R^7$; OH; CN; oxo; O—$C_{1-6}$alkyl; halogen; $C_{1-6}$alkyl; $C_{1-6}$haloalkyl; $C_{1-6}$alk-OH; $C_{3-6}$cycloalkyl; $C_{1-6}$alkaryl; $SO_2C_{1-6}$alkyl; $SO_2C_{2-6}$alkenyl; $NR^8$—C(O)—$C_{1-6}$alk-$NR^6R^7$; $NR^8$—C(O)—$C_{1-6}$alkyl; $NR^8$—C(O)—O—$C_{1-6}$alkyl; $NR^8$—C(O)—$C_{3-6}$cycloalkyl; $NR^8$—C(O)H; $NR^8$—C(O)—$C_{3-6}$cycloalkyl; $NR^8$—C(O)—$C_{1-6}$haloalkyl; $NR^8$—C(O)-alkynyl; $NR^8$—C(O)—$C_{6-10}$aryl; $NR^8$—C(O)-heteroaryl; $NR^8$—C(O)—$C_{1-6}$alk-CN; $NR^8$—C(O)—$C_{1-6}$alk-OH; $NR^8$—C(O)—$C_{1-6}$alk-$SO_2$—$C_{1-6}$alkyl; $NR^8$—C(O)—O—$C_{1-6}$ alkyl; $NR^8$—C(O)—$C_{1-6}$alk-$NR^6R^7$; $NR^8$—C(O)—$C_{1-6}$alk-O—$C_{1-6}$alkyl, wherein the $C_{1-6}$alk- is optionally substituted with a member selected from the group consisting of: OH, $OC_{1-6}$alkyl, and $NR^6R^7$; and $NR^8$—C(O)—$C_{0-6}$alk-heterocycloalkyl wherein the $C_{0-6}$alk is optionally substituted with oxo and the heterocycloalkyl is optionally substituted with $C_{1-6}$alkyl;

wherein $R^6$ and $R^7$ are each independently selected from the group consisting of H; $C_{1-6}$alkyl, $C_{3-6}$cycloalkyl, C(O)H, and CN;

$R^3$ is selected from the group consisting of H, CN, halogen, $C_{1-6}$haloalkyl, and $C_{1-6}$alkyl;

$R^4$ and $R^5$ are each independently selected from the group consisting of H; $C_{0-6}$alk-$NR^6R^7$; $C_{1-6}$alk-OH; $C_{0-6}$alk-$C_{3-6}$cycloalkyl optionally substituted with $C_{1-6}$alkyl; halogen; $C_{1-6}$alkyl; $OC_{1-6}$alkyl; $NR^6R^7$; $C_{1-6}$alk-O—$C_{1-6}$alkyl; $C_{1-6}$alk-NH—$C_{0-6}$alk-O—$C_{1-6}$alkyl; $C_{0-6}$alk-heterocycloalkyl optionally substituted with $C(O)C_{1-6}$alkyl or $C_{1-6}$alkyl; $C_{1-6}$alk-$NHSO_2$—$C_{1-6}$alkyl; $C_{1-6}$alk-$SO_2$—$C_{1-6}$alkyl; NHC(O)—$C_{1-6}$alkyl; and linker-PEG-Biotin;

$R^8$ is H or $C_{1-6}$alkyl;

A is selected from the group consisting of: a bond; pyridyl; phenyl; napthalenyl; pyrimidinyl; pyrazinyl; pyridazinyl; benzo[d][1,3]dioxolyl optionally substituted with halogen; benzothiophenyl; and pyrazolyl; optionally substituted with 1, 2, or 3 substituents each independently selected from the group consisting of: $C_{1-6}$alkyl; halogen; $SF_5$; $OC_{1-6}$alkyl; C(O)—$C_{1-6}$alkyl; and $C_{1-6}$haloalkyl;

E is selected from the group consisting of: O, a bond, C(O)—NH, $CH_2$, and $CH_2$—O;

G is selected from the group consisting of H; $C_{3-6}$cycloalkyl; phenyl; thiophenyl; $C_{1-6}$alkyl; pyrimidinyl; pyridyl; pyridazinyl; benzofuranyl; $C_{1-6}$haloalkyl; heterocycloalkyl that contains an oxygen heteroatom; phenyl-$CH_2$—O-phenyl; $C_{1-6}$alk-O—$C_{1-6}$alkyl; $NR^6R^7$; $SO_2C_{1-6}$alkyl; and OH; wherein the phenyl, pyridyl, pyridazinyl, benzofuranyl, or thiophenyl is optionally substituted with 1, 2, or 3 substituents each independently selected from the group consisting of halogen; $C_{1-6}$alkyl, $C_{1-6}$haloalkyl, $OC_{1-6}$haloalkyl, $C_{3-6}$cycloalkyl, $OC_{1-6}$alkyl, CN, OH, $C_{1-6}$alk-O—$C_{1-6}$alkyl, C(O)—$NR^6R^7$, and C(O)—$C_{1-6}$alkyl; and stereoisomers and isotopic variants thereof; and pharmaceutically acceptable salts thereof.

The present disclosure is also directed to the use of compounds of Formula (I):

(I)

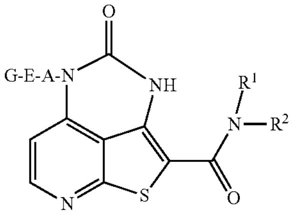

or a pharmaceutically acceptable salt, hydrate, polymorph or solvate thereof;

wherein $R^1$ is H or $C_{1-6}$alkyl;

$R^1$ and $R^2$, together with the nitrogen atom to which they are attached, form an optionally substituted ring that is a pyrrolidinyl ring or a piperidinyl ring;

wherein the pyrrolidinyl ring or piperidinyl ring formed from the joining of $R^1$ and $R^2$ are optionally substituted with 1, 2, or 3 substituents each independently selected from the group consisting of: $NR^8$—C(O)—C($R^3$)=$CR^4(R^5)$; $NR^6R^7$; OH; CN; oxo; O—$C_{1-6}$alkyl; halogen; $C_{1-6}$alkyl; $C_{1-6}$haloalkyl; $C_{1-6}$alk-OH; $C_{3-6}$cycloalkyl; $C_{1-6}$alkaryl; $SO_2C_{1-6}$alkyl; $SO_2C_{2-6}$alkenyl; —$NR^8$—C(O)—$C_{1-6}$alk-$NR^6R^7$; $NR^8$—C(O)—$C_{1-6}$alkyl; $NR^8$—C(O)—O—$C_{1-6}$alkyl; $NR^8$—C(O)—$C_{3-6}$ cycloalkyl; $NR^8$—C(O)H; $NR^8$—C(O)—$C_{1-6}$alkyl; $NR^8$—C(O)—$C_{3-6}$cycloalkyl;$NR^8$—C(O)—$C_{1-6}$haloalkyl; $NR^8$—C(O)-alkynyl; $NR^8$—C(O)—$C_{6-10}$aryl; $NR^8$—C(O)-heteroaryl; $NR^8$—C(O)—$C_{1-6}$alk-CN; $NR^8$—C(O)—$C_{1-6}$alk-OH; $NR^8$—C(O)—$C_{1-6}$alk-$SO_2$—$C_{1-6}$alkyl; $NR^8$—C(O)—O—$C_{1-6}$alkyl; $NR^8$—C(O)—$C_{1-6}$alk-$NR^6R^7$; $NR^8$—C(O)—$C_{1-6}$alk-O—$C_{1-6}$ alkyl wherein the $C_{1-6}$alk- is optionally substituted with OH, $OC_{1-6}$alkyl, or $NR^6R^7$; and $NR^8$—C(O)—$C_{0-6}$alk-heterocycloalkyl wherein the $C_{0-6}$alk is optionally substituted with oxo and the heterocycloalkyl is optionally substituted with $C_{1-6}$alkyl;

wherein $R^6$ and $R^7$ are each independently selected from the group consisting of: H, $C_{1-6}$alkyl, $C_{3-6}$cycloalkyl, C(O)H, and —CN;

$R^3$ is selected from the group consisting of: H, CN, halogen, $C_{1-6}$haloalkyl, and $C_{1-6}$alkyl;

$R^4$ and $R^5$ are each independently selected from the group consisting of: H; $C_{0-6}$alk-$NR^6R^7$; $C_{1-6}$alk-OH; $C_{0-6}$alk-$C_{3-6}$cycloalkyl optionally substituted with $C_{1-6}$alkyl; halogen; $C_{1-6}$alkyl; —$OC_{1-6}$alkyl; $NR^6R^7$; $C_{1-6}$alk-O—$C_{1-6}$alkyl; $C_{1-6}$alk-NH—$C_{0-6}$ alk-O—$C_{1-6}$alkyl; $C_{0-6}$alk-heterocycloalkyl optionally substituted with $C(O)C_{1-6}$alkyl or $C_{1-6}$alkyl; $C_{1-6}$alk-$NHSO_2$—$C_{1-6}$alkyl; $C_{1-6}$alk-$SO_2$—$C_{1-6}$alkyl; NHC(O)—$C_{1-6}$alkyl; or linker-PEG-Biotin;

$R^8$ is H or $C_{1-6}$alkyl;

A is selected from the group consisting of: a bond; pyridyl; phenyl; napthalenyl; pyrimidinyl; pyrazinyl; pyridazinyl; benzo[d][1,3]dioxolyl optionally substituted with halogen; benzothiophenyl; or pyrazolyl; optionally substituted with 1, 2, or 3 substituents independently selected from the group consisting of $C_{1-6}$alkyl, halogen, $SF_5$, $OC_{1-6}$alkyl, C(O)—$C_{1-6}$alkyl, and $C_{1-6}$haloalkyl;

E is selected from the group consisting of: O, a bond, C(O)—NH, $CH_2$, and $CH_2$—O;

G is selected from the group consisting of: H; $C_{3-6}$cycloalkyl; phenyl; thiophenyl; $C_{1-6}$alkyl; pyrimidinyl; pyridyl; pyridazinyl; benzofuranyl; —$C_{1-6}$haloalkyl; heterocycloalkyl that contains an oxygen heteroatom; phenyl-$CH_2$—O-phenyl; $C_{1-6}$alk-O—$C_{1-6}$alkyl; $NR^6R^7$; $SO_2C_{1-6}$alkyl; or OH; wherein the phenyl, pyridyl, pyridazinyl, benzofuranyl, or thiophenyl is optionally substituted with 1, 2, or 3 substituents each independently selected from the group consisting of: halogen, $C_{1-6}$alkyl, $C_{1-6}$haloalkyl, $OC_{1-6}$haloalkyl, $C_{3-6}$cycloalkyl, $OC_{1-6}$alkyl, CN, OH, $C_{1-6}$alk-O—$C_{1-6}$ alkyl, C(O)—$NR^6R^7$, and C(O)—$C_{1-6}$alkyl; and stereoisomers and isotopic variants thereof; and pharmaceutically acceptable salts thereof.

The present disclosure is also directed to the use of compounds of Formula (I):

(I)

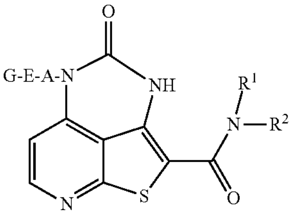

or a pharmaceutically acceptable salt, hydrate, polymorph or solvate thereof;

wherein $R^1$ is H;

$R^2$ is selected from the group consisting of: $CH_2$-cyclohexyl, wherein the cyclohexyl is optionally substituted with OH; 3-hydroxyadamantan-1-yl; and $C_{3-6}$cycloalkyl optionally substituted with 1, 2, or 3 substituents each independently selected from the group consisting of: OH, halogen, $C_{1-6}$alkyl, $C_{1-6}$haloalkyl, $OC_{1-6}$alkyl, CN, $NR^6R^7$, $NR^8$—C(O)H, $NR^8$—C(O)—$C_{1-6}$alkyl, $NR^8$—C(O)—$C_{1-6}$haloalkyl, $NR^8$—C(O)—O—$C_{1-6}$ alkyl, $NR^8$—C(O)—$C_{1-6}$alk-OH, $NR^8$—C(O)—$C_{1-6}$ alk-$NR^6R^7$, and $NR^8$—C(O)—C($R^3$)═C$R^4$($R^5$); wherein $R^3$ is selected from the group consisting of: H, CN, halogen, $C_{1-6}$haloalkyl, and $C_{1-6}$alkyl;

$R^4$ and $R^5$ are each independently selected from the group consisting of: H; $C_{0-6}$alk-$NR^6R^7$; $C_{1-6}$alk-O—$C_{1-6}$alkyl; $C_{3-6}$cycloalkyl; heterocycloalkyl optionally substituted with $C_{1-6}$alkyl; and -linker-PEG-Biotin;

$R^6$ and $R^7$ are each independently selected from the group consisting of: H, $C_{1-6}$alkyl, C(O)H, and CN; and $R^8$ is H;

or $R^1$ and $R^2$, together with the nitrogen atom to which they are attached, form a pyrrolidinyl ring optionally substituted with $NR^6R^7$, where $R^6$ and $R^7$ are each independently selected from the group consisting of H; $C_{1-6}$alkyl; $NR^8$—C(O)—$C_{1-6}$alkyl; and $NR^8$—C(O)—C($R^3$)═C$R^4$($R^5$), wherein $R^3$ is H or CN, $R^4$ is H and $R^5$ is H or cyclopropyl;

A is selected from the group consisting of pyridyl; phenyl; pyrimidinyl; pyrazinyl; pyridin-2(1H)-one; and pyridazinyl; wherein the A is optionally substituted with 1, 2, or 3 substituents each independently selected from the group consisting of: halogen, $C_{1-6}$alkyl, $C_{1-6}$haloalkyl, and $OC_{1-6}$alkyl;

E is selected from the group consisting of: O, a bond, and $CH_2$;

G is selected from the group consisting of H; halogen; $C_{1-6}$alkyl; $C_{1-6}$haloalkyl; NH($C_{1-6}$alkyl); $C_{3-6}$cycloalkyl; phenyl; pyrimidinyl; pyridyl; pyridazinyl; pyridin-2(1H)-one; heterocycloalkyl that contains an oxygen heteroatom; and phenyl-$CH_2$—O-phenyl, wherein the —O-phenyl is substituted with CN; wherein the phenyl, pyridyl, pyridazinyl, and pyridin-2(1H)-one is optionally substituted with 1, 2, or 3 substituents each independently selected from the group consisting of: halogen, $C_{1-6}$alkyl, $C_{1-6}$haloalkyl, $OC_{1-6}$haloalkyl, and $OC_{1-6}$alkyl; and stereoisomers or isotopic variant thereof; and pharmaceutically acceptable salts thereof.

According to the disclosure, $R^1$ is H or $C_{1-6}$alkyl. In some aspects, $R^1$ is $C_{1-6}$alkyl, for example, methyl, ethyl, n-propyl, isopropyl, n-butyl, s-butyl, or t-butyl. In preferred aspects, $R^1$ is H.

According to the disclosure, $R^2$ is a $C_{0-6}$ alk-cycloalkyl moiety that can be unsubstituted. In other aspects of the disclosure, $R^2$ is a $C_{0-6}$ alk-cycloalkyl moiety substituted with 1, 2, or 3 substituents, preferably 1 or 2 substituents, more preferably 1 substituent. In those aspects wherein $R^2$ is $C_0$ alk-cycloalkyl, the cycloalkyl is directly attached to the compound of Formula (I) through a bond. In those aspects wherein $R^2$ is a $C_{1-6}$ alk-cycloalkyl moiety, the cycloalkyl moiety is attached to the compound of Formula (I) through an aliphatic linker having 1, 2, 3, 4, 5, or 6 carbon atoms, wherein the $C_{1-6}$ alk includes, for example, —$CH_2$—, —CH($CH_3$)—, CH($CH_3$)—$CH_2$—, and —C($CH_3$)$_2$—. In preferred aspects, $R^2$ is $C_{0-1}$ alk-cycloalkyl, for example $C_0$ alk-cycloalkyl (i.e., cycloalkyl) or $C_1$ alk-cycloalkyl (i.e., $CH_2$-cycloalkyl).

In preferred aspects, the $R^2$ cycloalkyl moiety is a 3-, 4-, 5-, 6-, or 10-membered cycloalkyl, preferably a 5- or 6-membered cycloalkyl, with a 5-membered cycloalkyl being most preferred.

In some aspects of the disclosure, $R^2$ is $C_{0-6}$alk-cylopropyl, preferably $C_0$ alk-cylopropyl or $C_1$ alk-cylopropyl, optionally substituted with 1, 2, or 3 substituents as recited herein. In more preferred aspects, $R^2$ is $C_{0-6}$alk-cylopropyl, preferably $C_0$ alk-cylopropyl or $C_1$ alk-cylopropyl, substituted with 1 or 2 substituents as recited herein. The substituents can be attached through any position on the cylopropyl ring.

In some aspects of the disclosure, $R^2$ is $C_{0-6}$alk-cylobutyl, preferably $C_0$ alk-cylobutyl or $C_1$ alk-cylobutyl, optionally substituted with 1, 2, or 3 substituents as recited herein. In more preferred aspects, $R^2$ is $C_{0-6}$alk-cylobutyl, preferably $C_0$ alk-cylobutyl or $C_1$ alk-cylobutyl, substituted with 1 or 2 substituents as recited herein. The substituents can be attached through any position on the cylobutyl ring.

In preferred aspects of the disclosure, $R^2$ is $C_{0-6}$alk-cyclopentyl, preferably $C_0$ alk-cyclopentyl or $C_1$ alk-cyclopentyl, optionally substituted with 1, 2, or 3 substituents as recited herein. In more preferred aspects, $R^2$ is $C_{0-6}$alk-cyclopentyl, preferably $C_0$ alk-cyclopentyl or $C_1$ alk-cyclopentyl, substituted with 1 or 2 substituents as recited herein. The substituents can be attached through any position on the cyclopentyl ring.

In some aspects of the disclosure, $R^2$ is $C_{0-6}$alk-cyclohexyl, preferably $C_0$ alk-cyclohexyl or $C_1$ alk-cyclohexyl, optionally substituted with 1, 2, or 3 substituents as recited herein. In more preferred aspects, $R^2$ is $C_{0-6}$alk-cyclohexyl, preferably $C_0$ alk-cyclohexyl or $C_1$ alk-cyclohexyl, substituted with 1 or 2 substituents as recited herein. The substituents can be attached through any position on the cyclohexyl ring.

In some aspects of the disclosure, $R^2$ is $C_{0-6}$alk-adamantanyl, preferably $C_0$ alk-adamantanyl or $C_1$ alk-adamantanyl, optionally substituted with 1, 2, or 3 substituents as recited herein. In more preferred aspects, $R^2$ is $C_{0-6}$alk-adamantanyl, preferably $C_0$ alk-adamantanyl or $C_1$ alk-adamantanyl, substituted with 1 or 2 substituents as recited herein. The substituents can be attached through any position on the adamantanyl ring.

According to the disclosure, the $R^2$ cycloalkyl can be unsubstituted. In some aspects, the $R^2$ cycloalkyl is substituted with 1, 2, or 3 substituents. In preferred aspects, the $R^2$ cycloalkyl is substituted with 1 or 2 substituents, more preferably 1 substituent. In those aspects wherein the $R^2$ cycloalkyl is substituted, the substituents may be independently selected from the group consisting of $NR^8$—C(O)—C($R^3$)═C$R^4$($R^5$); $NR^6R^7$; OH; CN; oxo; O—$C_{1-6}$alkyl; halogen; $C_{1-6}$alkyl; $C_{1-6}$haloalkyl; $C_{1-6}$alk-OH; $C_{3-6}$cycloalkyl; $C_{1-6}$alkaryl; $SO_2C_{1-6}$alkyl; $SO_2C_{2-6}$alkenyl; $NR^8$—C(O)—$C_{1-6}$alk-$NR^6R^7$; $NR^8$—C(O)—$C_{1-6}$alkyl; $NR^8$—C(O)—O—$C_{1-6}$alkyl; $NR^8$—C(O)—$C_{3-6}$cycloalkyl; $NR^8$—C(O)H; $NR^8$—C(O)—$C_{3-6}$cycloalkyl; $NR^8$—C(O)—$C_{1-6}$ haloalkyl; $NR^8$—C(O)-alkynyl; $NR^8$—C(O)—$C_{6-10}$aryl; $NR^8$—C(O)-heteroaryl; $NR^8$—C(O)—$C_{1-6}$alk-CN; $NR^8$—C(O)—$C_{1-6}$alk-OH; $NR^8$—C(O)—$C_{1-6}$alk-$SO_2$—$C_{1-6}$alkyl; $NR^8$—C(O)—$C_{1-6}$alk-$NR^6R^7$; $NR^8$—C(O)—$C_{1-6}$alk-O—$C_{1-6}$alkyl wherein the $C_{1-6}$alk- is optionally substituted with OH, $OC_{1-6}$alkyl, or $NR^6R^7$; $NR^8$—C(O)—$C_{0-6}$alk-heterocycloalkyl wherein the -alk- is optionally substituted with oxo and the heterocycloalkyl is optionally substituted with $C_{1-6}$alkyl; and wherein $R^3$, $R^4$, $R^5$, $R^6$, $R^7$, and $R^8$ are as defined herein.

In some aspects, the $R^2$ cycloalkyl is substituted with an oxo moiety, for example one oxo moiety. In those aspects wherein the $R^2$ cycloalkyl is substituted with an oxo moiety, the cycloalkyl ring may optionally be substituted with one or two additional substituents as defined herein for the $R^2$ substituents.

In some aspects, the $R^2$ cycloalkyl is substituted with a halogen, for example a fluorine or chlorine or bromine. In some aspects, the $R^2$ cycloalkyl is substituted with one or two halogens, preferably one halogen. In those aspects wherein the $R^2$ cycloalkyl is substituted with a halogen, the cycloalkyl ring may optionally be substituted with one or two additional substituents as defined herein for the $R^2$ substituents.

In some aspects, the $R^2$ cycloalkyl is substituted with CN. In some aspects, the $R^2$ cycloalkyl is substituted with one or two CN, preferably one CN. In those aspects wherein the $R^2$ cycloalkyl is substituted with CN, the cycloalkyl ring may optionally be substituted with one or two additional substituents as defined herein for the $R^2$ substituents.

In some aspects, the $R^2$ cycloalkyl is substituted with OH. In some aspects, the $R^2$ cycloalkyl is substituted with one or two OH, preferably one OH. In those aspects wherein the $R^2$ cycloalkyl is substituted with OH, the cycloalkyl ring may optionally be substituted with one or two additional substituents as defined herein for the $R^2$ substituents.

In some aspects, the $R^2$ cycloalkyl is substituted with $NR^6R^7$ wherein $R^6$ and $R^7$ are each independently H; $C_{1-6}$alkyl, $C_{3-6}$cycloalkyl; C(O)H; or CN. In preferred aspects, $R^6$ and $R^7$ are each independently H or $C_{1-6}$alkyl. In those aspects wherein the $R^2$ cycloalkyl is substituted with $NR^6R^7$, the cycloalkyl ring may optionally be substituted with one or two additional substituents as defined herein for the $R^2$ substituents.

In some aspects, the $R^2$ cycloalkyl is substituted with $C_{1-6}$ alkyl, for example, $C_{1-5}$alkyl, $C_{1-4}$alkyl, $C_{1-3}$alkyl, $C_{1-2}$alkyl, or $C_1$alkyl. In some aspects, the $R^2$ cycloalkyl is substituted with one or two $C_{1-6}$alkyl, preferably one $C_{1-6}$alkyl. In those aspects wherein the $R^2$ cycloalkyl is substituted with $C_{1-6}$alkyl, the cycloalkyl ring may optionally be substituted with one or two additional substituents as defined herein for the $R^2$ substituents.

In some aspects, the $R^2$ cycloalkyl is substituted with $C_{1-6}$alk-OH, for example, $C_{1-5}$alk-OH, $C_{1-4}$alk-OH, $C_{1-3}$alk-OH, $C_{1-2}$alk-OH, or $C_1$alk-OH, wherein the —OH moiety can be attached to any carbon of the $C_{1-6}$alk group, preferably the ω carbon. In some aspects, the $R^2$ cycloalkyl is substituted with one or two $C_{1-6}$alk-OH, preferably one $C_{1-6}$alk-OH. In those aspects wherein the $R^2$ cycloalkyl is substituted with $C_{1-6}$alk-OH, the cycloalkyl ring may optionally be substituted with one or two additional substituents as defined herein for the $R^2$ substituents.

In some aspects, the $R^2$ cycloalkyl is substituted with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. In some aspects, the $R^2$ cycloalkyl is substituted with one or two $OC_{1-6}$alkyl, preferably one $OC_{1-6}$alkyl. In those aspects wherein the $R^2$ cycloalkyl is substituted with $OC_{1-6}$alkyl, the cycloalkyl ring may optionally be substituted with one or two additional substituents as defined herein for the $R^2$ substituents.

In some aspects, the $R^2$ cycloalkyl is substituted with a $C_{3-6}$cycloalkyl moiety, for example, a cyclopropyl, cyclobutyl, cyclopentyl, or cyclohexyl moiety. In some aspects, the $R^2$ cycloalkyl is substituted with one or two $C_{3-6}$cycloalkyl, preferably one $C_{3-6}$cycloalkyl. In those aspects wherein the $R^2$ cycloalkyl is substituted with $C_{3-6}$cycloalkyl, the cycloalkyl ring may optionally be substituted with one or two additional substituents as defined herein for the $R^2$ substituents.

In some aspects, the $R^2$ cycloalkyl is substituted with $C_{1-6}$alkaryl, for example, benzyl (i.e., $CH_2$-phenyl). In some aspects, the $R^2$ cycloalkyl is substituted with one or two $C_{1-6}$alkaryl, preferably one $C_{1-6}$alkaryl. In those aspects wherein the $R^2$ cycloalkyl is substituted with $C_{1-6}$alkaryl, the cycloalkyl ring may optionally be substituted with one or two additional substituents as defined herein for the $R^2$ substituents.

In some aspects, the $R^2$ cycloalkyl is substituted with $SO_2C_{1-6}$alkyl, for example, $SO_2C_{1-5}$alkyl, $SO_2C_{1-4}$alkyl, $SO_2C_{1-3}$alkyl, $SO_2C_{1-2}$alkyl, or $SO_2C_1$alkyl. In some aspects, the $R^2$ cycloalkyl is substituted with one or two $SO_2C_{1-6}$alkyl, preferably one $SO_2C_{1-6}$alkyl. In those aspects wherein the $R^2$ cycloalkyl is substituted with $SO_2C_{1-6}$alkyl, the cycloalkyl ring may optionally be substituted with one or two additional substituents as defined herein for the $R^2$ substituents.

In some aspects, the $R^2$ cycloalkyl is substituted with $SO_2C_{2-6}$alkenyl, for example, —$SO_2C_{2-5}$alkenyl, $SO_2C_{2-4}$ alkenyl, $SO_2C_{2-3}$alkenyl, or $SO_2C_2$alkenyl. In some aspects, the $R^2$ cycloalkyl is substituted with one or two $SO_2C_{2-6}$ alkenyl, preferably one $SO_2C_{2-6}$alkenyl. In those aspects wherein the $R^2$ cycloalkyl is substituted with $SO_2C_{2-6}$alkenyl, the cycloalkyl ring may optionally be substituted with one or two additional substituents as defined herein for the $R^2$ substituents.

In some aspects, the $R^2$ cycloalkyl is substituted with $NR^8$—C(O)H wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)H, preferably one $NR^8$—C(O)H. In those aspects wherein the $R^2$ cycloalkyl is substituted with $NR^8$—C(O)H, the cycloalkyl ring may optionally be substituted with one or two additional substituents as defined herein for the $R^2$ substituents.

In some aspects, the $R^2$ cycloalkyl is substituted with $NR^8$—C(O)—$C_{1-6}$alkyl, for example, $NR^8$—C(O)—$C_{1-5}$alkyl, $NR^8$—C(O)—$C_{1-4}$alkyl, $NR^8$—C(O)—$C_{1-3}$alkyl, $NR^8$—C(O)—$C_{1-2}$alkyl, or $NR^8$—C(O)—$C_1$alkyl, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)—$C_{1-6}$alkyl, preferably one $NR^8$—C(O)—$C_{1-6}$alkyl. In those aspects wherein the $R^2$ cycloalkyl is substituted with $NR^8$—C(O)—$C_{1-6}$alkyl, the cycloalkyl ring may optionally be substituted with one or two additional substituents as defined herein for the $R^2$ substituents.

In some aspects, the $R^2$ cycloalkyl is substituted with $NR^8$—C(O)—$C_{3-6}$cycloalkyl, for example, $NR^8$—C(O)-cyclopropyl, $NR^8$—C(O)-cyclobutyl, $NR^8$—C(O)-cyclopentyl, or $NR^8$—C(O)-cyclohexyl, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)—$C_{3-6}$cycloalkyl, preferably one $NR^8$—C(O)—$C_{3-6}$cycloalkyl. In those aspects wherein the $R^2$ cycloalkyl is substituted with $NR^8$—C(O)—$C_{3-6}$cycloalkyl, the cycloalkyl ring may optionally be substituted with one or two additional substituents as defined herein for the $R^2$ substituents.

In some aspects, the $R^2$ cycloalkyl is substituted with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like. In some aspects, the $R^2$ cycloalkyl is substituted with one or two $C_{1-6}$haloalkyl, preferably one $C_{1-6}$haloalkyl. In those aspects wherein the $R^2$ cycloalkyl is substituted with $C_{1-6}$haloalkyl, the cycloalkyl ring may optionally be substituted with one or two additional substituents as defined herein for the $R^2$ substituents.

In some aspects, the $R^2$ cycloalkyl is substituted with $NR^8$—C(O)—$C_{1-6}$haloalkyl, for example, $NR^8$—C(O)—$C_{1-5}$haloalkyl, $NR^8$—C(O)—$C_{1-4}$haloalkyl, $NR^8$—C(O)—$C_{1-3}$haloalkyl, $NR^8$—C(O)—$C_{1-2}$haloalkyl, or $NR^8$—C(O)—$C_1$haloalkyl, including $NR^8$—C(O)—$CF_3$, $NR^8$—C(O)—$CH_2CH_2F$, and the like, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)—$C_{1-6}$haloalkyl, preferably one $NR^8$—C(O)—$C_{1-6}$haloalkyl. In those aspects wherein the $R^2$ cycloalkyl is substituted with $NR^8$—C(O)—$C_{1-6}$haloalkyl, the cycloalkyl ring may optionally be substituted with one or two additional substituents as defined herein for the $R^2$ substituents.

In some aspects, the $R^2$ cycloalkyl is substituted with $NR^8$—C(O)—$C_{2-6}$alkynyl, for example, $NR^8$—C(O)—$C_{2-5}$alkynyl, $NR^8$—C(O)—$C_{2-4}$alkynyl, $NR^8$—C(O)—$C_{2-3}$alkynyl, or $NR^8$—C(O)—$C_2$alkynyl, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)—$C_{2-6}$alkynyl, preferably one $NR^8$—C(O)—$C_{2-6}$alkynyl. In those aspects wherein the $R^2$ cycloalkyl is substituted with $NR^8$—C(O)—$C_{2-6}$alkynyl, the cycloalkyl ring may optionally be substituted with one or two additional substituents as defined herein for the $R^2$ substituents.

In some aspects, the $R^2$ cycloalkyl is substituted with $NR^8$—C(O)—$C_{6-10}$aryl, for example, $NR^8$—C(O)-phenyl or $NR^8$—C(O)-napthalenyl, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)—$C_{6-10}$aryl, preferably one $NR^8$—C(O)—$C_{6-10}$aryl. In those aspects wherein the $R^2$ cycloalkyl is substituted with $NR^8$—C(O)—$C_{6-10}$aryl, the cycloalkyl ring may optionally be substituted with one or two additional substituents as defined herein for the $R^2$ substituents.

In some aspects, the $R^2$ cycloalkyl is substituted with $NR^8$—C(O)-heteroaryl, for example, $NR^8$—C(O)-pyrrolyl, $NR^8$—C(O)-thienyl, $NR^8$—C(O)-oxazolyl, $NR^8$—C(O)-pyrazolyl, $NR^8$—C(O)-pyridyl, $NR^8$—C(O)-pyrimidinyl, and the like, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)-heteroaryl, preferably one $NR^8$—C(O)-heteroaryl. In those aspects wherein the $R^2$ cycloalkyl is substituted with $NR^8$—C(O)-heteroaryl, the cycloalkyl ring may optionally be substituted with one or two additional substituents as defined herein for the $R^2$ substituents.

In some aspects, the $R^2$ cycloalkyl is substituted with $NR^8$—C(O)—$C_{1-6}$alk-CN, for example, $NR^8$—C(O)—$C_{1-5}$alk-CN, $NR^8$—C(O)—$C_{1-4}$alk-CN, $NR^8$—C(O)—$C_{1-3}$alk-CN, $NR^8$—C(O)—$C_{1-2}$alk-CN, or $NR^8$—C(O)-$C_1$alk-CN, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)—$C_{1-6}$alk-CN, preferably one $NR^8$—C(O)—$C_{1-6}$alk-CN. In those aspects wherein the $R^2$ cycloalkyl is substituted with $NR^8$—C(O)—$C_{1-6}$alk-CN, the cycloalkyl ring may optionally be substituted with one or two additional substituents as defined herein for the $R^2$ substituents.

In some aspects, the $R^2$ cycloalkyl is substituted with $NR^8$—C(O)—$C_{1-6}$alk-OH, for example, $NR^8$—C(O)—$C_{1-5}$alk-OH, $NR^8$—C(O)—$C_{1-4}$alk-OH, $NR^8$—C(O)—$C_{1-3}$alk-OH, $NR^8$—C(O)—$C_{1-2}$alk-OH, or $NR^8$—C(O)-$C_1$alk-OH, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)—$C_{1-6}$alk-OH, preferably one $NR^8$—C(O)—$C_{1-6}$alk-OH. In those aspects wherein the $R^2$ cycloalkyl is substituted with $NR^8$—C(O)—$C_{1-6}$alk-OH, the cycloalkyl ring may optionally be substituted with one or two additional substituents as defined herein for the $R^2$ substituents.

In some aspects, the $R^2$ cycloalkyl is substituted with $NR^8$—C(O)—$C_{1-6}$alk-$SO_2$—$C_{1-6}$alkyl, for example, $NR^8$—C(O)—$C_{1-5}$alk-$SO_2$—$C_{1-5}$alkyl, $NR^8$—C(O)—$C_{1-4}$alk-$SO_2$—$C_{1-4}$alkyl, $NR^8$—C(O)—$C_{1-3}$alk-$SO_2$—$C_{1-3}$alkyl, $NR^8$—C(O)—$C_{1-2}$alk-$SO_2$—$C_{1-2}$alkyl, or $NR^8$—C(O)-$C_1$alk-$SO_2$-$C_1$alkyl, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)—$C_{1-6}$alk-$SO_2$—$C_{1-6}$alkyl, preferably one $NR^8$—C(O)—$C_{1-6}$alk-$SO_2$—$C_{1-6}$alkyl. In those aspects wherein the $R^2$ cycloalkyl is substituted with $NR^8$—C(O)—$C_{1-6}$alk-$SO_2$—$C_{1-6}$alkyl, the cycloalkyl ring may optionally be substituted with one or two additional substituents as defined herein for the $R^2$ substituents.

In some aspects, the $R^2$ cycloalkyl is substituted with $NR^8$—C(O)—O—$C_{1-6}$alkyl, for example, $NR^8$—C(O)—O—$C_{1-5}$alkyl, $NR^8$—C(O)—O—$C_{1-4}$alkyl, $NR^8$—C(O)—O—$C_{1-3}$alkyl, $NR^8$—C(O)—O—$C_{1-2}$alkyl, or $NR^8$—C(O)—O—$C_1$alkyl, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)—O—$C_{1-6}$alkyl, preferably one $NR^8$—C(O)—O—$C_{1-6}$alkyl. In those aspects wherein the $R^2$ cycloalkyl is substituted with $NR^8$—C(O)—O—$C_{1-6}$alkyl, the cycloalkyl ring may optionally be substituted with one or two additional substituents as defined herein for the $R^2$ substituents.

In some aspects, the $R^2$ cycloalkyl is substituted with $NR^8$—C(O)—$C_{1-6}$alk-$NR^6R^7$, for example, $NR^8$—C(O)—$C_{1-5}$alk-$NR^6R^7$, $NR^8$—C(O)—$C_{1-4}$alk-$NR^6R^7$, $NR^8$—C(O)—$C_{1-3}$alk-$NR^6R^7$, $NR^8$—C(O)—$C_{1-2}$alk-$NR^6R^7$, or $NR^8$—C(O)-$C_1$alk-$NR^6R^7$, wherein $R^6$ and $R^7$ are each independently H; $C_{1-6}$alkyl, for example, $C_{1-5}$alkyl, $C_{1-4}$alkyl, $C_{1-3}$alkyl, $C_{1-2}$alkyl, or $C_1$alkyl; $C_{3-6}$cycloalkyl, for example, cyclopropyl, cyclobutyl, cyclopentyl, or cyclohexyl; C(O)H, or CN. In preferred aspects, $R^6$ and $R^7$ are each independently H, $C_{1-6}$alkyl; or $C_{3-6}$cycloalkyl, with H and $C_{1-6}$alkyl being preferred, and H and $C_{1-2}$alkyl being more preferred. In these aspects, $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In some aspects, the $R^2$ cycloalkyl is substituted with one or two $NR^8$—C(O)—$C_{1-6}$alk-$NR^6R^7$, preferably one $NR^8$—C(O)—$C_{1-6}$alk-$NR^6R^7$. In those aspects wherein the $R^2$ cycloalkyl is substituted with $NR^8$—C(O)—$C_{1-6}$alk-$NR^6R^7$, the cycloalkyl ring may optionally be substituted with one or two additional substituents as defined herein for the $R^2$ substituents.

In some aspects, the $R^2$ cycloalkyl is substituted with $NR^8$—C(O)—$C_{1-6}$alk-O—$C_{1-6}$alkyl, for example, $NR^8$—C(O)—$C_{1-5}$alk-O—$C_{1-5}$alkyl, $NR^8$—C(O)—$C_{1-4}$alk-O—$C_{1-4}$ alkyl, $NR^8$—C(O)—$C_{1-3}$alk-O—$C_{1-3}$alkyl, $NR^8$—C(O)—$C_{1-2}$alk-O—$C_{1-2}$alkyl, or $NR^8$—C(O)-$C_1$alk-O—$C_1$alkyl, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In certain aspects wherein the $R^2$ cycloalkyl is substituted with $NR^8$—C(O)—$C_{1-6}$alk-O—$C_{1-6}$ alkyl, the $C_{1-6}$alk- is optionally substituted with OH; $OC_{1-6}$alkyl, for example, $OC_{1-5}$alkyl, $OC_{1-4}$alkyl, $OC_{1-3}$alkyl, $OC_{1-2}$alkyl, or $OC_1$alkyl; or $NR^6R^7$, wherein $R^6$ and $R^7$ are each independently H; $C_{1-6}$alkyl, for example, $C_{1-5}$alkyl, $C_{1-4}$alkyl, $C_{1-3}$alkyl, $C_{1-2}$alkyl, or $C_1$alkyl; $C_{3-6}$cycloalkyl; C(O)H; or CN. In preferred aspects, $R^6$ and $R^7$ are each independently H, $C_{1-6}$alkyl; or $C_{3-6}$cycloalkyl, with H and $C_{1-6}$alkyl being preferred, and H and $C_{1-2}$alkyl being more preferred. In some aspects, the $C_{1-6}$alk- of the $NR^8$—C(O)—$C_{1-6}$alk-O—$C_{1-6}$alkyl moiety is substituted with OH. In other aspects, the $C_{1-6}$alk- is substituted with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. In some aspects, the $R^2$ cycloalkyl is substituted with one or two $NR^8$—C(O)—$C_{1-6}$alk-O—$C_{1-6}$alkyl, preferably one $NR^8$—C(O)—$C_{1-6}$alk-O—$C_{1-6}$alkyl. In those aspects wherein the $R^2$ cycloalkyl is substituted with $NR^8$—C(O)—$C_{1-6}$alk-O—$C_{1-6}$alkyl, the cycloalkyl ring may optionally be substituted with one or two additional substituents as defined herein for the $R^2$ substituents.

In some aspects, the $R^2$ cycloalkyl is substituted with $NR^8$—C(O)—$C_{0-6}$alk-heterocycloalkyl, for example, $NR^8$—C(O)—$C_{0-5}$alk-heterocycloalkyl, $NR^8$—C(O)—$C_{0-4}$ alk-heterocycloalkyl, $NR^8$—C(O)—$C_{0-3}$alk-heterocycloalkyl, $NR^8$—C(O)—$C_{0-2}$alk-heterocycloalkyl, $NR^8$—C(O)—$C_{0-1}$alk-heterocycloalkyl, $NR^8$—C(O)-$C_1$alk-heterocycloalkyl, or $NR^8$—C(O)-$C_0$alk-heterocycloalkyl, wherein $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. Preferred substituent heterocycloalkyl groups include tetrahydrofuranyl, piperidinyl, pyrrolidinyl, and the like. In certain aspects wherein the $R^2$ cycloalkyl is substituted with $NR^8$—C(O)—$C_{1-6}$alk-heterocycloalkyl the $C_{1-6}$alk- is optionally substituted with oxo. In certain aspects wherein the $R^2$ cycloalkyl is substituted with $NR^8$—C(O)—$C_{0-6}$alk-heterocycloalkyl, the substituent heterocycloalkyl moiety can be unsubstituted or substituted with $C_{1-6}$alkyl, for example, $C_{1-5}$alkyl, $C_{1-4}$alkyl, $C_{1-3}$alkyl, $C_{1-2}$alkyl, or $C_1$alkyl. In those aspects wherein the $R^2$ cycloalkyl is substituted with C(O)—$C_{0-6}$alk-heterocycloalkyl, the $R^2$ cycloalkyl ring may optionally be substituted with one or two additional substituents as defined herein for the $R^2$ substituents.

In some aspects, the $R^2$ cycloalkyl is substituted with $NR^8$—C(O)—C($R^3$)=$CR^4$($R^5$), wherein $R^3$, $R^4$, and $R^5$ are as described herein and $R^8$ is H or $C_{1-6}$alkyl, for example, $C_{1-5}$alkyl, $C_{1-4}$alkyl, $C_{1-3}$alkyl, $C_{1-2}$alkyl, or $C_1$alkyl. In preferred aspects, $R^8$ is H. In these aspects, $R^3$ is H; CN; halogen; $C_{1-6}$haloalkyl; or $C_{1-6}$alkyl. In some aspects, $R^3$ is H. In other aspects, $R^3$ is CN. In still other aspects, $R^3$ is halogen, for example F or Cl. In yet other aspects, $R^3$ is $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like. In further aspects, $R^3$ is $C_{1-6}$alkyl, for example, $C_{1-5}$alkyl, $C_{1-4}$alkyl, $C_{1-3}$alkyl, $C_{1-2}$alkyl, or $C_1$alkyl. In those aspects wherein the $R^2$ cycloalkyl is substituted with $NR^8$—C(O)—C($R^3$)=$CR^4$($R^5$), the cycloalkyl ring may optionally be substituted with one or two additional substituents as defined herein for the $R^2$ substituents.

In preferred aspects, the $R^2$ cycloalkyl is substituted with $NR^8$—C(O)—C($R^3$)=$CR^4$($R^5$); $NR^8$—C(O)—$C_{1-6}$alk-$NR^6R^7$; $NR^8$—C(O)—$C_{1-6}$alkyl; or $NR^6R^7$. In more preferred aspects, the $R^2$ cycloalkyl is substituted with $NR^8$—C(O)—C($R^3$)=$CR^4$($R^5$). In other preferred aspects, the $R^2$ cycloalkyl is substituted with $NR^8$—C(O)—$C_{1-6}$alk-$NR^6R^7$; $NR^8$—C(O)—$C_{1-6}$alkyl; or $NR^6R^7$; wherein $R^6$ and $R^7$ are each independently H or $C_{1-6}$alkyl.

In some preferred aspects, $R^2$ is $CH_2$-cyclohexyl, wherein the cyclohexyl is optionally substituted with OH; 3-hydroxyadamantan-1-yl; or $C_{3-6}$cycloalkyl optionally substituted with 1, 2, or 3 substituents each independently selected from the group consisting of OH, halogen, $C_{1-6}$alkyl, $C_{1-6}$haloalkyl, $OC_{1-6}$alkyl, CN, $NR^6R^7$, $NR^8$—C(O)H, $NR^8$—C(O)—$C_{1-6}$alkyl, $NR^8$—C(O)—$C_{1-6}$haloalkyl, $NR^8$—C(O)—O—$C_{1-6}$alkyl, $NR^8$—C(O)—$C_{1-6}$alk-OH, $NR^8$—C(O)—$C_{1-6}$alk-$NR^6R^7$, and $NR^8$—C(O)—C($R^3$)=$CR^4$($R^5$); wherein $R^3$ is selected from the group consisting of: H, CN, halogen, $C_{1-6}$haloalkyl, and $C_{1-6}$alkyl; $R^4$ and $R^5$ are each independently selected from the group consisting of: H; $C_{0-6}$alk-$NR^6R^7$; $C_{1-6}$alk-O—$C_{1-6}$alkyl; $C_{3-6}$cycloalkyl; heterocycloalkyl optionally substituted with $C_{1-6}$alkyl; and -linker-PEG-Biotin; $R^6$ and $R^7$ are each independently selected from the group consisting of: H, $C_{1-6}$alkyl, C(O)H, and CN; and $R^8$ is H. In some aspects, the $R^2$ is substituted with 1 or 2 substituents. In some aspects, the $R^2$ is substituted with at least one substituent, preferably 1 or 2 substituents, independently selected from the group consisting of OH, halogen, $C_{1-6}$alkyl, $C_{1-6}$haloalkyl, $OC_{1-6}$alkyl, and CN.

In some preferred aspects, $R^2$ is $CH_2$-cyclohexyl. In other preferred aspects, $R^2$ is $CH_2$-cyclohexyl wherein the cyclohexyl is substituted with OH.

In some preferred aspects, $R^2$ is 3-hydroxyadamantan-1-yl.

In other preferred aspects, $R^2$ is $C_{3-6}$cycloalkyl. In some other preferred aspects, $R^2$ is $C_{3-6}$cycloalkyl substituted with 1, 2, or 3 substituents. Those substituents can be independently selected from the group consisting of OH, halogen, $C_{1-6}$alkyl, $C_{1-6}$haloalkyl, $OC_1$-6alkyl, CN, $NR^6R^7$, $NR^8$—C(O)H, $NR^8$—C(O)—$C_{1-6}$alkyl, $NR^8$—C(O)—$C_{1-6}$haloalkyl, $NR^8$—C(O)—O—$C_{1-6}$alkyl, $NR^8$—C(O)—$C_{1-6}$alk-OH, $NR^8$—C(O)—$C_{1-6}$alk-$NR^6R^7$, and $NR^8$—C(O)—C($R^3$)=$CR^4$($R^5$).

In those aspects employing $R^4$ and $R^5$, that is, those aspects wherein the $R^2$ cycloalkyl is substituted with $NR^8$—C(O)—C($R^3$)=$CR^4$($R^5$), $R^4$ and $R^5$ are each independently H; halogen; $C_{0-6}$alk-$NR^6R^7$; $C_{1-6}$alkyl; $OC_{1-6}$alkyl; $C_{0-6}$alk-$C_{3-6}$cycloalkyl optionally substituted with $C_{1-6}$alkyl; $C_{0-6}$alk-heterocycloalkyl optionally substituted with —C(O) $C_{1-6}$alkyl or $C_{1-6}$alkyl; $C_{1-6}$alk-OH; $C_{1-6}$alk-O—$C_{1-6}$alkyl; $C_{1-6}$alk-NH—$C_{0-6}$alk-O—$C_{1-6}$alkyl; $C_{1-6}$alk-$NHSO_2$—$C_{1-6}$ alkyl; —$C_{1-6}$alk-$SO_2$—$C_{1-6}$alkyl; —NHC(O)—$C_{1-6}$alkyl; or linker-PEG-Biotin.

Within the scope of this disclosure, the double bond present in —$NR^8$—C(O)—C($R^3$)═$CR^4$($R^5$) may be of the Z or E configuration.

In some aspects, neither $R^4$ nor $R^5$ is H.

In most preferred aspects, each of $R^4$ and $R^5$ is H.

In some aspects, one of $R^4$ and $R^5$ is H. In certain of these aspects, the other of $R^4$ and $R^5$ is halogen, for example F or Cl.

In some aspects, one of $R^4$ and $R^5$ is H. In certain of these aspects, the other of $R^4$ and $R^5$ is $C_{1-6}$alkyl, for example, $C_{1-5}$alkyl, $C_{1-4}$alkyl, $C_{1-3}$alkyl, $C_{1-2}$alkyl, or $C_1$alkyl.

In some aspects, one of $R^4$ and $R^5$ is H. In certain of these aspects, the other of $R^4$ and $R^5$ is $OC_{1-6}$alkyl, for example, $OC_{1-5}$alkyl, $OC_{1-4}$alkyl, $OC_{1-3}$alkyl, $OC_{1-2}$alkyl, or $OC_1$alkyl.

In some aspects, one of $R^4$ and $R^5$ is H. In certain of these aspects, the other of $R^4$ and $R^5$ is $C_{0-6}$alk-$C_{3-6}$cycloalkyl, for example, $C_{0-5}$alk-$C_{3-5}$cycloalkyl, $C_{0-4}$alk-$C_{3-4}$cycloalkyl, $C_{0-3}$alk-$C_3$cycloalkyl, $C_{0-2}$alk-$C_{3-6}$cycloalkyl, $C_{0-1}$alk-$C_{3-6}$ cycloalkyl, $C_0$alk-$C_{3-6}$cycloalkyl or $C_1$alk-$C_{3-6}$cycloalkyl. In these aspects, the cycloalkyl moiety can be unsubstituted or can be substituted with $C_{1-6}$alkyl, for example, $C_{1-5}$alkyl, $C_{1-4}$alkyl, $C_{1-3}$alkyl, $C_{1-2}$alkyl, or $C_1$alkyl. The substitution can be a spiro-substitution or a non-spiro-substitution.

In some aspects, one of $R^4$ and $R^5$ is H. In certain of these aspects, the other of $R^4$ and $R^5$ is $C_{0-6}$alk-heterocycloalkyl, for example, $C_{1-6}$alk-heterocycloalkyl, $C_{0-4}$alk-heterocycloalkyl, $C_{0-3}$alk-heterocycloalkyl, $C_{0-2}$alk-heterocycloalkyl, $C_{0-1}$alk-heterocycloalkyl, $C_1$alk-heterocycloalkyl, or $C_0$alk-heterocycloalkyl. In these aspects, the substituent heterocycloalkyl is preferably an oxygen-containing heterocycloalkyl, for example, tetrahydropyranyl, tetrahydrofuranyl, or oxetanyl. In other aspects, the heterocycloalkyl is a nitrogen-containing heterocycloalkyl, for example, pyrrolidinyl, aziridinyl, or piperidinyl. In certain of these aspects, the substituent heterocycloalkyl can be substituted with $C(O)C_{1-6}$alkyl, for example, $C(O)C_{1-5}$alkyl, $C(O)C_{1-4}$alkyl, $C(O)C_{1-3}$alkyl, $C(O)C_{1-2}$alkyl, or $C(O)C_1$alkyl. In other aspects, the substituent heterocycloalkyl can be substituted with $C_{1-6}$alkyl, for example, $C_{1-5}$alkyl, $C_{1-4}$alkyl, $C_{1-3}$alkyl, $C_{1-2}$alkyl, or $C_1$alkyl.

In some aspects, one of $R^4$ and $R^5$ is H. In certain of these aspects, the other of $R^4$ and $R^5$ is $C_{1-6}$alk-OH, for example, $C_{1-5}$alk-OH, $C_{1-4}$alk-OH, $C_{1-3}$alk-OH, $C_{1-2}$alk-OH, or $C_1$alk-OH. The OH moiety can be attached to any carbon of the $C_{1-6}$alk group, preferably the ω carbon.

In some aspects, one of $R^4$ and $R^5$ is H. In certain of these aspects, the other of $R^4$ and $R^5$ is $C_{0-6}$alk-$NR^6R^7$, for example, $C_{0-5}$alk-$NR^6R^7$, $C_{0-4}$alk-$NR^6R^7$, $C_{0-3}$alk-$NR^6R^7$, $C_{0-2}$alk-$NR^6R^7$, $C_{0-1}$alk-$NR^6R^7$, $C_1$alk-$NR^6R^7$, or $C_0$alk-$NR^6R^7$, wherein $R^6$ and $R^7$ are each independently H; $C_{1-6}$alkyl, for example, $C_{1-5}$alkyl, $C_{1-4}$alkyl, $C_{1-3}$alkyl, $C_{1-2}$alkyl, or $C_1$alkyl; $C_{3-6}$cycloalkyl, for example, cyclopropyl, cyclobutyl, cyclopentyl, or cyclohexyl; C(O)H; or CN. In preferred aspects, $R^6$ and $R^7$ are each independently H; $C_{1-6}$alkyl; or $C_{3-6}$cycloalkyl, more preferably, $R^6$ and $R^7$ are each independently H or $C_{1-6}$alkyl.

In some aspects, one of $R^4$ and $R^5$ is H. In certain of these aspects, the other of $R^4$ and $R^5$ is $C_{1-6}$alk-O—$C_{1-6}$alkyl, for example, $C_{1-5}$alk-O—$C_{1-5}$alkyl, $C_{1-4}$alk-O—$C_{1-4}$alkyl, $C_{1-3}$alk-O—$C_{1-3}$alkyl, $C_{1-2}$alk-O—$C_{1-2}$alkyl, or $C_1$alk-O-$C_1$alkyl.

In some aspects, one of $R^4$ and $R^5$ is H. In certain of these aspects, the other of $R^4$ and $R^5$ is $C_{1-6}$alk-NH—$C_{0-6}$alk-O—$C_{1-6}$alkyl, for example, $C_{1-5}$alk-NH—$C_{0-6}$alk-O—$C_{1-5}$alkyl, $C_{1-4}$alk-NH—$C_{0-6}$alk-O—$C_{1-4}$alkyl, $C_{1-3}$alk-NH—$C_{0-6}$alk-O—$C_{1-3}$alkyl, $C_{1-2}$alk-NH—$C_{0-6}$alk-O—$C_{1-2}$alkyl, $C_1$alk-NH—$C_{0-6}$alk-O-$C_1$alkyl, $C_{1-5}$alk-NH—$C_{0-6}$alk-O—$C_{1-5}$alkyl, $C_{1-4}$alk-NH—$C_{1-5}$alk-O—$C_{1-4}$alkyl, $C_{1-3}$alk-NH—$C_{1-4}$ alk-O—$C_{1-3}$alkyl, $C_{1-2}$alk-NH—$C_{1-3}$alk-O—$C_{1-2}$alkyl, $C_1$alk-NH—$C_{1-2}$alk-O-$C_1$alky, or $C_{1-6}$alk-NH-$C_0$alk-O—$C_{1-6}$alkyl.

In some aspects, one of $R^4$ and $R^5$ is H. In certain of these aspects, the other of $R^4$ and $R^5$ is $C_{1-6}$alk-$NHSO_2$—$C_{1-6}$ alkyl, for example, $C_{1-5}$alk-$NHSO_2$—$C_{1-5}$alkyl $C_{1-4}$alk-$NHSO_2$—$C_1$-4alkyl, $C_{1-3}$alk-$NHSO_2$—$C_{1-3}$alkyl, $C_{1-2}$alk-$NHSO_2$—$C_{1-2}$alkyl, or $C_1$alk-$NHSO_2$-$C_1$alkyl.

In some aspects, one of $R^4$ and $R^5$ is H. In certain of these aspects, the other of $R^4$ and $R^5$ is $C_{1-6}$alk-$SO_2$—$C_{1-6}$alkyl, for example, $C_{1-5}$alk-$SO_2$—$C_{1-5}$alkyl, $C_{1-4}$alk-$SO_2$—$C_{1-4}$alkyl, $C_{1-3}$alk-$SO_2$—$C_{1-3}$alkyl, $C_{1-2}$alk-$SO_2$—$C_{1-2}$alkyl, or $C_1$alk-$SO_2$-$C_1$alkyl.

In some aspects, one of $R^4$ and $R^5$ is H. In certain of these aspects, the other of $R^4$ and $R^5$ is NHC(O)—$C_{1-6}$alkyl, for example, NHC(O)—$C_{1-5}$alkyl, NHC(O)—$C_{1-4}$alkyl, NHC(O)—$C_{1-3}$alkyl, NHC(O)—$C_{1-2}$alkyl, or NHC(O)—$C_1$alkyl.

In some aspects, one of $R^4$ and $R^5$ is H. In certain of these aspects, the other of $R^4$ and $R^5$ is linker-PEG-Biotin, preferably

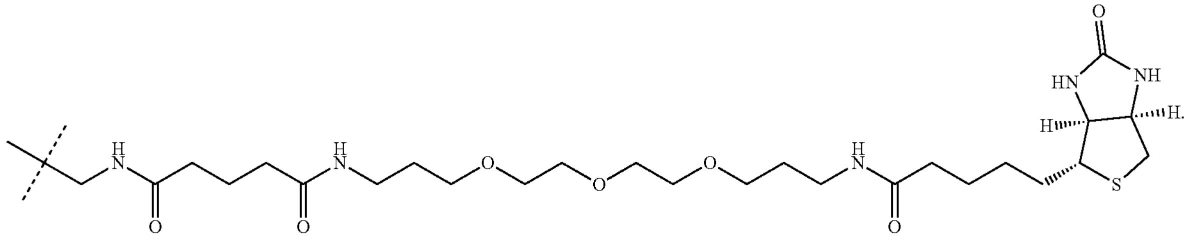

In preferred aspects, one of $R^4$ and $R^5$ is H and the other of $R^4$ and $R^5$ is $C_{1-6}$alkyl (e.g., methyl, t-butyl); cycloalkyl (e.g., cyclopropyl); $C_{1-6}$alk-$NR^6R^7$(e.g., $CH_2$—$NH_2$, $CH_2$—$NHCH_3$, $CH_2$—$N(CH_3)_2$, $C(CH_3)_2$—$NH_2$, $C(CH_3)_2$—$NHCH_3$, $C(CH_3)_2$—$N(CH_3)_2$; $C_{1-6}$alk-O—$C_{1-6}$alkyl (e.g., $C(CH_3)_2$—$OCH_3$, $C(CH_3)_2$—$OCH_2CH_3$); $C_{0-6}$alk-heterocycloalkyl substituted with $C_{1-6}$alkyl (e.g., $C(CH_3)$-oxetanyl).

In some aspects, or $R^1$ and $R^2$, together with the nitrogen atom to which they are attached, form an optionally substituted ring that is a pyrrolidinyl ring or a piperidinyl ring, for example, compounds of Formula (I)' or Formula (I)":

(I')

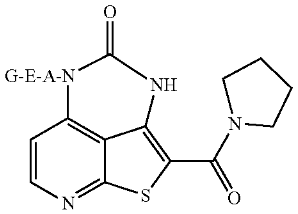

-continued (I'')

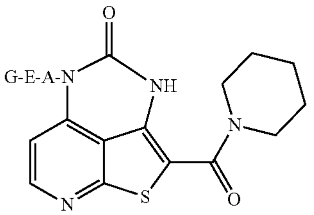

In these aspects, ring formed by the joining of $R^1$ and $R^2$ can be unsubstituted. In some aspects, the ring formed by the joining of $R^1$ and $R^2$ is substituted with 1, 2, or 3 substituents. In preferred aspects, the ring formed by the joining of $R^1$ and $R^2$ is substituted with 1 or 2 substituents, more preferably 1 substituent. In those aspects wherein the ring formed by the joining of $R^1$ and $R^2$ is substituted, the substituents may be independently selected from the group consisting of $NR^8$—C(O)—$C(R^3)$=$CR^4(R^5)$; $NR^6R^7$; OH; CN; oxo; O—$C_{1-6}$alkyl; halogen; $C_{1-6}$alkyl; $C_{1-6}$haloalkyl; $C_{1-6}$alk-OH; $C_{3-6}$cycloalkyl; $C_{1-6}$alkaryl; $SO_2C_{1-6}$alkyl; $SO_2C_{2-6}$alkenyl;—$NR^8$—C(O)—$C_{1-6}$alk-$NR^6R^7$; $NR^8$—C(O)—$C_{1-6}$alkyl; $NR^8$—C(O)—O—$C_{1-6}$alkyl; $NR^8$—C(O)—$C_{3-6}$cycloalkyl; $NR^8$—C(O)H; $NR^8$—C(O)—$C_{3-6}$cycloalkyl; $NR^8$—C(O)—$C_{1-6}$haloalkyl; $NR^8$—C(O)-alkynyl; $NR^8$—C(O)—$C_{6-10}$aryl; $NR^8$—C(O)-heteroaryl; $NR^8$—C(O)—$C_{1-6}$alk-CN; $NR^8$—C(O)—$C_{1-6}$alk-OH; $NR^8$—C(O)—$C_{1-6}$alk-$SO_2$—$C_{1-6}$alkyl; $NR^8$—C(O)—$C_{1-6}$alk-$NR^6R^7$; $NR^8$—C(O)—$C_{1-6}$alk-O—$C_{1-6}$alkyl wherein the $C_{1-6}$alk- is optionally substituted with —OH, $OC_{1-6}$alkyl, or $NR^6R^7$; $NR^8$—C(O)—$C_{0-6}$alk-heterocycloalkyl wherein the —$C_{0-6}$alk- is optionally substituted with oxo and the heterocycloalkyl is optionally substituted with $C_{1-6}$alkyl; and wherein $R^3$, $R^4$, $R^5$, $R^6$, $R^7$, and $R^8$ are as defined herein.

A preferred subgenus of Formula (I) is a compound of Formula (IA):

(I-A)

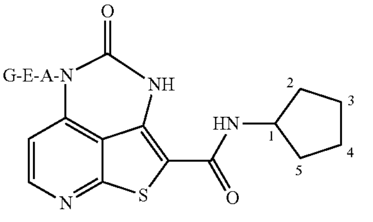

wherein the cyclopentyl ring is substituted at the 2 position with any of the $R^2$ substituents defined herein.

Other preferred subgenera of Formula (I) are:

(I-B-1)

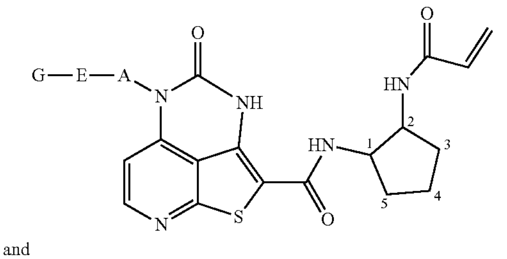

and

-continued (I-B-2)

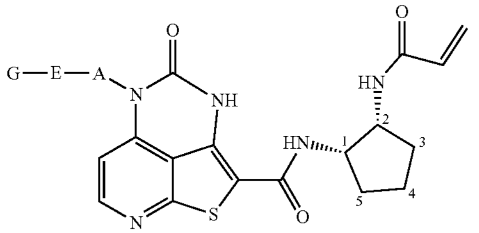

Within the scope of the disclosure, A can be a bond. Also within the scope of the disclosure, A can be pyridyl; phenyl; napthalenyl; pyrimidinyl; pyrazinyl; pyridazinyl; benzo[d][1,3]dioxolyl optionally substituted with halogen; benzothiophenyl; or pyrazolyl. Also within the disclosure, A can be pyridyl; phenyl; pyrimidinyl; pyrazinyl; pyridine-2(1H)-one, or pyridazinyl. Also according to the disclosure, any of the A moieties (excluding a bond) can be unsubstituted or substituted with 1, 2, or 3 substituents, preferably 1 or 2 substituents, more preferably 1 substituent, independently selected from the group consisting of $C_{1-6}$alkyl, for example, $C_{1-5}$alkyl, $C_{1-4}$alkyl, $C_{1-3}$alkyl, $C_{1-2}$alkyl, or $C_1$alkyl; halogen, for example F or Cl; $SF_5$; $OC_{1-6}$alkyl, for example, $OC_{1-5}$alkyl, $OC_{1-4}$alkyl, $OC_{1-3}$alkyl, $OC_{1-2}$alkyl, or $OC_1$alkyl; C(O)—$C_{1-6}$alkyl, for example, C(O)—$C_{1-5}$alkyl, C(O)—$C_{1-4}$alkyl, C(O)—$C_{1-3}$alkyl, C(O)—$C_{1-2}$alkyl, or C(O)—$C_1$alkyl; and $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like. Preferably, the A moieties can be substituted with 1, 2, or 3 substituents, preferably 1 or 2 substituents, independently selected from the group consisting of halogen, $C_{1-6}$alkyl, $C_{1-6}$haloalkyl, and $OC_{1-6}$alkyl.

In some aspects, A is pyridyl. The pyridyl can be attached to any of the compounds of Formula (I) (or its subgenera) through any ring carbon atom, but preferably it attached through the 2- or 3-position carbon. Preferably, the pyridyl is substituted with one or two substituents, preferably one substituent. The pyridyl substituent can be attached to any ring carbon atom of the pyridyl ring. In those aspects wherein the pyridyl is attached to the compound of Formula (I) through the 3-position carbon, the substituent is preferably attached to the pyridyl at the 2- or 4-position. The pyridyl can be substituted at any available ring carbon atom with $C_{1-6}$alkyl, for example, $C_{1-5}$alkyl, $C_{1-4}$alkyl, $C_{1-3}$alkyl, $C_{1-2}$alkyl, or $C_1$alkyl. The pyridyl can be substituted at any available ring carbon atom with halogen, for example F or Cl. The pyridyl can be substituted at any available ring carbon atom with $SF_5$. The pyridyl can be substituted at any available ring carbon atom with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. The pyridyl can be substituted at any available ring carbon atom with C(O)—$C_{1-6}$alkyl, for example, C(O)—$C_{1-5}$alkyl, C(O)—$C_{1-4}$alkyl, C(O)—$C_{1-3}$alkyl, C(O)—$C_{1-2}$alkyl, or C(O)—$C_1$alkyl. The pyridyl can be substituted at any available ring carbon atom with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like. Preferred substituents wherein A is pyridyl include $C_{1-6}$alkyl, with $C_1$alkyl being most preferred, and with one $C_1$alkyl substituent being more preferred. Other preferred substituents include halogen, in particular F and Cl.

In some aspects, A is phenyl. Preferably, the phenyl is substituted with one or two substituents, preferably one substituent. The phenyl can be substituted at any available ring carbon atom with $C_{1-6}$alkyl, for example, $C_{1-5}$alkyl, $C_{1-4}$alkyl, $C_{1-3}$alkyl, $C_{1-2}$alkyl, or $C_1$alkyl. The phenyl can be substituted at any available ring carbon atom with halogen, for example F or Cl. The phenyl can be substituted at any available ring carbon atom with —$SF_5$. The phenyl can be substituted at any available ring carbon atom with $OC_{1-6}$ alkyl, for example, $OC_{1-5}$alkyl, $OC_{1-4}$alkyl, $OC_{1-3}$alkyl, $OC_{1-2}$alkyl, or $OC_1$alkyl. The phenyl can be substituted at any available ring carbon atom with C(O)—$C_{1-6}$alkyl, for example, C(O)—$C_{1-5}$alkyl, C(O)—$C_{1-4}$alkyl, C(O)—$C_{1-3}$ alkyl, C(O)—$C_{1-2}$alkyl, or C(O)—$C_1$alkyl. The phenyl can be substituted at any available ring carbon atom with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like. The phenyl's substituent can be attached to any ring carbon atom of the phenyl ring, preferably ortho to the phenyl moiety's point of attachment to the compound of Formula (I). Preferred substituents wherein A is phenyl include $C_{1-6}$alkyl, with $C_1$alkyl being most preferred. Other preferred substituents include halogen, in particular F and Cl.

In some aspects, A is napthalenyl. Preferably, the napthalenyl is substituted with one or two substituents, preferably one substituent. The napthalenyl can be substituted at any available ring carbon atom with $C_{1-6}$alkyl, for example, $C_{1-5}$alkyl, $C_{1-4}$alkyl, $C_{1-3}$alkyl, $C_{1-2}$alkyl, or $C_1$alkyl. The napthalenyl can be substituted at any available ring carbon atom with halogen, for example F or Cl. The napthalenyl can be substituted at any available ring carbon atom with $SF_5$. The napthalenyl can be substituted at any available ring carbon atom with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. The napthalenyl can be substituted at any available ring carbon atom with C(O)—$C_{1-6}$alkyl, for example, C(O)—$C_{1-5}$alkyl, C(O)—$C_{1-4}$alkyl, C(O)—$C_{1-3}$alkyl, C(O)—$C_{1-2}$alkyl, or C(O)—$C_1$alkyl. The napthalenyl can be substituted at any available ring carbon atom with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like. The napthalenyl can be attached through any of its carbon atoms to the compound of Formula (I). The napthalenyl substituent can be attached to any ring carbon atom of the napthalenyl ring, preferably ortho to the napthalenyl moiety's point of attachment to the compound of Formula (I). Preferred substituents wherein A is napthalenyl include $C_{1-6}$alkyl, with $C_1$alkyl being most preferred. Other preferred substituents include halogen, in particular F and Cl.

In some aspects, A is pyrimidinyl. The pyrimidinyl can be attached to any of the compounds of Formula (I) (or its subgenera) through any ring carbon atom through any ring carbon atom. Preferably, the pyrimidinyl is substituted with one or two substituents, preferably one substituent. The pyrimidinyl can be substituted at any available ring carbon atom with $C_{1-6}$alkyl, for example, $C_{1-5}$alkyl, $C_{1-4}$alkyl, $C_{1-3}$alkyl, $C_{1-2}$alkyl, or $C_1$alkyl. The pyrimidinyl can be substituted at any available ring carbon atom with halogen, for example F or Cl. The pyrimidinyl can be substituted at any available ring carbon atom with $SF_5$. The pyrimidinyl can be substituted at any available ring carbon atom with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. The pyrimidinyl can be substituted at any available ring carbon atom with C(O)—$C_{1-6}$alkyl, for example, C(O)—$C_{1-5}$alkyl, C(O)—$C_{1-4}$alkyl, C(O)—$C_{1-3}$alkyl, C(O)—$C_{1-2}$alkyl, or C(O)—$C_1$alkyl. The pyrimidinyl can be substituted at any available ring carbon atom with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like. Preferred substituents wherein A is pyrimidinyl include $C_{1-6}$alkyl, with $C_1$alkyl being most preferred. Other preferred substituents include halogen, in particular F and Cl.

In some aspects, A is pyrazinyl. The pyrazinyl can be attached to any of the compounds of Formula (I) (or its subgenera) through any ring carbon atom. Preferably, the pyrazinyl is substituted with one or two substituents, preferably one substituent. The pyrazinyl can be substituted at any available ring carbon atom with $C_{1-6}$alkyl, for example, $C_{1-5}$alkyl, $C_{1-4}$alkyl, $C_{1-3}$alkyl, $C_{1-2}$alkyl, or $C_1$alkyl. The pyrazinyl can be substituted at any available ring carbon atom with halogen, for example F or Cl. The pyrazinyl can be substituted at any available ring carbon atom with $SF_5$. The pyrazinyl can be substituted at any available ring carbon atom with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. The pyrazinyl can be substituted at any available ring carbon atom with C(O)—$C_{1-6}$alkyl, for example, C(O)—$C_{1-5}$alkyl, C(O)—$C_{1-4}$alkyl, C(O)—$C_{1-3}$alkyl, C(O)—$C_{1-2}$alkyl, or C(O)—$C_1$alkyl. The pyrazinyl can be substituted at any available ring carbon atom with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like. Preferred substituents wherein A is pyrazinyl include $C_{1-6}$alkyl, with $C_1$alkyl being most preferred. Other preferred substituents include halogen, in particular F and Cl.

In some aspects, A is pyridazinyl. The pyridazinyl can be attached to any of the compounds of Formula (I) (or its subgenera) through any ring carbon atom. Preferably, the pyridazinyl is substituted with one or two substituents, preferably one substituent. The pyridazinyl can be substituted at any available ring carbon atom with $C_{1-6}$alkyl, for example, —$C_{1-5}$alkyl, $C_{1-4}$alkyl, $C_{1-3}$alkyl, $C_{1-2}$alkyl, or $C_1$alkyl. The pyridazinyl can be substituted at any available ring carbon atom with halogen, for example F or Cl. The pyridazinyl can be substituted at any available ring carbon atom with $SF_5$. The pyridazinyl can be substituted at any available ring carbon atom with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. The pyridazinyl can be substituted at any available ring carbon atom with C(O)—$C_{1-6}$alkyl, for example, C(O)—$C_{1-5}$alkyl, C(O)—$C_{1-4}$alkyl, C(O)—$C_{1-3}$alkyl, C(O)—$C_{1-2}$alkyl, or C(O)—$C_1$alkyl. The pyridazinyl can be substituted at any available ring carbon atom with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like. Preferred substituents wherein A is pyridazinyl include $C_{1-6}$alkyl, with $C_1$alkyl being most preferred. Other preferred substituents include halogen, in particular F and Cl.

In some aspects, A is benzo[d][1,3]dioxolyl. The benzo[d][1,3]dioxolyl can be attached to any of the compounds of Formula (I) (or its subgenera) through any ring carbon atom. The benzo[d][1,3]dioxolyl can be unsubstituted or can be substituted with one or two halogen, preferably F. Preferably, the benzo[d][1,3]dioxolyl is substituted with one or two other substituents. The benzo[d][1,3]dioxolyl can be substituted at any available ring carbon atom with $C_{1-6}$alkyl, for example, $C_{1-5}$alkyl, $C_{1-4}$alkyl, $C_{1-3}$alkyl, $C_{1-2}$alkyl, or $C_1$alkyl. The benzo[d][1,3]dioxolyl can be substituted at any available ring carbon atom with halogen, for example F or Cl. The benzo[d][1,3]dioxolyl can be substituted at any available ring carbon atom with —$SF_5$. The benzo[d][1,3]dioxolyl can be substituted at any available ring carbon atom with $OC_{1-6}$alkyl, for example, $OC_{1-5}$alkyl, $OC_{1-4}$alkyl, $OC_{1-3}$ alkyl, $OC_{1-2}$alkyl, or $OC_1$alkyl. The benzo[d][1,3]dioxolyl can be substituted at any available ring carbon atom with C(O)—$C_{1-6}$alkyl, for example, C(O)—$C_{1-5}$alkyl, C(O)—$C_{1-4}$alkyl, C(O)—$C_{1-3}$alkyl, C(O)—$C_{1-2}$alkyl, or C(O)—$C_1$alkyl. The benzo[d][1,3]dioxolyl can be substituted at any available ring carbon atom with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like.

In some aspects, A is benzothiophenyl. The benzothiophenyl can be attached to any of the compounds of Formula (I) (or its subgenera) through any ring carbon atom. Preferably, the benzothiophenyl is substituted with one or two substituents, preferably one substituent. The benzothiophenyl can be substituted at any available ring carbon atom with $C_{1-6}$alkyl, for example, $C_{1-5}$alkyl, $C_{1-4}$alkyl, $C_{1-3}$alkyl, $C_{1-2}$alkyl, or $C_1$alkyl. The benzothiophenyl can be substituted at any available ring carbon atom with halogen, for example F or Cl. The benzothiophenyl can be substituted at any available ring carbon atom with $SF_5$. The benzothiophenyl can be substituted at any available ring carbon atom with $OC_{1-6}$ alkyl, for example, $OC_{1-5}$alkyl, $OC_{1-4}$alkyl, $OC_{1-3}$alkyl, $OC_{1-2}$alkyl, or $OC_1$alkyl. The benzothiophenyl can be substituted at any available ring carbon atom with C(O)—$C_{1-6}$ alkyl, for example, C(O)—$C_{1-5}$alkyl, C(O)—$C_{1-4}$alkyl, C(O)—$C_{1-3}$alkyl, C(O)—$C_{1-2}$alkyl, or C(O)—$C_1$alkyl. The benzothiophenyl can be substituted at any available ring carbon atom with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like.

In some aspects, A is pyrazolyl. The pyrazolyl can be attached to any of the compounds of Formula (I) (or its subgenera) through any ring carbon atom. Preferably, the pyrazolyl is substituted with one or two substituents, preferably one substituent. The pyrazolyl can be substituted at any available ring carbon atom with $C_{1-6}$alkyl, for example, $C_{1-5}$alkyl, $C_{1-4}$alkyl, $C_{1-3}$alkyl, $C_{1-2}$alkyl, or $C_1$alkyl. The pyrazolyl can be substituted at any available ring carbon atom with halogen, for example F or Cl. The pyrazolyl can be substituted at any available ring carbon atom with $SF_5$. The pyrazolyl can be substituted at any available ring carbon atom with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. The pyrazolyl can be substituted at any available ring carbon atom with C(O)—$C_{1-6}$alkyl, for example, C(O)—$C_{1-5}$alkyl, C(O)—$C_{1-4}$alkyl, C(O)—$C_{1-3}$alkyl, C(O)—$C_{1-2}$alkyl, or C(O)—$C_1$alkyl. The pyrazolyl can be substituted at any available ring carbon atom with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like.

In preferred aspects, A is an unsubstituted or substituted phenyl, pyridyl, pyrimidyl, or pyrazinyl moiety, with pyridyl being particularly preferred. In those aspects wherein the phenyl, pyridyl, pyrimidyl, or pyrazinyl moiety is substituted, the preferred substituents include $C_{1-6}$alkyl (e.g., methyl) and halogen (e.g., F or $C_1$).

Additional preferred subgenera of Formula (I) are:

(I-D)

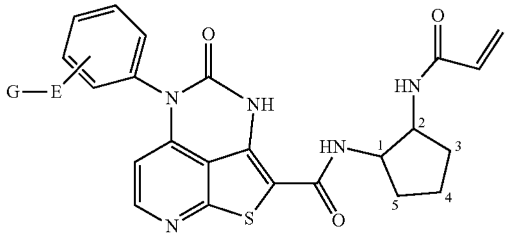

wherein the phenyl moiety can be unsubstituted or substituted with 1 or 2 substituents at any available carbon atom.

(I-E)

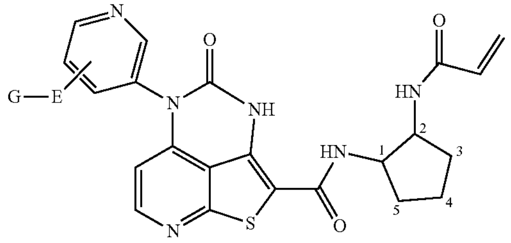

wherein the pyridyl moiety can be unsubstituted or substituted with 1 or 2 substituents at any available carbon atom.

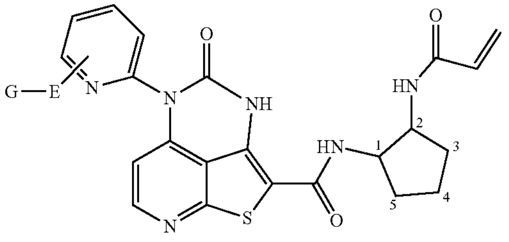

wherein the pyridyl moiety can be unsubstituted or substituted with 1 or 2 substituents at any available carbon atom.

According to the disclosure, E is O, a bond, C(O)—NH, $CH_2$, or $CH_2$—O. The E moiety can be attached through any available carbon atom on the A moiety. The E moiety can also be attached through any available carbon atom on the G moiety.

In some aspects, E is O, a bond, or $CH_2$. In preferred aspects, E is O. In other preferred aspects, E is a bond.

In some aspects of the disclosure, E is C(O)—NH, wherein the A-E-G moiety is A-C(O)—NH-G.

In other aspects of the disclosure, E is $CH_2$.

In yet other aspects of the disclosure, E is $CH_2$—O, wherein the A-E-G moiety is A-$CH_2$—O-G.

Additional preferred subgenera of Formula (I) are:

(I-G-1)

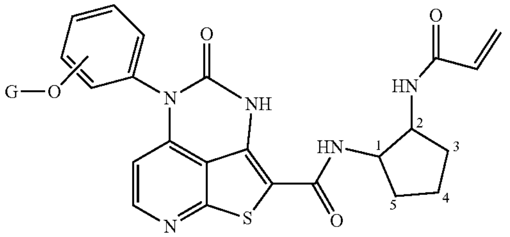

wherein the phenyl moiety can be unsubstituted or substituted with 1 or 2 substituents at any available carbon atom.

(I-G-2)

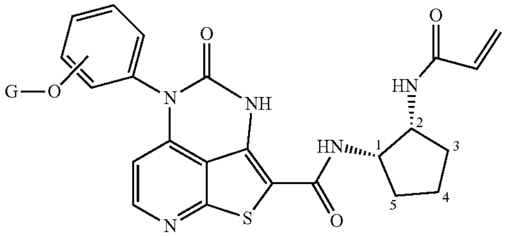

wherein the phenyl moiety can be unsubstituted or substituted with 1 or 2 substituents at any available carbon atom.

(I-H-1)

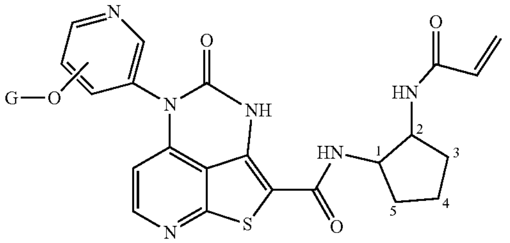

wherein the pyridyl moiety can be unsubstituted or substituted with 1 or 2 substituents at any available carbon atom.

(I-H-2)

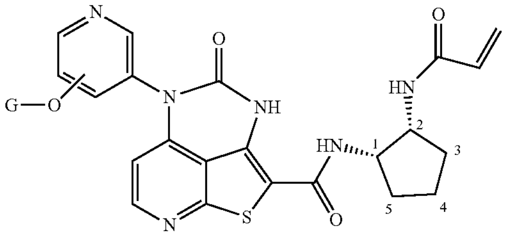

wherein the pyridyl moiety can be unsubstituted or substituted with 1 or 2 substituents at any available carbon atom.

(I-J-1)

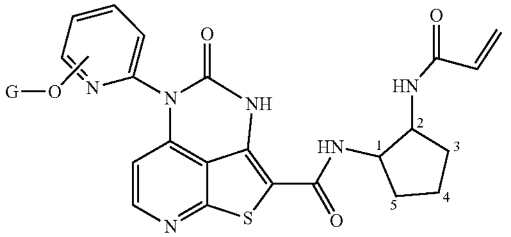

wherein the pyridyl moiety can be unsubstituted or substituted with 1 or 2 substituents at any available carbon atom.

(I-J-2)

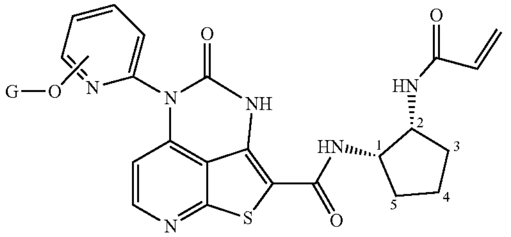

wherein the pyridyl moiety can be unsubstituted or substituted with 1 or 2 substituents at any available carbon atom.

Other preferred subgenera of Formula (I) are:

(I-K-1)

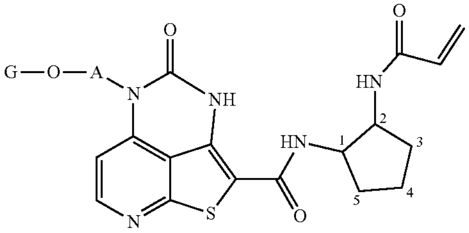

(I-K-2)

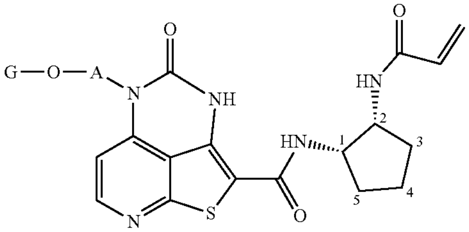

(I-L-1)

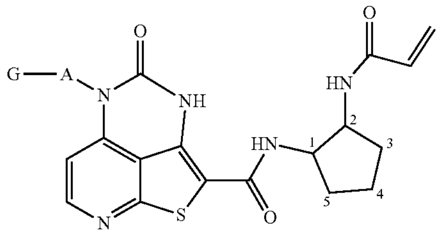

-continued (I-L-2)

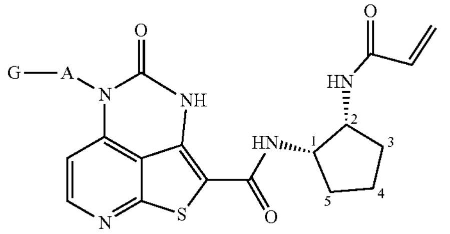

According to the disclosure, G is H; halogen; $C_{1-6}$alkyl; $C_{1-6}$haloalkyl; NH($C_{1-6}$alkyl); $C_{3-6}$cycloalkyl; phenyl; pyrimidinyl; pyridyl; pyridazinyl; pyridin-2(1H)-one; heterocycloalkyl that contains an oxygen heteroatom; and phenyl-$CH_2$—O-phenyl, wherein the —O-phenyl is substituted with CN; wherein the phenyl; pyridyl; pyridazinyl; and pyridin-2(1H)-one is optionally substituted with 1, 2, or 3 substituents each independently selected from the group consisting of: halogen, $C_{1-6}$alkyl, $C_{1-6}$haloalkyl, $OC_{1-6}$haloalkyl, and $OC_{1-6}$alkyl, Also according to the disclosure, G is H; $C_{3-6}$cycloalkyl; phenyl; thiophenyl; $C_{1-6}$alkyl; pyrimidinyl; pyridyl; pyridazinyl; benzofuranyl; $C_{1-6}$haloalkyl; heterocycloalkyl that contains an oxygen heteroatom; phenyl-$CH_2$—O-phenyl; $C_{1-6}$alk-O—$C_{1-6}$alkyl; $NR^6R^7$; $SO_2C_{1-6}$alkyl; or OH; wherein the phenyl; pyridyl; pyridazinyl; pyrimidinyl; benzofuranyl; or thiophenyl is optionally substituted with 1, 2, or 3 substituents independently selected from the group consisting of halogen; $C_{1-6}$alkyl; $C_{1-6}$haloalkyl; $OC_{1-6}$haloalkyl; $C_{3-6}$cycloalkyl; $OC_{1-6}$alkyl; CN; OH; $C_{1-6}$alk-O—$C_{1-6}$alkyl; C(O)—$NR^6R^7$; and C(O)—$C_{1-6}$alkyl.

In some aspects, G is H.

In other aspects, G is $C_{3-6}$cycloalkyl, for example, cyclopropyl, cyclobutyl, cyclopentyl, or cyclohexyl.

In some aspects, G is $C_{1-6}$alkyl, for example, $C_{1-5}$alkyl, $C_{1-41}$kyl, $C_{1-3}$alkyl, $C_{1-2}$alkyl, or $C_1$alkyl.

In some aspects, G is $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl, including $CF_3$, $CH_2CH_2F$, and the like.

In other aspects, G is a heterocycloalkyl that contains an oxygen heteroatom, for example, tetrahydropyranyl, tetrahydrofuranyl, or oxetanyl.

In preferred aspects, G is phenyl-$CH_2$—O-phenyl. In these aspects, the phenyl-$CH_2$—O-phenyl can be unsubstituted or substituted with 1, 2, or 3 substituents, preferably 1 or 2 substituents, more preferably 1 substituent, independently selected from the group consisting of halogen; $C_{1-6}$alkyl; $C_{1-6}$haloalkyl; $OC_{1-6}$haloalkyl; $C_{3-6}$cycloalkyl; $OC_{1-6}$ alkyl; CN; OH; $C_{1-6}$alk-O—$C_{1-6}$alkyl; C(O)—$NR^6R^7$; and C(O)—$C_{1-6}$alkyl. The one or both of the phenyl rings of the phenyl-$CH_2$—O-phenyl moiety can be substituted with halogen, for example F or Cl. The one or both of the phenyl rings of the -phenyl-$CH_2$—O-phenyl moiety can be substituted with $C_{1-6}$alkyl, for example, $C_{1-5}$alkyl, $C_{1-4}$alkyl, $C_{1-3}$alkyl, $C_{1-2}$alkyl, or $C_1$alkyl. The one or both of the phenyl rings of the phenyl-$CH_2$—O-phenyl moiety can be substituted with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl. The one or both of the phenyl rings of the phenyl-$CH_2$—O-phenyl moiety can be substituted with $OC_{1-6}$haloalkyl, for example, $OC_{1-5}$haloalkyl, $OC_{1-4}$haloalkyl, $OC_{1-3}$haloalkyl, $OC_{1-2}$haloalkyl, or $OC_1$haloalkyl. The one or both of the phenyl rings of the phenyl-$CH_2$—O-phenyl moiety can be substituted with $C_{3-6}$cycloalkyl, for example, cyclopropyl, cyclobutyl, cyclopentyl, or cyclohexyl. The one or both of the phenyl rings of the phenyl-$CH_2$—O-phenyl moiety can be substituted with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. The one or both of the phenyl rings of the phenyl-$CH_2$—O-phenyl moiety can be substituted with CN. The one or both of the phenyl rings of the phenyl-$CH_2$—O-phenyl moiety can be substituted with OH. The one or both of the phenyl rings of the phenyl-$CH_2$—O-phenyl moiety can be substituted with $C_{1-6}$alk-O—$C_{1-6}$alkyl, for example, $C_{1-5}$alk-O—$C_{1-5}$alkyl, $C_{1-4}$alk-O—$C_{1-4}$alkyl, $C_{1-3}$alk-O—$C_{1-3}$alkyl, $C_{1-2}$alk-O—$C_{1-2}$alkyl, or $C_1$alk-O—$C_1$alkyl. The one or both of the phenyl rings of the phenyl-$CH_2$—O-phenyl moiety can be substituted with C(O)—$NR^6R^7$, wherein $R^6$ and $R^7$ are preferably each independently H; $C_{1-6}$alkyl, for example, $C_{1-5}$alkyl, $C_{1-4}$alkyl, $C_{1-3}$alkyl, $C_{1-2}$alkyl, or $C_1$alkyl; or $C_{3-6}$cycloalkyl, for example, cyclopropyl, cyclobutyl, cyclopentyl, or cyclohexyl. More preferably, $R^6$ and $R^7$ are each independently H or $C_{1-6}$alkyl, for example, $C_{1-5}$alkyl, $C_{1-4}$alkyl, $C_{1-3}$alkyl, $C_{1-2}$alkyl, or $C_1$alkyl. The one or both of the phenyl rings of the phenyl-$CH_2$—O-phenyl moiety can be substituted with C(O)—$C_{1-6}$alkyl, for example, C(O)—$C_{1-65}$alkyl, C(O)—$C_{1-4}$alkyl, C(O)—$C_{1-3}$alkyl, C(O)—$C_{1-2}$alkyl, or C(O)—$C_1$alkyl.

In some aspects, G is $C_{1-6}$alk-O—$C_{1-6}$alkyl, for example, $C_{1-5}$alk-O—$C_{1-5}$alkyl, $C_{1-4}$alk-O—$C_{1-4}$alkyl, $C_{1-3}$alk-O—$C_{1-3}$alkyl, $C_{1-2}$alk-O—$C_{1-2}$alkyl, or $C_1$alk-O—$C_1$alkyl.

In other aspects, G is $NR^6R^7$, wherein $R^6$ and R are each independently H; $C_{1-6}$alkyl; $C_{3-6}$cycloalkyl; C(O)H, or CN. In these aspects, $R^6$ and $R^7$ are preferably each independently H; $C_{1-6}$alkyl, for example, $C_{1-5}$alkyl, $C_{1-4}$alkyl, $C_{1-3}$alkyl, $C_{1-2}$alkyl, or $C_1$alkyl; or $C_{3-6}$cycloalkyl, for example, cyclopropyl, cyclobutyl, cyclopentyl, or cyclohexyl. More preferably, $R^6$ and $R^7$ are each independently H or $C_{1-6}$alkyl, for example, $C_{1-5}$alkyl, $C_{1-4}$alkyl, $C_{1-3}$alkyl, $C_{1-2}$alkyl, or $C_1$alkyl.

In some aspects, G is $SO_2C_{1-6}$alkyl, for example, $SO_2C_{1-5}$ alkyl, $SO_2C_{1-4}$alkyl, —$SO_2C_{1-3}$alkyl, $SO_2C_{1-2}$alkyl, or $SO_2C_1$alkyl.

In some aspects, G is OH.

In preferred aspects, G is phenyl. In these aspects, the phenyl can be unsubstituted or substituted with 1, 2, or 3 substituents, preferably 1 or 2 substituents, more preferably 1 substituent, independently selected from the group consisting of halogen; $C_{1-6}$alkyl; $C_{1-6}$haloalkyl; $OC_{1-6}$haloalkyl; $C_{3-6}$cycloalkyl; $OC_{1-6}$alkyl; CN; OH; $C_{1-6}$alk-O—$C_{1-6}$alkyl; C(O)—$NR^6R^7$; and C(O)—$C_{1-6}$alkyl. The phenyl can be substituted with halogen, for example F or Cl. The phenyl can be substituted with $C_{1-6}$alkyl, for example, $C_{1-5}$alkyl, $C_{1-4}$alkyl, $C_{1-3}$alkyl, $C_{1-2}$alkyl, or $C_1$alkyl. The phenyl can be substituted with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl. The phenyl can be substituted with $OC_{1-6}$haloalkyl, for example, $OC_{1-5}$haloalkyl, $OC_{1-4}$haloalkyl, $OC_{1-3}$ haloalkyl, $OC_{1-2}$haloalkyl, or $OC_1$haloalkyl. The phenyl can be substituted with $C_{3-6}$cycloalkyl, for example, cyclopropyl, cyclobutyl, cyclopentyl, or cyclohexyl. The phenyl can be substituted with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. The phenyl can be substituted with CN. The phenyl can be substituted with OH. The phenyl can be substituted with $C_{1-6}$alk-O—$C_{1-6}$alkyl, for example, $C_{1-5}$alk-O—$C_{1-5}$alkyl, $C_{1-4}$alk-O—$C_{1-4}$alkyl, $C_{1-3}$alk-O—$C_{1-3}$alkyl, $C_{1-2}$alk-O—$C_{1-2}$alkyl, or $C_1$alk-O—$C_1$alkyl. The phenyl can be substituted with C(O)—$NR^6R^7$, wherein $R^6$ and $R^7$ are preferably each independently H; $C_{1-6}$alkyl, for example, $C_{1-5}$alkyl, $C_{1-4}$alkyl, $C_{1-3}$alkyl, $C_{1-2}$alkyl, or $C_1$alkyl; or $C_{3-6}$cycloalkyl, for example, cyclopropyl, cyclobutyl, cyclopentyl, or cyclohexyl. More preferably, $R^6$ and $R^7$ are each independently H or $C_{1-6}$alkyl, for example, $C_{1-5}$alkyl, $C_{1-4}$alkyl, $C_{1-3}$alkyl, $C_{1-2}$alkyl, or $C_1$alkyl. The phenyl can be substituted with C(O)—$C_{1-6}$alkyl, for example, C(O)—$C_{1-65}$alkyl, C(O)—$C_{1-4}$alkyl, C(O)—$C_{1-3}$ alkyl, C(O)—$C_{1-2}$alkyl, or C(O)—$C_1$alkyl.

In some aspects, G is pyridyl. In these aspects, the pyridyl can be unsubstituted or substituted with 1, 2, or 3 substituents, preferably 1 or 2 substituents, more preferably 1 substituent, independently selected from the group consisting of halogen; $C_{1-6}$alkyl; $C_{1-6}$haloalkyl; $OC_{1-6}$haloalkyl; $C_{3-6}$cycloalkyl; $OC_{1-6}$alkyl; CN; OH; $C_{1-6}$alk-O—$C_{1-6}$alkyl; C(O)—$NR^6R^7$; and C(O)—$C_{1-6}$alkyl. The pyridyl can be substituted with halogen, for example F or Cl. The pyridyl can be substituted with $C_{1-6}$alkyl, for example, $C_{1-5}$alkyl, $C_{1-4}$alkyl, $C_{1-3}$alkyl, $C_{1-2}$alkyl, or $C_1$alkyl. The pyridyl can be substituted with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl. The pyridyl can be substituted with $OC_{1-6}$ haloalkyl, for example, $OC_{1-5}$haloalkyl, $OC_{1-4}$haloalkyl, $OC_{1-3}$haloalkyl, $OC_{1-2}$haloalkyl, or $OC_1$haloalkyl. The pyridyl can be substituted with $C_{3-6}$cycloalkyl, for example, cyclopropyl, cyclobutyl, cyclopentyl, or cyclohexyl. The pyridyl can be substituted with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. The pyridyl can be substituted with CN. The pyridyl can be substituted with —OH. The pyridyl can be substituted with $C_{1-6}$alk-O—$C_{1-6}$alkyl, for example, $C_{1-5}$alk-O—$C_{1-5}$alkyl, $C_{1-4}$alk-O—$C_{1-4}$alkyl, $C_{1-3}$alk-O—$C_{1-3}$alkyl, $C_{1-2}$alk-O—$C_{1-2}$alkyl, or $C_1$alk-O—$C_1$alkyl. The pyridyl can be substituted with C(O)—$NR^6R^7$, wherein $R^6$ and $R^7$ are preferably each independently H; $C_{1-6}$alkyl, for example, $C_{1-5}$alkyl, $C_{1-4}$alkyl, $C_{1-3}$alkyl, $C_{1-2}$alkyl, or $C_1$alkyl; or $C_{3-6}$cycloalkyl, for example, cyclopropyl, cyclobutyl, cyclopentyl, or cyclohexyl. More preferably, $R^6$ and $R^7$ are each independently H or $C_{1-6}$alkyl, for example, $C_{1-5}$alkyl, $C_{1-4}$alkyl, $C_{1-3}$alkyl, $C_{1-2}$alkyl, or $C_1$alkyl. The pyridyl can be substituted with C(O)—$C_{1-6}$alkyl, for example, C(O)—$C_{1-65}$alkyl, C(O)—$C_{1-4}$alkyl, C(O)—$C_{1-3}$ alkyl, C(O)—$C_{1-2}$alkyl, or C(O)—$C_1$alkyl.

In some aspects, G is pyridazinyl. In these aspects, the pyridazinyl can be unsubstituted or substituted with 1, 2, or 3 substituents, preferably 1 or 2 substituents, more preferably 1 substituent, independently selected from the group consisting of halogen; $C_{1-6}$alkyl; $C_{1-6}$haloalkyl; $OC_{1-6}$haloalkyl; $C_{3-6}$cycloalkyl; $OC_{1-6}$alkyl; CN; OH; $C_{1-6}$alk-O—$C_{1-6}$alkyl; C(O)—$NR^6R^7$; and C(O)—$C_{1-6}$alkyl. The pyridazinyl can be substituted with halogen, for example F or Cl. The pyridazinyl can be substituted with $C_{1-6}$alkyl, for example, $C_{1-5}$alkyl, $C_{1-4}$alkyl, $C_{1-3}$alkyl, $C_{1-2}$alkyl, or $C_1$alkyl. The pyridazinyl can be substituted with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl. The pyridazinyl can be substituted with $OC_{1-6}$haloalkyl, for example, $OC_{1-5}$haloalkyl, $OC_{1-4}$haloalkyl, $OC_{1-3}$haloalkyl, $OC_{1-2}$haloalkyl, or $OC_1$haloalkyl. The pyridazinyl can be substituted with $C_{3-6}$cycloalkyl, for example, cyclopropyl, cyclobutyl, cyclopentyl, or cyclohexyl. The pyridazinyl can be substituted with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. The pyridazinyl can be substituted with CN. The pyridazinyl can be substituted with OH. The pyridazinyl can be substituted with $C_{1-6}$alk-O—$C_{1-6}$alkyl, for example, $C_{1-5}$alk-O—$C_{1-5}$alkyl, $C_{1-4}$alk-O—$C_{1-4}$alkyl, $C_{1-3}$alk-O—$C_{1-3}$alkyl, $C_{1-2}$alk-O—$C_{1-2}$alkyl, or $C_1$alk-O—$C_1$alkyl. The pyridazinyl can be substituted with C(O)—$NR^6R^7$, wherein $R^6$ and $R^7$ are preferably each independently H; $C_{1-6}$alkyl, for example, $C_{1-5}$alkyl, $C_{1-4}$alkyl, $C_{1-3}$alkyl, $C_{1-2}$alkyl, or $C_1$alkyl; or $C_{3-6}$cycloalkyl, for example, cyclopropyl, cyclobutyl, cyclopentyl, or cyclohexyl. More preferably, $R^6$ and $R^7$ are each independently H or $C_{1-6}$alkyl, for example, $C_{1-5}$alkyl, $C_{1-4}$alkyl, $C_{1-3}$alkyl, $C_{1-2}$alkyl, or $C_1$alkyl. The pyridazinyl can be substituted with C(O)—$C_{1-6}$alkyl, for example, C(O)—$C_{1-65}$alkyl, C(O)—$C_{1-4}$alkyl, C(O)—$C_{1-3}$alkyl, C(O)—$C_{1-2}$alkyl, or C(O)—$C_1$alkyl.

In some aspects, G is pyrimidinyl. In these aspects, the pyrimidinyl can be unsubstituted or substituted with 1, 2, or 3 substituents, preferably 1 or 2 substituents, more preferably 1 substituent, independently selected from the group consisting of halogen; $C_{1-6}$alkyl; $C_{1-6}$haloalkyl; $OC_{1-6}$haloalkyl; $C_{3-6}$cycloalkyl; $OC_{1-6}$alkyl; CN; OH; $C_{1-6}$alk-O—$C_{1-6}$alkyl; C(O)—$NR^6R^7$; and C(O)—$C_{1-6}$alkyl. The pyrimidinyl can be substituted with halogen, for example F or Cl. The pyrimidinyl can be substituted with $C_{1-6}$alkyl, for example, $C_{1-5}$alkyl, $C_{1-4}$alkyl, $C_{1-3}$alkyl, $C_{1-2}$alkyl, or $C_1$alkyl. The pyrimidinyl can be substituted with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl. The pyrimidinyl can be substituted with $OC_{1-6}$haloalkyl, for example, $OC_{1-5}$haloalkyl, $OC_{1-4}$haloalkyl, $OC_{1-3}$haloalkyl, $OC_{1-2}$haloalkyl, or $OC_1$haloalkyl. The pyrimidinyl can be substituted with $C_{3-6}$cycloalkyl, for example, cyclopropyl, cyclobutyl, cyclopentyl, or cyclohexyl. The pyrimidinyl can be substituted with $OC_{1-6}$alkyl, for example, $OC_{1-5}$alkyl, $OC_{1-4}$alkyl, $OC_{1-3}$alkyl, $OC_{1-2}$alkyl, or $OC_1$alkyl. The pyrimidinyl can be substituted with CN. The pyrimidinyl can be substituted with OH. The pyrimidinyl can be substituted with $C_{1-6}$alk-O—$C_{1-6}$alkyl, for example, $C_{1-5}$alk-O—$C_{1-5}$alkyl, $C_{1-4}$alk-O—$C_{1-4}$alkyl, $C_{1-3}$alk-O—$C_{1-3}$alkyl, $C_{1-2}$alk-O—$C_{1-2}$alkyl, or $C_1$alk-O—$C_1$alkyl. The pyrimidinyl can be substituted with C(O)—$NR^6R^7$, wherein $R^6$ and $R^7$ are preferably each independently H; $C_{1-6}$alkyl, for example, $C_{1-5}$alkyl, $C_{1-4}$alkyl, $C_{1-3}$alkyl, $C_{1-2}$alkyl, or $C_1$alkyl; or $C_{3-6}$cycloalkyl, for example, cyclopropyl, cyclobutyl, cyclopentyl, or cyclohexyl. More preferably, $R^6$ and $R^7$ are each independently H or $C_{1-6}$alkyl, for example, $C_{1-5}$alkyl, $C_{1-4}$alkyl, $C_{1-3}$alkyl, $C_{1-2}$alkyl, or $C_1$alkyl. The pyrimidinyl can be substituted with C(O)—$C_{1-6}$alkyl, for example, C(O)—$C_{1-65}$alkyl, C(O)—$C_{1-4}$alkyl, C(O)—$C_{1-3}$alkyl, C(O)—$C_{1-2}$alkyl, or C(O)—$C_1$alkyl.

In some aspects, G is benzofuranyl. In these aspects, the benzofuranyl can be unsubstituted or substituted with 1, 2, or 3 substituents, preferably 1 or 2 substituents, more preferably 1 substituent, independently selected from the group consisting of halogen; $C_{1-6}$alkyl; $C_{1-6}$haloalkyl; $OC_{1-6}$ haloalkyl; $C_{3-6}$cycloalkyl; $OC_{1-6}$alkyl; CN; OH; $C_{1-6}$alk-O—$C_{1-6}$alkyl; C(O)—$NR^6R^7$; and C(O)—$C_{1-6}$alkyl. The benzofuranyl can be substituted with halogen, for example F or Cl. The benzofuranyl can be substituted with $C_{1-6}$alkyl, for example, $C_{1-5}$alkyl, $C_{1-4}$alkyl, $C_{1-3}$alkyl, $C_{1-2}$alkyl, or $C_1$alkyl. The benzofuranyl can be substituted with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl. The benzofuranyl can be substituted with $OC_{1-6}$haloalkyl, for example, $OC_{1-5}$haloalkyl, $OC_{1-4}$haloalkyl, $OC_{1-3}$haloalkyl, $OC_{1-2}$haloalkyl, or $OC_1$haloalkyl. The benzofuranyl can be substituted with $C_{3-6}$cycloalkyl, for example, cyclopropyl, cyclobutyl, cyclopentyl, or cyclohexyl. The benzofuranyl can be substituted with $OC_{1-6}$alkyl, for example, $OC_{1-5}$alkyl, $OC_{1-4}$alkyl, $OC_{1-3}$ alkyl, $OC_{1-2}$alkyl, or $OC_1$alkyl. The benzofuranyl can be substituted with CN. The benzofuranyl can be substituted with OH. The benzofuranyl can be substituted with $C_{1-6}$alk-O—$C_{1-6}$alkyl, for example, $C_{1-5}$alk-O—$C_{1-5}$alkyl, $C_{1-4}$alk- O—$C_{1-4}$alkyl, $C_{1-3}$alk-O—$C_{1-3}$alkyl, $C_{1-2}$alk-O—$C_{1-2}$alkyl, or $C_1$alk-O—$C_1$alkyl. The benzofuranyl can be substituted with C(O)—$NR^6R^7$, wherein $R^6$ and $R^7$ are preferably each independently H; $C_{1-6}$alkyl, for example, $C_{1-5}$alkyl, $C_{1-4}$alkyl, $C_{1-3}$alkyl, $C_{1-2}$alkyl, or $C_1$alkyl; or $C_{3-6}$cycloalkyl, for example, cyclopropyl, cyclobutyl, cyclopentyl, or cyclohexyl. More preferably, $R^6$ and $R^7$ are each independently H or $C_{1-6}$alkyl, for example, $C_{1-5}$alkyl, $C_{1-4}$alkyl, $C_{1-3}$alkyl, $C_{1-2}$alkyl, or $C_1$alkyl. The benzofuranyl can be substituted with C(O)—$C_{1-6}$alkyl, for example, C(O)—$C_{1-65}$alkyl, C(O)—$C_{1-4}$alkyl, C(O)—$C_{1-3}$alkyl, C(O)—$C_{1-2}$alkyl, or C(O)—$C_1$alkyl.

In some aspects, G is thiophenyl. In these aspects, the thiophenyl can be unsubstituted or substituted with 1, 2, or 3 substituents, preferably 1 or 2 substituents, more preferably 1 substituent, independently selected from the group consisting of halogen; $C_{1-6}$alkyl; $C_{1-6}$haloalkyl; $OC_{1-6}$haloalkyl; $C_{3-6}$cycloalkyl; $OC_{1-6}$alkyl; CN; OH; $C_{1-6}$alk-O—$C_{1-6}$alkyl; C(O)—$NR^6R^7$; and C(O)—$C_{1-6}$alkyl. The thiophenyl can be substituted with halogen, for example F or Cl. The thiophenyl can be substituted with $C_{1-6}$alkyl, for example, $C_{1-5}$alkyl, $C_{1-4}$alkyl, $C_{1-3}$alkyl, $C_{1-2}$alkyl, or $C_1$alkyl. The thiophenyl can be substituted with $C_{1-6}$haloalkyl, for example, $C_{1-5}$haloalkyl, $C_{1-4}$haloalkyl, $C_{1-3}$haloalkyl, $C_{1-2}$haloalkyl, or $C_1$haloalkyl. The thiophenyl can be substituted with $OC_{1-6}$haloalkyl, for example, $OC_{1-5}$haloalkyl, $OC_{1-4}$haloalkyl, $OC_{1-3}$haloalkyl, $OC_{1-2}$haloalkyl, or $OC_1$haloalkyl. The thiophenyl can be substituted with $C_{3-6}$cycloalkyl, for example, cyclopropyl, cyclobutyl, cyclopentyl, or cyclohexyl. The thiophenyl can be substituted with $OC_{1-6}$alkyl, for example, $OC_{1-5}$alkyl, $OC_{1-4}$alkyl, $OC_{1-3}$ alkyl, $OC_{1-2}$alkyl, or $OC_1$alkyl. The thiophenyl can be substituted with CN. The thiophenyl can be substituted with OH. The thiophenyl can be substituted with $C_{1-6}$alk-O—$C_{1-6}$ alkyl, for example, $C_{1-5}$alk-O—$C_{1-5}$alkyl, $C_{1-4}$alk-O—$C_{1-4}$alkyl, $C_{1-3}$alk-O—$C_{1-3}$alkyl, $C_{1-2}$alk-O—$C_{1-2}$alkyl, or $C_1$alk-O—$C_1$alkyl. The thiophenyl can be substituted with C(O)—$NR^6R^7$, wherein $R^6$ and $R^7$ are preferably each independently H; $C_{1-6}$alkyl, for example, $C_{1-5}$alkyl, $C_{1-4}$alkyl, $C_{1-3}$alkyl, $C_{1-2}$alkyl, or $C_1$alkyl; or $C_{3-6}$cycloalkyl, for example, cyclopropyl, cyclobutyl, cyclopentyl, or cyclohexyl. More preferably, $R^6$ and $R^7$ are each independently H or $C_{1-6}$alkyl, for example, $C_{1-5}$alkyl, $C_{1-4}$alkyl, $C_{1-3}$alkyl, $C_{1-2}$alkyl, or $C_1$alkyl.

The thiophenyl can be substituted with C(O)—$C_{1-6}$alkyl, for example, C(O)—$C_{1-65}$alkyl, C(O)—$C_{1-4}$alkyl, C(O)—$C_{1-3}$alkyl, C(O)—$C_{1-2}$alkyl, or C(O)—$C_1$alkyl.

In preferred aspects, G is unsubstituted or substituted pyridyl, pyridizinyl, or pyrazinyl. In those aspects wherein G is substituted pyridyl, pyridizinyl, or pyrazinyl, preferred substituents include $C_{1-6}$alkyl (e.g., methyl). In other preferred aspects, G is $C_{1-6}$alkyl (e.g., isopropyl).

In preferred aspects, G is unsubstituted or substituted pyridyl, pyridizinyl, or pyrazinyl and E is $CH_2$ or O. In those aspects wherein G is substituted pyridyl, pyridizinyl, or pyrazinyl and E is $CH_2$ or O, preferred substituents include $C_{1-6}$alkyl (e.g., methyl). In other preferred aspects, G is $C_{1-6}$alkyl (e.g., isopropyl) and E is $CH_2$ or O.

In some preferred aspects, A-E-G is:

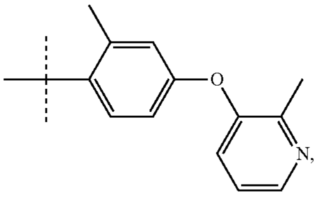

-continued

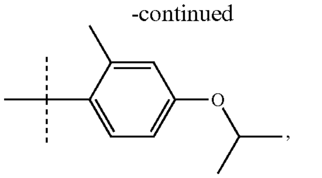

or

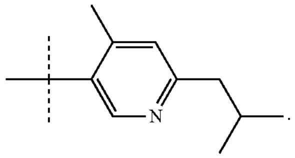

Preferred compounds of the Formula I include those wherein $R^1$ is H; $R^2$ is cyclopentyl substituted with 1 or 2 substituents wherein one of the substituents is $NR^8$—C(O)—C($R^3$)=$CR^4$($R^5$), wherein $R^3$, $R^4$, and $R^5$ are each H; A is phenyl or pyridyl, wherein the phenyl or pyridyl is substituted with $CH_3$; E is O or a bond; and G is phenyl or $C_{1-6}$alkyl. In more preferred aspects, $R^2$ is substituted with 1 substituent that is $NR^8$—C(O)—C($R^3$)=$CR^4$($R^5$). In preferred aspects, A-E-G is

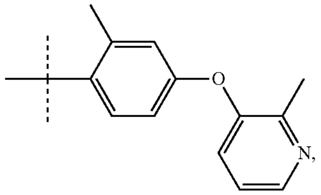

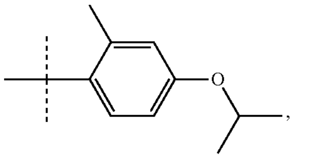

or

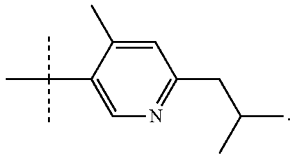

Preferred subgenera of Formula (I) include:

(I-M-1)

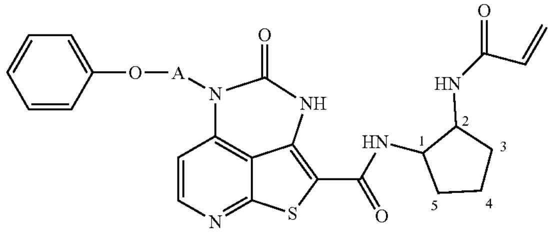

;

-continued
(I-M-2)
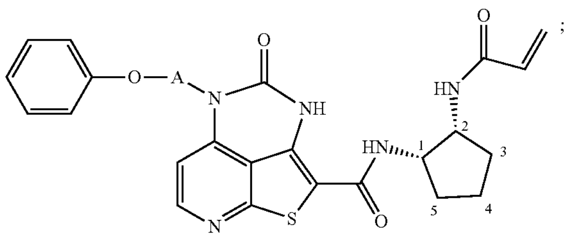
(I-V-1)
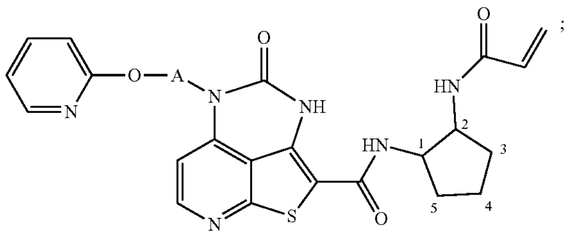
(I-V-2)
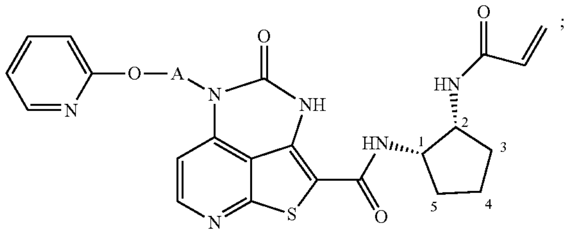
(I-W-1)
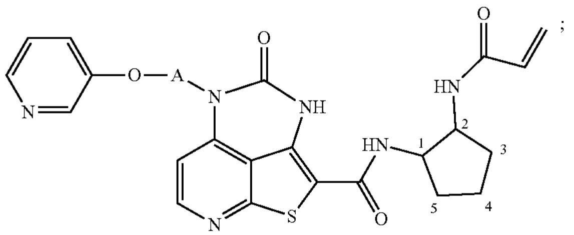
(I-W-2)
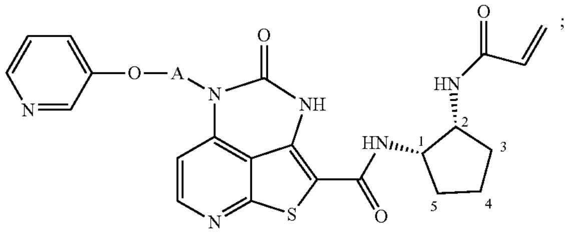
(I-Q-1)
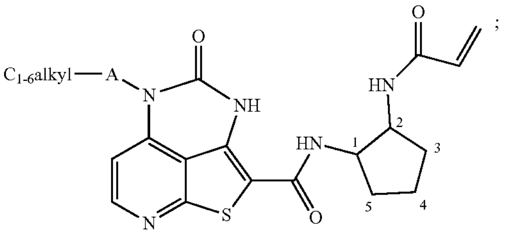
-continued
(I-Q-2)
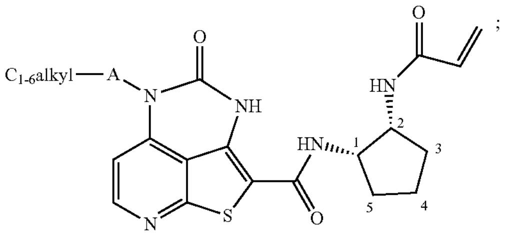
(I-P-1)
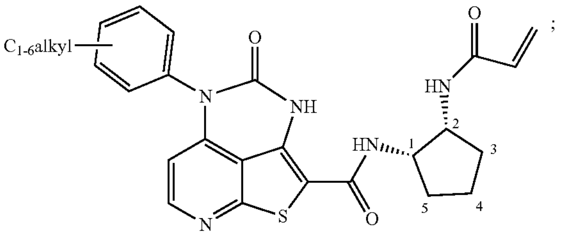
wherein the A phenyl is unsubstituted or substituted, preferably with $C_{1-6}$alkyl;
(I-P-2)
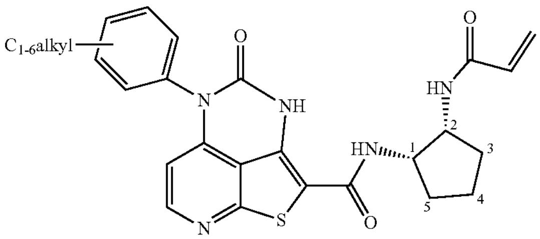
wherein the A phenyl is unsubstituted or substituted, preferably with $C_{1-6}$alkyl;
(I-T-1)
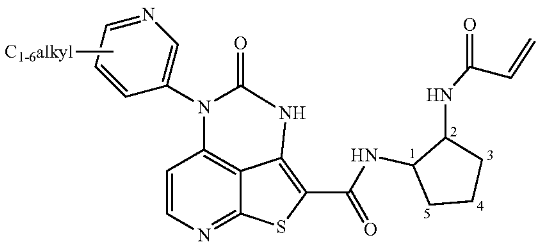
wherein the A pyridyl is unsubstituted or substituted, preferably with $C_{1-6}$alkyl;

(I-T-2)

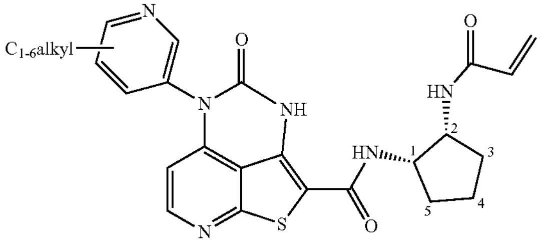

wherein the A pyridyl is unsubstituted or substituted, preferably with $C_{1-6}$alkyl;

(I-U-1)

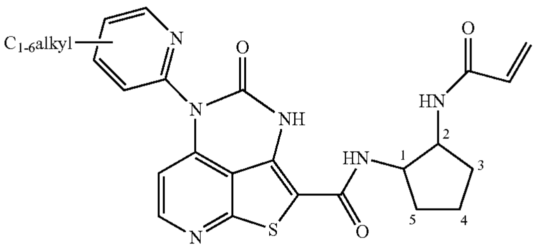

wherein the A pyridyl is unsubstituted or substituted, preferably with $C_{1-6}$alkyl;

(I-U-2)

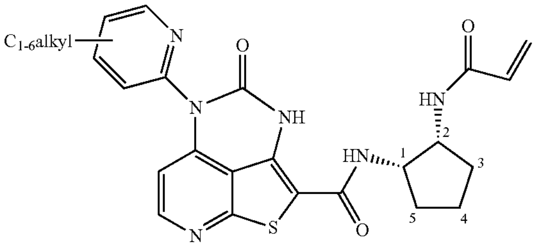

wherein the A pyridyl is unsubstituted or substituted, preferably with $C_{1-6}$alkyl;

(I-X-1)

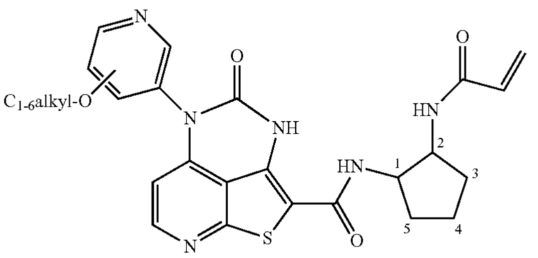

wherein the A pyridyl is unsubstituted or substituted, preferably with $C_{1-6}$alkyl;

(I-XU-2)

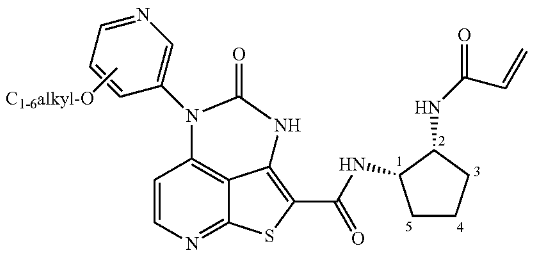

wherein the A pyridyl is unsubstituted or substituted, preferably with $C_{1-6}$alkyl;

(I-Y-1)

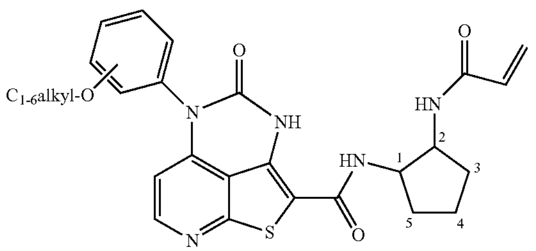

wherein the A phenyl is unsubstituted or substituted, preferably with $C_{1-6}$alkyl; and (I-Y-2)

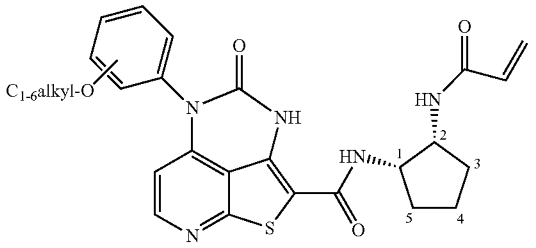

wherein the A phenyl is unsubstituted or substituted, preferably with $C_{1-6}$alkyl.

An additional aspect of the invention is a compound selected from the group consisting of:

N-((1S,4S)-4-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,3S)-3-Acrylamidocyclohexyl)-5-(2-methyl-4-phenoxyphenyl)-4-oxo-4,5-dihydro-3H-1-thia-3,5,8-triazaacenaphthylene-2-carboxamide;

N-((1S,4S)-4-Acrylamidocyclohexyl)-5-(2-methyl-4-phenoxyphenyl)-4-oxo-4,5-dihydro-3H-1-thia-3,5,8-triazaacenaphthylene-2-carboxamide;

N-((1R,2R)-2-Hydroxycyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Aminocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Hydroxycyclopentyl)-5-(2-methyl-4-phenoxyphenyl)-4-oxo-4,5-dihydro-3H-1-thia-3,5,8-triazaacenaphthylene-2-carboxamide;

N-((1R,2S)-2-(Dimethylamino)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Hydroxycyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2R)-2-Hydroxycyclopentyl)-5-(2-methyl-4-phenoxyphenyl)-4-oxo-4,5-dihydro-3H-1-thia-3,5,8-triazaacenaphthylene-2-carboxamide;

N-((1R,2S)-2-Aminocyclohexyl)-5-(2-methyl-4-phenoxyphenyl)-4-oxo-4,5-dihydro-3H-1-thia-3,5,8-triazaacenaphthylene-2-carboxamide;

N-((1R,2R)-2-Acetamidocyclopentyl)-5-(2-methyl-4-phenoxyphenyl)-4-oxo-4,5-dihydro-3H-1-thia-3,5,8-triazaacenaphthylene-2-carboxamide;

N-((1R,2S)-2-Aminocyclopentyl)-5-(2-methyl-4-phenoxyphenyl)-4-oxo-4,5-dihydro-3H-1-thia-3,5,8-triazaacenaphthylene-2-carboxamide;

N-((1R,4R)-4-Acrylamidocyclohexyl)-5-(2-methyl-4-phenoxyphenyl)-4-oxo-4,5-dihydro-3H-1-thia-3,5,8-triazaacenaphthylene-2-carboxamide;

N-((1R,2S)-2-(Dimethylamino)cyclohexyl)-5-(2-methyl-4-phenoxyphenyl)-4-oxo-4,5-dihydro-3H-1-thia-3,5,8-triazaacenaphthylene-2-carboxamide;

N-((1R,4R)-4-Hydroxycyclohexyl)-5-(2-methyl-4-phenoxyphenyl)-4-oxo-4,5-dihydro-3H-1-thia-3,5,8-triazaacenaphthylene-2-carboxamide;

N-((1S,4S)-4-Hydroxycyclohexyl)-5-(2-methyl-4-phenoxyphenyl)-4-oxo-4,5-dihydro-3H-1-thia-3,5,8-triazaacenaphthylene-2-carboxamide;

N-((1R,2S)-2-(Dimethylamino)cyclopentyl)-5-(2-methyl-4-phenoxyphenyl)-4-oxo-4,5-dihydro-3H-1-thia-3,5,8-triazaacenaphthylene-2-carboxamide;

N-((1R,4R)-4-Methoxycyclohexyl)-5-(2-methyl-4-phenoxyphenyl)-4-oxo-4,5-dihydro-3H-1-thia-3,5,8-triazaacenaphthylene-2-carboxamide;

N-((1S,4S)-4-((E)-2-Cyano-3-cyclopropylacrylamido)cyclohexyl)-5-(2-methyl-4-phenoxyphenyl)-4-oxo-4,5-dihydro-3H-1-thia-3,5,8-triazaacenaphthylene-2-carboxamide;

N-((1S,2S)-2-Hydroxycyclopentyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-((1R,2R)-2-(methylamino)cyclopentyl)-4-oxo-4,5-dihydro-3H-1-thia-3,5,8-triazaacenaphthylene-2-carboxamide;

N-((1R,2R)-2-Aminocyclopentyl)-5-(2-methyl-4-phenoxyphenyl)-4-oxo-4,5-dihydro-3H-1-thia-3,5,8-triazaacenaphthylene-2-carboxamide;

N-((1S,4S)-4-Cyanamidocyclohexyl)-5-(2-methyl-4-phenoxyphenyl)-4-oxo-4,5-dihydro-3H-1-thia-3,5,8-triazaacenaphthylene-2-carboxamide;

N-((1R,3S)-3-(Dimethylamino)cyclohexyl)-5-(2-methyl-4-phenoxyphenyl)-4-oxo-4,5-dihydro-3H-1-thia-3,5,8-triazaacenaphthylene-2-carboxamide;

N-((1S,4S)-4-Aminocyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-((1R,2R)-2-propionamidocyclopentyl)-4,5-dihydro-3H-1-thia-3,5,8-triazaacenaphthylene-2-carboxamide;

N-((1RS,2RS)-2-Hydroxycyclohexyl)-5-(2-methyl-4-phenoxyphenyl)-4-oxo-4,5-dihydro-3H-1-thia-3,5,8-triazaacenaphthylene-2-carboxamide;

N-Cyclopentyl-5-(2-methyl-4-phenoxyphenyl)-4-oxo-4,5-dihydro-3H-1-thia-3,5,8-triazaacenaphthylene-2-carboxamide;

N-((1R,2R)-2-(Dimethylamino)cyclopentyl)-5-(2-methyl-4-phenoxyphenyl)-4-oxo-4,5-dihydro-3H-1-thia-3,5,8-triazaacenaphthylene-2-carboxamide;

N-((1r,3s,5R,7S)-3-Hydroxyadamantan-1-yl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-(2-(methylamino)cyclohexyl)-4-oxo-4,5-dihydro-3H-1-thia-3,5,8-triazaacenaphthylene-2-carboxamide;

N-((1S,2S)-2-(Dimethylamino)cyclopentyl)-5-(2-methyl-4-phenoxyphenyl)-4-oxo-4,5-dihydro-3H-1-thia-3,5,8-triazaacenaphthylene-2-carboxamide;

N-((1R,2S)-2-Acetamidocyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-((1R,2S)-2-propionamidocyclopentyl)-4,5-dihydro-3H-1-thia-3,5,8-triazaacenaphthylene-2-carboxamide;

5-(2-Methyl-4-phenoxyphenyl)-4-oxo-N-((1R,2S)-2-propionamidocyclohexyl)-4,5-dihydro-3H-1-thia-3,5,8-triazaacenaphthylene-2-carboxamide;

N-((1RS,2RS)-2-Hydroxycyclohexyl)-5-(2-methyl-4-phenoxyphenyl)-4-oxo-4,5-dihydro-3H-1-thia-3,5,8-triazaacenaphthylene-2-carboxamide;

N-((1R,2S)-2-Acetamidocyclopentyl)-5-(2-methyl-4-phenoxyphenyl)-4-oxo-4,5-dihydro-3H-1-thia-3,5,8-triazaacenaphthylene-2-carboxamide;

N-((1R,2R)-2-Aminocyclohexyl)-5-(2-methyl-4-phenoxyphenyl)-4-oxo-4,5-dihydro-3H-1-thia-3,5,8-triazaacenaphthylene-2-carboxamide;

N-((1S,2R)-2-Hydroxycyclopentyl)-5-(2-methyl-4-phenoxyphenyl)-4-oxo-4,5-dihydro-3H-1-thia-3,5,8-triazaacenaphthylene-2-carboxamide;

N-((1S,2S)-2-Acetamidocyclopentyl)-5-(2-methyl-4-phenoxyphenyl)-4-oxo-4,5-dihydro-3H-1-thia-3,5,8-triazaacenaphthylene-2-carboxamide;

N-((1S,2S)-2-Aminocyclopentyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-((1S,2R)-2-propionamidocyclohexyl)-4,5-dihydro-3H-1-thia-3,5,8-triazaacenaphthylene-2-carboxamide;

N-((1R,2R)-2-(Dimethylamino)cyclohexyl)-5-(2-methyl-4-phenoxyphenyl)-4-oxo-4,5-dihydro-3H-1-thia-3,5,8-triazaacenaphthylene-2-carboxamide;

N-((1S,2R)-2-Acetamidocyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-4-oxo-N-((1S,2S)-2-propionamidocyclopentyl)-4,5-dihydro-3H-1-thia-3,5,8-triazaacenaphthylene-2-carboxamide;

5-(2-Methyl-4-phenoxyphenyl)-N-((1S,2S)-2-(methylamino)cyclopentyl)-4-oxo-4,5-dihydro-3H-1-thia-3,5,8-triazaacenaphthylene-2-carboxamide;

N-((1R,2R)-2-Acetamidocyclohexyl)-5-(2-methyl-4-phenoxyphenyl)-4-oxo-4,5-dihydro-3H-1-thia-3,5,8-triazaacenaphthylene-2-carboxamide;

N-((1S,2R)-2-(Dimethylamino)cyclohexyl)-5-(2-methyl-4-phenoxyphenyl)-4-oxo-4,5-dihydro-3H-1-thia-3,5,8-triazaacenaphthylene-2-carboxamide;

N-((1S,2R)-2-Aminocyclohexyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-((1S,2R)-2-(methylamino)cyclohexyl)-4-oxo-4,5-dihydro-3H-1-thia-3,5,8-triazaacenaphthylene-2-carboxamide;

N-((1S,2R)-2-(Dimethylamino)cyclopentyl)-5-(2-methyl-4-phenoxyphenyl)-4-oxo-4,5-dihydro-3H-1-thia-3,5,8-triazaacenaphthylene-2-carboxamide;
5-(2-Methyl-4-phenoxyphenyl)-4-oxo-N-((1R,2R)-2-propionamidocyclohexyl)-4,5-dihydro-3H-1-thia-3,5,8-triazaacenaphthylene-2-carboxamide;
N-((1S,2R)-2-Aminocyclopentyl)-5-(2-methyl-4-phenoxyphenyl)-4-oxo-4,5-dihydro-3H-1-thia-3,5,8-triazaacenaphthylene-2-carboxamide;
N-((1S,2S)-2-Formamidocyclohexyl)-5-(2-methyl-4-phenoxyphenyl)-4-oxo-4,5-dihydro-3H-1-thia-3,5,8-triazaacenaphthylene-2-carboxamide;
N-((1S,2S)-2-Acetamidocyclohexyl)-5-(2-methyl-4-phenoxyphenyl)-4-oxo-4,5-dihydro-3H-1-thia-3,5,8-triazaacenaphthylene-2-carboxamide;
N-((1S,2S)-2-Acrylamidocyclopentyl)-5-(*R)-(2-methyl-4-phenoxyphenyl)-4-oxo-4,5-dihydro-3H-1-thia-3,5,8-triazaacenaphthylene-2-carboxamide;
N-((1S,2R)-2-Acetamidocyclopentyl)-5-(2-methyl-4-phenoxyphenyl)-4-oxo-4,5-dihydro-3H-1-thia-3,5,8-triazaacenaphthylene-2-carboxamide;
N-((1S,2S)-2-Aminocyclohexyl)-5-(2-methyl-4-phenoxyphenyl)-4-oxo-4,5-dihydro-3H-1-thia-3,5,8-triazaacenaphthylene-2-carboxamide;
5-(2-Methyl-4-phenoxyphenyl)-4-oxo-N-((1S,2R)-2-propionamidocyclopentyl)-4,5-dihydro-3H-1-thia-3,5,8-triazaacenaphthylene-2-carboxamide;
5-(2-Methyl-4-phenoxyphenyl)-4-oxo-N-((1S,2S)-2-propionamidocyclohexyl)-4,5-dihydro-3H-1-thia-3,5,8-triazaacenaphthylene-2-carboxamide;
N-((1R,2R)-2-Hydroxycyclopentyl)-5-(*R)-(2-methyl-4-phenoxyphenyl)-4-oxo-4,5-dihydro-3H-1-thia-3,5,8-triazaacenaphthylene-2-carboxamide;
N-((1S,2S)-2-(Dimethylamino)cyclohexyl)-5-(2-methyl-4-phenoxyphenyl)-4-oxo-4,5-dihydro-3H-1-thia-3,5,8-triazaacenaphthylene-2-carboxamide;
5-(2-Methyl-4-phenoxyphenyl)-N-(4-(methylamino)cyclohexyl)-4-oxo-4,5-dihydro-3H-1-thia-3,5,8-triazaacenaphthylene-2-carboxamide;
N-((1S,4S)-4-Acetamidocyclohexyl)-5-(2-methyl-4-phenoxyphenyl)-4-oxo-4,5-dihydro-3H-1-thia-3,5,8-triazaacenaphthylene-2-carboxamide;
5-(2-Methyl-4-phenoxyphenyl)-4-oxo-N-((1S,4S)-4-propionamidocyclohexyl)-4,5-dihydro-3H-1-thia-3,5,8-triazaacenaphthylene-2-carboxamide;
N-((1S,4S)-4-(Dimethylamino)cyclohexyl)-5-(2-methyl-4-phenoxyphenyl)-4-oxo-4,5-dihydro-3H-1-thia-3,5,8-triazaacenaphthylene-2-carboxamide;
N-((1R,2R)-2-Acetamidocyclopentyl)-5-(*S)-(2-methyl-4-phenoxyphenyl)-4-oxo-4,5-dihydro-3H-1-thia-3,5,8-triazaacenaphthylene-2-carboxamide;
N-((1S,3R)-3-acrylamidocyclopentyl)-5-(2-methyl-4-phenoxyphenyl)-4-oxo-4,5-dihydro-3H-1-thia-3,5,8-triazaacenaphthylene-2-carboxamide;
5-(2-Methyl-4-phenoxyphenyl)-4-oxo-N-((1S,3R)-3-propionamidocyclopentyl)-4,5-dihydro-3H-1-thia-3,5,8-triazaacenaphthylene-2-carboxamide;
N-((1S,3R)-3-Acetamidocyclopentyl)-5-(2-methyl-4-phenoxyphenyl)-4-oxo-4,5-dihydro-3H-1-thia-3,5,8-triazaacenaphthylene-2-carboxamide;
N-((1S,3R)-3-(2-(Dimethylamino)acetamido)cyclopentyl)-5-(2-methyl-4-phenoxyphenyl)-4-oxo-4,5-dihydro-3H-1-thia-3,5,8-triazaacenaphthylene-2-carboxamide;
5-(2-Methyl-4-phenoxyphenyl)-N-((1S,3R)-3-(2-(methylamino)acetamido)cyclopentyl)-4-oxo-4,5-dihydro-3H-1-thia-3,5,8-triazaacenaphthylene-2-carboxamide;
N-((1S,3R)-3-(Dimethylamino)cyclopentyl)-5-(2-methyl-4-phenoxyphenyl)-4-oxo-4,5-dihydro-3H-1-thia-3,5,8-triazaacenaphthylene-2-carboxamide;
N-((1S,3R)-3-Hydroxycyclopentyl)-5-(2-methyl-4-phenoxyphenyl)-4-oxo-4,5-dihydro-3H-1-thia-3,5,8-triazaacenaphthylene-2-carboxamide;
N-((1S,3R)-3-(2-Aminoacetamido)cyclopentyl)-5-(2-methyl-4-phenoxyphenyl)-4-oxo-4,5-dihydro-3H-1-thia-3,5,8-triazaacenaphthylene-2-carboxamide;
N-((1S,3R)-3-Aminocyclopentyl)-5-(2-methyl-4-phenoxyphenyl)-4-oxo-4,5-dihydro-3H-1-thia-3,5,8-triazaacenaphthylene-2-carboxamide;
N-((1S,4S)-4-((E)-4-(Dimethylamino)but-2-enamido)cyclohexyl)-5-(2-methyl-4-phenoxyphenyl)-4-oxo-4,5-dihydro-3H-1-thia-3,5,8-triazaacenaphthylene-2-carboxamide;
5-(2-Methyl-4-phenoxyphenyl)-N-((1S,4S)-4-((E)-4-(methylamino)but-2-enamido)cyclohexyl)-4-oxo-4,5-dihydro-3H-1-thia-3,5,8-triazaacenaphthylene-2-carboxamide;
N-((1S,4S)-4-((E)-4-Aminobut-2-enamido)cyclohexyl)-5-(2-methyl-4-phenoxyphenyl)-4-oxo-4,5-dihydro-3H-1-thia-3,5,8-triazaacenaphthylene-2-carboxamide;
5-(2-Methyl-4-phenoxyphenyl)-N-((1S)-3-(methylamino)cyclopentyl)-4-oxo-4,5-dihydro-3H-1-thia-3,5,8-triazaacenaphthylene-2-carboxamide;
N-Cyclopentyl-5-(*S)-(2-methyl-4-phenoxyphenyl)-4-oxo-4,5-dihydro-3H-1-thia-3,5,8-triazaacenaphthylene-2-carboxamide;
N-Cyclopentyl-5-(*R)-(2-methyl-4-phenoxyphenyl)-4-oxo-4,5-dihydro-3H-thia-3,5,8-triazaacenaphthylene-2-carboxamide;
N-((1S,4S)-4-Hydroxycyclohexyl)-5-(*S)-(2-methyl-4-phenoxyphenyl)-4-oxo-4,5-dihydro-3H-1-thia-3,5,8-triazaacenaphthylene-2-carboxamide;
N-((1S,4S)-4-Hydroxycyclohexyl)-5-(*R)-(2-methyl-4-phenoxyphenyl)-4-oxo-4,5-dihydro-3H-1-thia-3,5,8-triazaacenaphthylene-2-carboxamide;
N-((1R,4R)-4-Hydroxycyclohexyl)-5-(*S)-(2-methyl-4-phenoxyphenyl)-4-oxo-4,5-dihydro-3H-1-thia-3,5,8-triazaacenaphthylene-2-carboxamide;
N-((1R,4R)-4-Hydroxycyclohexyl)-5-(*R)-(2-methyl-4-phenoxyphenyl)-4-oxo-4,5-dihydro-3H-1-thia-3,5,8-triazaacenaphthylene-2-carboxamide;
5-(*S)-(2-Methyl-4-phenoxyphenyl)-4-oxo-N-((1S,3R)-3-propionamidocyclopentyl)-4,5-dihydro-3H-1-thia-3,5,8-triazaacenaphthylene-2-carboxamide;
N-((1S,3R)-3-Acetamidocyclopentyl)-5-(*S)-(2-methyl-4-phenoxyphenyl)-4-oxo-4,5-dihydro-3H-1-thia-3,5,8-triazaacenaphthylene-2-carboxamide;
N-((1S,4S)-4-((*E)-2-Cyano-3-cyclopropylacrylamido)cyclohexyl)-5-(*S)-(2-methyl-4-phenoxyphenyl)-4-oxo-4,5-dihydro-3H-1-thia-3,5,8-triazaacenaphthylene-2-carboxamide;
N-((1S,4S)-4-((*E)-2-Cyano-3-cyclopropylacrylamido)cyclohexyl)-5-(*R)-(2-methyl-4-phenoxyphenyl)-4-oxo-4,5-dihydro-3H-1-thia-3,5,8-triazaacenaphthylene-2-carboxamide;
N-((1R,2R)-2-Aminocyclopentyl)-4-oxo-5-(4-phenoxyphenyl)-4,5-dihydro-3H-1-thia-3,5,8-triazaacenaphthylene-2-carboxamide;
5-(*S)-(2-Methyl-4-phenoxyphenyl)-4-oxo-N-((1S,4S)-4-propionamidocyclohexyl)-4,5-dihydro-3H-1-thia-3,5,8-triazaacenaphthylene-2-carboxamide;
5-(*R)-(2-Methyl-4-phenoxyphenyl)-4-oxo-N-((1S,4S)-4-propionamidocyclohexyl)-4,5-dihydro-3H-1-thia-3,5,8-triazaacenaphthylene-2-carboxamide;

N-((1S,4S)-4-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1S,4S)-4-Acetamidocyclohexyl)-5-(*R)-(2-methyl-4-phenoxyphenyl)-4-oxo-4,5-dihydro-3H-1-thia-3,5,8-triazaacenaphthylene-2-carboxamide;

N-(rac-(1,3-cis)-3-Aminocyclopentyl)-4-oxo-5-(4-phenoxyphenyl)-4,5-dihydro-3H-1-thia-3,5,8-triazaacenaphthylene-2-carboxamide;

N-((1R,2S)-2-Aminocyclopentyl)-4-oxo-5-(4-phenoxyphenyl)-4,5-dihydro-3H-1-thia-3,5,8-triazaacenaphthylene-2-carboxamide;

N-((1S,2R)-2-Aminocyclopentyl)-4-oxo-5-(4-phenoxyphenyl)-4,5-dihydro-3H-1-thia-3,5,8-triazaacenaphthylene-2-carboxamide;

N-((1S,4S)-4-(Dimethylamino)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1S,4S)-4-(Dimethylamino)cyclohexyl)-5-(*R)-(2-methyl-4-phenoxyphenyl)-4-oxo-4,5-dihydro-3H-1-thia-3,5,8-triazaacenaphthylene-2-carboxamide;

N-((1S,3R)-3-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,3R)-3-(2-(dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide;

5-(*S)-(2-Methyl-4-phenoxyphenyl)-N-((1S,3R)-3-(2-(methylamino)acetamido)cyclopentyl)-4-oxo-4,5-dihydro-3H-1-thia-3,5,8-triazaacenaphthylene-2-carboxamide;

N-((1R,2S)-2-acrylamidocyclopentyl)-4-oxo-5-(4-phenoxyphenyl)-4,5-dihydro-3H-1-thia-3,5,8-triazaacenaphthylene-2-carboxamide;

N-((1R,2R)-2-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

5-([1,1'-Biphenyl]-3-yl)-N-((1R,2 S)-2-acrylamidocyclohexyl)-4-oxo-4,5-dihydro-3H-1-thia-3,5,8-triazaacenaphthylene-2-carboxamide;

N-((1R,2S)-2-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1RS,3RS)-3-Acrylamidocyclopentyl)-4-oxo-5-(4-phenoxyphenyl)-4,5-dihydro-3H-1-thia-3,5,8-triazaacenaphthylene-2-carboxamide;

N-((1S,3R)-3-Acrylamidocyclopentyl)-5-(4-isopropoxy-2-methylphenyl)-4-oxo-4,5-dihydro-3H-1-thia-3,5,8-triazaacenaphthylene-2-carboxamide;

N-((1R,2R)-2-(2-(Dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide;

5-(*S)-(2-Methyl-4-phenoxyphenyl)-N-((1R,2R)-2-(2-(methylamino)acetamido)cyclopentyl)-4-oxo-4,5-dihydro-3H-1-thia-3,5,8-triazaacenaphthylene-2-carboxamide;

N-((1R,2R)-2-(2-Aminoacetamido)cyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,2R)-2-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Aminocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,2S)-2-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,3R)-3-Acrylamidocyclopentyl)-4-oxo-5-(4-phenoxyphenyl)-4,5-dihydro-3H-1-thia-3,5,8-triazaacenaphthylene-2-carboxamide;

N-((1R,2S)-2-Acrylamidocyclohexyl)-4-oxo-5-(4-phenoxyphenyl)-4,5-dihydro-3H-1-thia-3,5,8-triazaacenaphthylene-2-carboxamide;

N-((1S,4S)-4-Acrylamidocyclohexyl)-4-oxo-5-(4-phenoxyphenyl)-4,5-dihydro-3H-1-thia-3,5,8-triazaacenaphthylene-2-carboxamide;

N-((1R,2R)-2-Aminocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,3S)-3-Acrylamidocyclopentyl)-4-oxo-5-(4-phenoxyphenyl)-4,5-dihydro-3H-1-thia-3,5,8-triazaacenaphthylene-2-carboxamide;

5-(*S)-(2-Methyl-4-phenoxyphenyl)-N-((1R,2S)-2-(2-(methylamino)acetamido)cyclopentyl)-4-oxo-4,5-dihydro-3H-1-thia-3,5,8-triazaacenaphthylene-2-carboxamide;

N-((1S,2S)-2-(2-(Dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,2R)-2-Acrylamidocyclohexyl)-4-oxo-5-(4-phenoxyphenyl)-4,5-dihydro-3H-1-thia-3,5,8-triazaacenaphthylene-2-carboxamide;

5-(*S)-(2-Methyl-4-phenoxyphenyl)-N-((1R,2S)-2-(2-(methylamino)acetamido)cyclohexyl)-4-oxo-4,5-dihydro-3H-1-thia-3,5,8-triazaacenaphthylene-2-carboxamide;

N-((1R,2S)-2-Aminocyclohexyl)-4-oxo-5-(4-phenoxyphenyl)-4,5-dihydro-3H-1-thia-3,5,8-triazaacenaphthylene-2-carboxamide;

N-((1S,2R)-2-Acrylamidocyclopentyl)-4-oxo-5-(4-phenoxyphenyl)-4,5-dihydro-3H-1-thia-3,5,8-triazaacenaphthylene-2-carboxamide;

N-((1R,2S)-2-(2-(Dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1S,2S)-2-(2-Aminoacetamido)cyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-(2-Aminoacetamido)cyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-(2-(Dimethylamino)acetamido)cyclohexyl)-5-(*S)-(2-methyl-4-phenoxyphenyl)-4-oxo-4,5-dihydro-3H-1-thia-3,5,8-triazaacenaphthylene-2-carboxamide;

5-(*S)-(2-Methyl-4-phenoxyphenyl)-N-((1S,2S)-2-(2-(methylamino)acetamido)cyclopentyl)-4-oxo-4,5-dihydro-3H-1-thia-3,5,8-triazaacenaphthylene-2-carboxamide;

N-((1S,2S)-2-Acetamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,2S)-2-Aminocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Aminocyclohexyl)-5-(3-chloro-4-phenoxyphenyl)-4-oxo-4,5-dihydro-3H-1-thia-3,5,8-triazaacenaphthylene-2-carboxamide;

N-((1R,2S)-2-Acetamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,3R)-3-Hydroxycyclohexyl)-4-oxo-5-(4-phenoxyphenyl)-4,5-dihydro-3H-1-thia-3,5,8-triazaacenaphthylene-2-carboxamide;

N-((1R,2S)-2-Hydroxycyclopentyl)-4-oxo-5-(4-phenoxyphenyl)-4,5-dihydro-3H-1-thia-3,5,8-triazaacenaphthylene-2-carboxamide;

5-([1,1'-Biphenyl]-3-yl)-N-((1R,2S)-2-aminocyclohexyl)-4-oxo-4,5-dihydro-3H-1-thia-3,5,8-triazaacenaphthylene-2-carboxamide;

N-((1R,3S)-3-Hydroxycyclohexyl)-4-oxo-5-(4-phenoxyphenyl)-4,5-dihydro-3H-1-thia-3,5,8-triazaacenaphthylene-2-carboxamide;

N-((1S,3S)-3-Hydroxycyclohexyl)-4-oxo-5-(4-phenoxyphenyl)-4,5-dihydro-3H-1-thia-3,5,8-triazaacenaphthylene-2-carboxamide;

5-([1,1'-Biphenyl]-3-yl)-N-((1R,2R)-2-hydroxycyclopentyl)-4-oxo-4,5-dihydro-3H-1-thia-3,5,8-triazaacenaphthylene-2-carboxamide;

N-((1S,4S)-4-Aminocyclohexyl)-4-oxo-5-(4-phenoxyphenyl)-4,5-dihydro-3H-1-thia-3,5,8-triazaacenaphthylene-2-carboxamide;

N-(trans-(1R,4R)-4-Aminocyclohexyl)-4-oxo-5-(4-phenoxyphenyl)-4,5-dihydro-3H-1-thia-3,5,8-triazaacenaphthylene-2-carboxamide;

trans-N-((1RS,3RS)-3-Aminocyclopentyl)-4-oxo-5-(4-phenoxyphenyl)-4,5-dihydro-3H-1-thia-3,5,8-triazaacenaphthylene-2-carboxamide;

N-((1S,2S)-2-Aminocyclopentyl)-4-oxo-5-(4-phenoxyphenyl)-4,5-dihydro-3H-1-thia-3,5,8-triazaacenaphthylene-2-carboxamide;

N-((1R,2R)-2-Aminocyclohexyl)-4-oxo-5-(4-phenoxyphenyl)-4,5-dihydro-3H-1-thia-3,5,8-triazaacenaphthylene-2-carboxamide;

tert-Butyl ((1R,3S)-3-(4-oxo-5-(4-phenoxyphenyl)-4,5-dihydro-3H-1-thia-3,5,8-triazaacenaphthylene-2-carboxamido)cyclopentyl)carbamate;

tert-Butyl trans-((1R,4R)-4-(4-oxo-5-(4-phenoxyphenyl)-4,5-dihydro-3H-1-thia-3,5,8-triazaacenaphthylene-2-carboxamido)cyclohexyl)carbamate;

N-((1-Hydroxycyclohexyl)methyl)-4-oxo-5-(4-phenoxyphenyl)-4,5-dihydro-3H-1-thia-3,5,8-triazaacenaphthylene-2-carboxamide;

N-((1S,3R)-3-((E)-4-(Dimethylamino)but-2-enamido)cyclopentyl)-5-(4-isopropoxy-2-methylphenyl)-4-oxo-4,5-dihydro-3H-1-thia-3,5,8-triazaacenaphthylene-2-carboxamide;

N-((1S,2R)-2-(2-Aminoacetamido)cyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,2R)-2-(2-(Dimethylamino)acetamido)cyclopentyl)-5-(*S)-(2-methyl-4-phenoxyphenyl)-4-oxo-4,5-dihydro-3H-1-thia-3,5,8-triazaacenaphthylene-2-carboxamide;

5-(*S)-(2-Methyl-4-phenoxyphenyl)-N-((1S,2R)-2-(2-(methylamino)acetamido)cyclopentyl)-4-oxo-4,5-dihydro-3H-1-thia-3,5,8-triazaacenaphthylene-2-carboxamide;

N-((1S,3R)-3-Hydroxycyclohexyl)-4-oxo-5-(4-phenoxyphenyl)-4,5-dihydro-3H-1-thia-3,5,8-triazaacenaphthylene-2-carboxamide;

N-((1S,3R)-3-(2-(Dimethylamino)acetamido)cyclopentyl)-5-(4-isopropoxy-2-methylphenyl)-4-oxo-4,5-dihydro-3H-1-thia-3,5,8-triazaacenaphthylene-2-carboxamide;

4-Oxo-5-(2-phenylpyridin-4-yl)-N-((1S,2R)-2-propionamidocyclopentyl)-4,5-dihydro-3H-1-thia-3,5,8-triazaacenaphthylene-2-carboxamide;

N-((1R,2S)-2-Aminocyclohexyl)-5-(4-isopropoxy-2-methylphenyl)-4-oxo-4,5-dihydro-3H-1-thia-3,5,8-triazaacenaphthylene-2-carboxamide;

5-(4-Isopropoxy-2-methylphenyl)-N-((1S,3R)-3-(2-(methylamino)acetamido)cyclopentyl)-4-oxo-4,5-dihydro-3H-1-thia-3,5,8-triazaacenaphthylene-2-carboxamide;

N-((1S,2R)-2-Acetamidocyclopentyl)-5-(*S)-(2-methyl-4-phenoxyphenyl)-4-oxo-4,5-dihydro-3H-1-thia-3,5,8-triazaacenaphthylene-2-carboxamide;

tert-Butyl ((1S,4S)-4-(4-oxo-5-(4-phenoxyphenyl)-4,5-dihydro-3H-1-thia-3,5,8-triazaacenaphthylene-2-carboxamido)cyclohexyl)carbamate;

N-((1S,3R)-3-Aminocyclopentyl)-4-oxo-5-(4-phenoxyphenyl)-4,5-dihydro-3H-1-thia-3,5,8-triazaacenaphthylene-2-carboxamide;

N-((1R,2S)-2-Acrylamidocyclopentyl)-5-(*R)-(4-isopropoxy-2-methylphenyl)-4-oxo-4,5-dihydro-3H-1-thia-3,5,8-triazaacenaphthylene-2-carboxamide;

N-((1R,2S)-2-Acrylamidocyclopentyl)-5-(*S)-(4-methyl-2-phenoxypyrimidin-5-yl)-4-oxo-4,5-dihydro-3H-1-thia-3,5,8-triazaacenaphthylene-2-carboxamide;

N-((1R,2S)-2-Acrylamidocyclopentyl)-4-oxo-5-(6-phenylpyrimidin-4-yl)-4,5-dihydro-3H-1-thia-3,5,8-triazaacenaphthylene-2-carboxamide;

N-((1R,2S)-2-Acrylamidocyclohexyl)-4-oxo-5-(2-phenylpyridin-4-yl)-4,5-dihydro-3H-1-thia-3,5,8-triazaacenaphthylene-2-carboxamide;

N-((1R,2S)-2-Acrylamidocyclopentyl)-4-oxo-5-(2-phenylpyridin-4-yl)-4,5-dihydro-3H-1-thia-3,5,8-triazaacenaphthylene-2-carboxamide;

N-((1R,2S)-2-Aminocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclohexyl)-4-oxo-5-(6-phenoxypyridin-3-yl)-4,5-dihydro-3H-1-thia-3,5,8-triazaacenaphthylene-2-carboxamide;

N-((1R,2S)-2-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;

N-((1R,3R)-3-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,3R)-3-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2R)-2-Acrylamidocyclopentyl)-4-oxo-5-(6-phenoxypyridin-3-yl)-4,5-dihydro-3H-1-thia-3,5,8-triazaacenaphthylene-2-carboxamide;

N-((1R,2S)-2-Acrylamidocyclopentyl)-4-oxo-5-(6-phenoxypyridin-3-yl)-4,5-dihydro-3H-1-thia-3,5,8-triazaacenaphthylene-2-carboxamide;

N-((1R,2S)-2-Acrylamidocyclopentyl)-4-oxo-5-(5-phenoxypyridin-2-yl)-4,5-dihydro-3H-1-thia-3,5,8-triazaacenaphthylene-2-carboxamide;

N-((1S,3R)-3-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,3R)-3-Aminocyclohexyl)-5-(2-methyl-4-phenoxyphenyl)-4-oxo-4,5-dihydro-3H-1-thia-3,5,8-triazaacenaphthylene-2-carboxamide;

N-((1R,3R)-3-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Acrylamidocyclohexyl)-5-(6-cyclobutoxy-4-methylpyridin-3-yl)-4-oxo-4,5-dihydro-3H-1-thia-3,5,8-triazaacenaphthylene-2-carboxamide;

N-((1R,3R)-3-Acrylamidocyclopentyl)-5-(2-methyl-4-phenoxyphenyl)-4-oxo-4,5-dihydro-3H-1-thia-3,5,8-triazaacenaphthylene-2-carboxamide;

N-((1R,2R)-2-Acrylamidocyclopentyl)-4-oxo-5-(5-phenoxypyridin-2-yl)-4,5-dihydro-3H-1-thia-3,5,8-triazaacenaphthylene-2-carboxamide;

N-((1S,3R)-3-Acrylamidocyclopentyl)-5-(*R)-(4-isopropoxy-2-methylphenyl)-4-oxo-4,5-dihydro-3H-1-thia-3,5,8-triazaacenaphthylene-2-carboxamide;

N-((1R,2S)-2-Acrylamidocyclohexyl)-5-(6-cyclobutoxy-2-methylpyridin-3-yl)-4-oxo-4,5-dihydro-3H-1-thia-3,5,8-triazaacenaphthylene-2-carboxamide;

N-((1R,3S)-3-Acrylamidocyclopentyl)-4-oxo-5-(6-phenoxypyridin-3-yl)-4,5-dihydro-3H-1-thia-3,5,8-triazaacenaphthylene-2-carboxamide;

N-((1R,2S)-2-Acrylamidocyclopentyl)-4-oxo-5-(4-phenylpyridin-2-yl)-4,5-dihydro-3H-1-thia-3,5,8-triazaacenaphthylene-2-carboxamide;

N-((1S,3R)-3-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;

N-((1S,3R)-3-Acrylamidocyclopentyl)-5-(3-chloro-4-phenoxyphenyl)-4-oxo-4,5-dihydro-3H-1-thia-3,5,8-triazaacenaphthylene-2-carboxamide;

N-((1R,2S)-2-Acrylamidocyclopentyl)-4-oxo-5-(5-phenylpyridin-3-yl)-4,5-dihydro-3H-1-thia-3,5,8-triazaacenaphthylene-2-carboxamide;

5-([1,1'-Biphenyl]-3-yl)-N-((1R,2S)-2-acrylamidocyclopentyl)-4-oxo-4,5-dihydro-3H-1-thia-3,5,8-triazaacenaphthylene-2-carboxamide;

N-((1R,2S)-2-Acrylamidocyclopentyl)-4-oxo-5-(3-(pyridin-2-yl)phenyl)-4,5-dihydro-3H-1-thia-3,5,8-triazaacenaphthylene-2-carboxamide;

N-((1R,3R)-3-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,3S)-3-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2R)-2-Acrylamidocyclopentyl)-4-oxo-5-(2-phenylpyridin-4-yl)-4,5-dihydro-3H-1-thia-3,5,8-triazaacenaphthylene-2-carboxamide;

N-((1S,3R)-3-Acrylamidocyclopentyl)-4-oxo-5-(2-phenylpyridin-4-yl)-4,5-dihydro-3H-1-thia-3,5,8-triazaacenaphthylene-2-carboxamide;

N-((1R,2S)-2-Acrylamidocyclopentyl)-5-(2-methyl-4-(pyridin-3-yloxy)phenyl)-4-oxo-4,5-dihydro-3H-1-thia-3,5,8-triazaacenaphthylene-2-carboxamide;

N-((1R,2R)-2-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclopentyl)-4-oxo-5-(5-phenoxypyrazin-2-yl)-4,5-dihydro-3H-1-thia-3,5,8-triazaacenaphthylene-2-carboxamide;

N-((1R,2S)-2-Acrylamidocyclopentyl)-4-oxo-5-(3-(pyridin-3-yl)phenyl)-4,5-dihydro-3H-1-thia-3,5,8-triazaacenaphthylene-2-carboxamide;

N-((1R,2S)-2-Acrylamidocyclopentyl)-4-oxo-5-(6-phenylpyridazin-4-yl)-4,5-dihydro-3H-1-thia-3,5,8-triazaacenaphthylene-2-carboxamide;

N-((1R,2S)-2-Acrylamidocyclohexyl)-5-(*S)-(6-cyclobutoxy-2-methylpyridin-3-yl)-4-oxo-4,5-dihydro-3H-1-thia-3,5,8-triazaacenaphthylene-2-carboxamide;

N-((1R,2S)-2-Acrylamidocyclopentyl)-5-(4-isopropoxyphenyl)-4-oxo-4,5-dihydro-3H-1-thia-3,5,8-triazaacenaphthylene-2-carboxamide;

N-((1R,2S)-2-Acrylamidocyclopentyl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(2-isopropylpyridin-4-yl)-4-oxo-4,5-dihydro-3H-1-thia-3,5,8-triazaacenaphthylene-2-carboxamide;

N-((1R,3S)-3-Acrylamidocyclopentyl)-4-oxo-5-(2-phenylpyridin-4-yl)-4,5-dihydro-3H-1-thia-3,5,8-triazaacenaphthylene-2-carboxamide;

N-((1R,2S)-2-Acrylamidocyclohexyl)-5-(*S)-(6-isopropoxy-2-methylpyridin-3-yl)-4-oxo-4,5-dihydro-3H-1-thia-3,5,8-triazaacenaphthylene-2-carboxamide;

N-((1R,2S)-2-(3-Chloropropanamido)cyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclohexyl)-5-(6-isopropoxy-2-methylpyridin-3-yl)-4-oxo-4,5-dihydro-3H-1-thia-3,5,8-triazaacenaphthylene-2-carboxamide;

N-((1R,3R)-3-Acrylamidocyclopentyl)-4-oxo-5-(2-phenylpyridin-4-yl)-4,5-dihydro-3H-1-thia-3,5,8-triazaacenaphthylene-2-carboxamide;

N-((1R,2R)-2-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1RS,3RS)-3-Acrylamidocyclopentyl)-4-oxo-5-(5-phenoxypyridin-2-yl)-4,5-dihydro-3H-1-thia-3,5,8-triazaacenaphthylene-2-carboxamide;

N-((1R,3R)-3-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;

N-((1RS,3RS)-3-Acrylamidocyclohexyl)-4-oxo-5-(5-phenoxypyridin-2-yl)-4,5-dihydro-3H-1-thia-3,5,8-triazaacenaphthylene-2-carboxamide;

N-((1R,3R)-3-(2-(Dimethylamino)acetamido)cyclopentyl)-5-(2-methyl-4-phenoxyphenyl)-4-oxo-4,5-dihydro-3H-1-thia-3,5,8-triazaacenaphthylene-2-carboxamide;

N-((1R,2R)-2-Acrylamidocyclohexyl)-4-oxo-5-(5-phenoxypyridin-2-yl)-4,5-dihydro-3H-1-thia-3,5,8-triazaacenaphthylene-2-carboxamide;

N-((1R,2R)-2-Acrylamidocyclopentyl)-5-(*S)-(4-methyl-2-phenoxypyrimidin-5-yl)-4-oxo-4,5-dihydro-3H-1-thia-3,5,8-triazaacenaphthylene-2-carboxamide;

N-((1R,2S)-2-Acrylamidocyclopentyl)-5-(2-methyl-4-(pyridin-2-yloxy)phenyl)-4-oxo-4,5-dihydro-3H-1-thia-3,5,8-triazaacenaphthylene-2-carboxamide;

N-((1R,2S)-2-Acrylamidocyclohexyl)-5-(*S)-(6-cyclobutoxy-4-methylpyridin-3-yl)-4-oxo-4,5-dihydro-3H-1-thia-3,5,8-triazaacenaphthylene-2-carboxamide;

N-((1R,2S)-2-Acrylamidocyclohexyl)-5-(6-isopropoxy-4-methylpyridin-3-yl)-4-oxo-4,5-dihydro-3H-1-thia-3,5,8-triazaacenaphthylene-2-carboxamide;

N-((1R,2S)-2-Acrylamidocyclohexyl)-5-(6-(cyclopentyloxy)-4-methylpyridin-3-yl)-4-oxo-4,5-dihydro-3H-1-thia-3,5,8-triazaacenaphthylene-2-carboxamide;

N-((1R,2S)-2-Acrylamidocyclopentyl)-5-(2-methyl-4-(pyrimidin-2-yloxy)phenyl)-4-oxo-4,5-dihydro-3H-1-thia-3,5,8-triazaacenaphthylene-2-carboxamide;

N-((1R,2S)-2-Acrylamidocyclohexyl)-5-(6-isobutoxy-4-methylpyridin-3-yl)-4-oxo-4,5-dihydro-3H-1-thia-3,5,8-triazaacenaphthylene-2-carboxamide;

N-((1S,3S)-3-Acrylamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2R)-2-Acrylamidocyclohexyl)-4-oxo-5-(2-phenylpyridin-4-yl)-4,5-dihydro-3H-1-thia-3,5,8-triazaacenaphthylene-2-carboxamide;

N-((1R,3R)-3-Acetamidocyclopentyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-((1R,3R)-3-(2-(methylamino)acetamido)cyclopentyl)-4-oxo-4,5-dihydro-3H-1-thia-3,5,8-triazaacenaphthylene-2-carboxamide;

N-((1S,3R)-3-Aminocyclohexyl)-5-(*S)-(2-methyl-4-phenoxyphenyl)-4-oxo-4,5-dihydro-3H-1-thia-3,5,8-triazaacenaphthylene-2-carboxamide;

N-((1S,3S)-3-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,3R)-3-Acrylamidocyclohexyl)-4-oxo-5-(2-phenylpyridin-4-yl)-4,5-dihydro-3H-1-thia-3,5,8-triazaacenaphthylene-2-carboxamide;

N-((1R,2R)-2-Aminocyclopentyl)-5-(4-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclopentyl)-4-oxo-5-(4-((tetrahydro-2H-pyran-4-yl)oxy)phenyl)-4,5-dihydro-3H-1-thia-3,5,8-triazaacenaphthylene-2-carboxamide;

N-((1R,3R)-3-(2-Aminoacetamido)cyclopentyl)-5-(2-methyl-4-phenoxyphenyl)-4-oxo-4,5-dihydro-3H-1-thia-3,5,8-triazaacenaphthylene-2-carboxamide;

N-((1R,3R)-3-Aminocyclopentyl)-5-(2-methyl-4-phenoxyphenyl)-4-oxo-4,5-dihydro-3H-1-thia-3,5,8-triazaacenaphthylene-2-carboxamide;

N-((1R,3S)-3-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Acrylamidocyclohexyl)-5-(*R)-(6-isopropoxy-2-methylpyridin-3-yl)-4-oxo-4,5-dihydro-3H-1-thia-3,5,8-triazaacenaphthylene-2-carboxamide;

N-((1R,2R)-2-Acrylamidocyclohexyl)-4-oxo-5-(6-phenoxypyridin-3-yl)-4,5-dihydro-3H-1-thia-3,5,8-triazaacenaphthylene-2-carboxamide;

N-((1R,3S)-3-Aminocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,3S)-3-Acetamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Acrylamidocyclohexyl)-5-(*R)-(6-cyclobutoxy-2-methylpyridin-3-yl)-4-oxo-4,5-dihydro-3H-1-thia-3,5,8-triazaacenaphthylene-2-carboxamide;

N-((1S,3S)-3-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,3S)-3-Acetamidocyclopentyl)-5-(*S)-(2-methyl-4-phenoxyphenyl)-4-oxo-4,5-dihydro-3H-1-thia-3,5,8-triazaacenaphthylene-2-carboxamide;

N-((1S,3S)-3-(2-(Dimethylamino)acetamido)cyclopentyl)-5-(2-methyl-4-phenoxyphenyl)-4-oxo-4,5-dihydro-3H-1-thia-3,5,8-triazaacenaphthylene-2-carboxamide;

5-(2-Methyl-4-phenoxyphenyl)-N-((1S,3S)-3-(2-(methylamino)acetamido)cyclopentyl)-4-oxo-4,5-dihydro-3H-1-thia-3,5,8-triazaacenaphthylene-2-carboxamide;

N-((1S,3S)-3-Aminocyclohexyl)-5-(*S)-(2-methyl-4-phenoxyphenyl)-4-oxo-4,5-dihydro-3H-1-thia-3,5,8-triazaacenaphthylene-2-carboxamide;

5-(3-Chloro-4-phenoxyphenyl)-N-((1S,3R)-3-((E)-4-(dimethylamino)but-2-enamido)cyclopentyl)-4-oxo-4,5-dihydro-3H-1-thia-3,5,8-triazaacenaphthylene-2-carboxamide;

5-([1,1'-Biphenyl]-3-yl)-N-((1R,2S)-2-aminocyclopentyl)-4-oxo-4,5-dihydro-3H-1-thia-3,5,8-triazaacenaphthylene-2-carboxamide;

5-(*S)-(2-Methyl-4-phenoxyphenyl)-N-((1R,3S)-3-(2-(methylamino)acetamido)cyclohexyl)-4-oxo-4,5-dihydro-3H-1-thia-3,5,8-triazaacenaphthylene-2-carboxamide;

N-((1R,3S)-3-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,3S)-3-(2-(Dimethylamino)acetamido)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,3S)-3-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Aminocyclopentyl)-5-(*S)-(4-methyl-2-phenoxypyrimidin-5-yl)-4-oxo-4,5-dihydro-3H-1-thia-3,5,8-triazaacenaphthylene-2-carboxamide;

N-((1R,2R)-2-Aminocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2R)-2-Aminocyclopentyl)-5-(*S)-(4-methyl-2-phenoxypyrimidin-5-yl)-4-oxo-4,5-dihydro-3H-1-thia-3,5,8-triazaacenaphthylene-2-carboxamide;

N-((1R,2S)-2-Aminocyclohexyl)-4-oxo-5-(6-phenoxypyridin-3-yl)-4,5-dihydro-3H-1-thia-3,5,8-triazaacenaphthylene-2-carboxamide;

N-((1S,2R)-2-Acetamidocyclopentyl)-4-oxo-5-(2-phenylpyridin-4-yl)-4,5-dihydro-3H-1-thia-3,5,8-triazaacenaphthylene-2-carboxamide;

N-((1S,3S)-3-Aminocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Aminocyclohexyl)-4-oxo-5-(2-phenylpyridin-4-yl)-4,5-dihydro-3H-1-thia-3,5,8-triazaacenaphthylene-2-carboxamide;

N-((1R,3S)-3-Aminocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Aminocyclopentyl)-5-(*R)-(4-isopropoxy-2-methylphenyl)-4-oxo-4,5-dihydro-3H-1-thia-3,5,8-triazaacenaphthylene-2-carboxamide;

N-((1R,2S)-2-Aminocyclopentyl)-4-oxo-5-(2-phenylpyridin-4-yl)-4,5-dihydro-3H-1-thia-3,5,8-triazaacenaphthylene-2-carboxamide;

N-((1R,2R)-2-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;

N-((1R,2S)-2-Aminocyclopentyl)-4-oxo-5-(6-phenoxypyridin-3-yl)-4,5-dihydro-3H-1-thia-3,5,8-triazaacenaphthylene-2-carboxamide;

N-((1R,2S)-2-Acrylamidocyclohexyl)-5-(*R)-(6-cyclobutoxy-4-methylpyridin-3-yl)-4-oxo-4,5-dihydro-3H-1-thia-3,5,8-triazaacenaphthylene-2-carboxamide;

N-((1R,2S)-2-Aminocyclopentyl)-4-oxo-5-(4-phenylpyridin-2-yl)-4,5-dihydro-3H-1-thia-3,5,8-triazaacenaphthylene-2-carboxamide;

N-((1R,2R)-2-Hydroxycyclopentyl)-4-oxo-5-(2-phenylpyridin-4-yl)-4,5-dihydro-3H-1-thia-3,5,8-triazaacenaphthylene-2-carboxamide;

N-((1R,2R)-2-Aminocyclopentyl)-4-oxo-5-(6-phenoxypyridin-3-yl)-4,5-dihydro-3H-1-thia-3,5,8-triazaacenaphthylene-2-carboxamide;

N-((1R,2S)-2-Aminocyclopentyl)-5-(2-isopropylpyridin-4-yl)-4-oxo-4,5-dihydro-3H-1-thia-3,5,8-triazaacenaphthylene-2-carboxamide;

N-((1R,2S)-2-Aminocyclopentyl)-5-(4-isopropoxyphenyl)-4-oxo-4,5-dihydro-3H-1-thia-3,5,8-triazaacenaphthylene-2-carboxamide;

N-((1S,2S)-2-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;

N-((1R,2R)-2-Acrylamidocyclohexyl)-5-(*S)-(4-isopropoxy-2-methylphenyl)-4-oxo-4,5-dihydro-3H-1-thia-3,5,8-triazaacenaphthylene-2-carboxamide;

N-((1S, S)-3-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;

N-((1R,3S)-3-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;

N-((1R,3S)-3-Acrylamidocyclopentyl)-5-(*R)-(4-isopropoxy-2-methylphenyl)-4-oxo-4,5-dihydro-3H-1-thia-3,5,8-triazaacenaphthylene-2-carboxamide;

N-((1R,2R)-2-Aminocyclohexyl)-4-oxo-5-(6-phenoxypyridin-3-yl)-4,5-dihydro-3H-1-thia-3,5,8-triazaacenaphthylene-2-carboxamide;

N-((1R,2S)-2-Aminocyclopentyl)-4-oxo-5-(6-phenylpyridazin-4-yl)-4,5-dihydro-3H-1-thia-3,5,8-triazaacenaphthylene-2-carboxamide;

N-((1S,3S)-3-Acrylamidocyclohexyl)-4-oxo-5-(2-phenylpyridin-4-yl)-4,5-dihydro-3H-1-thia-3,5,8-triazaacenaphthylene-2-carboxamide;

N-((1R,2S)-2-Acetamidocyclopentyl)-4-oxo-5-(2-phenylpyridin-4-yl)-4,5-dihydro-3H-1-thia-3,5,8-triazaacenaphthylene-2-carboxamide;

N-((1R,2S)-2-Aminocyclopentyl)-4-oxo-5-(6-phenylpyrimidin-4-yl)-4,5-dihydro-3H-1-thia-3,5,8-triazaacenaphthylene-2-carboxamide;

N-((1S,3S)-3-Acrylamidocyclopentyl)-4-oxo-5-(2-phenylpyridin-4-yl)-4,5-dihydro-3H-1-thia-3,5,8-triazaacenaphthylene-2-carboxamide;

N-((1R,3S)-3-Acrylamidocyclohexyl)-4-oxo-5-(2-phenylpyridin-4-yl)-4,5-dihydro-3H-1-thia-3,5,8-triazaacenaphthylene-2-carboxamide;

N-((1R,2S)-2-Aminocyclopentyl)-4-oxo-5-(5-phenylpyridin-3-yl)-4,5-dihydro-3H-1-thia-3,5,8-triazaacenaphthylene-2-carboxamide;

N-((1R,2S)-2-Aminocyclopentyl)-4-oxo-5-(3-(pyridin-2-yl)phenyl)-4,5-dihydro-3H-1-thia-3,5,8-triazaacenaphthylene-2-carboxamide;

N-((1S,2R)-2-(2-(Methylamino)acetamido)cyclopentyl)-4-oxo-5-(2-phenylpyridin-4-yl)-4,5-dihydro-3H-1-thia-3,5,8-triazaacenaphthylene-2-carboxamide;

N-((1R,2S)-2-Aminocyclopentyl)-5-(2-methyl-4-((tetrahydro-2H-pyran-4-yl)oxy)phenyl)-4-oxo-4,5-dihydro-3H-1-thia-3,5,8-triazaacenaphthylene-2-carboxamide;

N-((1R,2S)-2-Aminocyclopentyl)-4-oxo-5-(4-((tetrahydro-2H-pyran-4-yl)oxy)phenyl)-4,5-dihydro-3H-1-thia-3,5,8-triazaacenaphthylene-2-carboxamide;

racemic cisN-((1RS,3RS)-3-Aminocyclopentyl)-4-oxo-5-(6-phenoxypyridin-3-yl)-4,5-dihydro-3H-1-thia-3,5,8-triazaacenaphthylene-2-carboxamide;

racemic transN-((1RS,3RS)-3-Aminocyclopentyl)-4-oxo-5-(6-phenoxypyridin-3-yl)-4,5-dihydro-3H-1-thia-3,5,8-triazaacenaphthylene-2-carboxamide;

N-((1R,2S)-2-Acrylamidocyclohexyl)-4-oxo-5-(5-phenoxypyridin-2-yl)-4,5-dihydro-3H-1-thia-3,5,8-triazaacenaphthylene-2-carboxamide;

N-((1RS,2RS)-2-Acrylamidocyclopentyl)-5-(2-methyl-6-phenoxypyridin-3-yl)-4-oxo-4,5-dihydro-3H-1-thia-3,5,8-triazaacenaphthylene-2-carboxamide;

N-((1RS,3RS)-3-Aminocyclopentyl)-5-(4-methyl-6-phenoxypyridin-3-yl)-4-oxo-4,5-dihydro-3H-1-thia-3,5,8-triazaacenaphthylene-2-carboxamide;

N-((1RS,3RS)-3-Acrylamidocyclopentyl)-4-oxo-5-(6-phenoxypyridin-3-yl)-4,5-dihydro-3H-1-thia-3,5,8-triazaacenaphthylene-2-carboxamide;

N-((1R,2S)-2-Acrylamidocyclohexyl)-4-oxo-5-(5-phenoxypyrazin-2-yl)-4,5-dihydro-3H-1-thia-3,5,8-triazaacenaphthylene-2-carboxamide;

N-((1R,2S)-2-acrylamidocyclopentyl)-4-oxo-5-(5-phenoxypyrimidin-2-yl)-4,5-dihydro-3H-1-thia-3,5,8-triazaacenaphthylene-2-carboxamide;

N-((1R,2S)-2-Acrylamidocyclohexyl)-4-oxo-5-(5-phenoxypyrimidin-2-yl)-4,5-dihydro-3H-1-thia-3,5,8-triazaacenaphthylene-2-carboxamide;

N-((1R,2S)-2-Acrylamidocyclohexyl)-5-(*S)-(6-isopropoxy-4-methylpyridin-3-yl)-4-oxo-4,5-dihydro-3H-1-thia-3,5,8-triazaacenaphthylene-2-carboxamide;

N-((1R,2S)-2-Acrylamidocyclopentyl)-4-oxo-5-(*S)-(4-(pyridin-3-yloxy)phenyl)-4,5-dihydro-3H-1-thia-3,5,8-triazaacenaphthylene-2-carboxamide;

N-((1R,2R)-2-Acrylamidocyclopentyl)-5-(*S)-(2-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclohexyl)-4-oxo-5-(2-phenoxypyrimidin-5-yl)-4,5-dihydro-3H-1-thia-3,5,8-triazaacenaphthylene-2-carboxamide;

N-((1R,2S)-2-Acrylamidocyclohexyl)-5-(*S)-(2-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclopentyl)-5-(*S)-(2-methyl-4-((tetrahydro-2H-pyran-4-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(2-methyl-4-(pyridazin-3-yloxy)phenyl)-4-oxo-4,5-dihydro-3H-1-thia-3,5,8-triazaacenaphthylene-2-carboxamide;

N-((1*S,3*S)-3-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2R)-2-Acrylamidocyclopentyl)-4-oxo-5-(5-phenoxypyrimidin-2-yl)-4,5-dihydro-3H-1-thia-3,5,8-triazaacenaphthylene-2-carboxamide;

N-((1*S,3*S)-3-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclohexyl)-5-(*S)-(6-(cyclopentyloxy)-4-methylpyridin-3-yl)-4-oxo-4,5-dihydro-3H-1-thia-3,5,8-triazaacenaphthylene-2-carboxamide;

N-((1R,2S)-2-Acrylamidocyclopentyl)-4-oxo-5-(2-phenoxypyrimidin-5-yl)-4,5-dihydro-3H-1-thia-3,5,8-triazaacenaphthylene-2-carboxamide;

N-((1R,2R)-2-Acrylamidocyclopentyl)-4-oxo-5-(5-phenoxypyrazin-2-yl)-4,5-dihydro-3H-1-thia-3,5,8-triazaacenaphthylene-2-carboxamide;
N-((1R,2S)-2-Acrylamidocyclohexyl)-5-(*S)-(6-isobutoxy-4-methylpyridin-3-yl)-4-oxo-4,5-dihydro-3H-1-thia-3,5,8-triazaacenaphthylene-2-carboxamide;
N-((1S,3R)-3-Acrylamidocyclopentyl)-4-oxo-5-(5-phenoxypyridin-2-yl)-4,5-dihydro-3H-1-thia-3,5,8-triazaacenaphthylene-2-carboxamide;
N-((1R,2R)-2-Acrylamidocyclopentyl)-4-oxo-5-(2-phenoxypyrimidin-5-yl)-4,5-dihydro-3H-1-thia-3,5,8-triazaacenaphthylene-2-carboxamide;
N-((1*S,3*S)-3-Acrylamidocyclohexyl)-4-oxo-5-(5-phenoxypyridin-2-yl)-4,5-dihydro-3H-1-thia-3,5,8-triazaacenaphthylene-2-carboxamide;
N-((1R,2R)-2-Acrylamidocyclopentyl)-5-(*S)-(4-isopropoxy-2-methylphenyl)-4-oxo-4,5-dihydro-3H-1-thia-3,5,8-triazaacenaphthylene-2-carboxamide;
5-([2,3'-Bipyridin]-4-yl)-N-((1R,2S)-2-acrylamidocyclopentyl)-4-oxo-4,5-dihydro-3H-1-thia-3,5,8-triazaacenaphthylene-2-carboxamide;
N-((1*R,2*S)-2-Aminocyclopentyl)-5-(*S)-(2-methyl-6-phenoxypyridin-3-yl)-4-oxo-4,5-dihydro-3H-1-thia-3,5,8-triazaacenaphthylene-2-carboxamide;
N-((1S,3R)-3-Acrylamidocyclopentyl)-4-oxo-5-(2-phenoxypyrimidin-5-yl)-4,5-dihydro-3H-1-thia-3,5,8-triazaacenaphthylene-2-carboxamide;
N-((1R,2S)-2-Acrylamidocyclopentyl)-4-oxo-5-(5-phenylpyridazin-3-yl)-4,5-dihydro-3H-1-thia-3,5,8-triazaacenaphthylene-2-carboxamide;
N-((1*S,3*S)-3-Acrylamidocyclopentyl)-4-oxo-5-(6-phenoxypyridin-3-yl)-4,5-dihydro-3H-1-thia-3,5,8-triazaacenaphthylene-2-carboxamide;
N-((1R,2R)-2-Acrylamidocyclohexyl)-5-(*S)-(2-methyl-6-phenoxypyridin-3-yl)-4-oxo-4,5-dihydro-3H-1-thia-3,5,8-triazaacenaphthylene-2-carboxamide;
N-((1S,3S)-3-Acrylamidocyclohexyl)-4-oxo-5-(6-phenoxypyridin-3-yl)-4,5-dihydro-3H-1-thia-3,5,8-triazaacenaphthylene-2-carboxamide;
N-((1R,2R)-2-Acrylamidocyclopentyl)-4-oxo-5-(3-(pyridin-3-yl)phenyl)-4,5-dihydro-3H-1-thia-3,5,8-triazaacenaphthylene-2-carboxamide;
5-([2,2'-Bipyridin]-4-yl)-N-((1R,2S)-2-acrylamidocyclopentyl)-4-oxo-4,5-dihydro-3H-1-thia-3,5,8-triazaacenaphthylene-2-carboxamide;
5-([2,3'-Bipyridin]-4-yl)-N-((1R,2R)-2-acrylamidocyclopentyl)-4-oxo-4,5-dihydro-3H-1-thia-3,5,8-triazaacenaphthylene-2-carboxamide;
N-((1R,2R)-2-Acrylamidocyclopentyl)-4-oxo-5-(3-(pyridin-2-yl)phenyl)-4,5-dihydro-3H-1-thia-3,5,8-triazaacenaphthylene-2-carboxamide;
N-((1*R,3*S)-3-Acrylamidocyclopentyl)-4-oxo-5-(5-phenoxypyridin-2-yl)-4,5-dihydro-3H-1-thia-3,5,8-triazaacenaphthylene-2-carboxamide;
N-((1*R,3*R)-3-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;
N-((1R,2S)-2-Acrylamidocyclopentyl)-5-(6-(isopropylamino)-4-methylpyridin-3-yl)-4-oxo-4,5-dihydro-3H-1-thia-3,5,8-triazaacenaphthylene-2-carboxamide;
N-((1*R,3*R)-3-Acrylamidocyclohexyl)-4-oxo-5-(6-phenoxypyridin-3-yl)-4,5-dihydro-3H-1-thia-3,5,8-triazaacenaphthylene-2-carboxamide;
N-((1*R,3*R)-3-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;
N-((1R,2S)-2-Aminocyclohexyl)-5-(*S)-(2-methyl-6-phenoxypyridin-3-yl)-4-oxo-4,5-dihydro-3H-1-thia-3,5,8-triazaacenaphthylene-2-carboxamide;
N-((1*R,3*R)-3-Acrylamidocyclopentyl)-4-oxo-5-(6-phenoxypyridin-3-yl)-4,5-dihydro-3H-1-thia-3,5,8-triazaacenaphthylene-2-carboxamide;
N-((1R,2S)-2-Aminocyclohexyl)-5-(*S)-(6-isobutyl-4-methylpyridin-3-yl)-4-oxo-4,5-dihydro-3H-1-thia-3,5,8-triazaacenaphthylene-2-carboxamide;
N-((1R,2R)-2-Aminocyclopentyl)-5-(2-isopropylpyridin-4-yl)-4-oxo-4,5-dihydro-3H-1-thia-3,5,8-triazaacenaphthylene-2-carboxamide;
N-((1R,2R)-2-Acrylamidocyclopentyl)-5-(2-isopropylpyridin-4-yl)-4-oxo-4,5-dihydro-3H-1-thia-3,5,8-triazaacenaphthylene-2-carboxamide;
N-((1R,2R)-2-Acrylamidocyclohexyl)-4-oxo-5-(2-phenoxypyrimidin-5-yl)-4,5-dihydro-3H-1-thia-3,5,8-triazaacenaphthylene-2-carboxamide;
N-((1R,2R)-2-Aminocyclopentyl)-5-(*S)-(2-methyl-6-phenoxypyridin-3-yl)-4-oxo-4,5-dihydro-3H-1-thia-3,5,8-triazaacenaphthylene-2-carboxamide;
N-((1R,2S)-2-Acetamidocyclohexyl)-5-(*S)-(2-methyl-6-phenoxypyridin-3-yl)-4-oxo-4,5-dihydro-3H-1-thia-3,5,8-triazaacenaphthylene-2-carboxamide;
N-((1R,2S)-2-Acrylamidocyclohexyl)-5-(*R)-(6-(cyclopentyloxy)-4-methylpyridin-3-yl)-4-oxo-4,5-dihydro-3H-1-thia-3,5,8-triazaacenaphthylene-2-carboxamide;
5-([2,2'-Bipyridin]-4-yl)-N-((1R,2R)-2-acrylamidocyclopentyl)-4-oxo-4,5-dihydro-3H-1-thia-3,5,8-triazaacenaphthylene-2-carboxamide;
5-(*S)-(2-Methyl-6-phenoxypyridin-3-yl)-4-oxo-N-((1R,2S)-2-propionamidocyclohexyl)-4,5-dihydro-3H-1-thia-3,5,8-triazaacenaphthylene-2-carboxamide;
N-((1*R,3*R)-3-Acrylamidocyclohexyl)-4-oxo-5-(5-phenoxypyridin-2-yl)-4,5-dihydro-3H-1-thia-3,5,8-triazaacenaphthylene-2-carboxamide;
N-((1R,2S)-2-Acetamidocyclopentyl)-5-(*S)-(2-methyl-6-phenoxypyridin-3-yl)-4-oxo-4,5-dihydro-3H-1-thia-3,5,8-triazaacenaphthylene-2-carboxamide;
5-(*S)-(2-Methyl-6-phenoxypyridin-3-yl)-4-oxo-N-((1R,2S)-2-propionamidocyclopentyl)-4,5-dihydro-3H-1-thia-3,5,8-triazaacenaphthylene-2-carboxamide;
N-((1R,2S)-2-Acrylamidocyclopentyl)-5-(*R)-(2-methyl-4-((tetrahydro-2H-pyran-4-yl)oxy)phenyl)-4-oxo-4,5-dihydro-3H-1-thia-3,5,8-triazaacenaphthylene-2-carboxamide;
N-((1R,2S)-2-Acrylamidocyclohexyl)-5-(*R)-(6-isopropoxy-4-methylpyridin-3-yl)-4-oxo-4,5-dihydro-3H-1-thia-3,5,8-triazaacenaphthylene-2-carboxamide;
N-((1R,2S)-2-Aminocyclopentyl)-4-oxo-5-(5-phenylpyridazin-3-yl)-4,5-dihydro-3H-1-thia-3,5,8-triazaacenaphthylene-2-carboxamide;
N-((1R,2R)-2-Aminocyclohexyl)-5-(*S)-(2-methyl-6-phenoxypyridin-3-yl)-4-oxo-4,5-dihydro-3H-1-thia-3,5,8-triazaacenaphthylene-2-carboxamide;
N-((1S,3R)-3-Acrylamidocyclohexyl)-4-oxo-5-(2-phenylpyridin-4-yl)-4,5-dihydro-3H-1-thia-3,5,8-triazaacenaphthylene-2-carboxamide;
N-((1R,2S)-2-Acrylamidocyclohexyl)-5-(*R)-(6-isobutoxy-4-methylpyridin-3-yl)-4-oxo-4,5-dihydro-3H-1-thia-3,5,8-triazaacenaphthylene-2-carboxamide;
5-(*S)-(2-Methyl-6-phenoxypyridin-3-yl)-4-oxo-N-((1R,2R)-2-propionamidocyclopentyl)-4,5-dihydro-3H-1-thia-3,5,8-triazaacenaphthylene-2-carboxamide;
N-((1R,2S)-2-Aminocyclopentyl)-5-(*S)-(6-isobutyl-4-methylpyridin-3-yl)-4-oxo-4,5-dihydro-3H-1-thia-3,5,8-triazaacenaphthylene-2-carboxamide;

N-((1R,3S)-3-Aminocyclopentyl)-5-(*S)-(4-methyl-6-phenoxypyridin-3-yl)-4-oxo-4,5-dihydro-3H-1-thia-3,5,8-triazaacenaphthylene-2-carboxamide;
N-((1R,3S)-3-Aminocyclohexyl)-5-(*S)-(4-methyl-6-phenoxypyridin-3-yl)-4-oxo-4,5-dihydro-3H-1-thia-3,5,8-triazaacenaphthylene-2-carboxamide;
N-((1R,2S)-2-Acrylamidocyclohexyl)-5-(*S)-(6-isobutyl-4-methylpyridin-3-yl)-4-oxo-4,5-dihydro-3H-1-thia-3,5,8-triazaacenaphthylene-2-carboxamide;
N-((1R,2R)-2-Acetamidocyclopentyl)-5-(*S)-(2-methyl-6-phenoxypyridin-3-yl)-4-oxo-4,5-dihydro-3H-1-thia-3,5,8-triazaacenaphthylene-2-carboxamide;
N-((1R,3S)-3-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;
N-((1R,3S)-3-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;
5-(*S)-(4-Methyl-6-phenoxypyridin-3-yl)-4-oxo-N-((1R,3S)-3-propionamidocyclopentyl)-4,5-dihydro-3H-1-thia-3,5,8-triazaacenaphthylene-2-carboxamide;
N-((1R,2R)-2-Acetamidocyclohexyl)-5-(*S)-(2-methyl-6-phenoxypyridin-3-yl)-4-oxo-4,5-dihydro-3H-1-thia-3,5,8-triazaacenaphthylene-2-carboxamide;
N-((1R,3S)-3-Acrylamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;
5-(*S)-(2-Methyl-6-phenoxypyridin-3-yl)-4-oxo-N-((1R,2R)-2-propionamidocyclohexyl)-4,5-dihydro-3H-1-thia-3,5,8-triazaacenaphthylene-2-carboxamide;
N-((1R,3S)-3-Acrylamidocyclopentyl)-5-(6-isobutoxy-4-methylpyridin-3-yl)-4-oxo-4,5-dihydro-3H-1-thia-3,5,8-triazaacenaphthylene-2-carboxamide;
N-((1R,3S)-3-Acrylamidocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide;
N-((1R,2S)-2-Acrylamidocyclopentyl)-5-(2-methyl-4-((2-methylpyridin-3-yl)oxy)phenyl)-4-oxo-4,5-dihydro-3H-1-thia-3,5,8-triazaacenaphthylene-2-carboxamide;
N-((1R,2S)-2-Acrylamidocyclopentyl)-5-(2-methyl-4-((6-methylpyridin-2-yl)oxy)phenyl)-4-oxo-4,5-dihydro-3H-1-thia-3,5,8-triazaacenaphthylene-2-carboxamide;
N-((1R,2S)-2-Acrylamidocyclopentyl)-5-(4-((6-methylpyridin-2-yl)oxy)phenyl)-4-oxo-4,5-dihydro-3H-1-thia-3,5,8-triazaacenaphthylene-2-carboxamide;
N-((1R,2S)-2-Acrylamidocyclopentyl)-5-(4-((6-methylpyridin-3-yl)oxy)phenyl)-4-oxo-4,5-dihydro-3H-1-thia-3,5,8-triazaacenaphthylene-2-carboxamide;
N-((1R,2S)-2-Acrylamidocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide;
N-((1R,2S)-2-Acrylamidocyclopentyl)-5-(4-((2-methylpyridin-3-yl)oxy)phenyl)-4-oxo-4,5-dihydro-3H-1-thia-3,5,8-triazaacenaphthylene-2-carboxamide;
N-((1R,2S)-2-Acrylamidocyclopentyl)-5-(*S)-(6-isobutoxy-4-methylpyridin-3-yl)-4-oxo-4,5-dihydro-3H-1-thia-3,5,8-triazaacenaphthylene-2-carboxamide;
N-((1R,2S)-2-Aminocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide;
N-((1R,2S)-2-Aminocyclohexyl)-5-(*S)-(4-methyl-6-phenoxypyridin-3-yl)-4-oxo-4,5-dihydro-3H-1-thia-3,5,8-triazaacenaphthylene-2-carboxamide;
N-((1R,2S)-2-Acrylamidocyclopentyl)-5-(2-cyclobutylpyridin-4-yl)-4-oxo-4,5-dihydro-3H-1-thia-3,5,8-triazaacenaphthylene-2-carboxamide;
N-((1R,2S)-2-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;
N-((1R,2S)-2-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;
N-((1R,2R)-2-Acrylamidocyclopentyl)-5-(2-cyclobutylpyridin-4-yl)-4-oxo-4,5-dihydro-3H-1-thia-3,5,8-triazaacenaphthylene-2-carboxamide;
5-(*S)-(2-Methyl-4-phenoxyphenyl)-4-oxo-N-((1R,2S)-2-propionamidocyclohexyl)-4,5-dihydro-3H-1-thia-3,5,8-triazaacenaphthylene-2-carboxamide;
5-(*S)-(4-Methyl-6-phenoxypyridin-3-yl)-4-oxo-N-((1R,2S)-2-propionamidocyclohexyl)-4,5-dihydro-3H-1-thia-3,5,8-triazaacenaphthylene-2-carboxamide;
N-((1R,2R)-2-Acrylamidocyclopentyl)-5-(*S)-(6-isobutyl-4-methylpyridin-3-yl)-4-oxo-4,5-dihydro-3H-1-thia-3,5,8-triazaacenaphthylene-2-carboxamide;
N-((1R,2S)-2-Acrylamidocyclopentyl)-5-(2-methyl-4-(((S)-tetrahydrofuran-3-yl)oxy)phenyl)-4-oxo-4,5-dihydro-3H-1-thia-3,5,8-triazaacenaphthylene-2-carboxamide;
N-((1R,2S)-2-Acrylamidocyclopentyl)-5-(2-methyl-4-((6-methylpyridin-3-yl)oxy)phenyl)-4-oxo-4,5-dihydro-3H-1-thia-3,5,8-triazaacenaphthylene-2-carboxamide;
5-(*S)-(4-Methyl-6-phenoxypyridin-3-yl)-4-oxo-N-((1R,3S)-3-propionamidocyclohexyl)-4,5-dihydro-3H-1-thia-3,5,8-triazaacenaphthylene-2-carboxamide;
N-((1R,2S)-2-Acrylamidocyclopentyl)-5-(2-methyl-4-(((R)-tetrahydrofuran-3-yl)oxy)phenyl)-4-oxo-4,5-dihydro-3H-1-thia-3,5,8-triazaacenaphthylene-2-carboxamide;
N-((1R,2S)-2-Acrylamidocyclopentyl)-4-oxo-5-(4-(pyridazin-3-yloxy)phenyl)-4,5-dihydro-3H-1-thia-3,5,8-triazaacenaphthylene-2-carboxamide;
5-(*S)-(4-Methyl-6-phenoxypyridin-3-yl)-4-oxo-N-((1R,3R)-3-propionamidocyclopentyl)-4,5-dihydro-3H-1-thia-3,5,8-triazaacenaphthylene-2-carboxamide;
N-((1S,4S)-4-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;
5-(*S)-(4-Methyl-6-phenoxypyridin-3-yl)-4-oxo-N-((1S,3R)-3-propionamidocyclopentyl)-4,5-dihydro-3H-1-thia-3,5,8-triazaacenaphthylene-2-carboxamide;
N-((1S,3R)-3-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;
N-((1R,3R)-3-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;
N-((1R,2R)-2-Hydroxycyclopentyl)-4-oxo-5-(4-phenoxyphenyl)-4,5-dihydro-3H-1-thia-3,5,8-triazaacenaphthylene-2-carboxamide;
N-((1R,3S)-3-Aminocyclopentyl)-5-(*S)-(6-(cyclopentyloxy)-4-methylpyridin-3-yl)-4-oxo-4,5-dihydro-3H-1-thia-3,5,8-triazaacenaphthylene-2-carboxamide;
N-((1S,3S)-3-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;
N-((1R,2S)-2-Acetamidocyclopentyl)-4-oxo-5-(4-phenoxyphenyl)-4,5-dihydro-3H-1-thia-3,5,8-triazaacenaphthylene-2-carboxamide;
N-((1R,2S)-2-Aminocyclopentyl)-5-(*S)-(6-isobutoxy-4-methylpyridin-3-yl)-4-oxo-4,5-dihydro-3H-1-thia-3,5,8-triazaacenaphthylene-2-carboxamide;
4-Oxo-5-(4-phenoxyphenyl)-N-((1R,2S)-2-propionamidocyclopentyl)-4,5-dihydro-3H-1-thia-3,5,8-triazaacenaphthylene-2-carboxamide;

5-(*S)-(4-Methyl-6-phenoxypyridin-3-yl)-4-oxo-N-((1S,3S)-3-propionamidocyclopentyl)-4,5-dihydro-3H-1-thia-3,5,8-triazaacenaphthylene-2-carboxamide;

N-((1S,3S)-3-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclohexyl)-5-(2-methyl-4-(pyridin-2-yloxy)phenyl)-4-oxo-4,5-dihydro-3H-1-thia-3,5,8-triazaacenaphthylene-2-carboxamide;

5-(*S)-(4-Methyl-6-phenoxypyridin-3-yl)-4-oxo-N-((1S,3S)-3-propionamidocyclohexyl)-4,5-dihydro-3H-1-thia-3,5,8-triazaacenaphthylene-2-carboxamide;

N-((1R,3S)-3-Acetamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2R)-2-Acrylamidocyclohexyl)-5-(*S)-(6-isobutyl-4-methylpyridin-3-yl)-4-oxo-4,5-dihydro-3H-1-thia-3,5,8-triazaacenaphthylene-2-carboxamide;

N-((1R,3S)-3-Aminocyclopentyl)-5-(*S)-(6-isobutoxy-4-methylpyridin-3-yl)-4-oxo-4,5-dihydro-3H-1-thia-3,5,8-triazaacenaphthylene-2-carboxamide;

N-((1R,2S)-2-Acrylamidocyclohexyl)-5-(2-methyl-4-(pyridazin-3-yloxy)phenyl)-4-oxo-4,5-dihydro-3H-1-thia-3,5,8-triazaacenaphthylene-2-carboxamide;

N-((1S,3R)-3-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

N-((1R,2S)-2-Acrylamidocyclohexyl)-4-oxo-5-(4-(pyridazin-3-yloxy)phenyl)-4,5-dihydro-3H-1-thia-3,5,8-triazaacenaphthylene-2-carboxamide;

5-(*S)-(2-Methyl-6-phenoxypyridin-3-yl)-4-oxo-N-((1S,3S)-3-propionamidocyclopentyl)-4,5-dihydro-3H-1-thia-3,5,8-triazaacenaphthylene-2-carboxamide;

N-((1S,3S)-3-Acetamidocyclopentyl)-5-(*S)-(2-methyl-6-phenoxypyridin-3-yl)-4-oxo-4,5-dihydro-3H-1-thia-3,5,8-triazaacenaphthylene-2-carboxamide;

N-((1S,3R)-3-Acrylamidocyclohexyl)-5-(*S)-(2-methyl-6-phenoxypyridin-3-yl)-4-oxo-4,5-dihydro-3H-1-thia-3,5,8-triazaacenaphthylene-2-carboxamide;

5-(*S)-(2-Methyl-6-phenoxypyridin-3-yl)-4-oxo-N-((1S,3R)-3-propionamidocyclohexyl)-4,5-dihydro-3H-1-thia-3,5,8-triazaacenaphthylene-2-carboxamide;

N-((1S,3R)-3-Acetamidocyclohexyl)-5-(*S)-(2-methyl-6-phenoxypyridin-3-yl)-4-oxo-4,5-dihydro-3H-1-thia-3,5,8-triazaacenaphthylene-2-carboxamide;

N-((1S,3R)-3-Aminocyclohexyl)-5-(*S)-(2-methyl-6-phenoxypyridin-3-yl)-4-oxo-4,5-dihydro-3H-1-thia-3,5,8-triazaacenaphthylene-2-carboxamide;

N-((1S,3S)-3-Aminocyclopentyl)-5-(*S)-(2-methyl-6-phenoxypyridin-3-yl)-4-oxo-4,5-dihydro-3H-1-thia-3,5,8-triazaacenaphthylene-2-carboxamide;

5-(*S)-(4-Methyl-6-phenoxypyridin-3-yl)-4-oxo-N-((1S,3R)-3-propionamidocyclohexyl)-4,5-dihydro-3H-1-thia-3,5,8-triazaacenaphthylene-2-carboxamide;

(S)-5-(2-Methyl-4-phenoxyphenyl)-2-(3-(methylamino)pyrrolidine-1-carbonyl)-3H-1-thia-3,5,8-triazaacenaphthylen-4(5H)-one;

(S)—N-(1-(5-(2-Methyl-4-phenoxyphenyl)-4-oxo-4,5-dihydro-3H-1-thia-3,5,8-triazaacenaphthylene-2-carbonyl)pyrrolidin-3-yl)propionamide;

(S)—N-(1-(5-(2-Methyl-4-phenoxyphenyl)-4-oxo-4,5-dihydro-3H-1-thia-3,5,8-triazaacenaphthylene-2-carbonyl)pyrrolidin-3-yl)acetamide;

(S)-2-(3-Aminopyrrolidine-1-carbonyl)-5-(2-methyl-4-phenoxyphenyl)-3H-1-thia-3,5,8-triazaacenaphthylen-4(5H)-one;

(S)-2-(3-(Dimethylamino)pyrrolidine-1-carbonyl)-5-(2-methyl-4-phenoxyphenyl)-3H-1-thia-3,5,8-triazaacenaphthylen-4(5H)-one;

N-((1R,3R)-3-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

5-(*S)-(4-Methyl-6-phenoxypyridin-3-yl)-4-oxo-N-((1R,3R)-3-propionamidocyclohexyl)-4,5-dihydro-3H-1-thia-3,5,8-triazaacenaphthylene-2-carboxamide;

N-((1R,2S)-2-Acrylamidocyclopentyl)-5-(*S)-(2-methyl-4-(pyridazin-3-yloxy)phenyl)-4-oxo-4,5-dihydro-3H-1-thia-3,5,8-triazaacenaphthylene-2-carboxamide;

N-((1R,2S)-2-Acrylamidocyclopentyl)-5-(*R)-(2-methyl-4-(pyridazin-3-yloxy)phenyl)-4-oxo-4,5-dihydro-3H-1-thia-3,5,8-triazaacenaphthylene-2-carboxamide;

N-((1R,2S)-2-Acrylamidocyclopentyl)-5-(*S)-(6-isopropoxy-4-methylpyridin-3-yl)-4-oxo-4,5-dihydro-3H-1-thia-3,5,8-triazaacenaphthylene-2-carboxamide;

N-((1R,3S)-3-Acrylamidocyclopentyl)-5-(*S)-(6-isopropoxy-4-methylpyridin-3-yl)-4-oxo-4,5-dihydro-3H-1-thia-3,5,8-triazaacenaphthylene-2-carboxamide;

N-((1R,2S)-2-Aminocyclopentyl)-5-(*S)-(6-isopropoxy-4-methylpyridin-3-yl)-4-oxo-4,5-dihydro-3H-1-thia-3,5,8-triazaacenaphthylene-2-carboxamide;

N-((1R,3S)-3-Aminocyclopentyl)-5-(*S)-(6-isopropoxy-4-methylpyridin-3-yl)-4-oxo-4,5-dihydro-3H-1-thia-3,5,8-triazaacenaphthylene-2-carboxamide;

N-((1S,3R)-3-Acrylamidocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1S,3R)-3-Aminocyclopentyl)-5-(*S)-(4-methyl-6-phenoxypyridin-3-yl)-4-oxo-4,5-dihydro-3H-1-thia-3,5,8-triazaacenaphthylene-2-carboxamide;

N-((1r,4r)-4-Acetamidocyclohexyl)-5-(*S)-(4-methyl-6-phenoxypyridin-3-yl)-4-oxo-4,5-dihydro-3H-1-thia-3,5,8-triazaacenaphthylene-2-carboxamide;

(S)—N-(1-(5-(2-Methyl-4-phenoxyphenyl)-4-oxo-4,5-dihydro-3H-1-thia-3,5,8-triazaacenaphthylene-2-carbonyl)pyrrolidin-3-yl)acrylamide;

(R)—N-(1-(5-(2-Methyl-4-phenoxyphenyl)-4-oxo-4,5-dihydro-3H-1-thia-3,5,8-triazaacenaphthylene-2-carbonyl)pyrrolidin-3-yl)acrylamide;

(S,E)-2-Cyano-3-cyclopropyl-N-(1-(5-(2-methyl-4-phenoxyphenyl)-4-oxo-4,5-dihydro-3H-1-thia-3,5,8-triazaacenaphthylene-2-carbonyl)pyrrolidin-3-yl)acrylamide;

(R,E)-2-Cyano-3-cyclopropyl-N-(1-(5-(2-methyl-4-phenoxyphenyl)-4-oxo-4,5-dihydro-3H-1-thia-3,5,8-triazaacenaphthylene-2-carbonyl)pyrrolidin-3-yl)acrylamide;

N-((1R,2S)-2-Acrylamidocyclopentyl)-4-oxo-5-(4-(pyridin-2-yloxy)phenyl)-4,5-dihydro-3H-1-thia-3,5,8-triazaacenaphthylene-2-carboxamide;

N-((1R,2S)-2-Acrylamidocyclopentyl)-5-(3-isopropylphenyl)-4-oxo-4,5-dihydro-3H-1-thia-3,5,8-triazaacenaphthylene-2-carboxamide;

N-((1R,2R)-2-Acrylamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2R)-2-Aminocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2R)-2-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Acrylamidocyclohexyl)-4-oxo-5-(4-(pyridin-2-yloxy)phenyl)-4,5-dihydro-3H-1-thia-3,5,8-triazaacenaphthylene-2-carboxamide;

5-(*S)-(2-Methyl-4-phenoxyphenyl)-N-((1S,2R)-2-(2-(methylamino)acetamido)cyclohexyl)-4-oxo-4,5-dihydro-3H-1-thia-3,5,8-triazaacenaphthylene-2-carboxamide;

N-((1S,2R)-2-(2-Aminoacetamido)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2R)-2-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1S,2R)-2-Acetamidocyclohexyl)-5-(*S)-(2-methyl-4-phenoxyphenyl)-4-oxo-4,5-dihydro-3H-1-thia-3,5,8-triazaacenaphthylene-2-carboxamide;

N-((1R,2R)-2-(2-(Dimethylamino)acetamido)cyclohexyl)-5-(*S)-(2-methyl-4-phenoxyphenyl)-4-oxo-4,5-dihydro-3H-1-thia-3,5,8-triazaacenaphthylene-2-carboxamide;

5-(*S)-(2-Methyl-4-phenoxyphenyl)-N-((1R,2R)-2-(2-(methylamino)acetamido)cyclohexyl)-4-oxo-4,5-dihydro-3H-1-thia-3,5,8-triazaacenaphthylene-2-carboxamide;

N-((1S,2R)-2-(2-(Dimethylamino)acetamido)cyclohexyl)-5-(*S)-(2-methyl-4-phenoxyphenyl)-4-oxo-4,5-dihydro-3H-1-thia-3,5,8-triazaacenaphthylene-2-carboxamide;

N-((1S,2R)-2-Aminocyclohexyl)-5-(*S)-(2-methyl-4-phenoxyphenyl)-4-oxo-4,5-dihydro-3H-1-thia-3,5,8-triazaacenaphthylene-2-carboxamide;

N-((1S,2R)-2-Acrylamidocyclohexyl)-5-(2-methyl-4-phenoxyphenyl)-4-oxo-4,5-dihydro-3H-1-thia-3,5,8-triazaacenaphthylene-2-carboxamide;

N-((1S,2R)-2-Aminocyclopentyl)-5-(*S)-(2-methyl-4-phenoxyphenyl)-4-oxo-4,5-dihydro-3H-1-thia-3,5,8-triazaacenaphthylene-2-carboxamide;

N-((1R,2S)-2-Aminocyclopentyl)-5-(4-isopropoxy-2-methylphenyl)-4-oxo-4,5-dihydro-3H-1-thia-3,5,8-triazaacenaphthylene-2-carboxamide;

N-((1S,3R)-3-Acetamidocyclopentyl)-5-(4-isopropoxy-2-methylphenyl)-4-oxo-4,5-dihydro-3H-1-thia-3,5,8-triazaacenaphthylene-2-carboxamide;

N-((1R,2S)-2-Aminocyclopentyl)-5-(3-isopropylphenyl)-4-oxo-4,5-dihydro-3H-1-thia-3,5,8-triazaacenaphthylene-2-carboxamide;

N-((1R,2R)-2-Hydroxycyclopentyl)-5-(4-isopropoxy-2-methylphenyl)-4-oxo-4,5-dihydro-3H-1-thia-3,5,8-triazaacenaphthylene-2-carboxamide;

N-((1S,2R)-2-Aminocyclohexyl)-4-oxo-5-(4-phenoxyphenyl)-4,5-dihydro-3H-1-thia-3,5,8-triazaacenaphthylene-2-carboxamide;

N-((1S,2S)-2-Acrylamidocyclopentyl)-5-(2-methyl-4-phenoxyphenyl)-4-oxo-4,5-dihydro-3H-1-thia-3,5,8-triazaacenaphthylene-2-carboxamide;

N-((1S,2R)-2-Acrylamidocyclopentyl)-5-(2-methyl-4-phenoxyphenyl)-4-oxo-4,5-dihydro-3H-1-thia-3,5,8-triazaacenaphthylene-2-carboxamide;

5-(4-(3-((2-Cyanophenoxy)methyl)phenoxy)-2-methylphenyl)-N-cyclohexyl-4-oxo-4,5-dihydro-3H-1-thia-3,5,8-triazaacenaphthylene-2-carboxamide;

N-(5-(4-(3-((2-Cyanophenoxy)methyl)phenoxy)-2-methylphenyl)-4-oxo-4,5-dihydro-3H-1-thia-3,5,8-triazaacenaphthylen-2-yl)cyclopropanecarboxamide;

N-Cyclohexyl-5-(2-methyl-4-phenoxyphenyl)-4-oxo-4,5-dihydro-3H-1-thia-3,5,8-triazaacenaphthylene-2-carboxamide;

N-Cyclohexyl-4-oxo-5-(4-phenoxyphenyl)-4,5-dihydro-3H-1-thia-3,5,8-triazaacenaphthylene-2-carboxamide;

N1-((E)-4-(((1S,2R)-2-(5-(6-isobutyl-4-methylpyridin-3-yl)-4-oxo-4,5-dihydro-3H-1-thia-3,5,8-triazaacenaphthylene-2-carboxamido)cyclopentyl)amino)-4-oxobut-2-en-1-yl)-N5-(15-oxo-19-((3aS,4S,6aR)-2-oxohexahydro-1H-thieno[3,4-d]imidazol-4-yl)-4,7,10-trioxa-14-azanonadecyl)glutaramide;

N-((1R,2S)-2-Acrylamidocyclopentyl)-5-(4-methyl-6-(pyrimidin-2-yloxy)pyridin-3-yl)-4-oxo-4,5-dihydro-3H-1-thia-3,5,8-triazaacenaphthylene-2-carboxamide;

N-((1R,2S)-2-((E)-2-Cyano-3-cyclopropylacrylamido)cyclopentyl)-5-(*S)-(6-isobutyl-4-methylpyridin-3-yl)-4-oxo-4,5-dihydro-3H-1-thia-3,5,8-triazaacenaphthylene-2-carboxamide;

N-((1R,2S)-2-Acrylamidocyclohexyl)-5-(4-methyl-6-(pyridazin-3-yloxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(2-methyl-6-(pyrimidin-2-yloxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(*S)-(4-methyl-6-oxo-1-(pyridazin-3-yl)-1,6-dihydropyridin-3-yl)-4-oxo-4,5-dihydro-3H-1-thia-3,5,8-triazaacenaphthylene-2-carboxamide;

N-((1R,2S)-2-Acrylamidocyclopentyl)-5-(*R)-(4-methyl-6-oxo-1-(pyridazin-3-yl)-1,6-dihydropyridin-3-yl)-4-oxo-4,5-dihydro-3H-1-thia-3,5,8-triazaacenaphthylene-2-carboxamide;

N-((1R,2S)-2-Acrylamidocyclopentyl)-5-(4-methyl-6-(pyridazin-3-yloxy)pyridin-3-yl)-4-oxo-4,5-dihydro-3H-1-thia-3,5,8-triazaacenaphthylene-2-carboxamide;

N-((1R,2S)-2-Acrylamidocyclohexyl)-5-(2-methyl-6-(pyridazin-3-yloxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(2-methyl-6-(pyridazin-3-yloxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(2-methyl-6-((2-methylpyridin-3-yl)oxy)pyridin-3-yl)-4-oxo-4,5-dihydro-3H-1-thia-3,5,8-triazaacenaphthylene-2-carboxamide;

N-((1R,2S)-2-Acrylamidocyclohexyl)-4-oxo-5-(5-(pyridazin-3-yloxy)pyridin-2-yl)-4,5-dihydro-3H-1-thia-3,5,8-triazaacenaphthylene-2-carboxamide;

N-((1R,2S)-2-Acrylamidocyclopentyl)-4-oxo-5-(5-(pyridazin-3-yloxy)pyridin-2-yl)-4,5-dihydro-3H-1-thia-3,5,8-triazaacenaphthylene-2-carboxamide;

N-((1R,2S)-2-Acrylamidocyclopentyl)-5-(6'-methyl-2-oxo-2H-[1,2'-bipyridin]-5'-yl)-4-oxo-4,5-dihydro-3H-1-thia-3,5,8-triazaacenaphthylene-2-carboxamide;

N-((1R,2S)-2-Acrylamidocyclopentyl)-5-(2-methyl-6-(pyridin-2-yloxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(5-((6-methylpyridin-2-yl)oxy)pyridin-2-yl)-4-oxo-4,5-dihydro-3H-1-thia-3,5,8-triazaacenaphthylene-2-carboxamide;

N-((1R,2S)-2-Acrylamidocyclopentyl)-4-oxo-5-(5-(pyridin-2-yloxy)pyridin-2-yl)-4,5-dihydro-3H-1-thia-3,5,8-triazaacenaphthylene-2-carboxamide;

N-((1R,2S)-2-Acrylamidocyclopentyl)-5-(5-((6-methylpyridin-3-yl)oxy)pyridin-2-yl)-4-oxo-4,5-dihydro-3H-1-thia-3,5,8-triazaacenaphthylene-2-carboxamide;

N-((1R,2S)-2-Acrylamidocyclopentyl)-5-(2-methyl-4-(pyrimidin-5-yloxy)phenyl)-4-oxo-4,5-dihydro-3H-1-thia-3,5,8-triazaacenaphthylene-2-carboxamide;

N-((1R,2S)-2-Acrylamidocyclopentyl)-5-(4-methyl-6-((6-methylpyridin-2-yl)oxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-4-oxo-5-(5-(pyrimidin-2-yloxy)pyridin-2-yl)-4,5-dihydro-3H-1-thia-3,5,8-triazaacenaphthylene-2-carboxamide;

N-((1R,2S)-2-Acrylamidocyclopentyl)-4-oxo-5-(5-(pyrimidin-5-yloxy)pyridin-2-yl)-4,5-dihydro-3H-1-thia-3,5,8-triazaacenaphthylene-2-carboxamide;

N-((1R,2S)-2-Acrylamidocyclopentyl)-5-(4-methyl-6-(pyrimidin-5-yloxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(4-methyl-6-((6-methylpyridin-3-yl)oxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(4-methyl-6-(pyridin-2-yloxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(4-methyl-6-((2-methylpyridin-3-yl)oxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(4-methyl-6-(pyridin-3-yloxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-4-oxo-5-(5-(pyridin-3-yloxy)pyridin-2-yl)-4,5-dihydro-3H-1-thia-3,5,8-triazaacenaphthylene-2-carboxamide;

N-((1R,2S)-2-Acrylamidocyclopentyl)-5-(2-methyl-6-(pyrimidin-5-yloxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(5-((2-methylpyridin-3-yl)oxy)pyridin-2-yl)-4-oxo-4,5-dihydro-3H-1-thia-3,5,8-triazaacenaphthylene-2-carboxamide;

N-((1R,2S)-2-Acrylamidocyclopentyl)-5-(2-methyl-6-(pyridin-3-yloxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(2-methyl-6-((6-methylpyridin-3-yl)oxy)pyridin-3-yl)-4-oxo-4,5-dihydro-3H-1-thia-3,5,8-triazaacenaphthylene-2-carboxamide;

N-((1R,2S)-2-Acrylamidocyclopentyl)-5-(*S)-(2-methyl-4-((6-methylpyridin-2-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(*R)-(2-methyl-4-((6-methylpyridin-2-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(*S)-(2-methyl-4-((6-methylpyridin-3-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(*R)-(2-methyl-4-((6-methylpyridin-3-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(*S)-(2-methyl-4-((2-methylpyridin-3-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(*R)-(2-methyl-4-((2-methylpyridin-3-yl)oxy)phenyl)-4-oxo-4,5-dihydro-3H-1-thia-3,5,8-triazaacenaphthylene-2-carboxamide;

N-((1R,2S)-2-Acrylamidocyclopentyl)-5-(*S)-(2-methyl-4-(pyrimidin-2-yloxy)phenyl)-4-oxo-4,5-dihydro-3H-1-thia-3,5,8-triazaacenaphthylene-2-carboxamide;

N-((1R,2S)-2-Acrylamidocyclopentyl)-5-(*R)-(2-methyl-4-(pyrimidin-2-yloxy)phenyl)-4-oxo-4,5-dihydro-3H-1-thia-3,5,8-triazaacenaphthylene-2-carboxamide;

N-((1R,2S)-2-Acrylamidocyclopentyl)-5-(*S)-(2-methyl-4-(pyridin-2-yloxy)phenyl)-4-oxo-4,5-dihydro-3H-1-thia-3,5,8-triazaacenaphthylene-2-carboxamide;

N-((1R,2S)-2-Acrylamidocyclopentyl)-5-(*R)-(2-methyl-4-(pyridin-2-yloxy)phenyl)-4-oxo-4,5-dihydro-3H-1-thia-3,5,8-triazaacenaphthylene-2-carboxamide;

N-((1R,2S)-2-((E)-2-Cyano-3-(3-methyloxetan-3-yl)acrylamido)cyclopentyl)-5-(*S)-(6-isobutyl-4-methylpyridin-3-yl)-4-oxo-4,5-dihydro-3H-1-thia-3,5,8-triazaacenaphthylene-2-carboxamide;

N—((E)-2-Cyano-4-ethoxy-4-methylpent-2-enamido)cyclopentyl)-5-(*S)-(6-isobutyl-4-methylpyridin-3-yl)-4-oxo-4,5-dihydro-3H-1-thia-3,5,8-triazaacenaphthylene-2-carboxamide;

N1-((E)-4-(((1S,2R)-2-(5-(6-isobutyl-4-methylpyridin-3-yl)-4-oxo-4,5-dihydro-3H-1-thia-3,5,8-triazaacenaphthylene-2-carboxamido)cyclopentyl)amino)-4-oxobut-2-en-1-yl)-N5-(15-oxo-19-((3aS,4S,6aR)-2-oxohexahydro-1H-thieno[3,4-d]imidazol-4-yl)-4,7,10-trioxa-14-azanonadecyl)glutaramide; and N-((1R,2S)-2-acrylamidocyclopentyl)-4-oxo-5-(4-(pyrimidin-5-yloxy)phenyl)-4,5-dihydro-3H-1-thia-3,5,8-triazaacenaphthylene-2-carboxamide; and isotopic variants, and pharmaceutically acceptable salts, hydrates, polymorph or solvates thereof.

An additional aspect of the invention is a compound selected from the group consisting of:

N-((1R,2S)-2-Acrylamidocyclopentyl)-5-(*R)-(4-isopropoxy-2-methylphenyl)-4-oxo-4,5-dihydro-3H-1-thia-3,5,8-triazaacenaphthylene-2-carboxamide;

N-((1R,2S)-2-Acrylamidocyclopentyl)-5-(*S)-(4-methyl-2-phenoxypyrimidin-5-yl)-4-oxo-4,5-dihydro-3H-1-thia-3,5,8-triazaacenaphthylene-2-carboxamide;

N-((1R,2S)-2-Acrylamidocyclohexyl)-4-oxo-5-(2-phenylpyridin-4-yl)-4,5-dihydro-3H-1-thia-3,5,8-triazaacenaphthylene-2-carboxamide;

N-((1R,2S)-2-Acrylamidocyclohexyl)-4-oxo-5-(6-phenoxypyridin-3-yl)-4,5-dihydro-3H-1-thia-3,5,8-triazaacenaphthylene-2-carboxamide;

N-((1R,2S)-2-Acrylamidocyclohexyl)-5-(*R)-(4-isopropoxy-2-methylphenyl)-4-oxo-4,5-dihydro-3H-1-thia-3,5,8-triazaacenaphthylene-2-carboxamide;

N-((1R,2R)-2-Acrylamidocyclopentyl)-5-(*S)-(4-methyl-2-phenoxypyrimidin-5-yl)-4-oxo-4,5-dihydro-3H-1-thia-3,5,8-triazaacenaphthylene-2-carboxamide;

N-((1R,2S)-2-Acrylamidocyclopentyl)-4-oxo-5-(5-phenoxypyrazin-2-yl)-4,5-dihydro-3H-1-thia-3,5,8-triazaacenaphthylene-2-carboxamide;

N-((1R,2S)-2-Acrylamidocyclohexyl)-4-oxo-5-(5-phenoxypyrimidin-2-yl)-4,5-dihydro-3H-1-thia-3,5,8-triazaacenaphthylene-2-carboxamide;

N-((1R,2S)-2-Acrylamidocyclohexyl)-5-(*S)-(6-isobutyl-4-methylpyridin-3-yl)-4-oxo-4,5-dihydro-3H-1-thia-3,5,8-triazaacenaphthylene-2-carboxamide; and N-((1R,2S)-2-Acrylamidocyclopentyl)-5-(*S)-(2-methyl-4-((2-methylpyridin-3-yl)oxy)phenyl)-4-oxo-4,5-dihydro-3H-1-thia-3,5,8-triazaacenaphthylene-2-carboxamide; and isotopic variants, and pharmaceutically acceptable salts, hydrates, polymorph or solvates thereof.

An additional aspect of the invention is a compound of Formula (I) having the Formula (IIa):

(IIa)

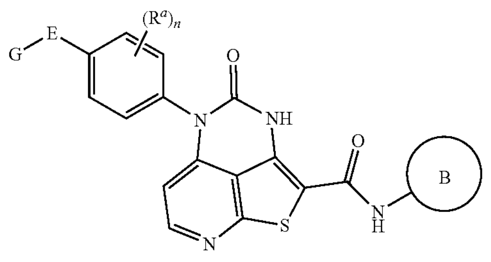

wherein $R^a$ is selected from the group consisting of: H, Cl and $CH_3$;

n is 0 or 1;

E is O;

G is selected from the group consisting of: $C_{1-6}$alkyl, phenyl, pyridyl, pyridyl substituted with $CH_3$, pyrimidinyl, pyridazinyl, tetrahydrofuranyl, tetrahydropyranyl, and

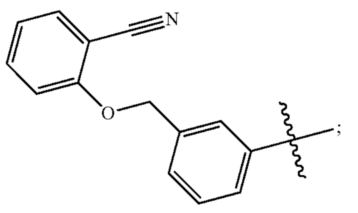 [SMILES: *c1cccc(COc2ccccc2C#N)c1]

Ring B is selected from the group consisting of:

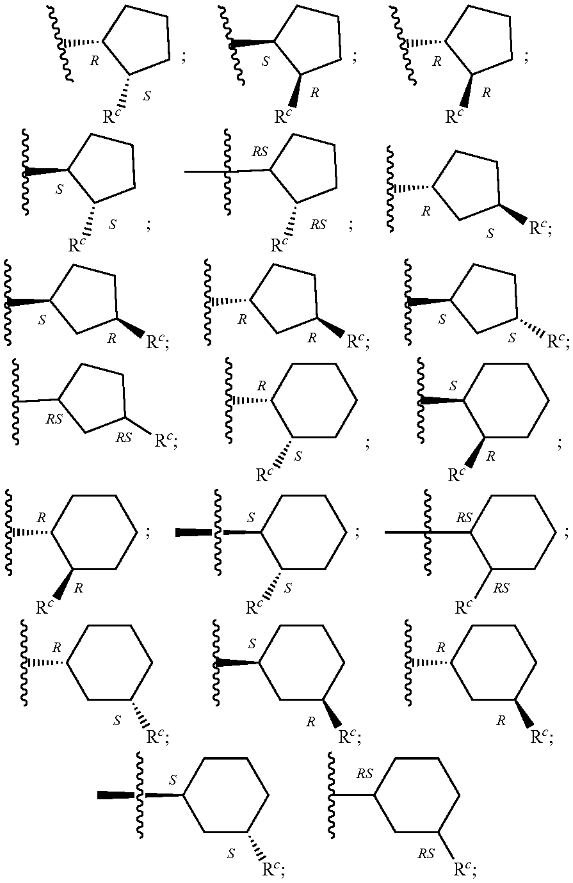

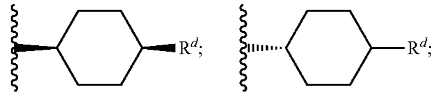

and

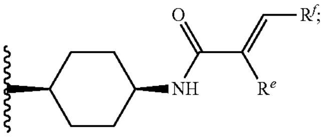

-continued

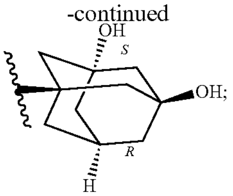

$R^c$ is selected from the group consisting of: OH, $OCH_3$, $NH_2$, $NH(CH_3)$, $N(CH_3)_2$, $NH(CO_2$-tert-butyl), $NH(C{=}O)C_{1-3}$alkyl, $NH(C{=}O)CH{=}CH_2$, $NH(C{=}O)CH_2NH_2$, $NH(C{=}O)CH_2NH(CH_3)$, $NH(C{=}O)CH_2N(CH_3)_2$, and $NH(C{=}O)CH{=}CHCH_2N(CH_3)_2$;

$R^d$ is selected from the group consisting of: OH, $OCH_3$, CN, $NH_2$, $NH(CH_3)$, $N(CH_3)_2$, $NH(CO_2$-tert-butyl), $NH(C{=}O)C_{1-3}$alkyl, and $NH(C{=}O)CH{=}CH_2$;

$R^e$ is H or CN; and $R^f$ is selected from the group consisting of: $CH_2NH_2$, $CH_2NH(CH_3)$, $CH_2N(CH_3)_2$, and cyclopropyl.

An additional aspect of the invention is a compound of Formula (I) having the Formula (IIa) wherein: $R^a$ is H or $CH_3$; n is 1; E is O; G is selected from the group consisting of: $C_{1-3}$alkyl, phenyl, pyridyl, and pyridyl substituted with $CH_3$; Ring B is selected from the group consisting of:

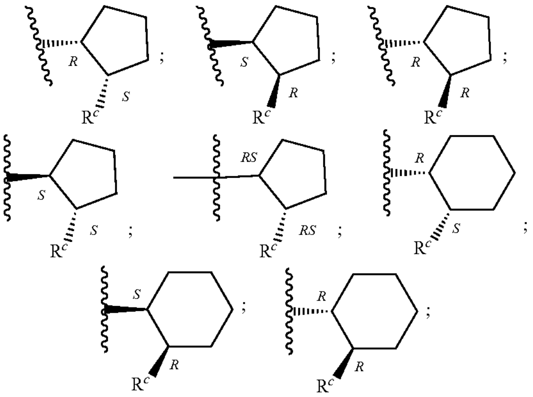

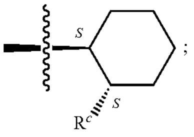

and

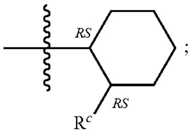

and $R^c$ is $NH(C{=}O)CH{=}CH_2$.

An additional aspect of the invention is a compound of Formula (I) having the Formula (IIb):

(IIb)

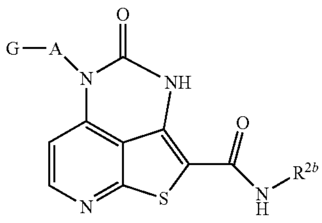

wherein

G-A is selected from the group consisting of:

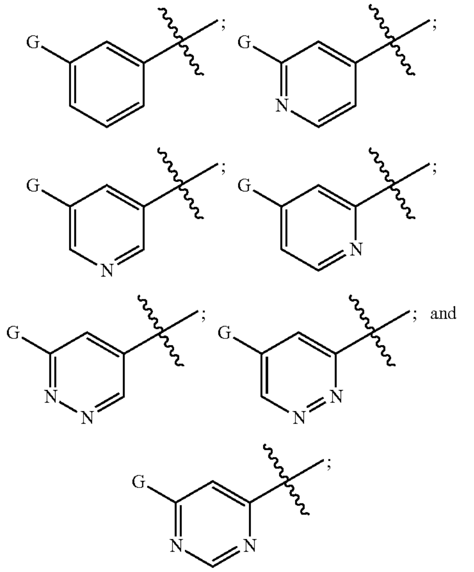

G is selected from the group consisting of: $C_{1-6}$alkyl, $C_{3-6}$cycloalkyl, phenyl, and pyridyl.

$R^{2b}$ is selected from the group consisting of:

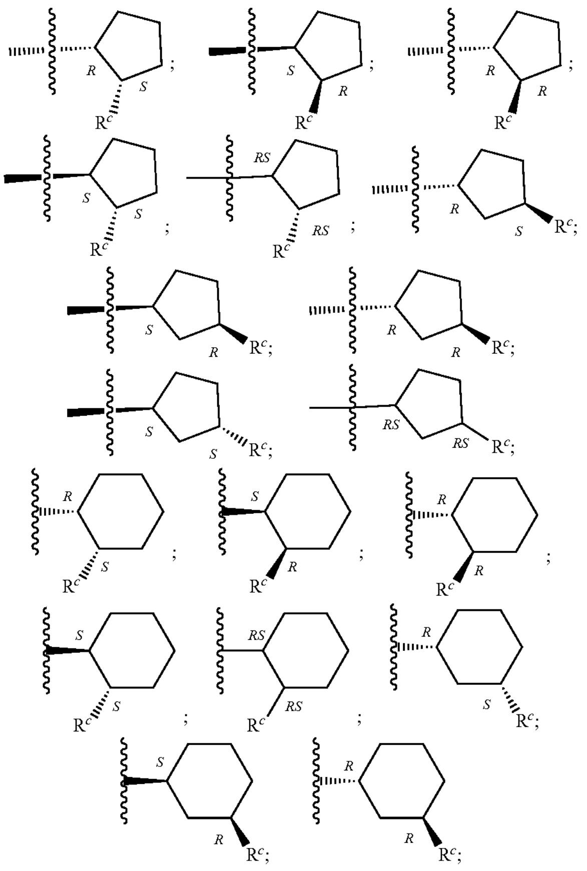

-continued

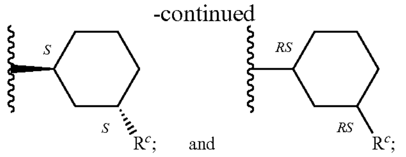

and $R^c$ is selected from the group consisting of: OH, $OCH_3$, $NH_2$, $NH(CH_3)$, $N(CH_3)_2$, $NH(CO_2$-tert-butyl), $NH(C{=}O)C_{1-3}$alkyl, $NH(C{=}O)CH{=}CH_2$, $NH(C{=}O)CH_2NH_2$, $NH(C{=}O)CH_2NH(CH_3)$, $NH(C{=}O)CH_2N(CH_3)_2$, and $NH(C{=}O)CH{=}CHCH_2N(CH_3)_2$.

An additional aspect of the invention is a compound of Formula (I) having the Formula (IIb) wherein: G-A is

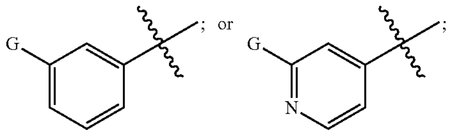

G is phenyl or pyridyl; $R^{2b}$ is selected from the group consisting of:

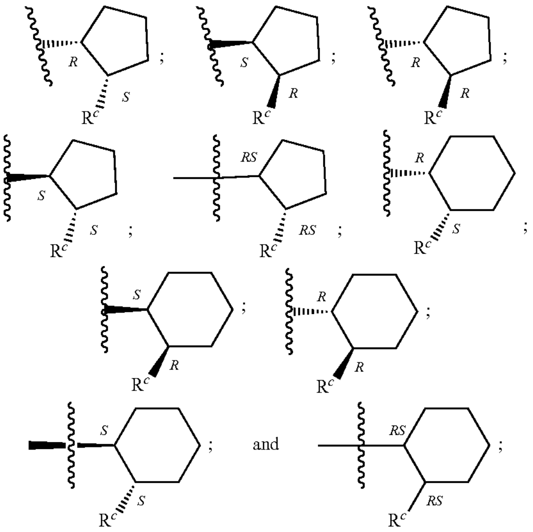

and $R^c$ is $NH(C{=}O)CH{=}CH_2$.

An additional aspect of the invention is a compound of Formula (I) having the Formula (IIc):

(IIc)

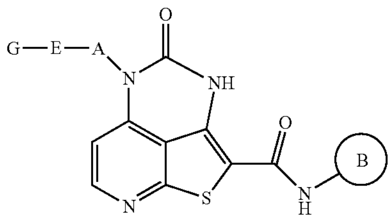

wherein

G-E-A is selected from the group consisting of:

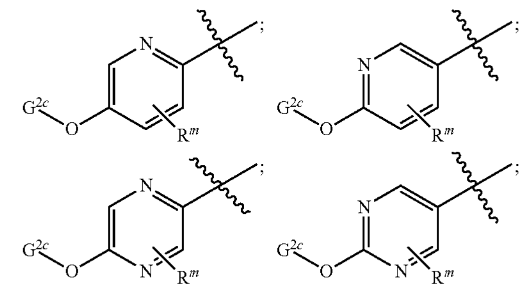

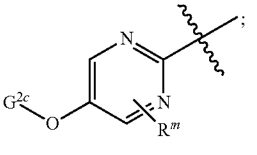

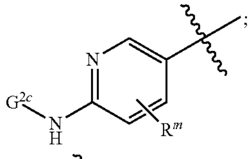

and

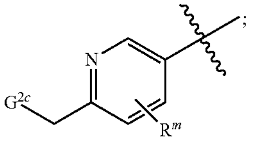

where $G^{2c}$ is selected from the group consisting of: $C_{1-6}$alkyl, phenyl, pyrimidinyl, pyridyl, pyridyl substituted with $CH_3$, and $C_{3-6}$cycloalkyl; and $R^m$ is H or $CH_3$;

Ring B is selected from the group consisting of:

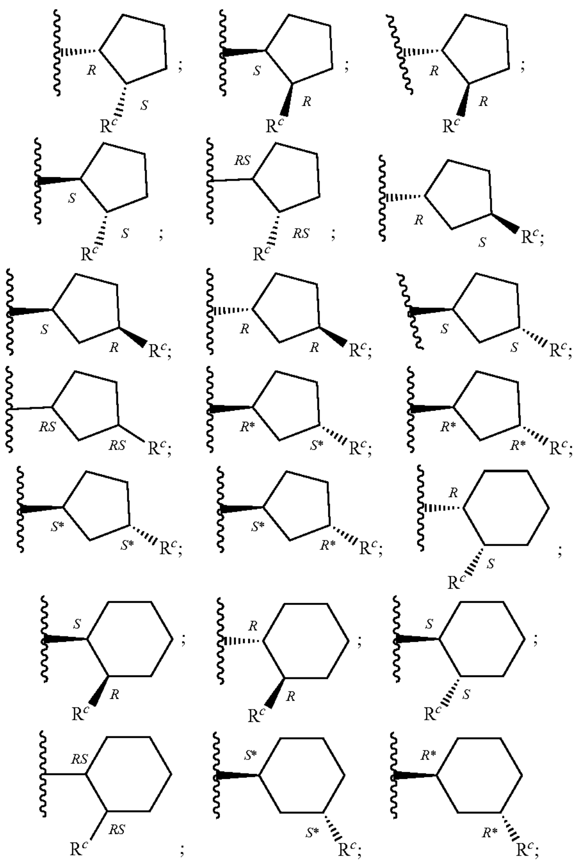

-continued

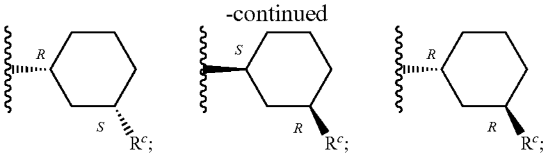

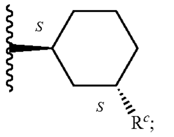

and

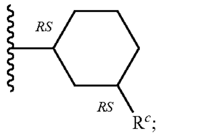

and $R^c$ is selected from the group consisting of: OH, $OCH_3$, $NH_2$, $NH(CH_3)$, $N(CH_3)_2$, $NH(CO_2$-tert-butyl), $NH(C{=}O)C_{1-3}$alkyl, $NH(C{=}O)CH{=}CH_2$, $NH(C{=}O)CH_2NH_2$, $NH(C{=}O)CH_2NH(CH_3)$, $NH(C{=}O)CH_2N(CH_3)_2$, and $NH(C{=}O)CH{=}CHCH_2N(CH_3)_2$.

An additional aspect of the invention is a compound of Formula (I) having the Formula (IIc) wherein:

An additional aspect of the invention is a compound of Formula (I) having the Formula (IIc): wherein G-E-A is

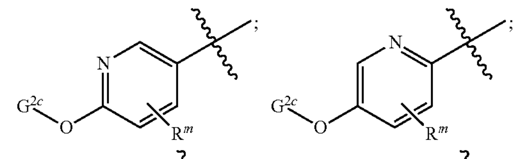

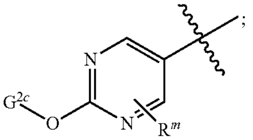

or

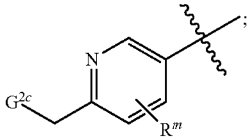

$G^{2c}$ is $C_{1-6}$alkyl, phenyl, or pyridyl; $R^m$ is H or $CH_3$; Ring B is

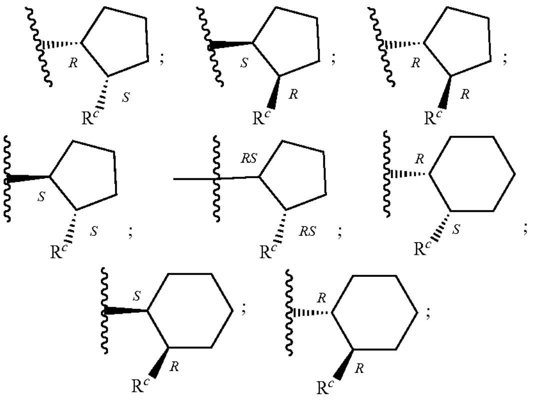

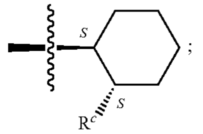

and

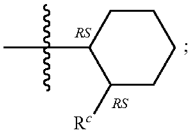

and $R^c$ is $NH(C{=}O)CH{=}CH_2$.

Method of Treatment

The disclosure also relates to methods of using the compounds described herein to treat subjects diagnosed with or suffering from a disease, disorder, or condition mediated by Bruton's tyrosine kinase. These methods are accomplished by administering to the subject a compound of the disclosure in an amount sufficient to inhibit Bruton's tyrosine kinase.

In a further aspect, provided herein are methods for inhibiting Bruton's tyrosine kinase in a subject in need of treatment by administering to the subject a composition containing a therapeutically effective amount of the compound of Formula (III). Some aspects of the disclosure are directed to methods of treating a subject suffering from a malignancy by administering to the subject a composition containing a therapeutically effective amount of the compound of Formula (III). In some aspects, the malignancy is, e.g., a lymphoma, a leukemia, a carcinoma, or a sarcoma. In some aspects the lymphoma includes, but is not limited tonon-Hodgkin's lymphoma (NHL (including B-cell NHL)), diffuse large B-cell lymphoma (DLBCL), mantle cell lymphoma (MCL), follicular lymphoma (FL), mucosa-associated lymphoid tissue (MALT) lymphoma, marginal zone lymphoma (MZL), T-cell lymphoma, Hodgkin's lymphoma, small lymphocytic lymphoma (SLL), Waldenstrom macroglobulinemia, and Burkitt's lymphoma. In some aspects, the leukemia includes, but is not limited to chronic lymphocytic leukemia (CLL), lymphoblastic T cell leukemia, chronic myelogenous leukemia (CML), hairy-cell leukemia, acute lymphoblastic T cell leukemia, plasmacytoma, immunoblastic large cell leukemia, megakaryoblastic leukemia, acute megakaryocyte leukemia, promyelocytic leukemia, erythroleukemia and multiple myeloma. In some aspects, the malignancy includes but is not limited to brain (gliomas), glioblastomas, breast cancer, colorectal/colon cancer, prostate cancer, lung cancer, non-small-cell lung cancer, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head & neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, Chronic graft versus host disease, and gastrointestinal stromal tumor. When used for the treatment of a malignancy, the compound of Formula (III) can be administered as a single agent. Alternatively, when used for the treatment of an malignancy, the compound of Formula (III) can be administered in combination with other agents known to be useful for the treatment of autoimmune diseases.

In a further aspect, provided herein are methods for inhibiting Bruton's tyrosine kinase in a subject in need of treatment by administering to the subject a composition containing a therapeutically effective amount of the compound of Formula (I). Some aspects of the disclosure are directed to methods of treating a subject suffering from a malignancy by administering to the subject a composition containing a therapeutically effective amount of the compound of Formula (I). In some aspects, the malignancy is a lymphoma, a leukemia, a carcinoma, or a sarcoma. In some aspects the lymphoma includes, but is not limited to, non-Hodgkin's lymphoma (NHL (including B-cell NHL)), diffuse large B-cell lymphoma (DLBCL), mantle cell lymphoma (MCL), follicular lymphoma (FL), mucosa-associated lymphoid tissue (MALT) lymphoma, marginal zone lymphoma (MZL), T-cell lymphoma, Hodgkin's lymphoma, small lymphocytic lymphoma (SLL), Waldenstrom macroglobulinemia, and Burkitt's lymphoma. In some aspects, the leukemia includes, but is not limited to chronic lymphocytic leukemia (CLL), lymphoblastic T cell leukemia, chronic myelogenous leukemia (CML), hairy-cell leukemia, acute lymphoblastic T cell leukemia, plasmacytoma, immunoblastic large cell leukemia, megakaryoblastic leukemia, acute megakaryocyte leukemia, promyelocytic leukemia, erythroleukemia and multiple myeloma. In some aspects, the malignancy includes, but is not limited to brain (gliomas), glioblastomas, breast cancer, colorectal/colon cancer, prostate cancer, lung cancer, non-small-cell lung cancer, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head & neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and gastrointestinal stromal tumor. In some aspects, provided herein are methods for the treatment of chronic graft versus host disease in a subject in ned thereof. When used for the treatment of a malignancy or other disease or condition, the compound of Formula (I) can be administered as a single agent. Alternatively, when used for the treatment of an malignancy or other disease or condition, the compound of Formula (I) can be administered in combination with one or more other agents known to be useful for the treatment of malignancies.

Other aspects of the disclosure are directed to methods of treating a subject suffering from a malignancy by administering to the subject a composition containing a therapeutically effective amount of a compound of Formula (III). In one aspect, the malignancy is diffuse large B-cell lymphoma (DLBCL), mantle cell lymphoma (MCL), follicular lymphoma (FL), marginal zone lymphoma (MZL), chronic lymphocytic leukemia (CLL), small lymphocytic lymphoma (SLL), Waldenstrom macroglobulinemia, and Chronic graft versus host disease. Malignancies that are particularly suited to being treated with compounds of the disclosure include diffuse large B-cell lymphoma (DLBCL), mantle cell lymphoma (MCL), follicular lymphoma (FL), marginal zone lymphoma (MZL), chronic lymphocytic leukemia (CLL), small lymphocytic lymphoma (SLL), Waldenstrom macroglobulinemia, and Chronic graft versus host disease. Other aspects of the disclosure are directed to methods of treating a subject suffering from chronic graft versus host disease by administering to the subject a composition containing a therapeutically effective amount of a compound of Formula (III).

In preferred aspects, the compound of Formula (III) can be used to treat diffuse large B-cell lymphoma (DLBCL), mantle cell lymphoma (MCL), follicular lymphoma (FL), marginal zone lymphoma (MZL), chronic lymphocytic leukemia (CLL), small lymphocytic lymphoma (SLL), Waldenstrom macroglobulinemia, and Chronic graft versus host disease.

The compound of Formula (III) can also be used to treat malignancies including, but not limited to, lymphomas, leukemias, carcinomas, and sarcomas, e.g. non-Hodgkin's lymphoma (NHL (including B-cell NHL)), diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chronic lymphocytic leukemia (CLL), small lymphocytic lymphoma (SLL), Waldenstrom macroglobulinemia, lymphoblastic T cell leukemia, chronic myelogenous leukemia (CML), hairy-cell leukemia, acute lymphoblastic T cell leukemia, plasmacytoma, immunoblastic large cell leukemia, megakaryoblastic leukemia, acute megakaryocyte leukemia, promyelocytic leukemia, erythroleukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head & neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor) as well as chronic graft versus host disease.

In treatment methods according to the disclosure, a therapeutically effective amount of a pharmaceutical agent according to the disclosure is administered to a subject suffering from or diagnosed as having such a disease, disorder, or condition. Therapeutically effective amounts or doses of the compounds of the present disclosure may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.0001 to about 1,000 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

In some aspects, the therapeutically effective amount of the compound of Formula (III) is from about 0.0001 mg to about 10,000 mg. In some aspects, the therapeutically effective amount of the compound of Formula (III) is from about 0.0001 mg to about 1,000 mg. In some aspects, the therapeutically effective amount of the compound of Formula (III) is from about 0.0001 mg to about 100 mg. In some aspects, the therapeutically effective amount of the compound of Formula (III) is from about 100 mg to about 200 mg. In some aspects, the therapeutically effective amount of the compound of Formula (III) is from about 100 mg to about 300 mg. In some aspects, the therapeutically effective amount of the compound of Formula (III) is from about 100 mg to about 400 mg. In some aspects, the therapeutically effective amount of the compound of Formula (III) is from about 100 mg to about 500 mg. In some aspects, the therapeutically effective amount of the compound of Formula (III) is from about 100 mg to about 600 mg. In some aspects, the therapeutically effective amount of the compound of Formula (III) is from about 100 mg to about 700 mg. In some aspects, the therapeutically effective amount of the compound of Formula (III) is from about 100 mg to about 800 mg. In some aspects, the therapeutically effective amount of the compound of Formula (III) is from about 100 mg to about 900 mg. In some aspects, the therapeutically effective amount of the compound of Formula (III) is from about 100 mg to about 1,000 mg. In some aspects, the therapeutically effective amount of the compound of Formula (III) is from about 140 mg to about 560 mg. In some aspects, the therapeutically effective amount of the compound of Formula (III) is about 140 mg. In some aspects, the therapeutically effective amount of the compound of Formula (III) is about 280 mg. In some aspects, the therapeutically effective amount of the compound of Formula (III) is about 560 mg.

The present invention also relates to the use of a therapeutically effective amount ranging from about 100 mg to about 1000 mg, alternatively from about 100 mg to about 600 mg, alternatively from about 140 mg to about 560 mg of a compound of Formula (III) or a pharmaceutically acceptable salt, hydrate, polymorph or solvate thereof, for treating a malignancy as described herein.

The present invention also relates to the use of a therapeutically effective amount ranging from about 100 mg to about 1000 mg, alternatively from about 100 mg to about 600 mg, alternatively from about 140 mg to about 560 mg of a compound of Formula (III) or a pharmaceutically acceptable salt, hydrate, polymorph or solvate thereof, for treating a malignancy that is affected by the inhibition of BTK.

The present invention also relates to a therapeutically effective amount ranging from about 100 mg to about 1000 mg, alternatively from about 100 mg to about 600 mg, alternatively from about 140 mg to about 560 mg of a compound of Formula (III) or a pharmaceutically acceptable salt, hydrate, polymorph or solvate thereof, for use in treating a malignancy as described herein.

The present invention also relates to a therapeutically effective amount ranging from about 100 mg to about 1000 mg, alternatively from about 100 mg to about 600 mg, alternatively from about 140 mg to about 560 mg of a compound of Formula (III) or a pharmaceutically acceptable salt, hydrate, polymorph or solvate thereof, for use in treating a malignancy that is affected by the inhibition of BTK.

The present invention also relates to a therapeutically effective amount ranging from about 100 mg to about 1000 mg, alternatively from about 100 mg to about 600 mg, alternatively from about 140 mg to about 560 mg of a compound of Formula (III) or a pharmaceutically acceptable salt, hydrate, polymorph or solvate thereof, for use in a method of treating a malignancy as described herein.

The present invention also relates to a therapeutically effective amount ranging from about 100 mg to about 1000 mg, alternatively from about 100 mg to about 600 mg, alternatively from about 140 mg to about 560 mg of a compound of Formula (III) or a pharmaceutically acceptable salt, hydrate, polymorph or solvate thereof, for use in a method of treating a malignancy that is affected by the inhibition of BTK.

The present invention also relates to the use of a therapeutically effective amount ranging from about 100 mg to about 1000 mg, alternatively from about 100 mg to about 600 mg, alternatively from about 140 mg to about 560 mg of a compound of Formula (III) or a pharmaceutically acceptable salt, hydrate, polymorph or solvate thereof, for the manufacture of a medicament for the treatment of a malignancy as described herein.

The present invention also relates to the use of a therapeutically effective amount ranging from about 100 mg to about 1000 mg, alternatively from about 100 mg to about 600 mg, alternatively from about 140 mg to about 560 mg of a compound of Formula (III) or a pharmaceutically acceptable salt, hydrate, polymorph or solvate thereof, for the manufacture of a medicament for the treatment of a malignancy that is affected by the inhibition of BTK.

In some aspects, the therapeutically effective amount of a compound of Formula (III) is determined by the resulting effect in the patient such as a particular pharmacokinetic or pharmacodynamic profile following administration. In some aspects, therapeutically effective amount of the compound of Formula (III) is an amount that results in a $C_{(max,day1)}$ (maximum concentration at day 1) of about 50 ng/ml to about 2,500 ng/ml. In some aspects, therapeutically effective amount of the compound of Formula (III) is an amount that results in a $C_{(max,day1)}$ of about 59.992 ng/ml to about 2,377.2 ng/ml. In some aspects, therapeutically effective amount of the compound of Formula (III) is an amount that results in a $C_{(max,day1)}$ of about 0.0001 ng/ml to about 10,000 ng/ml. In some aspects, therapeutically effective amount of the compound of Formula (III) is an amount that results in a $C_{(max,day1)}$ of about 0.0001 ng/ml to about 5,000 ng/ml. In some aspects, therapeutically effective amount of the compound of Formula (III) is an amount that results in a $C_{(max,day1)}$ of about 0.0001 ng/ml to about 2,500 ng/ml. In some aspects, therapeutically effective amount of the compound of Formula (III) is an amount that results in a $C_{(max,day1)}$ of about 0.0001 ng/ml to about 2,000 ng/ml. In some aspects, therapeutically effective amount of the compound of Formula (III) is an amount that results in a $C_{(max,day1)}$ of about 0.0001 ng/ml to about 1,500 ng/ml. In some aspects, therapeutically effective amount of the compound of Formula (III) is an amount that results in a $C_{(max,day1)}$ of about 0.0001 ng/ml to about 1,000 ng/ml. In some aspects, therapeutically effective amount of the compound of Formula (III) is an amount that results in a $C_{(max,day1)}$ of about 0.0001 ng/ml to about 750 ng/ml. In some aspects, therapeutically effective amount of the compound of Formula (III) is an amount that results in a $C_{(max,day1)}$ of about 0.0001 ng/ml to about 500 ng/ml. In some aspects, therapeutically effective amount of the compound of Formula (III) is an amount that results in a $C_{(max,day1)}$ of about 0.0001 ng/ml to about 250 ng/ml. In some aspects, therapeutically effective amount of the compound of Formula (III) is an amount that results in a $C_{(max,day1)}$ of about 0.0001 ng/ml to about 200 ng/ml. In some aspects, therapeutically effective amount of the compound of Formula (III) is an amount that results in a $C_{(max,day1)}$ of about 0.0001 ng/ml to about 100 ng/ml. In some aspects, therapeutically effective amount of the compound of Formula (III) is an amount that results in a $C_{(max,day1)}$ of about 0.0001 ng/ml to about 50 ng/ml. In some aspects, therapeutically effective amount of the compound of Formula (III) is an amount that results in a $C_{(max,day1)}$ of about 0.0001 ng/ml to about 10 ng/ml. In some aspects, the therapeutically effective amount of the compound of Formula (III) is an amount that results in a $C_{(max,day1)}$ of about 200 ng/ml to about 10,000 ng/ml. In some aspects, the therapeutically effective amount of the compound of Formula (III) is an amount that results in a $C_{(max,day1)}$ of about 239.97 to about 9,509 ng/ml. In some aspects, the therapeutically effective amount of the compound of Formula (III) is an amount that results in a $C_{(max,day1)}$ of about 429.75 ng/ml. In some aspects, the therapeutically effective amount of the compound of Formula (III) is an amount that results in a $C_{(max,day1)}$ of about 1,719 ng/ml.

In some aspects, the therapeutically effective amount of the compound of Formula (III) is an amount that results in a $C_{(max,ss)}$ (maximum concentration at steady state) of about 0.0001 ng/ml to about 10,000 ng/ml. In some aspects, the therapeutically effective amount of the compound of Formula (III) is an amount that results in a $C_{(max,ss)}$ of about 0.0001 ng/ml to about 5,000 ng/ml. In some aspects, the therapeutically effective amount of the compound of Formula (III) is an amount that results in a $C_{(max,ss)}$ of about 0.0001 ng/ml to about 4,000 ng/ml. In some aspects, the therapeutically effective amount of the compound of Formula (III) is an amount that results in a $C_{(max,ss)}$ of about 0.0001 ng/ml to about 3,000 ng/ml. In some aspects, the therapeutically effective amount of the compound of Formula (III) is an amount that results in a $C_{(max,ss)}$ of about 0.0001 ng/ml to about 2,500 ng/ml. In some aspects, the therapeutically effective amount of the compound of Formula (III) is an amount that results in a $C_{(max,ss)}$ of about 0.0001 ng/ml to about 2,000 ng/ml. In some aspects, the therapeutically effective amount of the compound of Formula (III) is an amount that results in a $C_{(max,ss)}$ of about 0.0001 ng/ml to about 1,000 ng/ml. In some aspects, the therapeutically effective amount of the compound of Formula (III) is an amount that results in a $C_{(max,ss)}$ of about 0.0001 ng/ml to about 750 ng/ml. In some aspects, the therapeutically effective amount of the compound of Formula (III) is an amount that results in a $C_{(max,ss)}$ of about 0.0001 ng/ml to about 500 ng/ml. In some aspects, the therapeutically effective amount of the compound of Formula (III) is an amount that results in a $C_{(max,ss)}$ of about 0.0001 ng/ml to about 250 ng/ml. In some aspects, the therapeutically effective amount of the compound of Formula (III) is an amount that results in a $C_{(max,ss)}$ of about 0.0001 ng/ml to about 100 ng/ml. In some aspects, the therapeutically effective amount of the compound of Formula (III) is an amount that results in a $C_{(max,ss)}$ of about 0.0001 ng/ml to about 50 ng/ml. In some aspects, the therapeutically effective amount of the compound of Formula (III) is an amount that results in a $C_{(max,ss)}$ of about 0.0001 ng/ml to about 10 ng/ml. In some aspects, therapeutically effective amount of the compound of Formula (III) is an amount that results in a $C_{(max,day1)}$ of about 50 ng/ml to about 2,500 ng/ml. In some aspects, the therapeutically effective amount of the compound of Formula (III) is an amount that results in a $C_{(max,ss)}$ of about 66.855 ng/ml to about 2,395.4 ng/ml. In some aspects, therapeutically effective amount of the compound of Formula (III) is an amount that results in a $C_{(max,day1)}$ of about 250 ng/ml to about 10,000 ng/ml. In some aspects, the therapeutically effective amount of the compound of Formula (III) is an amount that results in a $C_{(max,ss)}$ of about 267.42 to about 9,581.5 ng/ml. In some aspects, the therapeutically effective amount of the compound of Formula (III) is an amount that results in a $C_{(max,ss)}$ of about 435.1 ng/ml. In some aspects, the therapeutically effective amount of the compound of Formula (III) is an amount that results in a $C_{(max,ss)}$ of about 1,740.4 ng/ml.

In some aspects, the therapeutically effective amount of the compound of Formula (III) is an amount that results in a $AUC_{(day\ 1)}$ (area under the curve at day 1) of about 0.0001 ng·hr/ml to about 100,000 ng·hr/ml. In some aspects, the therapeutically effective amount of the compound of Formula (III) is an amount that results in a $AUC_{(day\ 1)}$ of about 0.0001 ng·hr/ml to about 75,000 ng·hr/ml. In some aspects, the therapeutically effective amount of the compound of Formula (III) is an amount that results in a $AUC_{(day\ 1)}$ of about 0.0001 ng·hr/ml to about 50,000 ng·hr/ml. In some aspects, the therapeutically effective amount of the compound of Formula (III) is an amount that results in a $AUC_{(day\ 1)}$ of about 0.0001 ng·hr/ml to about 25,000 ng·hr/ml. In some aspects, the therapeutically effective amount of the compound of Formula (III) is an amount that results in a $AUC_{(day\ 1)}$ of about 0.0001 ng·hr/ml to about 20,000 ng·hr/ml. In some aspects, the therapeutically effective amount of the compound of Formula (III) is an amount that results in a $AUC_{(day\ 1)}$ of about 0.0001 ng·hr/ml to about 15,000 ng·hr/ml. In some aspects, the therapeutically effective amount of the compound of Formula (III) is an amount that results in a $AUC_{(day\ 1)}$ of about 0.0001 ng·hr/ml to about 10,000 ng·hr/ml. In some aspects, the therapeutically effective amount of the compound of Formula (III) is an amount that results in a $AUC_{(day\ 1)}$ of about 0.0001 ng·hr/ml to about 5,000 ng·hr/ml. In some aspects, the therapeutically effective amount of the compound of Formula (III) is an amount that results in a $AUC_{(day\ 1)}$ of about 0.0001 ng·hr/ml to about 2,500 ng·hr/ml. In some aspects, the therapeutically effective amount of the compound of Formula (III) is an amount that results in a $AUC_{(day\ 1)}$ of about 0.0001 ng·hr/ml to about 2,000 ng·hr/ml. In some aspects, the therapeutically effective amount of the compound of Formula (III) is an amount that results in a $AUC_{(day\ 1)}$ of about 0.0001 ng·hr/ml to about 1,500 ng·hr/ml. In some aspects, the therapeutically effective amount of the compound of Formula (III) is an amount that results in a $AUC_{(day\ 1)}$ of about 0.0001 ng·hr/ml to about 1,000 ng·hr/ml. In some aspects, the therapeutically effective amount of the compound of Formula (III) is an amount that results in a $AUC_{(day\ 1)}$ of about 0.0001 ng·hr/ml to about 750 ng·hr/ml. In some aspects, the therapeutically effective amount of the compound of Formula (III) is an amount that results in a $AUC_{(day\ 1)}$ of about 0.0001 ng·hr/ml to about 500 ng·hr/ml. In some aspects, the therapeutically effective amount of the compound of Formula (III) is an amount that results in a $AUC_{(day\ 1)}$ of about 0.0001 ng·hr/ml to about 250 ng·hr/ml. In some aspects, the therapeutically effective amount of the compound of Formula (III) is an amount that results in a $AUC_{(day\ 1)}$ of about 0.0001 ng·hr/ml to about 200 ng·hr/ml. In some aspects, the therapeutically effective amount of the compound of Formula (III) is an amount that results in a $AUC_{(day\ 1)}$ of about 0.0001 ng·hr/ml to about 100 ng·hr/ml. In some aspects, the therapeutically effective amount of the compound of Formula (III) is an amount that results in a $AUC_{(day\ 1)}$ of about 0.0001 ng·hr/ml to about 10 ng·hr/ml. In some aspects, the therapeutically effective amount of the compound of Formula (III) is an amount that results in a $AUC_{(day\ 1)}$ of about 300 ng·hr/ml to about 15,000 ng·hr/ml.In some aspects, the therapeutically effective amount of the compound of Formula (III) is an amount that results in a $AUC_{(day\ 1)}$ of about 312.1 to about 11,517 ng·hr/ml. In some aspects, the therapeutically effective amount of the compound of Formula (III) is an amount that results in a $AUC_{(day\ 1)}$ of about 1,000 ng·hr/ml to about 50,000 ng·hr/ml. In some aspects, the therapeutically effective amount of the compound of Formula (III) is an amount that results in a $AUC_{(day\ 1)}$ of about 1,248.4 to about 46,068 ng·hr/ml. In some aspects, the therapeutically effective amount of the compound of Formula (III) is an amount that results in a $AUC_{(day\ 1)}$ of about 2,157.5 ng·hr/ml. In some aspects, the therapeutically effective amount of the compound of Formula (III) is an amount that results in a $AUC_{(day\ 1)}$ of about 8,629.9 ng·hr/ml.

In some aspects, the therapeutically effective amount of the compound of Formula (III) is an amount that results in a $AUC_{(ss)}$ (area under the curve at steady state) of about 0.0001 ng/hr/ml to about 100,000 ng·hr/ml. In some aspects, the therapeutically effective amount of the compound of Formula (III) is an amount that results in a $AUC_{(ss)}$ of about 0.0001 ng·hr/ml to about 75,000 ng·hr/ml. In some aspects, the therapeutically effective amount of the compound of Formula (III) is an amount that results in a $AUC_{(ss)}$ of about 0.0001 ng·hr/ml to about 50,000 ng·hr/ml. In some aspects, the therapeutically effective amount of the compound of Formula (III) is an amount that results in a $AUC_{(ss)}$ of about 0.0001 ng·hr/ml to about 40,000 ng·hr/ml. In some aspects, the therapeutically effective amount of the compound of Formula (III) is an amount that results in a $AUC_{(ss)}$ of about 0.0001 ng·hr/ml to about 30,000 ng·hr/ml. In some aspects, the therapeutically effective amount of the compound of Formula (III) is an amount that results in a $AUC_{(ss)}$ of about 0.0001 ng·hr/ml to about 20,000 ng·hr/ml. In some aspects, the therapeutically effective amount of the compound of Formula (III) is an amount that results in a $AUC_{(ss)}$ of about 0.0001 ng·hr/ml to about 15,000 ng·hr/ml. In some aspects, the therapeutically effective amount of the compound of Formula (III) is an amount that results in a $AUC_{(ss)}$ of about 0.0001 ng·hr/ml to about 10,000 ng·hr/ml. In some aspects, the therapeutically effective amount of the compound of Formula (III) is an amount that results in a $AUC_{(ss)}$ of about 0.0001 ng·hr/ml to about 5,000 ng·hr/ml. In some aspects, the therapeutically effective amount of the compound of Formula (III) is an amount that results in a $AUC_{(ss)}$ of about 0.0001 ng·hr/ml to about 2,500 ng·hr/ml. In some aspects, the therapeutically effective amount of the compound of Formula (III) is an amount that results in a $AUC_{(ss)}$ of about 0.0001 ng·hr/ml to about 2,000 ng·hr/ml. In some aspects, the therapeutically effective amount of the compound of Formula (III) is an amount that results in a $AUC_{(ss)}$ of about 0.0001 ng·hr/ml to about 1,000 ng·hr/ml. In some aspects, the therapeutically effective amount of the compound of Formula (III) is an amount that results in a $AUC_{(ss)}$ of about 0.0001 ng·hr/ml to about 750 ng·hr/ml. In some aspects, the therapeutically effective amount of the compound of Formula (III) is an amount that results in a $AUC_{(ss)}$ of about 0.0001 ng·hr/ml to about 500 ng·hr/ml. In some aspects, the therapeutically effective amount of the compound of Formula (III) is an amount that results in a $AUC_{(ss)}$ of about 0.0001 ng·hr/ml to about 250 ng·hr/ml. In some aspects, the therapeutically effective amount of the compound of Formula (III) is an amount that results in a $AUC_{(ss)}$ of about 0.0001 ng·hr/ml to about 200 ng·hr/ml. In some aspects, the therapeutically effective amount of the compound of Formula (III) is an amount that results in a $AUC_{(ss)}$ of about 0.0001 ng·hr/ml to about 100 ng·hr/ml. In some aspects, the therapeutically effective amount of the compound of Formula (III) is an amount that results in a $AUC_{(ss)}$ of about 0.0001 ng·hr/ml to about 10 ng·hr/ml. In some aspects, the therapeutically effective amount of the compound of Formula (III) is an amount that results in a $AUC_{(ss)}$ of about 300 ng·hr/ml to about 15,000 ng·hr/ml. In some aspects, the therapeutically effective amount of the compound of Formula (III) is an amount that results in a $AUC_{(ss)}$ of about 312.27 ng·hr/ml to about 13,015 ng·hr/ml. In some aspects, the therapeutically effective amount of the compound of Formula (III) is an amount that results in a $AUC_{(ss)}$ of about 0.0001 ng·hr/ml to about 20,000 ng·hr/ml. In some aspects, the therapeutically effective amount of the compound of Formula (III) is an amount that results in a $AUC_{(ss)}$ of about 1,249.1 ng·hr/ml to about 52,061 ng·hr/ml. In some aspects, the therapeutically effective amount of the compound of Formula (III) is an amount that results in a $AUC_{(ss)}$ of about 1,000 ng·hr/ml to about 55,000 ng·hr/ml. In some aspects, the therapeutically effective amount of the compound of Formula (III) is an amount that results in a $AUC_{(ss)}$ of about 2,249.7 ng·hr/ml. In some aspects, the therapeutically effective amount of the compound of Formula (III) is an amount that results in a $AUC_{(ss)}$ of about 8,998.9 ng·hr/ml.

In some aspects, the therapeutically effective amount of the compound of Formula (III) is an amount that results in a $BTKO_{(max/day1)}$ (maximum BTK occupancy at day 1) of about 100% occupancy. In some aspects, the therapeutically effective amount of the compound of Formula (III) is an amount that results in a $BTKO_{(max/day1)}$ of greater than about 99.95% occupancy. In some aspects, the therapeutically effective amount of the compound of Formula (III) is an amount that results in a $BTKO_{(max/day1)}$ of greater than about 99% occupancy. In some aspects, the therapeutically effective amount of the compound of Formula (III) is an amount that results in a $BTKO_{(max/day1)}$ of greater than about 98% occupancy. In some aspects, the therapeutically effective amount of the compound of Formula (III) is an amount that results in a $BTKO_{(max/day1)}$ of greater than about 95% occupancy. In some aspects, the therapeutically effective amount of the compound of Formula (III) is an amount that results in a $BTKO_{(max/day1)}$ of greater than about 90% occupancy. In some aspects, the therapeutically effective amount of the compound of Formula (III) is an amount that results in a $BTKO_{(max/day1)}$ of greater than about 85% occupancy. In some aspects, the therapeutically effective amount of the compound of Formula (III) is an amount that results in a $BTKO_{(max/day1)}$ of greater than about 80% occupancy. In some aspects, the therapeutically effective amount of the compound of Formula (III) is an amount that results in a $BTKO_{(max/day1)}$ of greater than about 75% occupancy. In some aspects, the therapeutically effective amount of the compound of Formula (III) is an amount that results in a $BTKO_{(max/day1)}$ of greater than about 70% occupancy. In some aspects, the therapeutically effective amount of the compound of Formula (III) is an amount that results in a $BTKO_{(max/day1)}$ of greater than about 65% occupancy. In some aspects, the therapeutically effective amount of the compound of Formula (III) is an amount that results in a $BTKO_{(max/day1)}$ of greater than about 60% occupancy. In some aspects, the therapeutically effective amount of the compound of Formula (III) is an amount that results in a $BTKO_{(max/day1)}$ of greater than about 55% occupancy. In some aspects, the therapeutically effective amount of the compound of Formula (III) is an amount that results in a $BTKO_{(max/day1)}$ of greater than about 50% occupancy. In some aspects, the therapeutically effective amount of the compound of Formula (III) is an amount that results in a $BTKO_{(max/day1)}$ of greater than about 45% occupancy. In some aspects, the therapeutically effective amount of the compound of Formula (III) is an amount that results in a $BTKO_{(max/day1)}$ of greater than about 40% occupancy. In some aspects, the therapeutically effective amount of the compound of Formula (III) is an amount that results in a $BTKO_{(max/day1)}$ of greater than about 35% occupancy. In some aspects, the therapeutically effective amount of the compound of Formula (III) is an amount that results in a $BTKO_{(max/day1)}$ of greater than about 30% occupancy. In some aspects, the therapeutically effective amount of the compound of Formula (III) is an amount that results in a $BTKO_{(max/day1)}$ of greater than about 25% occupancy. In some aspects, the therapeutically effective amount of the compound of Formula (III) is an amount that results in a $BTKO_{(max/day1)}$ of greater than about 20% occupancy. In some aspects, the therapeutically effective amount of the compound of Formula (III) is an amount that results in a $BTKO_{(max/day1)}$ of greater than about 15% occupancy. In some aspects, the therapeutically effective amount of the compound of Formula (III) is an amount that results in a $BTKO_{(max/day1)}$ of greater than about 10% occupancy. In some aspects, the therapeutically effective amount of the compound of Formula (III) is an amount that results in a $BTKO_{(max/day1)}$ of greater than about 5% occupancy.

In some aspects, the therapeutically effective amount of the compound of Formula (III) is an amount that results in a $BTKO_{(max/day1)}$ of about 0.0001% occupancy to about 100% occupancy. In some aspects, the therapeutically effective amount of the compound of Formula (III) is an amount that results in a $BTKO_{(max/day1)}$ of about 0.0001% occupancy to about 99.9% occupancy. In some aspects, the therapeutically effective amount of the compound of Formula (III) is an amount that results in a $BTKO_{(max/day1)}$ of about 0.0001% occupancy to about 99.95% occupancy. In some aspects, the therapeutically effective amount of the compound of Formula (III) is an amount that results in a $BTKO_{(max/day1)}$ of about 0.0001% occupancy to about 99% occupancy. In some aspects, the therapeutically effective amount of the compound of Formula (III) is an amount that results in a $BTKO_{(max/day1)}$ of about 0.0001% occupancy to about 98% occupancy. In some aspects, the therapeutically effective amount of the compound of Formula (III) is an amount that results in a $BTKO_{(max/day1)}$ of about 0.0001% occupancy to about 95% occupancy.

In some aspects, the therapeutically effective amount of the compound of Formula (III) is an amount that results in a $BTKO_{(max/day1)}$ of about 0.0001% occupancy to about 90% occupancy. In some aspects, the therapeutically effective amount of the compound of Formula (III) is an amount that results in a $BTKO_{(max/day1)}$ of about 0.0001% occupancy to about 85% occupancy. In some aspects, the therapeutically effective amount of the compound of Formula (III) is an amount that results in a $BTKO_{(max/day1)}$ of about 0.0001% occupancy to about 80% occupancy. In some aspects, the therapeutically effective amount of the compound of Formula (III) is an amount that results in a $BTKO_{(max/day1)}$ of about 0.0001% occupancy to about 75% occupancy. In some aspects, the therapeutically effective amount of the compound of Formula (III) is an amount that results in a $BTKO_{(max/day1)}$ of about 0.0001% occupancy to about 70% occupancy. In some aspects, the therapeutically effective amount of the compound of Formula (III) is an amount that results in a $BTKO_{(max/day1)}$ of about 0.0001% occupancy to about 60% occupancy. In some aspects, the therapeutically effective amount of the compound of Formula (III) is an amount that results in a $BTKO_{(max/day1)}$ of about 0.0001% occupancy to about 50% occupancy. In some aspects, the therapeutically effective amount of the compound of Formula (III) is an amount that results in a $BTKO_{(max/day1)}$ of about 0.0001% occupancy to about 40% occupancy. In some aspects, the therapeutically effective amount of the compound of Formula (III) is an amount that results in a $BTKO_{(max/day1)}$ of about 0.0001% occupancy to about 30% occupancy. In some aspects, the therapeutically effective amount of the compound of Formula (III) is an amount that results in a $BTKO_{(max/day1)}$ of about 0.0001% occupancy to about 20% occupancy. In some aspects, the therapeutically effective amount of the compound of Formula (III) is an amount that results in a $BTKO_{(max/day1)}$ of about 0.0001% occupancy to about 10% occupancy. In some aspects, the therapeutically effective amount of the compound of Formula (III) is an amount that results in a $BTKO_{(max/day1)}$ of about 0.0001% occupancy to about 1% occupancy.In some aspects, the therapeutically effective amount of the compound of Formula (III) is an amount that results in a $BTKO_{(max/day1)}$ of about 30.9% occupancy to about 99.8% occupancy. In some aspects, the therapeutically effective amount of the compound of Formula (III) is an amount that results in a $BTKO_{(max/day1)}$ of about 87.1% occupancy to about 100% occupancy. In some aspects, the therapeutically effective amount of the compound of Formula (III) is an amount that results in a $BTKO_{(max/day1)}$ of about 90.4% occupancy. In some aspects, the therapeutically effective amount of the compound of Formula (III) is an amount that results in a $BTKO_{(max/day1)}$ of about 95.9% occupancy.

In some aspects, the therapeutically effective amount of the compound of Formula (III) is an amount that results in a $BTKO_{(max/ss)}$ (maximum BTK occupancy at steady state) of about 100% occupancy. In some aspects, the therapeutically effective amount of the compound of Formula (III) is an amount that results in a $BTKO_{(max/ss)}$ of greater than about 99.95% occupancy. In some aspects, the therapeutically effective amount of the compound of Formula (III) is an amount that results in a $BTKO_{(max/ss)}$ of greater than about 99% occupancy. In some aspects, the therapeutically effective amount of the compound of Formula (III) is an amount that results in a $BTKO_{(max/ss)}$ of greater than about 98% occupancy. In some aspects, the therapeutically effective amount of the compound of Formula (III) is an amount that results in a $BTKO_{(max/ss)}$ of greater than about 95% occupancy. In some aspects, the therapeutically effective amount of the compound of Formula (III) is an amount that results in a $BTKO_{(max/ss)}$ of greater than about 90% occupancy. In some aspects, the therapeutically effective amount of the compound of Formula (III) is an amount that results in a $BTKO_{(max/ss)}$ of greater than about 85% occupancy. In some aspects, the therapeutically effective amount of the compound of Formula (III) is an amount that results in a $BTKO_{(max/ss)}$ of greater than about 80% occupancy. In some aspects, the therapeutically effective amount of the compound of Formula (III) is an amount that results in a $BTKO_{(max/ss)}$ of greater than about 75% occupancy. In some aspects, the therapeutically effective amount of the compound of Formula (III) is an amount that results in a $BTKO_{(max/ss)}$ of greater than about 70% occupancy. In some aspects, the therapeutically effective amount of the compound of Formula (III) is an amount that results in a $BTKO_{(max/ss)}$ of greater than about 65% occupancy. In some aspects, the therapeutically effective amount of the compound of Formula (III) is an amount that results in a $BTKO_{(max/ss)}$ of greater than about 60% occupancy. In some aspects, the therapeutically effective amount of the compound of Formula (III) is an amount that results in a $BTKO_{(max/ss)}$ of greater than about 55% occupancy. In some aspects, the therapeutically effective amount of the compound of Formula (III) is an amount that results in a $BTKO_{(max/ss)}$ of greater than about 50% occupancy. In some aspects, the therapeutically effective amount of the compound of Formula (III) is an amount that results in a $BTKO_{(max/ss)}$ of greater than about 45% occupancy. In some aspects, the therapeutically effective amount of the compound of Formula (III) is an amount that results in a $BTKO_{(max/ss)}$ of greater than about 40% occupancy. In some aspects, the therapeutically effective amount of the compound of Formula (III) is an amount that results in a $BTKO_{(max/ss)}$ of greater than about 35% occupancy. In some aspects, the therapeutically effective amount of the compound of Formula (III) is an amount that results in a $BTKO_{(max/ss)}$ of greater than about 30% occupancy. In some aspects, the therapeutically effective amount of the compound of Formula (III) is an amount that results in a $BTKO_{(max/ss)}$ of greater than about 25% occupancy. In some aspects, the therapeutically effective amount of the compound of Formula (III) is an amount that results in a $BTKO_{(max/ss)}$ of greater than about 20% occupancy. In some aspects, the therapeutically effective amount of the compound of Formula (III) is an amount that results in a $BTKO_{(max/ss)}$ of greater than about 15% occupancy. In some aspects, the therapeutically effective amount of the compound of Formula (III) is an amount that results in a $BTKO_{(max/ss)}$ of greater than about 10% occupancy. In some aspects, the therapeutically effective amount of the compound of Formula (III) is an amount that results in a $BTKO_{(max/ss)}$ of greater than about 5% occupancy.

In some aspects, the therapeutically effective amount of the compound of Formula (III) is an amount that results in a $BTKO_{(max/ss)}$ of about 0.0001% occupancy to about 100% occupancy. In some aspects, the therapeutically effective amount of the compound of Formula (III) is an amount that results in a $BTKO_{(max/ss)}$ of about 0.0001% occupancy to about 99.9% occupancy. In some aspects, the therapeutically effective amount of the compound of Formula (III) is an amount that results in a $BTKO_{(max/ss)}$ of about 0.0001% occupancy to about 99.95% occupancy. In some aspects, the therapeutically effective amount of the compound of Formula (III) is an amount that results in a $BTKO_{(max/ss)}$ of about 0.0001% occupancy to about 99% occupancy. In some aspects, the therapeutically effective amount of the compound of Formula (III) is an amount that results in a $BTKO_{(max/ss)}$ of about 0.0001% occupancy to about 98% occupancy. In some aspects, the therapeutically effective amount of the compound of Formula (III) is an amount that results in a $BTKO_{(max/ss)}$ of about 0.0001% occupancy to about 95% occupancy.

In some aspects, the therapeutically effective amount of the compound of Formula (III) is an amount that results in a $BTKO_{(max/ss)}$ of about 0.0001% occupancy to about 90% occupancy. In some aspects, the therapeutically effective amount of the compound of Formula (III) is an amount that results in a $BTKO_{(max/ss)}$ of about 0.0001% occupancy to about 85% occupancy. In some aspects, the therapeutically effective amount of the compound of Formula (III) is an amount that results in a $BTKO_{(max/ss)}$ of about 0.0001% occupancy to about 80% occupancy. In some aspects, the therapeutically effective amount of the compound of Formula (III) is an amount that results in a $BTKO_{(max/ss)}$ of about 0.0001% occupancy to about 75% occupancy. In some aspects, the therapeutically effective amount of the compound of Formula (III) is an amount that results in a $BTKO_{(max/ss)}$ of about 0.0001% occupancy to about 70% occupancy. In some aspects, the therapeutically effective amount of the compound of Formula (III) is an amount that results in a $BTKO_{(max/ss)}$ of about 0.0001% occupancy to about 60% occupancy. In some aspects, the therapeutically effective amount of the compound of Formula (III) is an amount that results in a $BTKO_{(max/ss)}$ of about 0.0001% occupancy to about 50% occupancy. In some aspects, the therapeutically effective amount of the compound of Formula (III) is an amount that results in a $BTKO_{(max/ss)}$ of about 0.0001% occupancy to about 40% occupancy. In some aspects, the therapeutically effective amount of the compound of Formula (III) is an amount that results in a $BTKO_{(max/ss)}$ of about 0.0001% occupancy to about 30% occupancy. In some aspects, the therapeutically effective amount of the compound of Formula (III) is an amount that results in a $BTKO_{(max/ss)}$ of about 0.0001% occupancy to about 20% occupancy. In some aspects, the therapeutically effective amount of the compound of Formula (III) is an amount that results in a $BTKO_{(max/ss)}$ of about 0.0001% occupancy to about 10% occupancy. In some aspects, the therapeutically effective amount of the compound of Formula (III) is an amount that results in a $BTKO_{(max/ss)}$ of about 0.0001% occupancy to about 1% occupancy. In some aspects, the therapeutically effective amount of the compound of Formula (III) is an amount that results in a $BTKO_{(max/ss)}$ of about 59.4% occupancy to about 99.9% occupancy. In some aspects, the therapeutically effective amount of the compound of Formula (III) is an amount that results in a $BTKO_{(max/ss)}$ of about 90.2% occupancy to about 100% occupancy. In some aspects, the therapeutically effective amount of the compound of Formula (III) is an amount that results in a $BTKO_{(max/ss)}$ of about 99.8% occupancy. In some aspects, the therapeutically effective amount of the compound of Formula (III) is an amount that results in a $BTKO_{(max/ss)}$ of about 99.8% occupancy.

In some aspects, the therapeutically effective amount of the compound of Formula (III) is an amount that results in a $BTKO_{(trough/day\ 1)}$ (trough BTK occupancy at day 1) of about 100% occupancy. In some aspects, the therapeutically effective amount of the compound of Formula (III) is an amount that results in a $BTKO_{(trough/day\ 1)}$ of greater than about 99.95% occupancy. In some aspects, the therapeutically effective amount of the compound of Formula (III) is an amount that results in a $BTKO_{(trough/day\ 1)}$ of greater than about 99% occupancy. In some aspects, the therapeutically effective amount of the compound of Formula (III) is an amount that results in a $BTKO_{(trough/day\ 1)}$ of greater than about 98% occupancy. In some aspects, the therapeutically effective amount of the compound of Formula (III) is an amount that results in a $BTKO_{(trough/day\ 1)}$ of greater than about 95% occupancy. In some aspects, the therapeutically effective amount of the compound of Formula (III) is an amount that results in a $BTKO_{(trough/day\ 1)}$ of greater than about 90% occupancy. In some aspects, the therapeutically effective amount of the compound of Formula (III) is an amount that results in a $BTKO_{(trough/day\ 1)}$ of greater than about 85% occupancy. In some aspects, the therapeutically effective amount of the compound of Formula (III) is an amount that results in a $BTKO_{(trough/day\ 1)}$ of greater than about 80% occupancy. In some aspects, the therapeutically effective amount of the compound of Formula (III) is an amount that results in a $BTKO_{(trough/day\ 1)}$ of greater than about 75% occupancy. In some aspects, the therapeutically effective amount of the compound of Formula (III) is an amount that results in a $BTKO_{(trough/day\ 1)}$ of greater than about 70% occupancy. In some aspects, the therapeutically effective amount of the compound of Formula (III) is an amount that results in a $BTKO_{(trough/day\ 1)}$ of greater than about 65% occupancy. In some aspects, the therapeutically effective amount of the compound of Formula (III) is an amount that results in a $BTKO_{(trough/day\ 1)}$ of greater than about 60% occupancy. In some aspects, the therapeutically effective amount of the compound of Formula (III) is an amount that results in a $BTKO_{(trough/day\ 1)}$ of greater than about 55% occupancy. In some aspects, the therapeutically effective amount of the compound of Formula (III) is an amount that results in a $BTKO_{(trough/day\ 1)}$ of greater than about 50% occupancy. In some aspects, the therapeutically effective amount of the compound of Formula (III) is an amount that results in a $BTKO_{(trough/day1)}$ of greater than about 45% occupancy. In some aspects, the therapeutically effective amount of the compound of Formula (III) is an amount that results in a $BTKO_{(trough/day\ 1)}$ of greater than about 40% occupancy. In some aspects, the therapeutically effective amount of the compound of Formula (III) is an amount that results in a $BTKO_{(trough/day\ 1)}$ of greater than about 35% occupancy. In some aspects, the therapeutically effective amount of the compound of Formula (III) is an amount that results in a $BTKO_{(trough/day\ 1)}$ of greater than about 30% occupancy. In some aspects, the therapeutically effective amount of the compound of Formula (III) is an amount that results in a $BTKO_{(trough/day\ 1)}$ of greater than about 25% occupancy. In some aspects, the therapeutically effective amount of the compound of Formula (III) is an amount that results in a $BTKO_{(trough/day\ 1)}$ of greater than about 20% occupancy. In some aspects, the therapeutically effective amount of the compound of Formula (III) is an amount that results in a $BTKO_{(trough/day\ 1)}$ of greater than about 15% occupancy. In some aspects, the therapeutically effective amount of the compound of Formula (III) is an amount that results in a $BTKO_{(trough/day\ 1)}$ of greater than about 10% occupancy. In some aspects, the therapeutically effective amount of the compound of Formula (III) is an amount that results in a $BTKO_{(trough/day\ 1)}$ of greater than about 5% occupancy.

In some aspects, the therapeutically effective amount of the compound of Formula (III) is an amount that results in a $BTKO_{(trough/day\ 1)}$ of about 0.0001% occupancy to about 100% occupancy. In some aspects, the therapeutically effective amount of the compound of Formula (III) is an amount that results in a $BTKO_{(trough/day\ 1)}$ of about 0.0001% occupancy to about 99.9% occupancy. In some aspects, the therapeutically effective amount of the compound of Formula (III) is an amount that results in a $BTKO_{(trough/day\ 1)}$ of about 0.0001% occupancy to about 99.95% occupancy. In some aspects, the therapeutically effective amount of the compound of Formula (III) is an amount that results in a $BTKO_{(trough/day\ 1)}$ Of about 0.0001% occupancy to about 99% occupancy. In some aspects, the therapeutically effective amount of the compound of Formula (III) is an amount that results in a $BTKO_{(trough/day\ 1)}$ Of about 0.0001% occupancy to about 98% occupancy. In some aspects, the therapeutically effective amount of the compound of Formula (III) is an amount that results in a $BTKO_{(trough/day\ 1)}$ Of about 0.0001% occupancy to about 95% occupancy.

In some aspects, the therapeutically effective amount of the compound of Formula (III) is an amount that results in a $BTKO_{(trough/day\ 1)}$ of about 0.0001% occupancy to about 90% occupancy. In some aspects, the therapeutically effective amount of the compound of Formula (III) is an amount that results in a $BTKO_{(trough/day\ 1)}$ of about 0.0001% occupancy to about 85% occupancy. In some aspects, the therapeutically effective amount of the compound of Formula (III) is an amount that results in a $BTKO_{(trough/day\ 1)}$ of about 0.0001% occupancy to about 80% occupancy. In some aspects, the therapeutically effective amount of the compound of Formula (III) is an amount that results in a $BTKO_{(trough/day\ 1)}$ of about 0.0001% occupancy to about 75% occupancy. In some aspects, the therapeutically effective amount of the compound of Formula (III) is an amount that results in a $BTKO_{(trough/day\ 1)}$Of about 0.0001% occupancy to about 70% occupancy. In some aspects, the therapeutically effective amount of the compound of Formula (III) is an amount that results in a $BTKO_{(trough/day\ 1)}$ of about 0.0001% occupancy to about 60% occupancy. In some aspects, the therapeutically effective amount of the compound of Formula (III) is an amount that results in a $BTKO_{(trough/day\ 1)}$ of about 0.0001% occupancy to about 50% occupancy. In some aspects, the therapeutically effective amount of the compound of Formula (III) is an amount that results in a $BTKO_{(trough/day\ 1)}$ of about 0.0001% occupancy to about 40% occupancy. In some aspects, the therapeutically effective amount of the compound of Formula (III) is an amount that results in a $BTKO_{(trough/day\ 1)}$ of about 0.0001% occupancy to about 30% occupancy. In some aspects, the therapeutically effective amount of the compound of Formula (III) is an amount that results in a $BTKO_{(trough/day\ 1)}$ of about 0.0001% occupancy to about 20% occupancy. In some aspects, the therapeutically effective amount of the compound of Formula (III) is an amount that results in a $BTKO_{(trough/day\ 1)}$ of about 0.0001% occupancy to about 10% occupancy. In some aspects, the therapeutically effective amount of the compound of Formula (III) is an amount that results in a $BTKO_{(trough/day\ 1)}$ of about 0.0001% occupancy to about 1% occupancy. In some aspects, the therapeutically effective amount of the compound of Formula (III) is an amount that results in a $BTKO_{(trough/day\ 1)}$ of about 63.9% occupancy to about 97.3% occupancy. In some aspects, the therapeutically effective amount of the compound of Formula (III) is an amount that results in a $BTKO_{(trough/day\ 1)}$ of about 23.3% occupancy to about 91.3% occupancy. In some aspects, the therapeutically effective amount of the compound of Formula (III) is an amount that results in a $BTKO_{(trough/day\ 1)}$ of about 77.4% occupancy. In some aspects, the therapeutically effective amount of the compound of Formula (III) is an amount that results in a $BTKO_{(trough/day\ 1)}$ of about 85.4% occupancy.

In some aspects, the therapeutically effective amount of the compound of Formula (III) is an amount that results in a $BTKO_{(trough/ss)}$ (trough BTK occupancy at steady state) of about 100% occupancy. In some aspects, the therapeutically effective amount of the compound of Formula (III) is an amount that results in a $BTKO_{(trough/ss)}$ of greater than about 99.95% occupancy. In some aspects, the therapeutically effective amount of the compound of Formula (III) is an amount that results in a $BTKO_{(trough/ss)}$ of greater than about 99% occupancy. In some aspects, the therapeutically effective amount of the compound of Formula (III) is an amount that results in a $BTKO_{(trough/ss)}$ of greater than about 98% occupancy. In some aspects, the therapeutically effective amount of the compound of Formula (III) is an amount that results in a $BTKO_{(trough/ss)}$ of greater than about 95% occupancy. In some aspects, the therapeutically effective amount of the compound of Formula (III) is an amount that results in a $BTKO_{(trough/ss)}$ of greater than about 90% occupancy. In some aspects, the therapeutically effective amount of the compound of Formula (III) is an amount that results in a $BTKO_{(trough/ss)}$ of greater than about 85% occupancy. In some aspects, the therapeutically effective amount of the compound of Formula (III) is an amount that results in a $BTKO_{(trough/ss)}$ of greater than about 80% occupancy. In some aspects, the therapeutically effective amount of the compound of Formula (III) is an amount that results in a $BTKO_{(trough/ss)}$ of greater than about 75% occupancy. In some aspects, the therapeutically effective amount of the compound of Formula (III) is an amount that results in a $BTKO_{(trough/ss)}$ of greater than about 70% occupancy. In some aspects, the therapeutically effective amount of the compound of Formula (III) is an amount that results in a $BTKO_{(trough/ss)}$ of greater than about 65% occupancy. In some aspects, the therapeutically effective amount of the compound of Formula (III) is an amount that results in a $BTKO_{(trough/ss)}$ of greater than about 60% occupancy. In some aspects, the therapeutically effective amount of the compound of Formula (III) is an amount that results in a $BTKO_{(trough/ss)}$ of greater than about 55% occupancy. In some aspects, the therapeutically effective amount of the compound of Formula (III) is an amount that results in a $BTKO_{(trough/ss)}$ of greater than about 50% occupancy. In some aspects, the therapeutically effective amount of the compound of Formula (III) is an amount that results in a $BTKO_{(trough/ss)}$ of greater than about 45% occupancy. In some aspects, the therapeutically effective amount of the compound of Formula (III) is an amount that results in a $BTKO_{(trough/ss)}$ of greater than about 40% occupancy. In some aspects, the therapeutically effective amount of the compound of Formula (III) is an amount that results in a $BTKO_{(trough/ss)}$ of greater than about 35% occupancy. In some aspects, the therapeutically effective amount of the compound of Formula (III) is an amount that results in a $BTKO_{(trough/ss)}$ of greater than about 30% occupancy. In some aspects, the therapeutically effective amount of the compound of Formula (III) is an amount that results in a $BTKO_{(trough/ss)}$ of greater than about 25% occupancy. In some aspects, the therapeutically effective amount of the compound of Formula (III) is an amount that results in a $BTKO_{(trough/ss)}$ of greater than about 20% occupancy. In some aspects, the therapeutically effective amount of the compound of Formula (III) is an amount that results in a $BTKO_{(trough/ss)}$ of greater than about 15% occupancy. In some aspects, the therapeutically effective amount of the compound of Formula (III) is an amount that results in a $BTKO_{(trough/ss)}$ of greater than about 10% occupancy. In some aspects, the therapeutically effective amount of the compound of Formula (III) is an amount that results in a $BTKO_{(trough/ss)}$ of greater than about 5% occupancy.

In some aspects, the therapeutically effective amount of the compound of Formula (III) is an amount that results in a $BTKO_{(trough/ss)}$ of about 50.2% occupancy to about 95.4% occupancy. In some aspects, the therapeutically effective amount of the compound of Formula (III) is an amount that results in a $BTKO_{(trough/ss)}$ of about 0.0001% occupancy to about 100% occupancy. In some aspects, the therapeutically effective amount of the compound of Formula (III) is an amount that results in a $BTKO_{(trough/ss)}$ of about 0.0001% occupancy to about 99.9% occupancy. In some aspects, the therapeutically effective amount of the compound of Formula (III) is an amount that results in a $BTKO_{(trough/ss)}$ of about 0.0001% occupancy to about 99.95% occupancy. In some aspects, the therapeutically effective amount of the compound of Formula (III) is an amount that results in a $BTKO_{(trough/ss)}$ of about 0.0001% occupancy to about 99% occupancy. In some aspects, the therapeutically effective amount of the compound of Formula (III) is an amount that results in a $BTKO_{(trough/ss)}$ of about 0.0001% occupancy to about 98% occupancy. In some aspects, the therapeutically effective amount of the compound of Formula (III) is an amount that results in a $BTKO_{(trough/ss)}$ of about 0.0001% occupancy to about 95% occupancy.

In some aspects, the therapeutically effective amount of the compound of Formula (III) is an amount that results in a $BTKO_{(trough/ss)}$ of about 0.0001% occupancy to about 90% occupancy. In some aspects, the therapeutically effective amount of the compound of Formula (III) is an amount that results in a $BTKO_{(trough/ss)}$ of about 0.0001% occupancy to about 85% occupancy. In some aspects, the therapeutically effective amount of the compound of Formula (III) is an amount that results in a $BTKO_{(trough/ss)}$ of about 0.0001% occupancy to about 80% occupancy. In some aspects, the therapeutically effective amount of the compound of Formula (III) is an amount that results in a $BTKO_{(trough/ss)}$ of about 0.0001% occupancy to about 75% occupancy. In some aspects, the therapeutically effective amount of the compound of Formula (III) is an amount that results in a $BTKO_{(trough/ss)}$ of about 0.0001% occupancy to about 70% occupancy. In some aspects, the therapeutically effective amount of the compound of Formula (III) is an amount that results in a $BTKO_{(trough/ss)}$ of about 0.0001% occupancy to about 60% occupancy. In some aspects, the therapeutically effective amount of the compound of Formula (III) is an amount that results in a $BTKO_{(trough/ss)}$ of about 0.0001% occupancy to about 50% occupancy. In some aspects, the therapeutically effective amount of the compound of Formula (III) is an amount that results in a $BTKO_{(trough/ss)}$ of about 0.0001% occupancy to about 40% occupancy. In some aspects, the therapeutically effective amount of the compound of Formula (III) is an amount that results in a $BTKO_{(trough/ss)}$ of about 0.0001% occupancy to about 30% occupancy. In some aspects, the therapeutically effective amount of the compound of Formula (III) is an amount that results in a $BTKO_{(trough/ss)}$ of about 0.0001% occupancy to about 20% occupancy. In some aspects, the therapeutically effective amount of the compound of Formula (III) is an amount that results in a $BTKO_{(trough/ss)}$ of about 0.0001% occupancy to about 10% occupancy. In some aspects, the therapeutically effective amount of the compound of Formula (III) is an amount that results in a $BTKO_{(trough/ss)}$ of about 0.0001% occupancy to about 1% occupancy. In some aspects, the therapeutically effective amount of the compound of Formula (III) is an amount that results in a $BTKO_{(trough/ss)}$ of about 75.5% occupancy to about 99.3% occupancy. In some aspects, the therapeutically effective amount of the compound of Formula (III) is an amount that results in a $BTKO_{(trough/ss)}$ of about 80.7% occupancy. In some aspects, the therapeutically effective amount of the compound of Formula (III) is an amount that results in a $BTKO_{(trough/ss)}$ of about 86.0% occupancy. In some aspects, the therapeutically effective amount of the compound of Formula (III) is administered once a day. In some aspects, the therapeutically effective amount of the compound of Formula (III) is administered twice a day. In some aspects, the therapeutically effective amount of the compound of Formula (III) is administered three times a day. In some aspects the therapeutically effective amount of the compound of formula (III) is administered orally.

In some aspects, the the compound of Formula (III) is used as a front line therapy, second line therapy, third line therapy, fourth line therapy, fifth line therapy, or sixth line therapy. In some aspects, the compound of Formula (III) treats a refractory hematological malignancy. In some aspects, the compound of Formula (III) is used as a maintenance therapy. In some aspects, the compound of Formula (III is administered until disease progression, unacceptable toxicity, or individual choice.

In addition, the compounds of the disclosure may be used in combination with additional active ingredients in the treatment of the above conditions. The additional active ingredients may be coadministered separately with a compound of the disclosure or included with such an agent in a pharmaceutical composition according to the disclosure. The combination may serve to increase efficacy (e.g., by including in the combination a compound potentiating the potency or effectiveness of an active agent according to the disclosure), decrease one or more side effects, or decrease the required dose of the active agent according to the disclosure.

The compounds of the disclosure are used, alone or in combination with one or more additional active ingredients, to formulate pharmaceutical compositions of the disclosure. A pharmaceutical composition of the disclosure comprises: (a) an effective amount of at least one compound in accordance with the disclosure; and (b) a pharmaceutically acceptable excipient.

In some aspects, the compound of Formula (III) can be administered in combination with one or more additional therapeutic agent. In some aspects, the one of more additional therapeutic agent is a Bcl2 inhibitor. In some aspects, the Bcl2 inhibitor is 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin5-yloxy)benzamide) also known as venetoclax. In some aspects, 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin5-yloxy)benzamide) is administerd according to a weekly ramp up dosage regimen comprising administering about 20 mg/day for the first week, about 50 mg/day for the second week, about100 mg/day for the third week, 200 mg/day for the third week, and 400 mg/day for the fourth week and beyond. In some aspects, the 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin5-yloxy)benzamide) is administered orally. In some aspects, the compound of Formula (III) can be administered in combination with 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin5-yloxy)benzamide) and rituximab. In some aspects, the compound of Formula (III) can be administered in combination with 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin5-yloxy)benzamide) and obinutuzumab. In some aspects, the compound of Formula (III) and Bcl2 inhibitor can be administeredsimultaneously, concurrently or sequentially with no specific intervening time limits.

In some aspects, the compound of Formula (III) can be administered in combination with one or more additional therapeutic agent. In some aspects, the one of more additional therapeutic agents are cyclophospharnide, doxorubicin, vincristine, prednisone and rituximab (R—CHOP).

In some aspects, a method of treating non-Hodgkin's lymphoma (NHL) in a subject comprises administering a therapeutically effective dose of about 140 mg to about 560 mg of compound of Formula (III). In some aspects, therapeutically effective amount of the compound of Formula (III) is an amount that results in a $C_{(max,day1)}$ of about 429.75 ng/ml to about 1,719 ng/ml. In some aspects, the therapeutically effective amount of the compound of Formula (III) is an amount that results in a $C_{(max,ss)}$ of about 435.1 ng/ml to about 1,740.4 ng/ml. In some aspects, the administration of the compound of Formula (III) is once daily or twice daily. In some aspects, the compound of Formula (III) is administered in combination with R—CHOP. In some aspects, the compound of Formula (III) is administered in combination with venetoclax. The venetoclax is administerd according to a weekly ramp up dosage regimen comprising administering about 20 mg/day for the first week, about 50 mg/day for the second week, about100 mg/day for the third week, 200 mg/day for the third week, and 400 mg/day for the fourth week and beyond. In some aspects, the NHL is relapsed or refractory NHL.

In some aspects, a method of treating diffuse large B-cell lymphoma (DLBCL) in a subject comprises administering a therapeutically effective dose of about 140 mg to about 560 mg of compound of Formula (III). In some aspects, therapeutically effective amount of the compound of Formula (III) is an amount that results in a $C_{(max,day1)}$ of about 429.75 ng/ml to about 1,719 ng/ml. In some aspects, the therapeutically effective amount of the compound of Formula (III) is an amount that results in a $C_{(max,ss)}$ of about 435.1 ng/ml to about 1,740.4 ng/ml. In some aspects, the administration of the compound of Formula (III) is once daily or twice daily. In some aspects, the compound of Formula (III) is administered in combination with R—CHOP. In some aspects, the compound of Formula (III) is administered in combination with venetoclax. The venetoclax is administerd according to a weekly ramp up dosage regimen comprising administering about 20 mg/day for the first week, about 50 mg/day for the second week, about100 mg/day for the third week, 200 mg/day for the third week, and 400 mg/day for the fourth week and beyond. In some aspects, the DLBCL is relapsed or refractory DLBCL.

In some aspects, a method of treating mantle cell lymphoma (MCL) in a subject comprises administering a therapeutically effective dose of about 140 mg to about 560 mg of compound of Formula (III). In some aspects, therapeutically effective amount of the compound of Formula (III) is an amount that results in a $C_{(max,day1)}$ of about 429.75 ng/ml to about 1,719 ng/ml. In some aspects, the therapeutically effective amount of the compound of Formula (III) is an amount that results in a $C_{(max,ss)}$ of about 435.1 ng/ml to about 1,740.4 ng/ml. In some aspects, the administration of the compound of Formula (III) is once daily or twice daily. In some aspects, the compound of Formula (III) is administered in combination with R—CHOP. In some aspects, the compound of Formula (III) is administered in combination with venetoclax. The venetoclax is administerd according to a weekly ramp up dosage regimen comprising administering about 20 mg/day for the first week, about 50 mg/day for the second week, about100 mg/day for the third week, 200 mg/day for the third week, and 400 mg/day for the fourth week and beyond. In some aspects, the MCL is relapsed or refractory MCL.

In some aspects, a method of treating follicular lymphoma (FL) in a subject comprises administering a therapeutically effective dose of about 140 mg to about 560 mg of compound of Formula (III). In some aspects, therapeutically effective amount of the compound of Formula (III) is an amount that results in a $C_{(max,day1)}$ of about 429.75 ng/ml to about 1,719 ng/ml. In some aspects, the therapeutically effective amount of the compound of Formula (III) is an amount that results in a $C_{(max,ss)}$ of about 435.1 ng/ml to about 1,740.4 ng/ml. In some aspects, the administration of the compound of Formula (III) is once daily or twice daily. In some aspects, the compound of Formula (III) is administered in combination with R—CHOP. In some aspects, the compound of Formula (III) is administered in combination with venetoclax. The venetoclax is administerd according to a weekly ramp up dosage regimen comprising administering about 20 mg/day for the first week, about 50 mg/day for the second week, about100 mg/day for the third week, 200 mg/day for the third week, and 400 mg/day for the fourth week and beyond. In some aspects, the FL is relapsed or refractory FL.

In some aspects, a method of treating marginal zone lymphoma (MZL) in a subject comprises administering a therapeutically effective dose of about 140 mg to about 560 mg of compound of Formula (III). In some aspects, therapeutically effective amount of the compound of Formula (III) is an amount that results in a $C_{(max,day1)}$ of about 429.75 ng/ml to about 1,719 ng/ml. In some aspects, the therapeutically effective amount of the compound of Formula (III) is an amount that results in a $C_{(max,ss)}$ of about 435.1 ng/ml to about 1,740.4 ng/ml. In some aspects, the administration of the compound of Formula (III) is once daily or twice daily. In some aspects, the compound of Formula (III) is administered in combination with R—CHOP. In some aspects, the compound of Formula (III) is administered in combination with venetoclax. The venetoclax is administerd according to a weekly ramp up dosage regimen comprising administering about 20 mg/day for the first week, about 50 mg/day for the second week, about100 mg/day for the third week, 200 mg/day for the third week, and 400 mg/day for the fourth week and beyond. In some aspects, the MZL is relapsed or refractory MZL.

In some aspects, a method of treating chronic lymphocytic leukemia (CLL) in a subject comprises administering a therapeutically effective dose of about 140 mg to about 560 mg of compound of Formula (III). In some aspects, therapeutically effective amount of the compound of Formula (III) is an amount that results in a $C_{(max,day1)}$ of about 429.75 ng/ml to about 1,719 ng/ml. In some aspects, the therapeutically effective amount of the compound of Formula (III) is an amount that results in a $C_{(max,ss)}$ of about 435.1 ng/ml to about 1740.4 ng/ml. In some aspects, the administration of the compound of Formula (III) is once daily or twice daily. In some aspects, the compound of Formula (III) is administered in combination with R—CHOP. In some aspects, the compound of Formula (III) is administered in combination with venetoclax. The venetoclax is administerd according to a weekly ramp up dosage regimen comprising administering about 20 mg/day for the first week, about 50 mg/day for the second week, about100 mg/day for the third week, 200 mg/day for the third week, and 400 mg/day for the fourth week and beyond. In some aspects, the CLL is relapsed or refractory CLL.

In some aspects, a method of treating small lymphocytic lymphoma (SLL) in a subject comprises administering a therapeutically effective dose of about 140 mg to about 560 mg of compound of Formula (III). In some aspects, therapeutically effective amount of the compound of Formula (III) is an amount that results in a $C_{(max,day1)}$ of about 429.75 ng/ml to about 1,719 ng/ml. In some aspects, the therapeutically effective amount of the compound of Formula (III) is an amount that results in a $C_{(max,ss)}$ of about 435.1 ng/ml to about 1,740.4 ng/ml. In some aspects, the administration of compound of Formula (III) is once daily or twice daily. In some aspects, the compound of Formula (III) is administered in combination with R—CHOP. In some aspects, the compound of Formula (III) is administered in combination with venetoclax. The venetoclax is administerd according to a weekly ramp up dosage regimen comprising administering about 20 mg/day for the first week, about 50 mg/day for the second week, about100 mg/day for the third week, 200 mg/day for the third week, and 400 mg/day for the fourth week and beyond. In some aspects, the SLL is relapsed or refractory SLL.

In some aspects, a method of treating Waldenstrom macroglobulinemia (WM) in a subject comprises administering a therapeutically effective dose of about 140 mg to about 560 mg of compound of Formula (III). In some aspects, therapeutically effective amount of the compound of Formula (III) is an amount that results in a $C_{(max,day1)}$ of about 429.75 ng/ml to about 1,719 ng/ml. In some aspects, the therapeutically effective amount of the compound of Formula (III) is an amount that results in a $C_{(max,ss)}$ of about 435.1 ng/ml to about 1,740.4 ng/ml. In some aspects, the administration of compound of Formula (III) is once daily or twice daily. In some aspects, the compound of Formula (III) is administered in combination with R—CHOP. In some aspects, the compound of Formula (III) is administered in combination with venetoclax. The venetoclax is administerd according to a weekly ramp up dosage regimen comprising administering about 20 mg/day for the first week, about 50 mg/day for the second week, about100 mg/day for the third week, 200 mg/day for the third week, and 400 mg/day for the fourth week and beyond. In some aspects, the WM is relapsed or refractory WM.

In some aspects, the compound of Formula (III) can be administered in combination with one or more additional therapeutic agents selected from the group consisting of a chemotherapeutic agent, a steroid, an immunotherapeutic agent, a targeted therapy, and any combination thereof. In some aspects, the one or more additional therapeutic agent includes, but is not limited to a B cell receptor pathway inhibitor B cell receptor signaling inhibitor, a PI3K inhibitor, an IAP inhibitor, an mTOR inhibitor, a radioimmunotherapeutic, a DNA damaging agent, a proteosome inhibitor, a histone deacetylase inhibitor, a protein kinase inhibitor, a hedgehog inhibitor, an Hsp90 inhibitor, a telomerase inhibitor, a Jakl/2 inhibitor, a protease inhibitor, a PKC inhibitor, a PARP inhibitor, and any combination thereof. In some aspects, the B cell receptor pathway inhibitor includes, but is not limited to a CD79A inhibitor, a CD79B inhibitor, a CD 19 inhibitor, a Lyn inhibitor, a Syk inhibitor, a PI3K inhibitor, a Blnk inhibitor, a PLCy inhibitor, a PKCP inhibitor, or an inhibitor of mitogen-activated protein kinase signaling, (e.g., U0126, PD98059, PD184352, PD0325901, ARRY-142886, SB239063, SP600125, BAY 43-9006, wortmannin, LY294002) or a combination thereof. In some aspects, the one or more additional therapeutic agents include, but are not limited to chlorambucil, ifosphamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, cyclophosphamide, hydroxydaunorubicin, vincristine, prednisone, rituximab, bendamustine, etoposide, prednisolone, and any combination thereof. In some aspects, the one or more therapeutic agents is a nitrogen mustard including but not limited to bendamustine, chlorambucil, chlormethine, cyclophosphamide, ifosfamide, melphalan, prednimustine, trofosfamide; Alkyl Sulfonates such as, but not limited to busulfan, mannosulfan, treosulfan; Ethylene Imines, carboquone, thiotepa, triaziquone; Nitrosoureas such as, but not limited to carmustine, fotemustine, lomustine, nimustine, ranimustine, semustine, streptozocin; Epoxides such as. but not limited to etoglucid; Other Alkylating Agents such as, but not limited to dacarbazine, mitobronitol, pipobroman. temozolomide; Folic Acid Analogues such as, but not limited to methotrexate, pemetrexed, pralatrexate, ralitrexed; Purine Analogs such as, but not limited to cladrbine, clofarabine, fludarabine, mercaptopurine, nelarabine tioguanine; Pyrirmidine Analogs such as, but not limited to azacitidine, capecitabine, carmofur, cytarabine, decitabine, fluorouracil, gemcitabine, tegafur: *Vinca*; Alkaloids such as for example vinblastine, vincristine, vindesine, vinflunine, vinorelbine: Podophyllotoxin Derivatives such as, but not limited to etoposide, teniposide; Colchicine derivatives such as, but not limited to demecolcine; Taxanes such as. but not limited to docetaxel, paclitaxel, paclitaxel poliglumex: Other Plant Alkaloids and Natural Products such as, but not limited to trabectedin: Actinomycines such as, but not limited to dactinomycin; Antracyclines such as for example aclarubicin, daunorubicin, doxorubicin, epirubicin, idarubicin, mitoxantrone, pirarubicin valrubicin, zorubincin; Other Cytotoxic Antibiotics such as, but not limited to bleomycin, ixabepilone, mitomycin, plicamycin; Platinum Compounds such as for example carboplatin, cisplatin, oxaliplatin, satraplatin; Methylhydrazines such as, but not limited to procarbazine; Sensitizers such as, but not limited to aminolevulinic acid, efaproxiral, methyl aminolevulinate, porfimer sodium, temoporfin; Protein Kinase Inhibitors such as. but not limited to dasatinib, erlotinib, everolimus, gefitinib, imatinib, lapatinib, nilotinib, pazopanib, sorafenib, sunitinib, temsirolimus; Other Antineoplastic Agents such as, but not limited to alitretinoin, altretamine, amzacrine anagrelide, arsenic trioxide, asparaginase, bexarotene., bortezomib. celecoxib. denileukin diftitox, estramustine, hydroxycarbamide, irinotecan, lonidamine. masoprocol, miltefosine, mitoguazone, mitotane, oblimersen, pegaspargase, pentostatin, romidepsin, sitimagene ceradenovec, tiazofurine, topotecan, tretinoin, vorinostat; Estrogens such as, but not limited to diethylstilbenol, ethinylestradiol, fosfestrol polyestradiol phosphate: Progestogens such as, but not limited to gestonorone, medroxyprogesterone, megestrol; Gonadotropin Releasing Hormone Analogs such as, but not limited to buserelin; goserelin. leuprorelin, triptorelin; Anti-Estrogens such as but not limited to fulvestrant, tamoxifen toremifene; Anti-Androgens such as, but not limited to bicalutamide, flutamide, nilutamide, Enzyme Inhibitors, aminoglutethimide, anastrozole, exemestane, formestane, letrozole, vorozole; Other Hormone Antagonists such as, but not limited to abarelix, degarelix; Immunostimulants such as. but not limited to histamine dihydrochloride. mifamurtide. pidotimod, plerixafor, roquinimex, thymopentin: Immunosuppressants such as, but not limited to everolimus, gusperimus, leflunomide, mycophenolic acid, sirolimus; Calcineurin Inhibitors such as, but not limited to ciclosporin, tacrolimus; Other Immunosuppressants such as, but not limited to azathioprine, lenalidomide, methotrexate, thalidomide; and Radiopharmaceuticals such as, but not limited to, iobenguane, interferons, interleukins, Tumor Necrosis Factors, Growth Factors, or the like., immunostimulants such as, but not limited to ancestim, filgrastim, lenograstim, molgramostim, pegfilgrastim, sargramostimn; Iterferons such as, but not limited to interferon alfa natural, interferon alfa-2a, interferon alfa-2b, interferon alfacon-1, interferon alfa-n1, interferon beta natural, interferon beta-1a, interferon beta-1b, interferon gamma, peginterferon alfa-2a, peginterferon alfa-2b; Interleukins such as. but not limited to aldesleukin, oprelvekin: Other Immunostimulants such as, but not limited to BCG vaccine, glatiramer acetate, histamine dihydrochloride, immunocyanin, lentinan. melanoma vaccine, mifamurtide, pegademase, pidotimod, plerixafor, poly I:C, poly ICLC, roquinimex, tasonermin, thymopentin; Immunosuppressants such as, but not limited to abatacept, abetimus, alefacept, antilymphocyte immunoglobulin (horse), antithymocyte immunoglobulin (rabbit), eculizumab, efalizumab, everolimus, gusperimus, leflunomide, muromab-CD3, mycophenolic acid, natalizumab, sirolimus; TNF alpha Inhibitors such as for example adalimumab, afelimomab, certolizumab pegol, etanercept, golimumab, infliximab; Interleukin Inhibitors such as, but not limited to anakinra, basiliximab, canakinumab, daclizumab, mepolizumab, rilonacept, tocilizumab, ustekinumab; Calcineunrin Inhibitors such as, but not limited to ciclosporin, tacrolimus; Other Immunosuppressants such as, but not limited to azathioprine, lenalidomide, methotrexate, thalidomide, Adalimumab, Alemtuzumab, Basiliximab, Bevacizumab, Cetuximab, Certolizumab pegol, Daclizumab, Eculizumab, Efalizumab, Gemtuzumab, Ibritumomab tiuxetan, Infliximab, Muromonab-CD3, Natalizumab, Panitumumab; Ranibizumab, Rituximab; Tositumomab, Trastuzumab, Additional cancer treatment regimens include Monoclonal Antibodies such as, but not limited to alemtuzumab, bevacizumab, catumaxomab, cetuximab. edrecolomab, gemtuzumab, ofatumumab, panitumumab, rituximab, trastuzumab, Immunosuppressants, eculizumab, efalizumab, muromab-CD3, natalizumab; TNF alpha Inhibitors such as, but not limited to adalimumab, afelimomab, certolizumab pegol, golimumab, infliximab. Interleukin Inhibitors, basiliximab, canakinumab, daclizumab, mepolizumab. tocilizumab, ustekinumab, Radiopharmaceuticals, ibritumomab tiuxetan, tositumomab: Others Monoclonal Antibodies such as, but not limited to abagovomab, adecatumumab, alemtuzumab, anti-CD30 monoclonal antibody Xmab2513, anti-MET monoclonal antibody MetMab, aolizumab, apomab, arcitumomab, basiliximab, bispecific antibody 2B1, blinatumomab, brentuximab vedotin, capromab pendetide, cixutumumab, claudiximab, conatumumab, dacetuzumab, denosumab, eculizumab, epratuzumab, epratuzumab, ertumaxomab, etaracizumab, figitumumab, fresolimumab, galiximab, ganitumab, gemtuzumab ozogamicin, glembatumumab. ibritumomab, inotuzumab ozogamicin, ipilimumab, lexatumumab. lintuzumab, lintuzumab, lucatumumab, mapatumumab, matuzumab, milatuzumab, monoclonal antibody CC49, necitumumab, nimotuzumab, ofatumumab, oregovomab, pertuzumab, ramacurimab, ranibizumab, siplizumab, sonepcizumab, tanezumab. tositumomab, trastuzumab, tremelimumab, tucotuzumab celmoleukin, veltuzumab, visilizumab, volociximab, zalutumumab, Additional cancer treatment regimens include agents that affect the tumor micro-environment such as, but not limited to cellular signaling network (e.g. phosphatidylinositol 3-kinase (PI3K) signaling pathway, signaling from the B-cell receptor and the IgE receptor), In some aspects, the one or more therapeutic agent is a PI3K signaling inhibitor or a s c kinase inhibitor. In one aspect., the syk inhibitor is R788. In another aspect is a PKCy inhibitor such as, but not limited to, enzastaurin. Examples of agents that affect the tumor micro-environment include but are not limited to PI3K signaling inhibitor, syc kinase inhibitor, Protein Kinase Inhibitors such as, but not limited to dasatnib, erlotinib, esverolimus, gefitinib, iinatinib, lapatinib, nilotinib, pazonanib, sorafenib, sunitinib, temnsirollmus; Other Angiogenesis Inhibitors such as, but not limited to GT-111, JI-101, R1530; Other Kinase Inhibitors such as for example AC220, AC480, ACF-041 AMG$^{9}$00X AP24534, Ary-614, AT7519, AT9283, A-951, axitinib, AZDI 152, AZD7762, AZD8055, AZD8931, bafetinib, BAY 73-4506, BGJ398, BGT226, BT 811283, B16727, BIBF 1120., BIBW 2992, BMS-690154 BMS-777607 BMS-863231 BSK-461364. CAL-101, CEP-11981, CYC116, DCC-2036, dinaciclib, dovitinib lactate, E7050, EMD 1214(63, ENMD-2076, fostarnatinib disodiurn GSK2256098, GSK690693, INCB18424, INNO-406, JNJ-26483327, JX-594, KX2-391, linifanib, LY2603618, MGCD265, MK-0457, MKI496, MLN8054, MLN8237, MP470, NMS-1116354, NMS-1286937, ON 01919.Na, OSI-027, OSL-930 Btk inhibitor PF-00562271, PF-02341'66, PF-03814735, PF-04217903, PF-04554878, PF-4691502, PF-3758309, PHA-739358, PLC3397, progenipoietin, R547, R763, ramucirunab, regorafenib. R05185426, SAR103168, S3333333CH 727965, SGi176, SGX523, SNS-314 TAK-593, TAK-901, T258, TLN-232. TTP607, XL147, XL228, XL281R05126766, XL418 XL765, inhibitors of mitogen-activated protein kinase signaling such as, but not limited to U0126, PD98059, PD184352, PD0325901, ARRY-142886, SB239063, SP600125, BAY 43-9006, wortmannin, or LY294002: Syk inhibitors; mTOR inhibitors; and antibodies (e.g., rituxan), Adriamycin, Dactinomycin, Bleomycin, Vinblastine, Cisplatin, acivicin; aclarubicin; acodazole hydrochloride; acronine; adozelesin; aldesleukin; altretamine: ambomycin; ametantrone acetate; aminoglutethimide: amsacrine; anastrozole; anthramycin; asparaginase; asperlin: azacitidine; azetepa; azotomycin; batimastat: benzodepa; bicalutamide; bisantrene hydrochloride; bisnafide dimesylate: bizelesin: bleomycin sulfate; brequinar sodium; bropirimine; busulfan; cactinomycin; calusterone; caracemide; carbetimer; carboplatin: carmustine: carubicin hydrochloride: carzelesin; cedefingol; chloranmbucil; cirolemycin; cladribine; crisnatol mesylate; cyclophosphamide; cytarabine; dacarbazine: daunorubicin hydrochloride; decitabine; dexormaplatin; dezaguanine; dezaguanine mesylate; diaziquone; doxorubicin: doxorubicin hydrochloride; droloxifene; droloxifene citrate: dromostanolone propionate; duazomycin; edatrexate; eflornithine hydrochoride; elsamitrucin; enloplatin; enpromate; epipropidine; epirubicin hydrochloride; erbulozole: esorubicin hydrochloride; estramustine; estramustine phosphate sodium; etanidazole; etoposide: etoposide phosphate: etoprine, fadrozole hydrochoride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine: interleukin II (including recombinant interleukin II, or rIL2), interferon alfa-2a; interferon alfa-2b; interferon alfanl interferon alfa-n3; interferon beta-1 a; interferon gamma-1 b: iproplatin: irinotecan hydrochloride; lanreotide acetate; letrozole: leuprolide acetate; liarozole hydrochloride: lometrexol sodium; lomustine; losoxantrone hydrochloride; masoprocol; maytansine; mechlorethamine hydrochloride: megestrol acetate: melengestrol acetate; melphalan; menogaril; mercaptopurine; methotrexate; methotrexate sodium metoprine; meturedepa; mitindomide; mitocarcin; mitocromin mitogillin; mitomalcin; mitomycin; mitosper; mitotane; mitoxantrone hydrochloride; mycophenolic acid: nocodazole; nogalamycin; ormaplatin; oxisuran; pegaspargase; peliomycin; pentamustine; peplomycin sulfate, perfosfamide, pipobroman; piposulfan; piroxantrone hydrochloride; plicamycin; plomestane; porfimer sodium: porfiromycin; prednimustine: procarbazine hydrochloride; puromycin; puromycin hydrochloride; pyrazofurin; riboprine; rogletimide; safingol; safingol hydrochloride; semustine; simtrazene; sparfosate sodium: sparsomycin: Spiro germanium hydrochloride; spiromustine: spiroplatin; streptonigrin; streptozocin; sulofenur; talisomycin; tecogalan sodium; tegafur; teloxantrone hydrochloride; temoporfm; teniposide; teroxirone; testolactone; thiamiprine: thioguanine; thiotepa; tiazofurin; tirapazamine; toremifene citrate: trestolone acetate: triciribine phosphate: trimetrexate; trimetrexate glucuronate; triptorelin; tubulozole hydrochloride; uracil mustard: uredepa: vapreotide; verteporfin: vinblastine sulfate; vincristine sulfate; vindesine; vindesine sulfate: vinepidine sulfate: vinglycinate sulfate; vinleurosine sulfate: vinorelbine tartrate; vinrosidine sulfate: vinzolidine sulfate; vorozole; zeniplatin; zinostatin; zorubicin hydrochloride; 20-epi-L 25 dihydroxyvitamin D3; 5-ethynyluracil; abiraterone; aclarubicin: acylfulvene; adecypenol; adozelesin: aldesleukin; ALL-TK antagonists; altretamine; amaranthine; amidox; amifostine; aminolevulinic acid; amrubicin; amsacrine; anagrelide; anastrozole; andrographolide; angiogenesis inhibitors; antagonist D; antagonist G; antarelix: anti-dorsalizing morphogenetic protein-1; antiandrogen, prostatic carcinoma: antiestrogen; antineoplaston; antisense oligonucleotides; aphidicolin glycinate; apoptosis gene modulators; apoptosis regulators: apurinic acid: ara-CDP-DL-PTBA; arginine deaminase; asulacrine: atamestane; atrimustine: axinastatin 1; axinastatin 2; axinastatin 3; azasetron; azatoxin; azatyrosine; baccatin 111 derivatives; balanol; batimastat: BCR/ABL antagonists; benzochlorins; benzoylstaurosporine; beta lactam derivatives: beta-alethine; betaclamycin B; betulinic acid; bFGF inhibitor; bicalutamide; bisantrene; bisaziridinylspermine; bisnafide; bistratene A: bizelesin: breflate: bropirimine;

budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700: cartilage derived inhibitor; carzelesin: casein kinase inhibitors (ICOS): castanospermine: cecropin B; cetrorelix; chlorins; chloroquinoxaline sulfonamide: cicaprost; cis-porphyrin; cladribine; clomifene analogues; clotrimazole: collismycin A; collismycin B: combretastatin A4; combretastatin analogue: conagenin; crambescidin 816: crisnatol; cryptophycin 8; cryptophycin A derivarives: curacin A: cyclopentanthraquinones: cycloplatam; cypemycin; cytarabine ocfosfate: cytolytic factor; cytostatin; daclix-imab: decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab: elfomithine; elemene; emitefur; epirubicin: epristeride: etanautine analogue; estrogen agonists; estrogen antagonists; etanidazole; etoposide phosphate: exemestane; fadrozole; fazarabine; fenretinide: filgrastim: finasteride; flavopiridol; flezelastine: fluasterone; fludarabine; fluorodaunorunicin hydrochloride: forfenimex; formestane; fostriecin; fotemustine; gadolinium texaphyrin; gallium nitrate; galocitabine; ganirelix; gelatinase inhibitors: gemcitabine: glutathione inhibitors; hepsulfam; heregulin: hexamethylene bisacetamide; hypericin; ibandronic acid; idarubicin; idoxifene; idramantone; ilmofosine; ilomastat; imidazoacridones: resiquimod; immunostimulant peptides; insulin-such as for example growth factor-1 receptor inhibitor; interferon agonists: interferons; interleukins: iobenguane; iododoxorubicin; ipomeanol, 4-: iroplact; irsogladme; isobengazole; isohomohalicondrin B: itasetron; jasplakinolide; kahalalide F; lamellarin-N triacetate; lanreotide; leinamycin; lenograstim: lentinan sulfate: leptolstatin; letrozole; leukemia inhibiting factor; leukocyte alpha interferon: leuprolide+estrogen+progesterone; leuprorelin: levamisole; liarozole; linear polyamine analogue; lipophilic disaccharide peptide; lipophilic platinum compounds;lissoclinamide 7; lobaplatin; lombricine; lometrexol: lonidamine; losoxantrone: lovastatin; loxoribine; lurtotecan; lutetium texaphyrin; lysofylline: lytic peptides; maitansine; mannostatin A; marimastat: masoprocol; maspin matrilysin inhibiters; matrix metalloproteinase inhibitors: menogaril: merbarone; meterelin; methioninase: metoclopramide; MIF inhibitor; mifepristone; miltefosine; mirimostim; mismatched double stranded RNA; mitoguazone; mitolactol; mitomycin analogues: mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor I -based therapy; mustard anticancer agent; mycaperoxide B mycobacterial cell wall extract; myriaporone; N-acetyldinaline: N-substituted benzamides; nafarelin; nagrestip; naloxone -pentazocine; napavin; naphterpin; nartograstim; nedaplatin; nemorubicin; neridronic acid; neutral endopeptidase, nilutamide; nisamycin; nitric oxide modulators: nitroxide antioxidant: nitrullyn; 06-benzylguanine; octreotide; okicenone; oligonucleotides; onapristone; ondansetron; ondansetron; oracin; oral cytokine inducer: ormaplatin; osaterone; oxaliplatin; oxaunomycin; palauarmine; palmitoylrhizoxin; pamidronic acid; panaxytriol; panomifene: parabactin; pazelliptine; pegaspargase; peldesine: pentosan polysulfate sodium; pentostatin; pentrozole; perflubron; perfosfamide; perillyl alcohol; phenazinomycin; phenylacetates: phosphatase inhibitors; picibanil; pilocarpine hydrochloride; pirarubicin; piritrexim; placetin A; placetin B; plasminogen activator inhibitor; platinum complex: platinum compounds; platinum-triamine complex: porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors purine nucleoside phosphorylase inhibitors; purpurins; pyrazoloacridine: pyridoxylated hemoglobin polyoxyethylerie conjugate: raf antagonists; raltitrexed; ramosetron: ras farnesyl protein transferase inhibitors; ras inhibitors; ras-GAP inhibitor: retelliptine demethylated; rhenium Re 186 etidronate; rhizoxin; ribozymes; RII retinamide: rogletimide; rohitukine; romurtide: roquinimex: rubiginone Bl; ruboxyl; safingol; saintopin; SarCNU; sarcophytol A: sargramostim Sdi 1 mimetics; semustine; senescence derived inhibitor 1: sense oligonucleotides; signal transduction inhibitors: signal transduction modulators: single chain antigen-binding protein: sizofiran; sobuzoxane; sodium borocaptate: sodium phenylacetate; solverol; somatomedin binding protein: sonermin: sparfosic acid; spicamycin D; spiromustine; splenopentin; spongistatin 1; squalamine; stein cell inhibitor; stem-cell division inhibitors; stipiamide; stromelysin inhibitors: sulfinosine; superactive vasoactive intestinal peptide antagonist: suradista: suramin: swainsonine; synthetic glycosaminoglycans: tallimustine; tamoxifen methiodide; tauromustine; tazarotene; tecogalan sodium: tegafur; tellurapyrylium: telomerase inhibitors: temoporfin; temozolomide: teniposide; tetrachlorodecaoxide; tetrazomine; thaliblastine; thiocoraline; thrombopoietin: thrombopoietin mimetic; thymalfasin; thymopoietin receptor agonist; thyronine; thyroid stimulating hormone; tin ethyl etiopurpurin; tirapazamine; titanocene bichloride; topsentine; toremifene; totipotent stem cell factor; translation inhibitors; tretinoin: triacetyluridine: triciribine; trimetrexate, triptorelin: tropisetron; turosteride; tyrosine kinase inhibitors: tyrphostins; UBC inhibitors; ubenimex: urogenital sinus-derived growth inhibitory factor: urokinase receptor antagonists; vapreotide; variolin B: vector system, erythrocyte gene therapy: velaresol; veramine; verdins; verteporfin; vinorelbine; vinxaltine: vitaxin; vorozole: zanoterone: zeniplatin zilascorb; and zinostatin stimalamer. Yet other anticancer agents that can be employed in combination with the compound of Formula (III) include alkylating agents, antimetabolites, natural products, or hormones, such as, but not limited to nitrogen mustards (such as, but not limited to mechloroethamine, cyclophosphamide, chlorambucil, etc.), alkyl sulfonates (such as, but not limited to busulfan), nitrosoureas (such as, but not limited to carmustine, lomusitne, etc.). or triazenes (decarbazine, etc.). Examples of antimetabolites include but are not limited to folic acid analog (such as, but not limited to methotrexate), or pyrimidine analogs (such as, but not limited to Cytarabine), purine analogs (such as, but not limited to mercaptopurine, thioguanine, pentostatin). Examples of alkylating agents that can be employed in combination the compounds of Formula (III) include, but are not limited to, nitrogen mustards (such as, but not limited to mechloroethamine, cyclophosphamide, chlorambucil, meiphalan, etc.), ethylenimine and methylmelamines (such as, but not limited to hexamethlymelamine. thiotepa). alkyl sulfonates (such as, but not limited to busulfan), nitrosoureas (such as, but not limited to carmustine, lomusitne, semustine, streptozocin, etc.), or triazenes (decarbazine, etc.). Examples of antimetabolites include, but are not limited to folic acid analog (such as, but not limited to methotrexate), or pyrimidine analogs (such as. but not limited to fluorouracil, floxouridine, Cytarabine), purine analogs (such as, but not limited to mercaptopurine, thioguanine, pentostatin. Examples of anti-cancer agents which act by arresting cells in the G2-M phases due to stabilized microtubules and which can be used in combination with a Btk inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP—XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4. Spongistatin 5, Spongistatin 6, Spongistatin 7, Spongistatin 8, and Spongistatin 9), Cemadotin hydrochloride (also known as LU-103793 and NSC-D-669356). Epothilones (such as Epothilone A, Epothilone B, Epothilone C (also known as desoxyepothilone A or dEpoA), Epothilone D (also referred to as KOS-861 dEpoB, and desoxy epothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477—P), LS-4477 (Pharmacia), LS-4559 (Pharmacia), RPR-112378 (A ventis), Vincristine sulfate, DZ-3358 (Daiichi, FR—182877 (Fujisawa, also known as WS-9885B), GS-164 (Takeda), GS-198 (Takeda), KAR-2 (Hungarian Academy of Sciences). BSF-223651 (BASF, also known as ILX-651 and LU-223651), SAH-49960 (Lilly/Novartis), SDZ-268970 (Lilly/Novartis), AM-97 (Armad/Kyowa Hakko), AM--132 (Armad), AM-138 (Armad/ Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HICI, and RPR-258062A), Vitilevuamide, Tubulysin A, Canadensol, Centaureidin (also known as NSC—106969), T-138067 (Tularik, also known as T-67, TL-138067 and TI-138067), COBRA-I (Parker Hughes Institute, also known as DDE-261 and WH1-261), H10 (Kansas State University, 116 (Kansas State University), Oncocidin Al (also known as BTO-956 and DIME), DDE-313 (Parker Hughes Institute), Fijianolide B, Laulimalide, SPA-2 (Parker Hughes Institute) SPA-1 (Parker Hughes institute, also known as SPIKET-P), 3-IAABL (Cytoskeleton/Mt. Sinai School of Medicine, also known as MF-569), Narcosine (also known as NSC-5366). Nascapine, D-24851 (Asta *Medica*), A-105972 (Abbott), Hemiasterlin, 3-B AABU (Cytoskeleton/Mt. Sinai School of Medicine, also known as MF-191), TMPN (Arizona State University, Vanadocene acetylacetonate, T-138026 (Tularik), Monsatrol, Indanocine (also know % n as NSC-698666), 3-1AABE (Cytoskeleton/Mt. Sinai School of Medicine), A-204197 (Abbott), T-607 (Tuiarik, also known as T-900607), RPR—115781 (Avemris), Eleutherobins (such as Desmethyleleutherobm, Desaetyleleutherobin, Isoeleutherobin A, and Z-Eleutherobin), Caribaeoside, Caribaeolin, Halichondrin B, D-64131 (Asta *Medica*). D-68144 (Asta *Medica*). Diazonamide A, A-293620 (Abbott), NPI-2350 (Nereus), Taccalonolide A, TUB-245 (A ventis), A-259754 (Abbott), Diozostatin, (−)-Phenylahistin (also known as NSCL-96F037), D-68838 (Asta *Medica*), D-68836 (Asta *Medica*), Myoseverin B. D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC—12983 (NCI), Resverastatin phosphate sodium., BPR—OY-007 (National Health Research Institutes), and SSR-250411 (Sanofi).

In some aspects, the compound of Formula (III) and additional therapeutic agent can be administered simultaneously, concurrently or sequentially with no specific intervening time limits.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the disclosure can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the disclosure mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the disclosure may be mixed with a solid, semisolid, or liquid diluent. Soft gelatin capsules may be prepared by mixing the compound of the disclosure with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this disclosure may also be administered by non-oral routes. For example, the compositions may be formulated for rectal administration as a suppository. For parenteral use, including intravenous, intramuscular, intraperitoneal, or subcutaneous routes, the compounds of the disclosure may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 μg/kg/minute of compound, admixed with a pharmaceutical carrier over a period ranging from several minutes to several days.

For topical administration, the compounds may be mixed with a pharmaceutical carrier at a concentration of about 0.10% to about 10% of drug to vehicle. Another mode of administering the compounds of the disclosure may utilize a patch formulation to affect transdermal delivery.

Compounds of the disclosure may alternatively be administered in methods of this disclosure by inhalation, via the nasal or oral routes, e.g., in a spray formulation also containing a suitable carrier.

Compounds of the disclosure can be prepared using the knowledge of one skilled in the art in combination with the present disclosure. For example, compounds of the disclosure can be prepared according to the schemes and examples disclosed in U.S. Pat. Nos. 10,717,745, 10,934,310 and PCT application publication WO2017100662, each of which is hereby incorporated in its entirety.

Aspects of the present disclosure also include the use of BTK binding assays to determine efficacy and dosing regimens for the use of BTK inhibitors including, but not limited to the compounds disclosed herein. In some aspects, a BTK binding assay is used to determine the level of BTK occupancy by a BTK inhibitor including the compounds of the present disclosure. In some aspects, the BTK inhibitor is a compound of Formula (I) or a pharmaceutically acceptable salt, hydrate, polymorph or solvate thereof. In some aspects, the BTK inhibitor is a compound of Formula (III) or a pharmaceutically acceptable salt, hydrate, polymorph or solvate thereof.

Aspects of the present disclosure are directed to companion diagnostic methods and kits for use in combination with a therapy comprising administration of a BTK inhibitor such as the compound of Formula (III) or a pharmaceutically acceptable salt, hydrate, polymorph or solvate thereof. Such methods and kits are described in WO 2014/059368 which is hereby incorporated by reference in its entirety.

Described herein are companion diagnostic methods and kits for use in combination with a therapy comprising administration of a BTK inhibitor. In some aspects, the companion diagnostic methods provided involve protein occupancy assays for one or more inhibitors of BTK. Accordingly, described herein are protein occupancy assays for BTK inhibitors. Described herein in certain aspects is protein occupancy assay that is an ELISA probe assay. In some aspects, the ELISA probe assay is plate based electrochemilummescent assay to determine the relative amount of a BTK that has not been bound by a BTK inhibitor. For example, in some aspects, the BTK inhibitor binds to the active site of the BTK and forms a disulfide bond with a cysteine residue. In some aspects, the assays involves binding an activity probe to free BTK that have not been bound by the BTK inhibitor. In some aspects, the activity probe comprises a BTK inhibitor attached to a detectable label (e.g., biotin) via a linker (e.g., a long chain linker). Labeling of samples with the probe allows for the detection of BTK not occupied by drug. In some aspects, the probe conjugated with the BTK is captured by a streptavidin coated plate. In some aspects, excess un-conjugated probe competes with probe labeled BTK for binding to streptavidin. Also described herein are methods for determining the efficacy of inhibitors of the BTK. Further described herein are methods for using the protein occupancy assays in the diagnosis, prognosis, and determination and modification of therapeutic regimens in the treatment of diseases associated with activation of BTK, including diseases wherein inhibition of BTK provides therapeutic benefit to a patient having the disease. In some aspects, the patient is diagnosed as having a disease or disorder associated with aberrant activation of BTK, such as, for example, a malignancy. Further disclosed herein are diagnostic assays for diagnosing, prognosing, and monitoring a disease or condition benefitting from treatment with a BTK inhibitor. Also disclosed herein are diagnostic assays for identifying responders to BTK inhibitor therapy, determining therapeutic regimens, and detecting resistance to BTK inhibitor therapy.Some aspects are methods for determining the efficacy of a protein modulator (e.g., inhibitor drug) on a target (e.g., target protein kinase). In some aspects, methods are provided for determining the efficacy of a BTK inhibitor on a target kinase (e.g., BTK). In some aspects, the method comprises: (a) contacting a sample comprising a BTK with a probe to form a probe-bound target kinase; (b) detecting the amount of the probe-bound target kinase in the sample; and (c) determining the efficacy of the BTK inhibitor based on the amount of probe-bound target kinase. In some aspects, the method further comprises contacting the sample with the BTK inhibitor prior to step (a) (e.g., combining the sample with the probe). In some aspects, detecting the amount of the probe-bound target kinase comprises administering a compound, reagent or buffer to detect the probe-bound kinase. In some aspects, the compound, reagent or buffer comprises horseradish peroxidase (HRP), detection antibody buffer, read buffer, wash buffer. In some aspects, detecting the presence or absence of the probe-bound target kinase comprises quantifying the amount of probe-bound target kinase. In some aspects, the quantifying step comprises fluorescence, immunofluorescence, chemiluminescence, or electrochemiluminescence. In some aspects, determining the efficacy of the BTK inhibitor comprises determining occupancy of the target kinase by the BTK inhibitor. In some aspects, the amount of probe-bound target kinase inversely correlates with the efficacy of the BTK inhibitor. For example, if a drug-treated sample (e.g., a sample that is contacted with the drug prior to contact with the probe such as a blood sample or tumor tissue) is contacted with the probe, then as the amount of probe-bound target kinases (e.g., unoccupied target kinases) detected increases, the efficacy of the drug decreases. In another example, if a drug-treated sample is contacted with the probe, then as the amount of probe-bound target kinase (e.g., unoccupied target kinases) detected decreases, the efficacy of the drug increases. In some aspects, the amount of probe-bound target kinases directly correlates with the efficacy of the drug. For example, if an untreated sample (e.g., a sample that is not contacted with the drug prior to contact with the probe) is contacted with the probe, then as the amount of probe-bound target kinase detected increases, the efficacy of the drug also increases. In another example, if an untreated sample (e.g., a sample that is not contacted with the drug prior to contact with the probe) is contacted with the probe, then as the amount of probe-bound target kinase detected decreases, the efficacy of the drug decreases. In some aspects, a drug is determined to be effective when the drug binds at least about 50% of the target kinases. Alternatively, a drug is determined to be effective when the drug binds at least about 60% of the target kinases. In some aspects, a drug is determined to be effective when the drug binds at least about 65%, 70%, 75%, 80%, 85%, 90%, 95%, 97%, or 99% of the targets. In some aspects, the assay is performed on a sample obtained from a patient that has been administered a BTK inhibitor. In some aspects, the sample is obtained about 1 hour, 2 hours, 4 hours, 6 hours, 8 hours, 10 hours, 12 hours, 14 hours, 16 hours, 18 hours, 20 hours, 22 hours, 24 hours, 30 hours, 36 hours, 42 hours, 48 hours, 3 days, 4, days, 5 days, 6 days, 1 week, 2 weeks or longer after administration of the BTK inhibitor. In some aspects, the probe comprises an agent and a label. In some instances, the agent is fused to the label. In other instances, the agent is attached to the label. In another instance, the agent is attached to the label by a linker. In some aspects, the agent and the drug are essentially the same. In some aspects, the probe comprises a label. In some aspects, the probe comprises a label and a linker. In some aspects, the agent and the drug are at least about 20% identical, at least about 30% identical, at least about 40% identical, at least about 50% identical, at least about 60% identical, at least about 70% identical, at least about 80% identical, at least about 90% identical, or at least about 95% identical. In other aspects, the agent and the drug are different. In some aspects, the agent and the drug are at least about 5% different, at least about 10% different, at least about 20% different, at least about 30% different, at least about 40% different, at least about 50% different, at least about 60%) different, at least about 70% different, at least about 80% different, at least about 90% different, or at least about 95% different.

Disclosed herein are protein occupancy assay kits comprising a linker, a label, an agent, or any combination thereof. In one aspect is a protein occupancy assay kit comprising a linker and a label, wherein the linker is capable of attaching the label to an agent and the agent is a protein modulator. In another aspect is a protein occupancy assay kit comprising an agent, a linker, and a label, wherein the linker is capable of attaching to the agent and the label, thereby attaching the agent to the label. In some aspects is a protein occupancy assay kit comprising a probe, wherein the probe comprises an agent attached to a label. In some aspects is a protein occupancy assay kit comprising a probe, wherein the probe comprises an agent attached to a linker. In some aspects is a protein occupancy assay kit comprising an agent and a solid support, wherein the agent is attached to the solid support. In another aspect is a protein occupancy assay kit comprising a label and a solid support, wherein the label is attached to the solid support. In another aspect is a protein occupancy assay kit comprising a probe and a solid support, wherein the probe comprises an agent, a linker, a label, or any combination thereof. In some aspects is a protein occupancy assay kit comprising a target (e.g., protein) and a solid support, wherein the target is attached to the solid support. In some aspects, any of the kits disclosed herein further comprise a label. In some aspects, any of the kits disclosed herein further comprise a linker. In some aspects, any of the kits disclosed herein further comprise an agent. In some aspects, any of the kits disclosed herein further comprise a plurality of linkers, wherein the linkers are capable of attaching to another linker, an agent, a label, or any combination thereof. In some aspects, any of the kits disclosed herein further comprise a probe. In some aspects the probe comprises an agent, a linker, a label, or any combination thereof. In some aspects, any of the kits disclosed herein further comprise a target (e.g., protein). Exemplary aspects of agents, linkers, labels, probes, solid supports, and targets are disclosed herein. Further disclosed herein are exemplary methods for attaching probes or targets to solid supports.

In some aspects, the methods, kits, and compositions disclosed herein comprise a probe. In some aspects, the probe comprises an agent and a label. In some aspects, the agent and label are attached. In other aspects, the probe comprises an agent and a linker. In some aspects, the agent and linker are attached. In another aspect, the probe comprises an agent, a linker, and a label. In some aspects, the agent, linker and/or label are attached to each other. In some aspects, the probe comprises a label. In another aspect, the probe comprises a label and a linker. In some aspects, the label and the linker are attached. In some aspects, attachment is by chemical methods, enzymatic methods, or cross-linking methods. In some aspects, the probe is attached to a solid support. Exemplary aspects of agents, linkers, labels, and solid supports are disclosed herein.

Any of the assays and systems disclosed herein can be useful in researching and validating drugs. Provided herein are methods for validating a drug comprising (a) contacting a sample comprising a target with a probe to form a probe-bound target; (b) detecting the presence or absence of the probe-bound target; and (c) determining occupancy of the target by a drug based on the presence or absence of the probe-bound target, thereby validating the drug.

Further provided herein are methods for determining occupancy of a target comprising: a) combining a sample comprising a target with a probe; b) detecting the presence or absence of a probe-bound target; and c) determining occupancy of the target by a drug based on the presence or absence of the probe-bound target.

In some aspects, the method further comprises capturing the target prior to step (a) contacting the sample with the probe. In some aspects, the target is captured by an antibody. In some aspects, the antibody is an anti-target antibody. In some aspects, the antibody is attached to a solid support. In some aspects, the solid support is a microplate. In some aspects, the microplate is a MSD microplate.

In yet other aspects, the method further comprises contacting the probe-bound target with a primary detection agent. In some aspects, the primary detection agent comprises an antibody, a bead, a dye, or a fluorophore. In some aspects, the primary detection agent comprises an antibody. In some aspects, the antibody is an anti-BTK antibody. In some aspects, the method further comprises contacting the detection agent with a secondary detection agent. In some aspects, the secondary detection agent comprises an antibody, a bead, a dye, or a fluorophore. In some aspects, the primary detection agent is labeled. In some aspects, the secondary detection agent is labeled. In some aspects, the label is an electrochemiluminescent tag. In some aspects, the electrochemiluminescent tag comprises Tris(bipyridine)ruthenium(II) dicfiloride. In some aspects, the electrochemiluminescent tag is Ruthenium (II) tris-bipyridine, N-hydroxysuccinimide. In some aspects, the label is a SULFO TAG.

In some aspects, detecting the presence or absence of the probe-bound target comprises contacting the sample with a solid support. In some aspects, the solid support comprises a bead. In some aspects, the bead is a streptavidin bead. In some aspects, the bead is a magnetic bead. In some aspects, the bead is a labeled bead. In some aspects, the bead is a labeled streptavidin bead. In some aspects, the bead is a labeled with an electrochemiluminescent tag. In some aspects, the electrochemiluminescent tag comprises Tris (bipyridine)ruthenium(II) dicfiloride. In some aspects, the electrochemiluminescent tag is Ruthenium (II) tris-bipyridine, N-hydroxysuccinimide. In some aspects, the bead is a SULFO TAG bead. In some aspects, the bead is a SULFO TAG streptavidin bead.

In some aspects, the bead interacts with the probe. In some aspects, the probe comprises a label. In some aspects, the label comprises biotin. In some aspects, the bead interacts with biotin. In some aspects, the bead forms a conjugate with the probe-bound target. In some aspects, the bead is conjugated to the probe.

In some aspects, detecting the presence or absence of the probe-bound target comprises detecting the probe-bound target or a portion thereof. In some aspects, detecting the presence or absence of the probe-bound target comprises detecting the bead or a portion thereof. In some aspects, detecting the presence or absence of the probe-bound target comprises detecting the labeled bead. In some aspects, detecting the presence or absence of the probe-bound target comprises detecting an electrochemiluminescent tag. In some aspects, the electrochemiluminescent tag comprises Tris(bipyridine)ruthenium(II) dichloride. In some aspects, the electrochemiluminescent tag is Ruthenium (II) tris-bipyridine, N-hydroxysuccinimide. In some aspects, detecting the presence or absence of the probe-bound target comprises detecting a SULFO TAG. In some aspects, the detecting step comprises luminescence. In some aspects, the detecting step comprises electrochemiluminescence.

In some aspects, the method further comprises purification of the probe-bound target. In some aspects, the probe-bound target is an unoccupied target. In some aspects, the probe-bound target is a drug-occupied target. In another aspect, purification of the probe-bound target comprises magnetic separation of probe-bound targets from non-probe-bound targets.

In some aspects, the sample is a pre -treated sample, wherein the pre-treated sample is contacted with a drug prior to contact with the probe. In some aspects, the sample is a non-treated sample, wherein the sample is not contacted with a drug prior to contact with the label.

In some aspects, the probe comprises an agent. In some aspects, the probe comprises an agent and a linker. In some aspects, the probe comprises a label. In some aspects, the probe comprises a label and a linker. In some aspects, the agent is a BTK inhibitor. In some aspects, the agent is a compound of Formula (III). In some aspects, the BTK inhibitor is a reversible BTK inhibitor. In some aspects, the agent is a, the BTK inhibitor is an irreversible BTK inhibitor. In some aspects, the agent is a, the BTK inhibitor is a selective, covalent BTK inhibitor. In some aspects, the agent is a, the BTK inhibitor forms a covalent bond with a cysteine residue of a Bruton's tyrosine kinase (BTK). In some aspects, the cysteine residue is cysteine 481. In some aspects, the agent is a, the BTK inhibitor is a compound of Formula (III).

In some aspects, validating the drug comprises determining the efficacy of the drug on a target. In some aspects, determining occupancy of the target by the drug comprises quantifying the presence or absence of probe-bound targets. In some aspects, the drug is effective when the occupancy of the target is at least about 50%, 60%, 65%, 70%, 75%, 80%, 85%, 90%, 95%, 97%, or 99%.

Any of the methods, assays and systems can be used to inform therapeutic treatment and the over-all health care management of a subject informing method for determining a therapeutic regimen. In some aspects, is a method for determining a therapeutic regimen comprising: (a) combining a sample comprising a target with a probe; (b) detecting the presence or absence of a probe-bound target; and (c) determining a therapeutic regimen based on the presence or absence of the probe-bound target. Further disclosed herein is a method for determining efficacy of a test agent comprising: (a) combining a sample comprising a target with a probe; (b) detecting the presence or absence of a probe-bound target; and (c) determining efficacy of a test agent based on the presence or absence of the probe-bound target. Further disclosed herein is a method for identifying drug responders comprising: (a) combining a sample comprising a target with a probe; (b) detecting the presence or absence of a probe-bound target; and (c) identifying drug responders based on the presence or absence of the probe-bound target. Further disclosed herein is a method for identifying BTK inhibitors comprising: (a) combining a sample comprising a target with a probe; (b) detecting the presence or absence of a probe-bound target; and (c) identifying kinase modulators based on the presence or absence of the probe-bound target. Disclosed herein is a method for determining drug resistance comprising: (a) combining a sample comprising a target with a probe; (b) detecting the presence or absence of a probe-bound target; and (c) determining drug resistance based on the presence or absence of the probe-bound target.

In some aspects, the methods, assays, and systems disclosed herein comprise contacting sample comprising a target with a probe. Suitable samples for use in any of the methods, assays, and systems disclosed herein comprise, but are not limited to, a whole blood sample, peripheral blood sample, lymph sample, tissue sample, tumor biopsy sample, bone marrow sample, or other bodily fluid sample. In some aspects, the sample is a sample containing one or more cell types, or a lysate thereof, derived from a whole blood sample, peripheral blood sample, lymph sample, tissue sample, tumor biopsy sample, bone marrow sample, or other bodily fluid sample. Examples of bodily fluids include, but are not limited to, smears, sputum, biopsies, secretions, cerebrospinal fluid, bile, blood, lymph fluid, saliva, and urine. In some aspects, cells of the sample are isolated from other components of the sample prior to use in the methods provided. In some aspects, particular cell types of the sample are isolated from other cell types of the sample prior to use in the methods provided. For example, in some aspects, peripheral blood mononuclear cells (PBMCs, e.g., lymphocytes, monocytes and macrophages) of a blood sample are isolated from other cell types of the blood sample prior to use in the methods provided. For example, in some aspects, lymphocytes (e.g., B cells, T cells or NK cells) of the sample are isolated from other cell types of the sample prior to use in the methods provided. For example, in some aspects, B cells of the sample are isolated from other cell types of the sample prior to use in the methods provided. In some aspects, cells of the sample are lysed prior to use in the methods provided. For example, in some aspects, cancer cells are isolated from normal cells of the sample prior to use in the methods provided.

Any of the samples disclosed herein comprises complex populations of cells, which can be assayed as a population, or separated into sub-populations. Such cellular and acellular samples can be separated by centrifugation, elutriation, density gradient separation, apheresis, affinity selection, panning, FACS, filtration, centrifugation with Hypaque, etc. By using antibodies specific for markers identified with particular cell types, a relatively homogeneous population of cells can be obtained. Alternatively, a heterogeneous cell population can be used.

Once a sample is obtained, it can be used directly, frozen, or maintained in appropriate culture medium for short periods of time. Methods to isolate one or more cells for use according to the methods of this invention are performed according to standard techniques and protocols well-established in the art. In some aspects, the sample is obtained from a subject. Such subject can be a human or a domesticated animal such as a cow, chicken, pig, horse, rabbit, dog, cat, or goat. In some aspects, the cells used in the present invention are taken from a patient. Samples derived from an animal, e.g., human, can include, for example whole blood, sweat, tears, saliva, ear flow, sputum, lymph, bone marrow suspension, lymph, urine, saliva, semen, vaginal flow, cerebrospinal fluid, brain fluid, ascites, milk, secretions of the respiratory, intestinal or genitourinary tracts fluid, a lavage of a tissue or organ (e.g., lung) or tissue which has been removed from organs, such as breast, lung, intestine, skin, cervix, prostate, pancreas, heart, liver and stomach.

To obtain a blood sample, any technique known in the art can be used, e.g., a syringe or other vacuum suction device. A sample can be optionally pre -treated or processed prior to enrichment. Examples of pre-treatment steps include the addition of a reagent such as a stabilizer, a preservative, a fixant, a lysing reagent, a diluent, a drug, an anti-apoptotic reagent, an anti-coagulation reagent, an anti-thrombotic reagent, magnetic property regulating reagent, a buffering reagent, an osmolality regulating reagent, a pH regulating reagent, and/or a cross-linking reagent. For example, when a blood sample is obtained, a preservative such an anticoagulation agent and/or a stabilizer can be added to the sample prior to enrichment.

A sample, such as a blood sample, can be analyzed under any of the methods, assays and systems disclosed herein within 1 week, 6 days, 5 days, 4 days, 3 days, 2 days, 1 day, 12 hrs, 6 hrs, 3 hrs, 2 hrs, or 1 hr from the time the sample is obtained.

In some aspects, a sample can be combined with an enzyme or compound that selectively lyses one or more cells or components in the sample. For example, in a blood sample, platelets and/or enucleated red blood cells are selectively lysed to generate a sample enriched in nucleated cells. The cells of interest can subsequently be separated from the sample using methods known in the art.

When obtaining a sample from a subject (e.g., blood sample), the amount can vary depending upon subject size and the condition being screened. In some aspects, up to 50, 40, 30, 20, 10, 9, 8, 7, 6, 5, 4, 3, 2, or 1 mL of a sample is obtained. In some aspects, 1-50, 2-40, 3-30, or 4-20 mL of sample is obtained. In some aspects, more than 5, 10, 15, 20, 25, 30, 35, 40, 45, 50, 55, 60, 65, 70, 75, 80, 85, 90, 95 or 100 mL of a sample is obtained.

Aspects of the present disclosure include methods of modifying the dose and/or frequency of dosing of a BTK inhibitor. Aspects of the present disclosure include methods of determining a BTK inhibitor treatment regimen in a subject. Aspects of the present disclosure include methods of monitoring the efficacy of BTK inhibitor inhibitor therapy in a subject. In some aspects, a BTK occupancy of greater than about 75% is indicative that the BTK inhibitor is therapeutically effective. In some aspects, a BTK occupancy of greater than about 80% is indicative that the BTK inhibitor is therapeutically effective. In some aspects, a BTK occupancy of greater than about 90% is indicative that the BTK inhibitor is therapeutically effective. In some aspects, a BTK occupancy of greater than about 95% is indicative that the BTK inhibitor is therapeutically effective. In some aspects, a BTK occupancy of greater than about 99% is indicative that the BTK inhibitor is therapeutically effective. In some aspects, a BTK occupancy of greater than about 100% is indicative that the BTK inhibitor is therapeutically effective. Aspects of the present disclosure include methods of predicting a subjects' response to BTK inhibitor therapy. In some aspects, a BTK occupancy of greater than about 75% is indicative that a patient will response to a particular BTK inhibitor. Aspects of the present disclosure also include methods for determining drug target occupancy in a patient.

Aspects of the present disclosure include the use of a A BTK lanthascreen binding assay to determine the BTK occupancy by a BTK inhibitor. In some aspects, a BTK lanthascreen binding assay monitors compound binding to unphosphorylated-BTK kinase domain (UP-BTK), by competing with a fluorescent labeled tracer. In some aspects, UP-BTK, consisting of the kinase domain of non-phosphorylated BTK protein (389-659aa), is produced in a Baculovirus/insect cell expression system. In some aspects, into a 384-well plate, 2 ng of GST-tagged human BTK (389-659aa) is incubated with a BTK inhibitor compound, 50 nM of Tracer 236 and 2 nM anti-GST antibody for 60 minutes using an optimized Lanthascreen™ assay. In some aspects, after 60 minutes, plates are read at 340 nM and 615/665 nM in a multifunctional plate reader such as an Infinite F500 (Tecan). In some aspects, data is analyzed using Xlfit™ version 5.3 from ID Business Solutions (Guildford), Microsoft Excel add-in.

In some aspects, binding of a BTK inhibitor to BTK in the assay described herein may be indicative of the the BTK inhibitors' function when used to treat a disease or condition in a patient in need thereof. In some aspects, a BTK occupancy of greater than about 75% is indicative that the BTK inhibitor is therapeutically effective. In yet other aspects, binding of a BTK inhibitor to BTK in the assay described herein may provide insight into the optimal dosage and frequency of administration of a BTK inhibitor. In some aspects, a BTK occupancy of greater than about 75% is indicative that the BTK inhibitor is being administered at an optimal dose and/or frequency. In some aspects, binding of a BTK inhibitor to BTK in the assay described herein may be predictive of a compounds ability to inhibit BTK and thereby treat a disease or condition disclosed herein. In some aspects, a BTK occupancy of greater than about 75% is indicative that the BTK inhibitor is effectively ingibiting BTK. In yet other aspects binding of a BTK inhibitor to BTK in the assay described herein may be predictive of the in vivo activity of a particular BTK inhibitor based on having similar BTK occupancy in the assay. In some aspects, a BTK occupancy of greater than about 75% is indicative that the BTK inhibitor is therapeutically effective in vivo.

EXAMPLES

Example 1:: A Phase I First In Human Pharmacokinetic and Pharmacodynamic Study of the Compound of Formula (III), A Potent and Selective Covalent Inhibitor of the Bruton's Tyrosine Kinase

Introduction

Bruton's tyrosine kinase (BTK) is a nonreceptor tyrosine kinase expressed in most hematopoietic cells except for T cells, natural killer cells, and plasma cells. BTK activity is critical to the development and differentiation of B cells and acts as a modulator of signaling via the B-cell receptor (BCR). Given the key role of BTK in oncogenic BCR signaling and the fact that BCR signaling is necessary to sustain B-cell malignancies, recent efforts have focused on developing BTK inhibitors for the treatment of these malignancies.

Currently, four small-molecule, irreversible, covalent, variably selective BTK inhibitors are approved as oral monotherapy for the treatment of B-cell malignancies. Ibrutinib (IMBRUVICA®), the first-in-class and most potent of the currently approved BTK inhibitors, is approved in numerous countries around the world for treatment of mantle-cell lymphoma, chronic lymphocytic leukemia (CLL)/small lymphocytic lymphoma (SLL), Waldenstrom macroglobulinemia, and marginal zone lymphoma, as well as chronic graft vs host disease. Subsequently, several selective second-generation BTK inhibitors like acalabrutinib, zanubrutinib, and tirabrutinib have been developed. Acalabrutinib and zanubrutinib have received United States Food and Drug Administration approval for the treatment of mantle-cell lymphoma. Additionally, acalabrutinib is approved for treating patients with CLL/SLL and zanubrutinib is approved for marginal zone lymphoma and Waldenstrom macroglobulinemia. Whereas, tirabrutinib has been approved in Japan for the treatment of recurrent or refractory primary central nervous system lymphoma. All four BTK inhibitors bind to cysteine-481 in the adenosine triphosphate binding site. Acalabrutinib and tirabrutinib are the most selective for BTK followed by zanubrutinib and then ibrutinib. With a shorter half-life than ibrutinib, acalabrutinib and zanubrutinib are dosed twice-daily, to maintain >95% BTK occupancy (BTKO), with a lower risk of off-target effects. However, side effects such as infection, atrial fibrillation and bleeding can limit the clinical benefits of these agents. Thus, there is a clinical need for novel, more specific BTK inhibitors with less toxicity that might improve efficacy with a shorter duration of therapy.

Compound of Formula (III) is being developed as an orally active, potent, covalent, and highly selective BTK inhibitor as a potential treatment for patients with B-cell malignancies or autoimmune disorders. This first-in-human (FIH) study was designed to assess the safety, tolerability, pharmacokinetics (PK), and pharmacodynamics (PD; BTKO) of compound of Formula (III) when orally administered as either single-ascending doses (SAD) or multiple-ascending doses (MAD) in healthy participants. The effects of gender, food, and solid capsule formulation on the safety, tolerability, PK, and PD BTKO of a single oral dose of compound of Formula (III) were also evaluated.

Data from this study have also been used to investigate the currently accepted paradigm that meaningful BTK inhibitor efficacy requires >90-95% BTKO. The dynamics of BTKO depend both on PK exposure and on the kinetics of target turnover, which is best captured with a quantitative PK/PD model.

Methods

Study Participants—Volunteers aged 18-58 years, with a body mass index (BMI) of 18-30 kg/$m^2$, body weight ≥50 kg, and who were considered healthy based on medical history, physical examination, clinical laboratory evaluation, and 12-lead electrocardiogram (ECG) were enrolled in this study. Females were required to be surgically sterile or postmenopausal. Key exclusion criteria were history of, or current, clinically significant medical illness and history of malignancy within 5 years.

The Independent Ethics Committee associated with the study site reviewed and approved the study protocol and amendments. The study was conducted in accordance with the ethical principles that have their origin in the Declaration of Helsinki and that are consistent with the International Conference on Harmonization for Good Clinical Practices guidelines and applicable local and regulatory requirements. Written informed consent was obtained prior to study enrollment.

Study Design—This phase 1, randomized, double-blind, placebo-controlled, single-center study (NCT03607513; EudraCT 2018-000428-32) was conducted between July 2018 and August 2019 at the Janssen Clinical Pharmacology Unit in Merksem, Belgium.The study comprised two distinct parts; Part 1 examined SAD of compound of Formula (III) and Part 2 assessed MAD of compound of Formula (III).

Part 1

Figure 1:
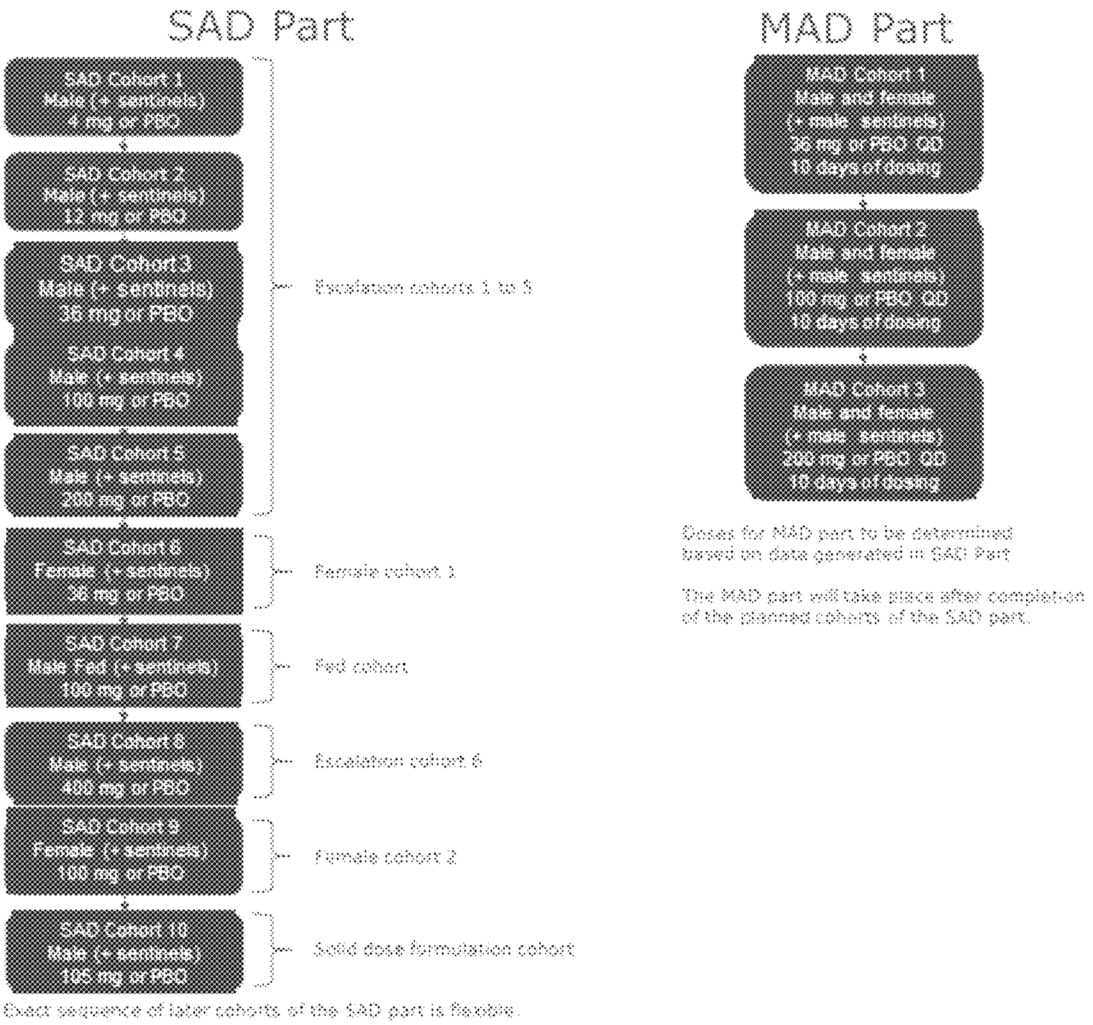

Safety, tolerability, PK, and BTKO were assessed for six doses of compound of Formula (III) oral solution (4, 12, 36, 100, 200, 400 mg) in participants under fasted conditions. The SAD part comprised 10 cohorts of 8 participants each (FIG. 1). In each cohort receiving compound of Formula (III) oral solution (Cohorts 1-9), 6 participants were randomized to receive compound of Formula (III) and 2 to receive placebo. All participants in Cohort 10 received compound of Formula (III) as an oral capsule. All 10 cohorts included 2 sentinel participants who were dosed ~24 hours prior to the rest of the cohort. In cohorts receiving compound of Formula (III) oral solution, 1 sentinel participant received compound of Formula (III) and the other received placebo.

Six male escalating dose cohorts received a single oral dose of 4, 12, 36, 100, 200, 400 mg compound of Formula (III) or placebo solution under fasted conditions. Gender effects were assessed in 2 female cohorts whose participants received either a 36 or 100 mg dose of compound of Formula (III) or placebo as an oral solution under fasted conditions. Food effects were evaluated in a male cohort receiving compound of Formula (III) 100 mg or placebo as an oral solution after a high-fat breakfast.

Safety, tolerability, and PK of a solid dose formulation of compound of Formula (III) were assessed in an additional male cohort (Cohort 10) that received 3×35 mg (105 mg) of compound of Formula (III) in the fasted state. Since all the participants received the same dose of compound of Formula (III), this cohort was not blinded.

Part 2

Safety, tolerability, PK, and BTKO following multiple compound of Formula (III) doses were evaluated in 3 dose escalation cohorts with a total of 18 participants (males: 9, females: 9) receiving active study drug. In each cohort, 3 males and 3 females were randomized to receive 36 mg once-daily (QD), 100 mg QD, or 200 mg QD compound of Formula (III) oral solution and 3 participants (males: 2; female: 1) to receive placebo. Two male participants in each cohort served as sentinel participants: one received compound of Formula (III) and other received placebo ~48 hours prior to other participants in the cohort. All safety and tolerability data (through the follow-up visit), PK data (through at least 24 hours after last dose administration), and all available PD data were reviewed from each cohort before a decision was made to dose escalate.

The doses administered during Part 2 were determined based on safety, tolerability, PK, and PD data obtained from preceding cohorts and on data obtained in Part 1 of the study, considering predicted PK and target occupancy of compound of Formula (III) after repeated dosing.

Study Assessments

Safety—Safety evaluations were based upon the type, incidence, and severity of treatment-emergent adverse events (TEAEs) reported throughout the study, and concomitant medication reporting, clinical laboratory tests, physical examinations, vital sign measurements, and ECGs assessed at pre-defined time points. The TEAEs and serious TEAEs were coded using the Medical Dictionary for Regulatory Activities (MedDRA Version 21.0) and summarized by system-organ class (SOC) and preferred terms.

Pharmacokinetics

Sample collection—For the PK assessment of compound of Formula (III), venous blood samples (2 to 4 mL each) were collected predose and at 15 min, 0.5, 1, 1.5, 2, 2.5, 3, 4, 6, 8, 12, 24, 36, 48, and 72 hours post-dose in Part 1. In Part 2, samples were collected predose and at 15 min, 0.5, 1, 1.5, 2, 2.5, 3, 4, 6, 8, 12 hours post-dose on day 1, predose and 1 hour post-dose on days 2-9, and predose and at 15 min, 0.5, 1, 1.5, 2, 2.5, 3, 4, 6, 8, 12, 24, 48, and 72 hours after the last dose on day 10. Plasma samples were analyzed to determine concentrations of compound of Formula (III) using a scientific validated, specific, and sensitive liquid chromatography-mass spectrometry (LC-MS/MS) method.

The PK analysis for the compound of Formula (III) samples was performed using a non-compartmental method with validated Phoenix® WinNonlin® (version 8.0, Certara L.P.). Estimated PK parameters included maximum observed plasma concentration ($C_{max}$), time to reach Cmax ($t_{max}$), minimum observed plasma concentration during dosing interval (Cmin), area under the plasma concentration-time curve during the 24-hour dosing interval ($AUC_{0-24}$), AUC from time 0 to time of last measurable concentration ($AUC_{last}$), AUC from time 0 to infinite time ($AUC_{\infty}$), dominant half-life (t1/2, dom), apparent elimination half-life (t1/2, λz), the observed accumulation ratio based on Cmax (ARCmax), the observed accumulation ratio based on AUC ($AR_{AUC}$), amount of drug excreted into the urine as a percent dose, and renal clearance of drug ($CL_R$).

Pharmacodynamics (BTKO)—In Part 1, venous blood samples (8 mL) were collected predose and at 1, 2, 4, 8, 12, 24, 48, and 72 hours post-dose for measuring free BTK levels in peripheral blood mononuclear cells (PBMCs) and calculating % BTKO. In Part 2, blood samples were taken on day 1 predose and at 2, 4, and 8 hours after dosing; days 2-10 predose and 4 hours post-dose; and at 24, 48, and 72 hours after the last dose and at the follow-up visit.

After PBMCs were isolated from whole blood, they were lysed and prepared for the measurement of BTK occupancy using a custom streptavidin-coated Meso Scale Discovery (MSD) immunoassay. Percent occupancy was calculated as 100%×([Baseline free BTK−Free BTK with treatment]/Baseline Free BTK).

PK/PD modeling and simulation—In the PK/PD model, a two-compartment population PK (popPK) model with a first-order absorption and elimination was used to fit the PK data. The model was parameterized in terms of apparent clearance (CL/F), apparent volume of distribution of the central compartment ($V_2$/F), apparent inter-compartmental clearance (Q/F), apparent volume of distribution of the peripheral compartment ($V_3$/F), and first-order absorption rate constant ($K_a$). Inter-individual variability was included on CL/F, $V_2$/F, Q/F, and $K_a$. Following the development of the popPK model, the PK/PD model was subsequently developed based on individual estimates from the popPK model.

Figure 2:
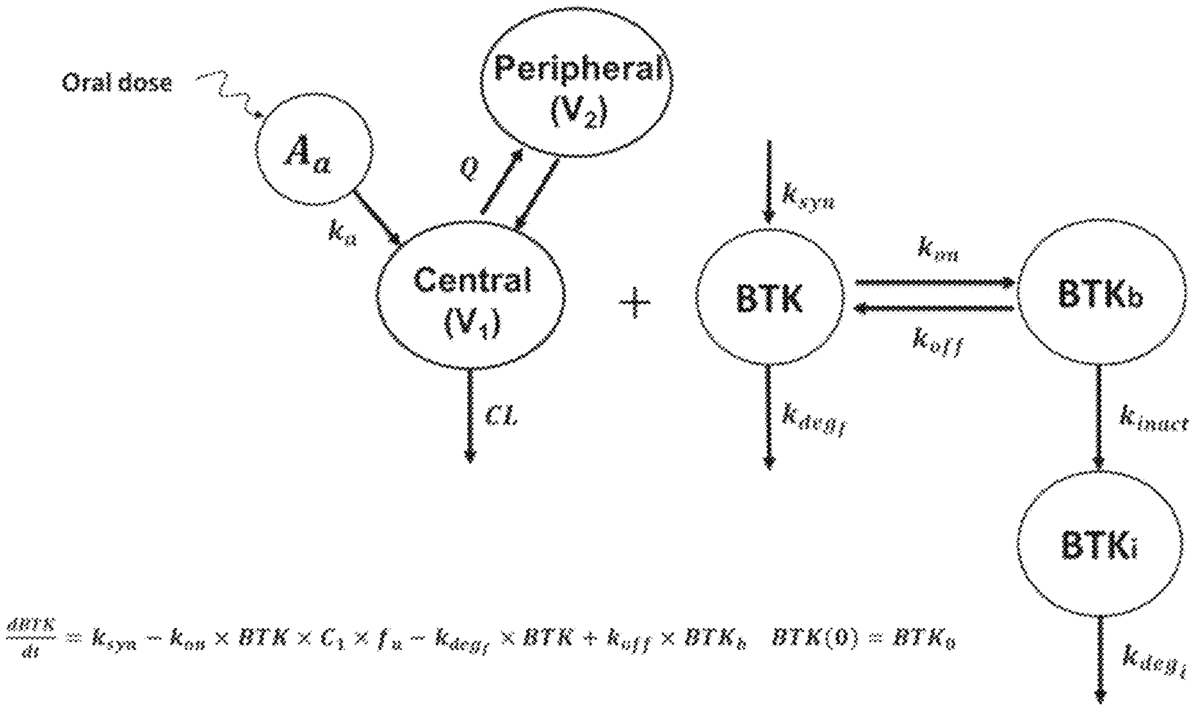

A mechanistic covalent binding model (FIG. 2) was used to describe the receptor occupancy of compound of Formula (III). The equations describing the binding model are shown in equations 1-5.

$$f_u = 1.4 + \frac{4.43 \times C^2}{2076^2 + C^2} \quad (1)$$

where $f_u$ is the compound of Formula (III) unbound fraction and C is the concentration in nM. Free fraction equation was developed using data from the study that evaluated the concentration dependence of compound of Formula (III) binding to the proteins in human plasma using an equilibrium dialysis technique.

$$\frac{dBTK}{dt} = k_{syn} - k_{on} \times BTK \times C_1 \times f_u - k_{deg_f} \times BTK + k_{off} \times BTK_b \qquad BTK(0) = BTK_0 \quad (2)$$

$$\frac{dBTK_b}{dt} = k_{on} \times BTK \times C_1 \times f_u - k_{off} \times BTK_b - k_{inact} \times BTK_b \qquad BTK_b(0) = 0 \quad (3)$$

$$\frac{dBTK_i}{dt} = k_{inact} \times BTK_b - k_{deg_i} \times BTK_i \quad BTK_i(0) = 0 \quad (4)$$

$$\%BTK \text{ occupancy} = \frac{BTK_b + BTK_i}{BTK + BTK_b + BTK_i} \quad (5)$$

where symbols represent the free BTK protein concentration (BTK), drug-BTK complex (BTKb) and covalently bound complex (BTKi). The rate constants in the equations include zero-order rate of BTK synthesis ($k_{syn}$); the first-order rate of free BTK degradation ($k_{degf}$); the first-order rate of covalently bound complex degradation ($K_{degi}$); association rate drug-BTK binding ($k_{on}$); dissociation rate drug-BTK binding ($k_{off}$). $C_1$ is the concentration in central compartment. $BTK_0$ is the baseline value of BTK. The degradation rate of free BTK and covalently bound complex is assumed to be the same.

In order to refine predictions of % BTKO after multiple dosing for the MAD cohorts and to help select a starting dose for the subsequent first-in-patient oncology study, a prior mechanistic PK/PD model based on in vitro and in vivo BTKO data was updated with clinical PK/BTKO data collected from SAD cohorts of the FIH study. The semi-mechanistic PK/PD model was used to simulate % BTKO following various dose regimen. The evaluated dosing regimens included 12 mg, 36 mg, 70 mg, 100 mg, 140 mg, 200 mg QD dose. The participants for simulation were randomly sampled from the analysis dataset (n=1000). The BTKO was targeted at 90% as meaningful clinical efficacy. The observed % BTKO in MAD cohort were compared with the model predictions.

Once MAD data were available, the semi-mechanistic PK/PD model was updated with the acquired data from SAD and MAD cohorts. The covariates assessed in the popPK analysis were shown in Table 4. All covariate effects in the popPK analysis were evaluated on clearance from the central compartment (CL/F) only, except for body weight, food effect, and drug formulation. Body weight was included in the structural model (as a covariate on the CL/F, $V_2$/F, Q/F). Body weight was investigated as a covariate by using an allometric function with power value of 0.75 for clearance parameters and 1 for volume parameters. Food effect and drug formulation were evaluated on $K_a$. The covariates model selection was conducted using a full-model approach with backward elimination (nominal p<0.001, i.e., a change in the objective function value of 10.83 with 1 degree of freedom). A covariate model was initially developed using all statistically significant covariates of interest, and was then reduced by removing covariates with effect sizes less than 10% of the typical values of the respective PK parameters. This reduced model was regarded as the final mode which was subsequently used for PD model. Model selection was determined by graphical assessment, statistically significant difference in the objective function value between competing models. The performance of the final model was evaluated using a prediction-corrected visual predictive check (pcVPC; n=1000 replicates).

Software

The semi-mechanistic PK/PD model was performed using NONMEM (version 7.3.0, ICON Development Solutions LLC, Ellicott City, MD, United States). The use of NONMEM, including model qualification procedures, were facilitated within the environment of Perl-speaks-NONMEM (version 4.6.0, a compatible front-end program for NONMEM. Data management, exploratory analyses, diagnostic graphics, and post processing of the data and NONMEM outputs were performed using R (version 3.4.1, The R Project for Statistical Computing, statistical software). All analyses were performed in a validated environment, High Performance Pharmacometrics Platform System (Rudraya Sonic version 4 or higher), based on Good Automated Manufacturing Practice and in accordance with 21 CFR Part 11 and Good Clinical Practice regulations.

Statistical Analysis

Considering this was a phase 1 FIH study, formal statistical sample size calculation was not appropriate and was not performed. The number of participants enrolled was consistent with the customary size employed in such early development dose-escalation studies, and was expected to allow clinical judgment of safety and tolerability, and to allow meaningful assessment of the PK and PD profile.

Compound of Formula (III) plasma concentration data and its derived PK parameters, % BTKO, and safety were summarized using descriptive statistics. The PK analysis set included participants who received at least one dose of compound of Formula (III). The PD analysis set consisted of all participants who received at least 1 dose of compound of Formula (III) or placebo, and had at least 1 post-dose PD assessment. Safety analysis included all participants who received at least one dose of compound of Formula (III) or placebo.

Results

Participant Disposition and Demographics

In Part 1, 60 participants received a single dose of compound of Formula (III) and 18 received placebo. To assess multiple doses in Part 2, 18 participants received compound of Formula (III) and 9 participants received placebo. Overall, the demographic characteristics were similar across groups in either Part 1 or Part 2. Most participants were Caucasian (Part 1: 74/78 [94.9%]; Part 2: 26/27 [96.3%]). In Part 1, the mean age of participants was 45.8 years (range: 21 to 58 years) and mean body mass index (BMI) was 24.93 kg/$m^2$ (range: 19.4 to 29.2 kg/m2). In Part 2, the mean age was 48.6 years (range: 25 to 58 years) and mean BMI was 24.95 kg/m2 (range: 19.1 to 29.9 kg/$m^2$).

Safety

Overall, the nature and incidence of TEAEs were similar in compound of Formula (III) -treated and placebo-treated participants after single and multiple dosing. In Part 1 and Part 2, 24 (40.0%) and 14 (77.8%) participants receiving compound of Formula (III) had at least 1 TEAE, as compared to 9 (50.0%) and 9 (100.0%) participants in the corresponding placebo groups (Table 1). All TEAEs were rated as mild to moderate in severity.

TABLE 1

TEAEs Reported for ≥10% of Total Population in any Treatment Group (compound of Formula (III) or Placebo; Safety Analysis Set)

PART 1

| | | compound of Formula (III) | | | | | | | | |
|---|---|---|---|---|---|---|---|---|---|---|
| | | Fasted | | | | | | Solid | Fed | Total compound |
| TEAEs, n (%) | Placebo n = 18 | 4 mg n = 6 | 12 mg n = 5 | 36 mg n = 12 | 100 mg n = 11 | 200 mg n = 6 | 400 mg n = 6 | 105 mg n = 6 | 100 mg n = 8 | of Formula (III) N = 60 |
| Patients with ≥1 TEAEs | 9 (50.0) | 2 (33.3) | 3 (60.0) | 4 (33.3) | 4 (36.4) | 4 (66.7) | 3 (50.0) | 3 (50.0) | 1 (12.5) | 24 (40.0) |
| Headache | 3 (16.7) | 1 (16.7) | 2 (40.0) | 2 (16.7) | 0 | 1 (16.7) | 0 | 1 (16.7) | 1 (12.5) | 8 (13.3) |
| Administration site irritation* | 2 (11.1) | 1 (16.7) | 0 | 0 | 0 | 1 (16.7) | 0 | 0 | 0 | 2(3.3) |

PART 2

| | Placebo | compound of Formula (III) | | | |
|---|---|---|---|---|---|
| | n = 9 | 36 mg n = 6 | 100 mg n = 6 | 200 mg n = 6 | Total compound of Formula (III) N = 18 |
| Patients with ≥1 TEAEs | 9 (100.0) | 4 (66.7) | 5 (83.3) | 5 (83.3) | 14 (77.8) |
| Administration site irritation* | 1 (11.1) | 1 (16.7) | 2 (33.3) | 0 | 3 (16.7) |
| Injection site hematoma* | 0 | 0 | 2 (33.3) | 0 | 2 (11.1) |

TABLE 1-continued

TEAEs Reported for ≥10% of Total Population in any Treatment Group (compound of Formula (III) or Placebo; Safety Analysis Set)

| | | | | | |
|---|---|---|---|---|---|
| Injection site reaction* | 0 | 1 (16.7) | 1 (16.7) | 0 | 2 (11.1) |
| Fatigue | 3 (33.3) | 0 | 0 | 1 (16.7) | 1 (5.6) |
| Vessel puncture site hematoma* | 1 (11.1) | 0 | 1 (16.7) | 0 | 1 (5.6) |
| Abdominal discomfort | 1 (11.1) | 1 (16.7) | 1 (16.7) | 0 | 2 (11.1) |
| Regurgitation | 1 (11.1) | 1 (16.7) | 0 | 1 (16.7) | 2 (11.1) |
| Abdominal pain | 2 (22.2) | 0 | 0 | 1 (16.7) | 1 (5.6) |
| Diarrhea | 4 (44.4) | 0 | 1 (16.7) | 0 | 1 (5.6) |
| Flatulence | 1 (11.1) | 1 (16.7) | 0 | 0 | 1 (5.6) |
| Nausea | 1 (11.1) | 0 | 0 | 0 | 0 |
| Oral dysaesthesia | 1 (11.1) | 0 | 0 | 0 | |
| Paresthesia | 0 | 2 (33.3) | 0 | 0 | 2 (11.1) |
| Dizziness | 1 (11.1) | 0 | 0 | 1 (16.7) | 1 (5.6) |
| Headache | 2 (22.2) | 0 | 0 | 1 (16.7) | 1 (5.6) |
| Somnolence | 1 (11.1) | 0 | 1 (16.7) | 0 | 1 (5.6) |
| Dysgeusia | 1 (11.1) | 0 | 0 | 0 | 0 |
| Back pain | 0 | 1 (16.7) | 0 | 0 | 1 (16.7) |
| Myalgia | 1 (11.1) | 0 | 1 (16.7) | 0 | 0 |
| Abnormal dreams | 1 (11.1) | 0 | 0 | 0 | 0 |
| Skin irritation | 1 (11.1) | 0 | 0 | 0 | 0 |
| Skin reaction | 0 | 1 (16.7) | 0 | 1 (16.7) | 2 (11.1) |
| Hot flush | 0 | 0 | 1 (16.7) | 1 (16.7) | 2 (11.1) |
| Vertigo | 1 (11.1) | 0 | 0 | 0 | 0 |
| Vision blurred | 1 (11.1) | 0 | 0 | 1 (16.7) | 1 (5.6) |
| Lipase increased | 1 (11.1) | 0 | 0 | 0 | 0 |
| Dehydration | 1 (11.1) | 0 | 0 | 0 | 0 |
| Cough | 1 (11.1) | 0 | 0 | 0 | 0 |
| Increased bronchial secretion | 1 (11.1) | 0 | 0 | 0 | 0 |
| Oropharyngeal pain | 1 (11.1) | 0 | 0 | 0 | 0 |
| Nasopharyngitis | 1 (11.1) | 0 | 0 | 0 | 0 |

TEAEs = treatment-emergent adverse events

*"Vessel puncture site hematoma" were due to bruising at the site of indwelling catheters for blood draws.

The TEAEs of "skin irritation" and "skin reaction" were due to ECG electrode adhesive.

In Part 1, among compound of Formula (III) -treated participants, the most common (≥5%) TEAEs were headache (13.3% versus 16.7% in placebo) and nasal congestion (5% versus 0 in placebo). In Part 2, administration site irritation (ECG electrode adhesive site irritation) was the most frequently reported TEAE (compound of Formula (III), 16.7% [3/18] versus placebo, 11.1% [0 to 1/9]), followed by abdominal discomfort, back pain, hot flush, paresthesia, regurgitation, and skin reaction (reaction at ECG electrode adhesive site) (compound of Formula (III), 11.1% [2/18] versus placebo, 11.1% [0 to 1/9] for each). Only 1 participant from Part 2 (compound of Formula (III) 200 mg group) discontinued after 8 days of dosing due to a TEAE of mild 'transaminases increased, and levels returned to within the normal range at follow-up, 12 days after administration of the last dose of compound of Formula (III).

There were no dose-related, gender-related, or food-related differences in TEAEs reported in either of the parts. No serious TEAEs or TEAEs considered probably or very likely related to the study drug were reported. Also, no clinically significant changes were observed in laboratory parameters, vital signs, physical examinations, or ECGs.

TABLE 2

Mean (SD) of compound of Formula (III) Pharmacokinetic Parameters Following Single Dose of compound of Formula (III) in Healthy Participants (PK Analysis Set)

| Formulation Treatment, Condition | N | $C_{max}$ (ng/mL) | $C_{max}$/Dose (ng/mL) | $t_{max}^{a}$ (h) | $AUC_{0\text{-}24\,h}$ (h · ng/mL) | $AUC_{last}$ (h · ng/mL) | $AUC_{\infty}$ (h · ng/mL) | $AUC_{\infty}$/Dose (h · ng/mL/mg) | $t_{1/2,\,\lambda z}$ (h) | $t_{1/2,\,dom}$ (h) |
|---|---|---|---|---|---|---|---|---|---|---|
| Oral Solution | | | | | | | | | | |
| 4 mg, Male Fasted | 6 | 43.5 (9.61) | 10.9 (2.40) | 1 (1-1.5) | 157 (51.0) | 154 (48.9) | 155 (49.8) | 38.9 (12.5) | 1.6 (0.2) | 1.6 (0.2) |
| 12 mg, Male Fasted | 5 | 88.0 (18.9) | 733 (1.58) | 1 (1-1.5) | 319 (108) | 316 (109) | 317 (109) | 26.4 (9.07) | 1.6 (0.5) | 1.5 (0.2) |
| 36 mg, Male Fasted | 6 | 200 (51.8) | 5.55 (1.44) | 1 (0.5-1) | 649 (213) | 649 (214) | $644\ (239)^{b}$ | 17.9 (6.64) | $2.1\ (0.4)^{b}$ | 1.6 (0.1) |

TABLE 2-continued

Mean (SD) of compound of Formula (III) Pharmacokinetic Parameters Following Single Dose of compound of Formula (III) in Healthy Participants (PK Analysis Set)

| Formulation Treatment, Condition | N | $C_{max}$ (ng/mL) | $C_{max}$/Dose (ng/mL) | $t_{max}$[a] (h) | $AUC_{0-24\ h}$ (h · ng/mL) | $AUC_{last}$ (h · ng/mL) | $AUC_{\infty}$ (h · ng/mL) | $AUC_{\infty}$/Dose (h · ng/mL/mg) | $t_{1/2,\ \lambda z}$ (h) | $t_{1/2,\ dom}$ (h) |
|---|---|---|---|---|---|---|---|---|---|---|
| 100 mg, Male Fasted | 6 | 923 (334) | 9.23 (3.34) | 0.5 (0.5-1) | 2135 (709) | 2145 (718) | 20.6 (760)[b] | 20.6 (7.60) | 5.0 (3.3)[b] | 1.9 (0.2) |
| 200 mg, Male Fasted | 6 | 1210 (413) | 6.06 (2.07) | 1 (0.5-1) | 2748 (752) | 277 (763) | 2778 (761) | 13.9 (3.80) | 12.87 (8.4) | 1.8 (0.2) |
| 400 mg, Male Fasted | 6 | 1920 (1280) | 4.80 (3.20) | 0.75 (0.5-2) | 3704 (1639) | 3828 (1616) | 4197 (1885)[b] | 9.11 (4.68) | 13.2 (11.3)[c] | 2.2 (0.3) |
| 36 mg, Female Fasted | 6 | 233 (44.5) | 6.46 (1.24) | 1 (1-1.5) | 819 (296) | 816 (299) | 22.7 (8.30) | 1.9 (0.5) | 1.9 (0.5) | 1.6 (0.2) |
| 100 mg, Female Fasted | 5 | 650 (199) | 6.50 (1.99) | 0.5 (0.25-1) | 1420 (519) | 1459 (494) | 1338 (460)[c] | 13.4 (4.60) | 11.67 (7.8)[c] | 1.6 (0.2) |
| 100 mg, Male Fed | 6 | 277 (81.1) | 2.77 (0.811) | 2.5 (1-4) | 1716 (403) | 1752 (420) | 1757 (420) | 17.6 (4.20) | 10.8 (5.2) | 2.0 (0.5) |
| Oral Capsule | | | | | | | | | | |
| 105 mg (3 x 35 mg), Male Fasted | 8 | 345 (200) | 3.28 (1.91) | 1.5 (1-2) | 1323 (710) | 1452 (731) | 1505 (797)[d] | 14.3 (7.59) | 14.2 (4.5)[d] | 1.9 (0.3) |

[a]Data presented as Median (Minimum-Maximum);
[b]n = 5;
[c]n = 4;
[d]n = 6.
AUC = area under the plasma concentration versus time curve;
$AUC_{0-24\ h}$ = AUC from time 0 to 24 horns post-dose;
$AUC_{last}$ = AUC from time 0 to the time corresponding to the last quantifiable concentration;
$AUC_{\infty}$ = AUC from time 0 to infinity with extrapolation of the terminal phase;
AUC/Dose = AUC normalized for dose;
$C_{max}$ = maximum observed plasma concentration;
$C_{max}$/Dose = Cmax normalized for dose;
SD = standard deviation;
$t_{1/2,\ \lambda z}$ = terminal half-life;
$t_{1/2,eff}$ = dominant half-life;
$t_{max}$ = time correspondent to the maximum observed plasma concentration Pharmacokinetics Part 1

Figure 3:
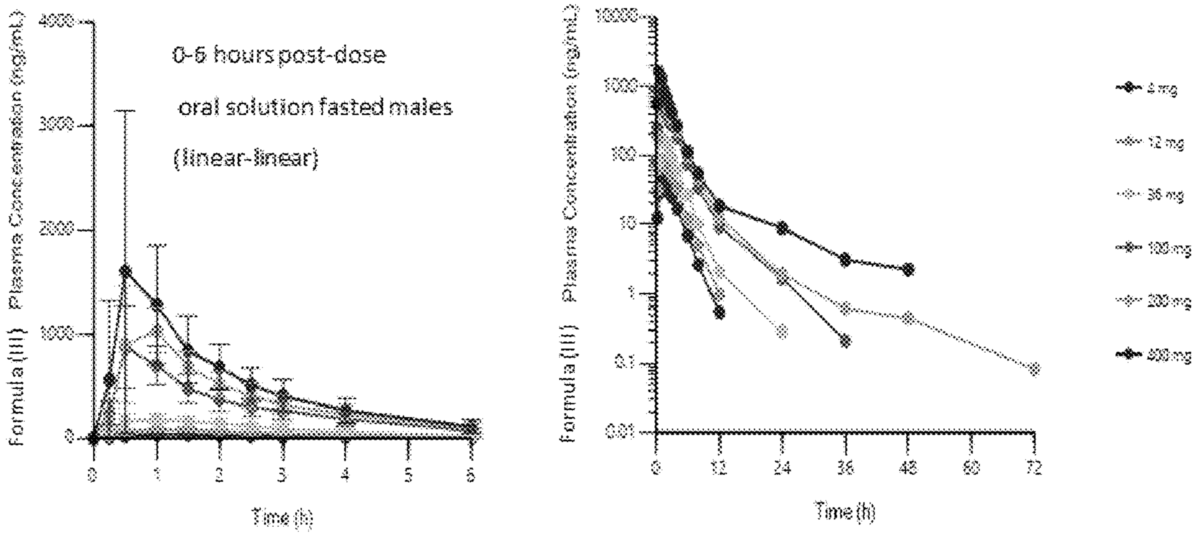
FIG. 3 depicts SAD fasted male cohorts plasma concentrations by time.

Following a single dose of compound of Formula (III) oral solution under fasted conditions in healthy males, peak plasma concentrations occurred within 1 hour and then declined in a multi-exponential manner (FIG. 3). Compound of Formula (III)was rapidly absorbed into the systemic circulation as indicated by a median tmax of 0.5 to 1 hours post-dose. Mean $C_{max}$, $AUC_{last}$, and $AUC_{\infty}$ of compound of Formula (III) increased over the dose range of 4 to 400 mg but less than dose proportionally with increasing doses (Table 2). Mean $t_{1/2,\ dorm}$ values were similar, ranging from 1.5 to 2.2 hours in the dose range of 4 to 400 mg. Mean $t_{1/2,\ \lambda z}$ increased with dose, with mean values ranging from 1.6 to 13.2 hours. At the lowest doses (4, 12, and 36 mg), the Mean $t_{1/2,\ \lambda z}$ was similar to the Mean $t_{1/2,\ dorm}$ as the plasma concentrations were approaching the lower limit of quantitation (LLOQ) between 12 and 24 hours post-dose.

Gender Effects

The PK parameters in male and female participants were overlapping following a single dose of 36 mg and 100 mg of compound of Formula (III) as an oral solution under fasted conditions. For 36 mg dose cohorts, mean $C_{max}$ and AUCs in females were slightly higher than in males by approximately 17-27%; however, in females dosed with the 100 mg dose, these values were lower than in males by approximately 30-35% (Table 2).

Mean $t_{1/2}$ of the initial fast decay ($t_{1/2,\ dorm}$) was 1.6 hours in fasted females irrespective of the dose of compound of Formula (III) (36 mg or 100 mg) and was comparable to the mean $t_{1/2,dorm}$ reported for male participants (36 mg: 1.6 hours; 100 mg: 1.9 hours). The $t_{1/2,\ \lambda z}$ in female participants increased with dose, with values of 1.9 hours and 11.6 hours for the 36 mg and 100 mg dose groups, respectively.

Food Effects

Figure 4:
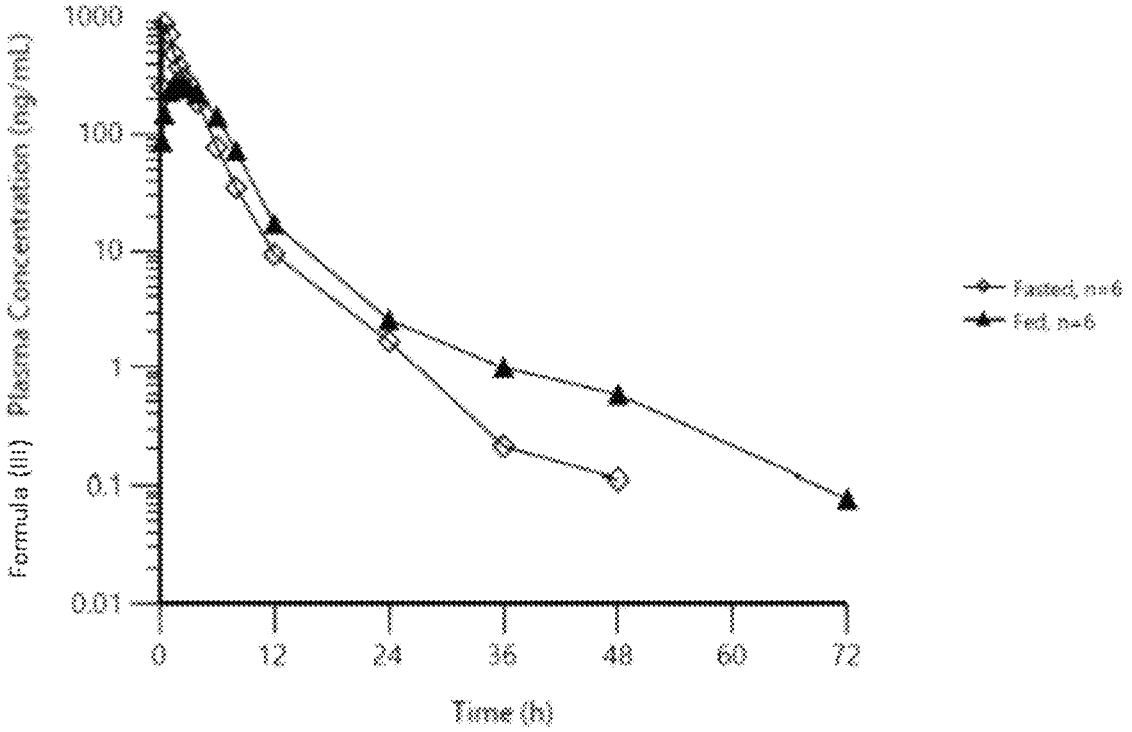
FIG. 4 depicts the arithmetic mean of the compound of formula (III) plasma concentration-time profiles following a single dose of 100 mg of the compound of Formula (III) oral solution in healthy male subjects under fasted or fed conditions (high-fat breakfast) (log-linear) (Phase I Study-SAD part: Pharmacokinetic Analysis Set).

Administration of a single dose of 100 mg compound of Formula (III) following a high-fat meal delayed peak of the concentration-time profile (median $t_{max}$: 2.5 hours versus 0.5 hours [100 mg fasted cohort]) (FIG. 4), and lowered the plasma $C_{max}$ by approximately 70% without much affecting overall exposure (Table 2). Mean AUCs of the fed cohort were approximately 15 to 20% lower compared with the fasted cohort (Table 2). The rate of decline in plasma concentrations was similar between fasted and fed male cohorts, with mean $t_{1/2,\ dorm}$ of 1.9 and 2.0 hours, respectively. Mean $t_{1/2,\ \lambda z}$ in fed participants fell within the range of values estimated across the dose range of 4 mg to 400 mg in the fasted cohorts (Table 2).

Capsule Formulation

Following a single dose of 105 mg compound of Formula (III) administered as 3x35 mg capsules, the peak of the plasma concentration-time profile was slightly delayed, with a median $t_{max}$ of 1.5 hours versus 0.5 hours for 100 mg oral solution (Table 2). Mean $C_{max}$/Dose of the capsule formulation was approximately 64% lower while mean AUCs/Dose was approximately 31% to 41% lower compared with the oral solution.

Part 2

Figure 5:
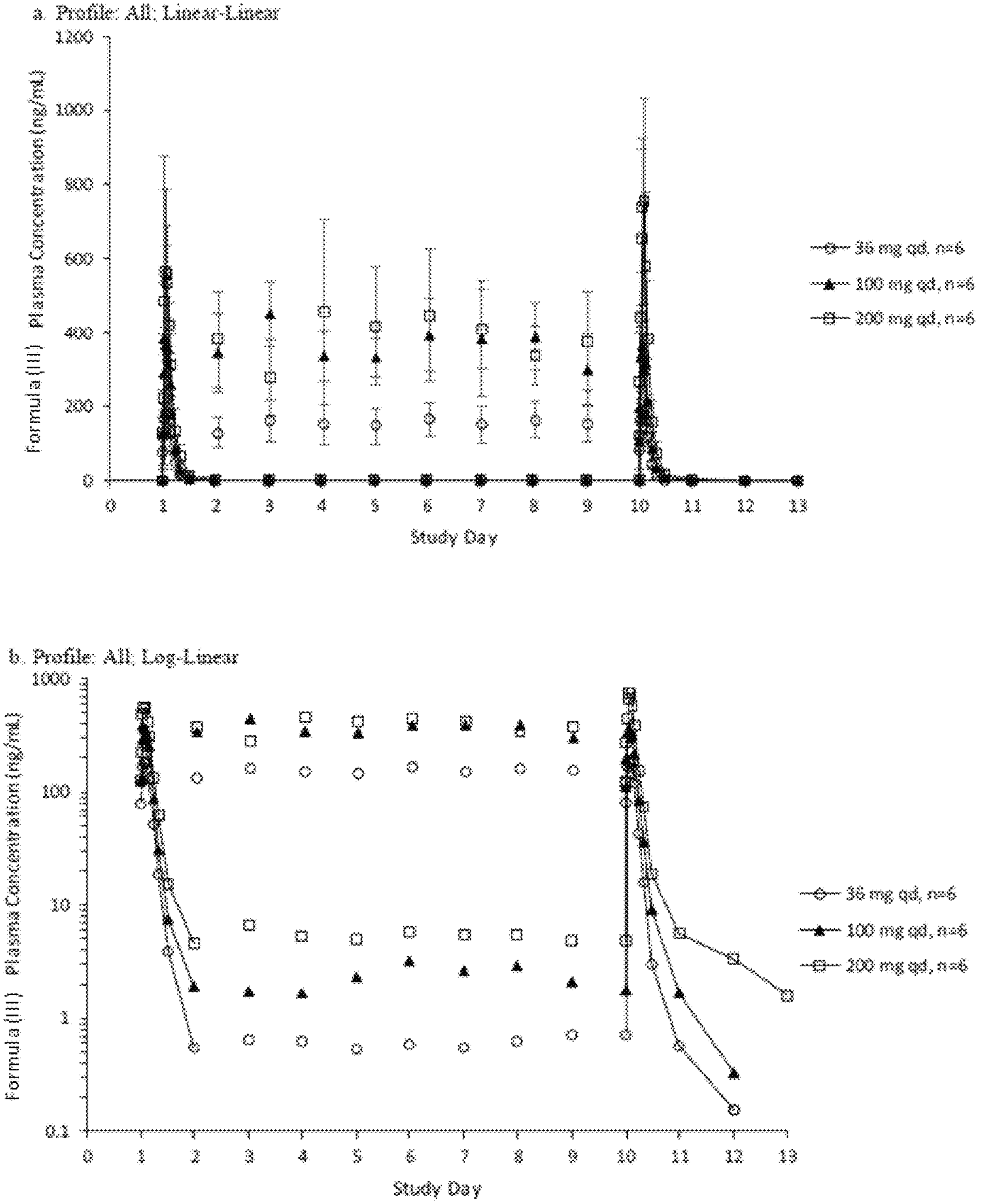
FIG. 5 depicts mean (SD) compound of Formula (III) plasma concentration-time profiles following multiple doses of the compound of Formula (III) oral solution in healthy male and female subjects under fed conditions (standard breakfast).

On day 1, the mean PK profiles increased with dose, and compound of Formula (III) was rapidly absorbed with median $t_{max}$ ranging from 1.25 to 1.77 hours post-dose (Table 3). Mean predose and 1-hour post-dose concentrations remained similar across days 2-9 within each dose group, suggesting that compound of Formula (III) plasma concentrations reached steady-state by the second dose (FIG. 5). Compared to the profiles observed on day 1, the day 10 plasma concentration-time profiles were similar or slightly higher but subsequently decreased in a multi-exponential manner (FIG. 5). No accumulation of compound of Formula (III) was observed following daily dosing of 36 mg and 100 mg, with mean (SD) $AR_{AUC}$=0.968 (0.101) and 0.950 (0.237), respectively. Minor accumulation was observed after multiple doses of 200 mg compound of Formula (III) with mean (SD) $AR_{AUC}$=1.21 (0.180). Renal elimination of unchanged compound of Formula (III) was negligible following daily oral doses of 200 mg compound of Formula (III) (Table 3).

TABLE 3

Mean (SD) of compound of Formula (III) Pharmacokinetic Parameters Following Multiple Doses of compound of Formula (III) Oral Solution in Healthy Males and Females under Fed Conditions (PK Analysis set)

| Treatment | $C_{max}$ (ng/mL) | $t_{max}$[a] (h) | $AUC_{0-24\ h}$ (h · ng/mL) | $C_{min}$ (ng/mL) | $t_{1/2,\ \lambda z}$ (h) | $t_{1/2,\ dom}$ (h) | $AR_{Cmax}$ | $AR_{AUC}$ | $Ae_{\%\ dose}$ | $CL_R$ (L/h) |
|---|---|---|---|---|---|---|---|---|---|---|
| Day 1 | | | | | | | | | | |
| 36 mg QD | 193 (39.2) | 1.50 (1.00-2.50) | 925 (210) | NA | NA | NA | NA | NA | NA | NA |
| 100 mg QD | 464 (141) | 1.25 (1.00-3.00) | 1821 (499) | NA | NA | NA | NA | NA | NA | NA |
| 200 mg QD | 719 (299) | 1.77 (1.00-3.00) | 2565 (577) | NA | NA | NA | NA | NA | 0.234 (0.0662) | 0.186 (0.0544) |
| Day 10 | | | | | | | | | | |
| 36 mg QD | 199 (36.9) | 2.00 (1.00-2.50) | 889 (182) | 0.552 (0.198) | 4.9 (3.3)[b] | 1.5 (0.1) | 1.04 (0.129) | 0.968 (0.101) | NA | NA |
| 100 mg QD | 424 (70.4) | 1.53 (1.00-3.00) | 1692 (546) | 1.51 (0.545) | 9.6 (3.6) | 1.8 (0.2) | 0.968 (0.234) | 0.950 (0.237) | NA | NA |
| 200 mg QD | 839 (252) | 2.00 (1.50-2.50) | 3164 (965) | 4.96 (1.85) | 23.1 (12.2)[c] | 1.9 (0.1) | 1.21 (0.180) | 1.21 (0.180) | 0.234 (0.0723) | 0.186 (0.0453) |

[a]Data presented as Median (Minimum-Maximum);
[b]n = 3;
[c]n = 4
$Ae_{\%\ dose}$ = amount excreted into the urine as a percent of dose, calculated as ratio of Ae to the dose administered × 100;
$AR_{AUC}$ = the observed accumulation ratio based on AUC;
$AR_{Cmax}$ = the observed accumulation ratio based on Cmax;
AUC = area under the plasma concentration versus time curve;
$AUC_{0-24\ h}$ = AUC from time 0 to 24 hours post-dose;
$C_{max}$ = maximum observed plasma concentration;
$C_{min}$, minimum observed plasma concentration;
CLR = renal clearance;
SD = standard deviation;
$t_{1/2,\ \lambda z}$ = terminal half-life;
$t_{1/2,\ eff}$ = dominant half-life;
$t_{max}$ = time correspondent to the maximum observed plasma concentration

TABLE 4

Covariates Assessed in Population Pharmacokinetic Analysis Using All Data from SAD and MAD

| Categories | Covariates | Type |
|---|---|---|
| Demographic characteristics | Weight [BWT], Age [AGE] | Continuous |
| | Sex [SEX], Race [RACE] | Discrete |
| Renal Function | Baseline creatinine clearance [CRCL], Estimated glomerular filtration rate [eGFR] | Continuous |
| Clinical laboratory characteristics | Baseline albumin [BALB], Baseline aspartate aminotransferase [AST], Baseline alanine aminotransferase [ALT], Baseline alkaline phosphatase [ALP], Total bilirubin [TB] | Continuous |
| Food Effects | Nutritional status [NUTR] | Discrete |
| Formulation | Dosage form [FORM] | Discrete |

MAD, multiple-ascending dose;
SAD, single-ascending dose.

Pharmacodynamics

Figure 6:
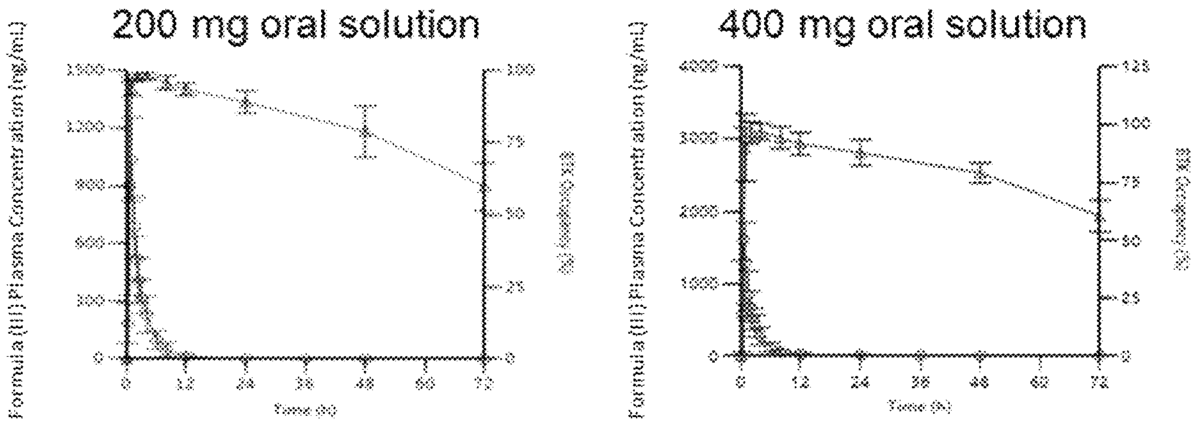
FIG. 6 depicts BTK occupancy and plasma concentrations by time following single doses of the compound of Formula (III) oral solution in fasted males.

BTKO following single oral solution dose in fasted state—In male participants, the % BTKO increased with increasing compound of Formula (III) doses and approached 100% at 4 hours after administration of doses ≥100 mg (FIG. 6). While plasma concentrations of compound of Formula (III) decreased to <LLOQ 12 hours post-dose, the duration of BKTO was up to 72 hours for cohorts dosed with ≥100 mg compound of Formula (III) (FIG. 6). At the follow-up visit (7-14 days post last dose), the mean % BTKO values were ≤42% in all treatment groups, with high variability in some groups. The emerging PK and BTKO data demonstrated that BTKO was closely linked with compound of Formula (III) AUCss rather than $C_{max}$.

Compared with fasted administration of the solution formulation (100 mg), the peak mean % BTKO value was delayed and slightly lower following administration of the solution formulation after a high-fat breakfast (100 mg) (fed state: 73% [at 8 hours post-dose]; fasted state: 86% [at 4 hours post-dose]).

The mean % BTKO values in females receiving 36 mg or 100 mg compound of Formula (III) were similar to male participants receiving the same doses. At 4 hours following administration of the 36 mg dose, the mean % BTKO values were 39% in males and 55% in females, and were 86% versus 81%, respectively when dosed with 100 mg compound of Formula (III).

BTKO following single capsule formulation dose in fasted state—The mean % BTKO was reduced in males dosed with 105 mg compound of Formula (III) capsule formulation compared with fasted administration of 100 mg oral solution. At 4 hours post-dose, mean % BTKO was ≈37% lower for 105 mg capsule formulation (54%) than the 100 mg oral solution (86%), and ≈30% lower at 24 hours post-dose (53% versus76%, respectively).

BTKO following multiple doses of compound of Formula (III) oral solution -Accumulation of % BTKO in PBMCs was observed after multiple once-daily dosing with compound of Formula (III). At 4 hours post-dose, the mean % BTKO increased from 34% (day 1) to 80% (day 10) in the 36 mg dose group and from 61% (day 1) to 91% (day 10) in the 100 mg group. Whereas, in the 200 mg dose group, mean % BTKO was evident from day 1 (94%) and maintained on day 10 (98%). Mean % BTKO at all 3 compound of Formula (III) doses (36, 100, and 200 mg) remained high (68% to 79%) 24 hours after the day 10 dose. At the follow-up visit (7 to 14 days post-dose), the mean % BTKO values were <40% in all treatment groups with high variability in some groups.

PK/PD modeling and simulation—compound of Formula (III) plasma concentrations from the first 5 SAD cohorts were best described with a 2-compartment model, including a first-order absorption and first-order elimination with IIV on CL/F, $V_1$/F, $V_2$/F, Q/F and $K_a$. Additionally, correlation terms were included between CL/F and Vi/F. The PK/PD model was subsequently developed based on individual estimates from the popPK model to describe free BTK, with IIV on baseline free BTK and associate rate $k_{on}$. Parameter estimates are shown in Table 5 and goodness-of-fit plots are shown in FIG. 9 and FIG. 10. All model parameters were estimated reasonably well with relative standard errors ≤20% for all the structural PK/PD parameter estimates. Based on the PK/PD model, simulations were conducted to predict % BTK occupancy in the MAD cohorts (FIG. 5). The model-predicted % BTKO in the MAD cohorts based on data from the SAD cohorts was consistent with observed % BTKO (Table 6).

TABLE 5

Parameter Estimates of the PK/PD Model Using (A) First 5 SAD Cohorts data (B) All SAD and MAD Data

| Parameter, unit | Estimate | RSE (%) | IIV (% CV) | RSE (%) | Shrinkage (%) |
|---|---|---|---|---|---|
| (A) | | | | | |
| popPK parameters[b] | | | | | |
| CL/F (L/h) | 49.4 | 8.68 | 44.0 | 25.2 | 1.18 |
| $V_1$/F (L) | 108.9 | 8.62 | 40.6 | 25.1 | 2.93 |
| $V_2$/F (L) | 43.0 | 17.7 | | | |
| Q/F (L/h) | 1.57 | 12.0 | 49.1 | 42.2 | 21.8 |
| Ka (l/h) | 1.94 | 11.2 | 44.5 | 33.7 | 12.5 |
| Covar (CL/F, $V_1$/F) | 0.174 | 25.4 | | | |
| Proportional residual error (% CV) | 24.5 | 8.43 | | | |
| Additive residual error (ng/mL)[c] | 0.0289 | — | | | |
| PD parameters[b] | | | | | |
| $k_{on}$ (l/nM/h) | 0.0447 | 13.3 | 31.6 | 125.5 | 64.8 |
| $k_{off}$ (l/h)[d] | $5.7 \times 10^{-5} \times 60 \times 60$ | — | | | |
| $k_{inact}$ (l/s)[d] | $7.8 \times 10^{-4}$ | — | | | |
| $BTK_0$ (nM) | 0.0815 | 3.63 | 34.0 | 29.1 | 8.82 |
| $K_{degi}/K_{degf}$ (l/h)[d] | 0.0116 | — | | | |
| Additive residual error (nM) | 0.0208 | 12.4 | | | |

[a]CL/F = apparent clearance; IIV = inter-individual variability, calculated as $(\text{variance})^{1/2} \times 100\%$; Ka = first-order absorption rate constant; $k_{on}$ = association rate; $k_{off}$ = dissociate rate; $k_{inac}$t = covalent binding rate; $k_{deg}$ = BTK degradation rate; Q/F = apparent inter-compartmental clearance; RSE = relative standard error; $V_1$/F = apparent volume of distribution of the central compartment; $V_2$/F = apparent volume of distribution of the peripheral compartment.

[b]popPK was examined using Cohort 1-5 data, PD was assessed with Cohort 2-5 data.

[c]Additive residual error was fixed to 0.0289 ng/mL based on a calculation of the probability distribution characteristic associated with LLOQ of 0.1 ng/mL.

[d]koff was obtained from Woyach Supplemental Data 2014, kinact was from lab measurement, kdegi/kdegf was calculated with ln(2)/60, assuming BTK turnover half-life was 60 h.

| Parameter, unit | Estimate | RSE (%) | IIV (% CV) | RSE (%) | Shrinkage (%) |
|---|---|---|---|---|---|
| (B) | | | | | |
| popPK parameters[b] | | | | | |
| CL/F (L/h)[c] | 62.4 | 5.10 | 46.0 | 17.4 | 0.42 |
| BWT on CL/F | 0.75 | — | | | |
| $V_1$/F (L)[d] | 129.6 | 4.92 | 41.7 | 19.7 | 2.76 |
| BWT on $V_1$/F | 1 | — | | | |
| $V_2$/F (L)[e] | 49.5 | 15.2 | 139.9 | 19.7 | 10.1 |
| BWT on $V_2$/F | 1 | — | | | |
| Q/F (L/h)[f] | 2.85 | 13.7 | 132.5 | 19.6 | 8.92 |
| BWT on Q/F | 0.75 | — | | | |
| $K_a$ (l/h)[g] | 1.97 | 8.14 | 44.3 | 22.0 | 11.5 |
| NURT = Fed, standard meal on Ka | 0.339 | 12.3 | | | |
| FORM = Oral Capsule on Ka | 0.325 | 19.2 | | | |
| Covar (CL/F, $V_1$/F) | 0.185 | 18.5 | | | |
| Covar (Q/F, $V_2$/F) | 1.74 | 19.9 | | | |
| Proportional residual error (% CV) | 28.1 | 2.21 | | | |

TABLE 5-continued

Parameter Estimates of the PK/PD Model Using (A) First 5 SAD Cohorts data (B) All SAD and MAD Data

| Parameter, unit | Estimate | RSE (%) | IIV (% CV) | RSE (%) | Shrinkage (%) |
|---|---|---|---|---|---|
| Additive residual error (ng/mL) | 0.0483 | 33.9 | | | |
| PD parameters[b] | | | | | |
| $k_{on}$ (l/nM/h) | 0.0509 | 10.2 | 43.2 | 45.7 | 50.4 |
| $k_{off}$ (l/h)[h] | $5.7 \times 10^{-5} \times 60 \times 60$ | — | | | |
| $k_{inact}$ (l/s)[h] | $7.8 \times 10^{-4}$ | — | | | |
| $BTK_0$ (nM) | 0.0802 | 3.01 | 24.6 | 19.4 | 11.2 |
| $K_{degi}/K_{degf}$ (l/h)[h] | 0.0116 | — | | | |
| Additive residual error (nM) | 0.0220 | 0.748 | | | |

[a]BWT = baseline body weight in kilograms; CL/F = apparent clearance; FORM = Dosage form (1 = Oral solution, 2 = Oral Capsule); IIV = inter-individual variability, calculated as $(\text{variance})^{1/2} \times 100\%$; Ka = first-order absorption rate constant; $k_{on}$ = association rate; $k_{off}$ = dissociate rate; $k_{inac}$t = covalent binding rate; $k_{deg}$ = BTK degradation rate; NURT = Nutritional status (0 = Fasted, 1 = Fed, standard meal); Q/F = apparent inter-compartmental clearance; RSE = relative standard error; $V_1/F$ = apparent volume of distribution of the central compartment; $V_2/F$ = apparent volume of distribution of the peripheral compartment.

[b]popPK and PD were examined using data from both SAD and MAD data.

[c] $$\frac{CL}{F}\ (\text{L/h}) = 62.4 \times \left(\frac{BWT}{75.5}\right)^{0.75}$$

[d] $$\frac{V1}{F}\ (\text{L}) = 129.6 \times \left(\frac{BWT}{75.5}\right)^{1}$$

[e] $$\frac{V2}{F}\ (\text{L}) = 49.5 \times \left(\frac{BWT}{75.5}\right)^{1}$$

[f] $$\frac{Q}{F}\ (\text{L}) = 2.85 \times \left(\frac{BWT}{75.5}\right)^{0.75}$$

[g] $$Ka\left(\frac{1}{\text{h}}\right) = 1.97 \times 0.339^{NUTR=Fed,standard\ meal} \times 0.325^{FORM=Oral\ Capsule}$$

[h]koff was obtained from Woyach Supplemental Data 2014, kinact was from lab measurement, kdegi/kdegf was calculated with ln(2)/60, assuming BTK turnover half life was 60 h.

TABLE 6

Comparison of Simulated and Observed Data

| | Median of Simulations (n = 1000) based on Phase 1 SAD Oral Solution data | | | Median Observed Day 10 Oral Solution Data | | |
|---|---|---|---|---|---|---|
| Dose (mg) | BTKO at 24 hr,ss (%)[b] | Max BTKO at ss (%)[b] | Average BTKO (%)[b,c] | BTKO at 24 hr, ss (%) | Max BTKO at ss (%) | Calculated Average BTKO (%) |
| 12 QD | 43.4 | 52.0 | 48.3 | — | — | — |
| 36 QD | 66.7 | 79.9 | 74.3 | 69.5 | 78.9 | 74.2 |
| 70 QD | 75.6 | 91.5 | 84.7 | — | — | — |
| 100 QD | 78.8 | 96.0 | 88.3 | 84.1 | 94.1 | 89.1 |
| 105 QD | 79.1 | 96.3 | 88.7 | — | — | — |

TABLE 6-continued

Comparison of Simulated and Observed Data

| Dose (mg) | Median of Simulations (n = 1000) based on Phase 1 SAD Oral Solution data: BTKO at 24 hr,ss (%)[b] | Max BTKO at ss (%)[b] | Average BTKO (%)[b,c] | Median Observed Day 10 Oral Solution Data: BTKO at 24 hr, ss (%) | Max BTKO at ss (%) | Calculated Average BTKO (%) |
|---|---|---|---|---|---|---|
| 140 QD | 80.3 | 98.2 | 90.4 | — | — | — |
| 200 QD | 81.6 | 99.3 | 91.5 | 78.9 | 98.8 | 88.8 |

[a]popPK was examined using Cohort 1-5 data, popPD was assessed with Cohort 2-5 data;
[b]The values are median of 1000 simulations;
[c]Average RO at steady-state (ss) was calculated as $AUMC_{ss/tau}$
$AUMC_{ss/tau}$ = Area under the first moment of the plasma concentration-time curve for the dosing interval at steady-state;
BTKO = Bruton's tyrosine kinase occupancy;
PopPK = population pharmacokinetics;
popPD = population pharmacodynamics;
QD, once daily;
SAD = single-ascending dose;
ss = steady-state.

The PK/PD model was updated again with the data acquired from FIH study. The PK/PD dataset contained 1509 compound of Formula (III) concentration-time datapoints and 1335 free BTK datapoints from 105 participants. compound of Formula (III) plasma concentrations from both SAD and MAD cohorts were described with a 2-compartmnet model, including a first-order absorption and first-order elimination with IIV on CL/F, $V_1$/F, $V_2$/F, Q/F and $K_a$. Additionally, correlation terms were included between CL/F and $V_1$/F, Q/F and $V_2$/F. The residual error was best described by a combined additive and proportional error model. The covariate effects retained in the final popPK model were the effects of body weight on CL/F, $V_1$/F, $V_2$/F and Q/F, the food effects and drug formulation effects on $K_a$. Other covariates tested were not statistically significant. pcVPC are shown in FIG. 11, the final PKPD model adequately captured the median concentration-time profiles.

DISCUSSION

In the overall context of pharmacotherapy, the BTK inhibitors are promising novel agents that have significantly expanded the arsenal of therapies available for the treatment of various types of B-cell malignancies. This FIH phase 1 study demonstrated that an oral solution of compound of Formula (III), a novel BTK inhibitor, can be administered as a single dose up to 400 mg and multiple daily doses up to 200 mg for 10 days with no safety signals of concern. A maximum % BTKO of ≥90% (mean) was achieved after single and multiple doses of compound of Formula (III) of ≥100 mg. The high variability was seen between the reported % BTKO for the same doses in SAD and MAD cohorts. This high variability in BTKO can be attributed to the food effect; in SAD cohorts, participants were dosed in a fasted state, while in MAD cohorts, participants were not fasted.

The safety profile showed that TEAEs occurred in 40% of participants following single dosing and in 78% participants after multiple dosing of compound of Formula (III). The most common TEAEs after single dosing were headache and nasal congestion, and administration site irritation, abdominal discomfort, back pain, hot flush, paresthesia, regurgitation, and skin reaction were most common after multiple dosing. All the events were of mild to moderate severity and resolved by the end of the study. All TEAEs reported in both parts of the study resolved by follow-up and there was no apparent increase in frequency or type of TEAEs with increasing dose of compound of Formula (III). Also, no gender- or food-related differences were reported in incidence and severity of TEAEs. There were no clinically relevant ECG changes or relevant cardiac or cardiovascular TEAEs.

The PK profiles of compound of Formula (III) demonstrated rapid absorption with peak concentrations reached within 1 hour after single doses and 2 hours after multiple doses. After reaching $C_{max}$, the plasma concentration of compound of Formula (III) declined rapidly in a multiexponential fashion. The PK were linear but less than dose-proportional over a 4 to 400 mg single-dose range and a 36 to 200 mg QD multiple-dose range at steady-state, with little to no accumulation and no time dependency observed after 10 days repeated dosing. Gender did not have a substantial effect on PK of compound of Formula (III). Food delayed the $t_{max}$ and decreased the $C_{max}$ by approximately 70%; and overall exposure was approximately 15 to 20% lower in the fed versus fasted state. The capsule formulation affected the PK profile, showing slower absorption and ~64% lower $C_{max}$ and 31% to 41% lower AUC compared with a similar dose of the oral solution.

Pharmacodynamics were assessed as % BTKO in PBMCs. Target occupancy was dose-dependent, approaching complete maximal BTKO following single and multiple doses of compound of Formula (III) ≥100 mg, typically within 4 hours of administration. The duration of BTKO was long-lasting, remaining detectable 72 hours post dose for cohorts who received ≥100 mg compound of Formula (III). Following multiple oral doses of compound of Formula (III), mean BTKO values appeared to reach steady-state by between days 3 and 7. Although little accumulation of plasma concentrations of compound of Formula (III) was observed, lower variability in BTKO was observed following multiple doses compared with single dose administration. This was particularly evident in samples taken within a few hours of dosing, at the time when peak plasma concentrations of compound of Formula (III) would have been achieved. As mean compound of Formula (III) plasma concentrations declined and approached the LLOQ within 24 hours after the last dose on Day 10, mean BTKO in all dose groups remained above 65% and 30% at 24 hours and 72 hours post-dose, respectively. These findings are in line with target occupancy data reported for other covalent BTK inhibitors. Although there are no published target occupancy data in healthy volunteers for ibrutinib, acalabrutinib, and zanubrutinib in healthy volunteers; a median BTKO of ≥95i was observed in patients with B-cell lymphoma or chronic lymphocytic leukemia in peripheral blood. A semi-mechanistic PK/PD model was developed to describe the irreversible BTK inhibition of compound of Formula (III). The PK/PD model with the first 5 SAD cohorts' clinical data was used to predict % BTKO and to aid in the selection of doses for Part 2 (i.e., MAD portion) of this study. The PK/PD model guided the decision of dose-escalation. The model-predicted % BTKO in the MAD cohorts based on data from the SAD cohorts were consistent with observed MAD % BTKO once data became available. Food effects and dosage formulation effects were identified as covariates significantly contributing to the observed compound of Formula (III) PK variability when the PK/PD model was further updated when all the data from the FIH Study was available.

Single doses of 4 to 400 mg compound of Formula (III) and multiple-doses of 36 to 200 mg compound of Formula (III) QD×10 days were safe and well tolerated and had favorable PK/PD properties for continued development. The observed data, PK/BTKO modeling, and data from the oral capsule cohort guided the selection of 140 mg QD as the starting dose regimen for the first-in-patient studies in B-cell non-Hodgkin lymphoma and CLL as a single agent and in combination (NCT04210219 and NCT04657224).

activates phospholipase-Cγ, leading to calcium mobilization and activation of NF-κB and mitogen-activated protein kinase pathways.

Given the key role of BTK in oncogenic BCR signaling, BTK inhibitors have been extensively studied in B-cell hematologic malignancies. Multiple lines of evidence suggest that signaling through the BCR is necessary to sustain the viability of B-cell malignancies. For example, expression of a functional BCR is maintained throughout lymphoma progression. Selective knockdown of BCR components by RNA interference results in apoptosis in multiple B-cell lymphoma cell lines. Furthermore, activation of NF-κB via BCR signaling is critical for the survival of several B-cell tumors, including the activated B-cell subtype of diffuse large B-cell lymphoma (ABC-DLBCL). B-cell receptor signaling has also been shown to be the major pathway activated in proliferating chronic lymphocytic leukemia cells and is, therefore, a primary therapeutic target. Finally, BCR signaling may also lead to increased occlusion within the stromal microenvironment in tissues, and blocking this protective interaction can lead to efflux of the tumor cells into the circulation, where they are more easily killed by chemotherapeutic agents.

Three small-molecule BTK inhibitors—ibrutinib, acalabrutinib, and zanubrutinib (FIG. 12) are approved for the treatment of hematologic malignancies. Despite the success of these drugs, the treatment of hematological malignancies remains challenging due to a substantial portion of patients not achieving complete response or experiencing relapse. Therefore, additional highly selective and safe BTK inhibitors are needed to with the potential to achieve transformational efficacy with synergistic combination therapies.

TABLE 7

Comparison of Simulated and Observed Data

| | Simulations (n = 1000) based on Phase 1 SAD Oral Solution data | | | Median Observed Day 10 Oral Solution Data | | |
|---|---|---|---|---|---|---|
| Dose (mg) | BTKO at 24 hr, ss (%)[b] | Max BTKO at ss (%)[b] | Average BTKO (%)[b,c] | BTKO at 24 hr, ss (%) | Max BTKO at ss (%) | Calculated Ave BTKO (%) |
| 12 QD | 43.2 | 51.8 | 48.0 | — | — | — |
| 36 QD | 66 | 79.7 | 74.1 | 69.5 | 78.9 | 74.2 |
| 70 QD | 75.6 | 91.5 | 84.6 | — | — | — |
| 100 QD | 78.7 | 96 | 88.3 | 84.1 | 94.1 | 89.1 |
| 105 QD | 79 | 96.3 | 88.7 | — | — | — |
| 140 QD | 80.1 | 98.3 | 90.3 | — | — | — |
| 200 QD | 81.4 | 99.4 | 91.49 | 78.9 | 98.8 | 88.8 |

[a]popPK was examined using Cohort 1-5 data, popPD was assessed with Cohort 2-5 data;
[b]The values are median of 1000 simulations;
[c]Average RO at steady state (ss) was calculated as AUMCss/tau

Example 2—Discovery and Preclinical Properties of Compound of Formula (III), a Potent and Selective Covalent Inhibitor of Bruton's Tyrosine Kinase Introduction—Bruton's tyrosine kinase (BTK), a member of the Tec family of nonreceptor cytoplasmic tyrosine kinases, plays a critical role in B cell activation via the B cell receptor (BCR). Bruton's tyrosine kinase also plays a critical role in macrophage activation via Fcγ receptors, platelet microparticle production in the inflamed joint, and osteoclast activation. The BTK protein is expressed in most hematopoietic cells, with the exception of T cells, plasma cells, and natural killer cells. The upstream Src-family kinases (BLK, LYN, and FYN1,10) and SYK tyrosine kinases activate BTK, which in turn phosphorylates and The approved BTK inhibiting drugs 1-3 validate covalent targeting BTK as a viable strategy for achieving high kinase selectivity and sustained target occupancy. The BTK Cys481 residue is present in an analogous position for only 10 other human kinases (BMX, TEC, ITK, TXK, EGFR, ERBB2, ERBB4, JAK3, BLK, MKK7), thus providing an opportunity for covalent bond formation with a small fraction of the kinome. Furthermore, an irreversible covalent inhibition mechanism can achieve an extended pharmacodynamic effect with a transient pharmacokinetic exposure when the protein re-synthesis rate is low. The re-synthesis rate of BTK has been estimated at 3.6-31.4% per day in patients with chronic lymphocytic leukemia, and a corresponding extended pharmacodynamic effect with clinical BTK inhibitors has been reported.

RESULTS AND DISCUSSION—Selectivity—The compound of Formula (III) was evaluated in three selectivity panels to assess the potential for off-target pharmacology (Table 8). In a panel of diverse proteins including receptors, enzymes, and ion channels, The compound of Formula (III) did not bind >50% at 10 μM for any of the 54 test targets. The kinase off-target profile of The compound of Formula (III) was assessed in a full human wild-type panel using radiometric kinase activity assays (KinaseProfiler™ and $IC_{50}$Profiler™; Eurofins Scientific) (Table 9; FIG. 23). The compound of Formula (III) inhibited 4/278 kinases >50% at 1 micromolar, identifying BTK and the three other kinases having analogous Cys residues with the potential for covalent inhibition (BMX, TEC, BLK). Subsequence concentration-response experiment confirmed BMX and TEC $IC_{50}$<1 micromolar, however the $IC_{50}$ does not measure the rate component of a potential covalent interaction with these homologous kinases. The cellular kinase selectivity of The compound of Formula (III) was established in native Ramos B cell kinome assays (KiNativ™; ActivX) confirmed BTK as the primary target with inhibition of BLK and TEC inhibition detected (Table 10).

TABLE 8

In Vitro Inhibition of Various Receptors at 10 μM by the compound of Formula (III)

| Target | % Inhibition at 10 μM | Target | % Inhibition at 10 μM |
|---|---|---|---|
| **Study 1** | | | |
| A1 (h) | — | Y1 (h) | 44.4 |
| A2A (h) | — | Y2 (h) | — |
| A3 (h) | — | NT1 (h) (NTS1) | — |
| alpha 1 | — | delta 2(h) (DOP) | — |
| alpha 2 | — | kappa (KOP) | — |
| beta 1 (h) | — | mu (h) (MOP) | — |
| AT1 (h) | — | ORL1 (h) (NOP) | 14.6 |
| BZD (central) | — | 5-HT1A (h) | — |
| B2 (h) | — | 5-HT1B | — |
| CCKA (h) (CCK1) | 23.7 | 5-HT2A (h) | — |
| D1 (h) | — | 5-HT3 (h) | — |
| D2S (h) | — | 5-HT5A (h) | — |
| ETA (h) | — | 5-HT6 (h) | — |
| GABA | — | 5-HT7 (h) | — |
| GAL2 (h) | — | sst (non-selective) | — |
| CXCR2 (h) (IL-8B) | — | VIP1 (h) (VPAC1) | — |
| CCR1 (h) | — | Vla(h) | — |
| H1 (h) | — | $Ca^{2+}$ channel | — |
| H2 (h) | — | $K^{+}V$ channel | 12.2 |
| MC4 (h) | — | $SK^{+}Ca$ channel | — |
| MT1 (h) | 13.4 | $Na^{+}$ channel (site 2) | — |
| M1 (h) | — | $Cl^{-}$ channel | 25.1 |
| M2 (h) | — | NE transporter (h) | — |
| M3 (h) | — | DA transporter (h) | — |
| NK2 (h) | 16 | 5-HT Transporter (h) | — |
| NK3 (h) | 38.9 | | |
| **Study 2** | | | |
| Beta2 (h) | — | GR (h) | — |
| CB1 (h) | — | AR (h) | — |
| CB2 (h) | — | Ca channel | — |
| NMDA | — | PDE3A (h) | — |
| mGluR5 (h) | — | PDE4D2 (h) | — |
| MAO-A | 14 | Ach (h) | 11 |
| N neuronal α4β2 (h) | — | | |

Study 3

| Assay | Receptor | Agonist $IC_{50}$, μM | Agonist Comments | Antagonist $IC_{50}$, μM | Antagonist Comments |
|---|---|---|---|---|---|
| ADRB1 | Adrenergic beta | ND | ND | >12.5 | n = 2 |
| ADRB2 | Adrenergic beta | ND | ND | >12.5 | n = 2 |
| D2L | Dopamine 2L | ND | ND | >12.5 | n = 2 |
| DOP | Opioid delta | ND | ND | >10 | n = 2 20% |
| H1 | Histamine H1 | >10 | n = 2 | >10 | n = 2 |

—, no inhibition observed;
ND, not determined.

TABLE 9

| Summary of Kinase Selectivity Profiling | |
|---|---|
| Assay [test concentration] | Result |
| Eurofins KinaseProfiler ™ [1 µM][a] | 98% inhibition of BTK; 92% inhibition of BMX; 88% inhibition of TEC; 54% inhibition of BLK; |
| Eurofins $IC_{50}$ Profiler ™ [10-point concentration response][b] | BTK $IC_{50}$ = 0.558 µM; BMX $IC_{50}$ ¯ 0.172 µM; TEC $IC_{50}$ = 0.303 µM; BLK $IC_{50}$ ¯ 3.128 µM; |

[b]Direct filter-binding radiometric kinase activity assay. No other kinases with $IC_{50}$ <10 µM

[a]Direct filter-binding radiometric kinase activity assay (278 human wild type kinases). No other kinases with >50% inhibition at 1 µM of the compound of formula (III).

TABLE 10

| Summary of ActivX KiNativ ™ Kinase Selectivity Profiling[a] | |
|---|---|
| Kinase[b] | % Inhibition |
| BTK (activation loop labeling) | 94.4 |
| BTK (Lys labelling) | 90.3 |
| TEC | 77.6 |
| BLK (activation loop labelling) | 61.9 |

[a]Native cellular kinases: Ramos cell lysates; test concentration, 1 µM.

In vitro Absorption, Distribution, Metabolism, and Excretion—The compound of Formula (III) was assessed at a concentration of 5 µM in cell permeability models. In the Caco-2 model, the compound of Formula (III) demonstrated moderate-to-high permeability with evidence for efflux (Table 11). In the MDCK cell line over-expressing MDR1 (Pgp), the efflux ratio was >115, and the A to B permeability increased in the presence of the Pgp inhibitor elacridar, indicating that the compound of Formula (III) is a high permeability Pgp substrate. The compound of Formula (III) is highly plasma protein bound with a percent free of 3.1% in human, which was commensurate to free concentrations observed in pre-clinical species. In blood to plasma partitioning studies, the compound of Formula (III) primarily distributes into the blood in rat and resides primarily in plasma for dog and human.

In human hepatocytes, the compound of Formula (III) is metabolized by CYP3A through mono-oxidations and N-dealkylations and by GSH conjugation to its acrylamide functionality. It bears moderate metabolic stability in hepatocytes across species and is slowly metabolized in human intestinal microsomes fortified with NADPH.

TABLE 11

Permeability and Efflux Potential of the Compound of Formula (III) in Caco-2 and MDCK MDR1 Cell Lines

| | $P_{app}$, $10^{-6}$ cm/s | | Efflux Ratio |
|---|---|---|---|
| Cell Line | Ato B | B to A | (BA/AB) |
| Caco-2 | | | |
| Compound of formula (III) | 6.69 | 54.9 | 8.2 |
| Propranolol | 31.6 | 30.1 | 0.95 |
| Atenolol | 0.317 | 0.477 | 1.5 |
| Talinolol | 0.232 | 8.71 | 37.5 |
| MDCK-MDR1 (NIH) | | | |
| Compound of formula (III) alone | <0.483 | 55.4 | >115 |

TABLE 11-continued

Permeability and Efflux Potential of the Compound of Formula (III) in Caco-2 and MDCK MDR1 Cell Lines

| | $P_{app}$, $10^{-6}$ cm/s | | Efflux Ratio |
|---|---|---|---|
| Cell Line | Ato B | B to A | (BA/AB) |
| compound of formula (III) with elacridar | 16.7 | | |
| Propranolol[3] | 28.6 | 38.3 | 1.3 |
| Prazosin alone[a] | 1.8 | 70.1 | 38.2 |
| Prazosin with elacridar[a] | 17.5 | | |

$P_{app}$, apparent permeability coefficient.

[a]Values reported as mean of n = 2.

TABLE 12

| ADME Properties of the compound of formula (III) | |
|---|---|
| Assay | Result |
| Caco-2 permeability, $P_{app}$, $10^{-6}$ cm/sec | 6.69 (AB), 54.9 (BA) |
| Plasma protein binding, % free[a] | 2.4 (Ms), 3.7 (R), 6.3 (D), 3.2 (Mk), 3.1 (H) |
| Blood:plasma ratio | 1.37 (R), 0.75 (D), 0.69 (Mk), 0.67 (H) |
| Hepatocyte metabolic stability, extraction ratio | 0.52 (R), 0.67 (D), 0.78 (Mk), 0.51 (H) |
| Intestinal microsomal stability, $CL_{int}$ µL/min/mg | <3.9 (R), <3.9 (D), 14.1 (H) |

ADME, absorption, distribution, metabolism, and excretion; Ms, CD-1 mouse; R, Sprague Dawley rat; D, beagle dog; Mk, cynomolgus monkey; H, Human.

[a]2.5 µM concentration.

[b]Intravenous administration.

The potential of the compound of Formula (III) to inhibit human CYP450s in vitro was investigated up to test concentrations of 50 µM by incubating the compound of Formula (III) with specific CYP probe substrates in human liver microsomes and measuring probe metabolite formation. The compound of Formula (III) did not show significant inhibition of CYP1A2, 2A6, 2B6, 2C19, or 2E1; moderate inhibition was observed for CYP2C8 ($IC_{50}$: 16 µM), 2D6 (26 µM), and 3A4 (25-µM for midazolam), and more potent inhibition was observed for CYP2C9 (3.0 µM for diclofenac and 5.3 µM for tolbutamide) (Table 13).

TABLE 13

Inhibition by the compound of formula (III) of Major CYP Isoforms in Human Liver Microsomes

| Isoform | CYP Probe Substrate | Compound of Formula (III) $IC_{50}$, µM |
|---|---|---|
| 1A2 | Phenacetin | >50 |
| 2A6 | Coumarin | >50 |
| 2B6 | Bupropion | >50 |
| 2C8 | Amodiaquine | 16 |
| 2C9 | Tolbutamide | 5.3 |
| 2C9 | Diclofenac | 3.0 |
| 2C19 | S-Mephenytoin | >50 |
| 2D6 | Dextromethorphan | 26 |
| 2E1 | Chlorzoxazone | >50 |
| 3A4 | Testosterone | 40 |
| 3A4 | Midazolam | 25 |
| 3A4 | Nifedipine | >50 |

$IC_{50}$, half maximal inhibitory concentration.

Preclinical PK Profile—Pharmacokinetics of the compound of Formula (III) in pre-clinical species was characterized by a low (monkey) to moderate (rat and dog)

clearance and a moderate volume of distribution (all species) affording a short drug half-life ranging from 0.4 h (rat) to 4.0 h (monkey) (Table 14). It was rapidly absorbed across pre-clinical species with a $t_{max}$ achieved within the first two hours after oral administration from a 20% hydroxy propyl beta cyclodextrin solution and had moderate to high oral bioavailability ranging from 28-75%. Notably, commensurate drug exposure of the compound of Formula (III) was achieved from a crystalline suspension relative to solution, whereas the initial lead compound did not achieve significant oral bioavailability when dosed as a crystalline suspension.

TABLE 14

Rat, Dog, and Monkey PK Data Following Oral and IV Administration of the compound of Formula (III)

| Species | CL, mL/min/kg | $V_{ss}$, L/kg | IV $T_{1/2}$, h | F, % | Oral $C_{max}$, ng/mL | Oral $AUC_{inf}$, ng/mL · h | $T_{max}$, h |
|---|---|---|---|---|---|---|---|
| Rat | 55 ± 2 | 1.9 ± 0.2 | 0.4 ± 0.0 | 28 ± 6[a]; 41 ± 19[b] | 189 ± 81[a]; 133 ± 53[b] | 425 ± 96[a] 626 ± 290[b] | 0.5 ± 0.0[a]; 1.7 ± 0.6[b] |
| Dog | 11 ± 3 | 0.8 ± 0.2 | 1.1 ± 0.1 | 51 ± 10 | 890 ± 286 | 1964 ± 421 | 0.8 ± 0.3 |
| Monkey | 3.1 ± 0.3 | 0.7 ± 0.0 | 4.0 ± 0.2 | 75 ± 17 | 1006 ± 94 | 10044 ± 2273 | 1.7 ± 0.6 |

[a]5 mg/kg solution PO; formulated from amorphous material in 20% hydroxy propyl beta cyclodextrin solution.
[b]5 mg/kg suspension PO; formulated from crystalline material as suspension in 0.5% HPMC suspension.
Data presented as mean ± SD (n = 3 animals).

In vitro cellular target engagement—The dose-response of BTK occupancy was assessed using a Ramos B cell occupancy assay. Irreversible reaction with Cys491 excludes it from further reaction and enables selective detection of the free (unreacted) BTK with a chemical probe, which utilizes the same binding site and reaction mechanism as the compound of formula (III). The probe carries a biotin sidechain to tag free BTK with an affinity handle to enable detection by ELISA. The mean±SD $IC_{50}$ was 0.021±0.007 μM (n=11) (FIG. 13). The kinetics of BTK occupancy in Human B cells were assessed using 5 concentrations of the compound of formula (III) (3, 10, 30, 100, and 300 nM). Occupancy increased in magnitude and speed with increasing concentration, reaching full occupancy within 40 minutes for the 2 highest concentrations (100 and 300 nM) (FIG. 14).

In Vivo BTK Engagement—BTK receptor occupancy and plasma concentrations of the Compound of Formula (III) increased in a dose-dependent manner following a single oral dose in rat (FIG. 15). Doses of 2 mg/kg or higher consistently achieved sustained target occupancy after 8 and 24 hours (>75% following a 2 mg/kg dose, ≥88% following a 3 mg/kg dose, and ≥99% following a 10 mg/kg dose). Target occupancy was maintained at 24 h even after parent drug plasma levels decreased, indicating persistent BTK occupancy, a hallmark of the covalent mechanism. Considering that 70% to 80% BTK target engagement for 7 to 8 hours in a chronic dosing regimen is associated with anti-inflammatory activity in rodent efficacy models, 75% target engagement at 7.5 hours was identified as the desired level of target engagement.

In vivo activity in collagen-induced arthritis—A rat CIA model in female Wistar rats was used to define the impact of the compound of Formula (III) on chronic inflammation and derive PK-PD correlations (FIG. 16). YiSaipu™ (recombinant human tumor necrosis factor-α receptor (type II): IgGI Fc (rhTNFR:Fc) fusion protein; biogeneric version of Etanercept™) was used as a comparator. The compound of Formula (III) attenuated hind paw inflammation in a dose-dependent manner. A dose of 2 mg/kg/day or higher of the compound of Formula (III) achieved an effect on inflammation equivalent to the anti-TNFα comparator treatment, corresponding to $C_{max}$ of 46.6 ng/mL and $AUC_{last}$ of 324 ng/mL*h. The doses required to achieve meaningful efficacy correlated with a BTK target occupancy threshold of >75% over 24 hours based on the preceding target engagement studies.

In Vitro Activity in DLBCL Cell Lines—NFκB signaling regulates the secretion of multiple cytokines, including interleukin (IL)-6 and IL-10. Secretion of IL-6 and -10 by ABC-DLBCL OCI-LY-10 cells was measured using a MesoScale assay. The mean±SEM $IC_{50}$ values of the compound of Formula (III) across 6 independent experiments was determined to be 16±3 nM for IL-6 and 18±7 nM for IL-10. To determine the anti-proliferative activity of the compound of formula (III), several ABC-DLBCL cell lines—OCI-LY-3, OCI-LY-10, TMD8, and HBL-1—were treated for 8 days. In CD79b-mutant ABC-DLBCL cell lines (OCI-LY10, TMD8, HBL-1), the compound of Formula (III) showed antiproliferative activity with $IC_{50}$ values below 100 nM (FIG. 17; Table 15). The OCI-LY-3 cell line, which harbors a CARD11 mutation downstream of BTK in the NF-κB signaling pathway, was completely insensitive to the compound of Formula (III) up to 2 μM. In 2 experiments, OCI-LY-3 cells were insensitive to the compound of Formula (III) at all concentrations up to 10 μM. These results support a first in-human trial of the compound of Formula (III) in patients with lymphomas driven by the classical NF-κB pathway.

TABLE 15

Antiproliferative Activity of the compound of Formula (III) in ABC-DLBCL Cell Lines (8 Days)

| Cell Line | $IC_{50}$, μM (n = 4) |
|---|---|
| OCI-LY10 (CD79b/Myd88/A20 mutant) | 0.018 |
| TMD8 (CD79b/Myd88/A20 mutant) | 0.034 |
| HBL1 (CD79b/Myd88/A20 mutant) | 0.030 |
| OCI-LY3 (Myd88/CARD11/A20 mutant) | >2 |

$IC_{50}$, half maximal inhibitory concentration.

In Vivo Efficacy in ABC-DLBCL Xenograft and PDX Mouse Models of Lymphoma-To evaluate the effect of the compound of Formula (III) on NFκB signaling in vivo, we analyzed circulating human IL-10 levels in serum of NSG mice implanted with OCI-LY10 DLBCL tumors treated with 0, 1, 3, 10, 30 and 100 mg/kg compound of Formula (III) at 2, 4, 8, 12, 16 and 24 hours after single dose administration. Human IL-10 levels dropped to around 50% of vehicle control 2 hours after dosing, lowering even further after 4 hours to below 20%, 10% and 5% of vehicle control IL-10 levels in 10 mg/kg, 30 mg/kg and 100 mg/kg compound of Formula (III) treatment groups, respectively, and remaining low up to 12 hours. Some rebound to 23% of vehicle control levels for 30 mg/kg and 100 mg/kg and to 39% for the 10 mg/kg dosing group are observed 16 hours after compound administration, while IL-10 levels normalize after 24 hours (FIG. 18).

To evaluate the duration of signaling shutdown and occupancy of BTK protein after compound administration, we determined the amount of free BTK protein in OCI-LY10 DLBCL tumor lysates harvested using an BTK occupancy assay. No BTK occupancy was observed in OCI-LY10 DLBCL tumor lysates of animals dosed with 1 and 3 mg/kg the compound of Formula (III). However, 54%, 90% and 95% BTK protein occupancy was observed 4 hours after the compound of Formula (III) dosing at dose levels of 10, 30 and 100 mg/kg, respectively. BTK protein occupancy levels remained high with 71%, 94% and 96%, respectively, at 12 hours and 70%, 91% and 85%, respectively after 24 hours. (FIG. 19). The antitumor efficacy of compound of Formula (III) was assessed in mice bearing established SC OCI-LY10 human CD79b mutant DLBCL xenografts in female NSG mice, dosed either once (QD) or twice (BID) a day. Analysis of tumor growth inhibition was performed 14 days into the 21-day treatment period (Day 45) as that was the last day when 2/3 of the vehicle controls remained on the study. Compound of Formula (III) induced tumor growth inhibition in the OCI-LY10 model at all dose levels. Treatment with 10, 30 and 100 mg/kg the compound of Formula (III) administered QD inhibited tumor growth by 24%, 35% and 51% TGI (30, 45, and 65% ΔTGI) respectively, as compared with vehicle treated control mice ($p<0.05$). BID treatments with 5, 15 and 50 mg/kg the compound of Formula (III) elicited slightly more pronounced tumor growth inhibition with 26%, 51% and 78% TGI (34, 66, and 102% ΔTGI) ($p<0.05$) (FIG. 20). In the LY2298 xenograft model (CD79b/MyD88 mut), monotherapy of the compound of Formula (III) treatment moderately inhibits in vivo growth of LY2298 DLBCL PDX model while Venetoclax did not show efficacy in this model (FIG. 21). The combination therapy of the compound of Formula (III) and Venetoclax showed in vivo synergistic efficacy with tumor growth inhibition of 76.6% ($P<0.001$). Taken together, the in vivo data support a first in-human trial of the compound of Formula (III) in combination with Venetoclax in patients with B cell lymphomas.

The compound of Formula (III) Inhibits B-cell receptor activation—Rat whole blood assays were used to assess the ability of the compound of Formula (III) to inhibit activation of primary B cells in whole blood. The assay used anti-IgD stimulation to trigger B-cell activation. Cell activation in freshly isolated blood was quantified by staining for cell surface expression of B220 to identify B cells and a cell activation marker CD86. The compound of Formula (III) inhibited B-cell activation in rat whole blood with an IC50 of 0.0410±0.0117 μM (n=2) and a 95% CI of 0.0248 to 0.0572 μM (FIG. 22).

CONCLUSIONS—In summary, we have identified a highly selective and potent irreversible BTK inhibitor, the compound of Formula (III). Preclinical characterization predicts a low dose should achieve BTK inactivation based upon potency and pharmacokinetic properties. The molecule demonstrated highly favorable preclinical tolerability and ADME profile. The compound of Formula (III) demonstrated potent effects in cellular assays and efficacy in in vivo models of autoimmunity and lymphoma. In addition, in vivo efficacy data indicates combination therapy of the compound of Formula (III)together with Venetoclax results in synergistic efficacy. Together, these data suggest that the compound of Formula (III)has potential utility in both autoimmune indications and B cell lymphomas, potentially using combination approaches.

EXPERIMENTAL SECTION—Experimental Details -All solvents and chemicals were used as purchased without further purification. Nuclear magnetic resonance spectra were obtained on Bruker model DRX spectrometers. Chemical shifts (6) are expressed in parts per million, relative to internal tetramethylsilane; coupling constants (J) are in Hz. The following abbreviations are used to describe peak patterns when appropriate: s (singlet), d (doublet), t (triplet), q (quartet), qt (quintet), m (multiplet), app (apparent), and br (broad). HPLC-MS chromatograms and spectra were obtained using one of the following methods: (1) Agilent 1200 HPLC and G6100 system on X-Bridge ShieldRP18 (50×2.1 mm, 5 μm) and a gradient system of 0.05% $NH_4OH$ in $H_2O/CH_3CN$, 100:0 to 5:95 over 7.5 min, then 100:0 for 2.5 min at a temperature of 40° C.; (2) Agilent 1200 HPLC and G6100 system on Phenomenex Luna-C18 (50×2 mm, 5 μm) and a gradient system of 0.1% TFA in $H_2O$/0.05% TFA in $CH_3CN$, 100:0 to 15:85 over 7.5 min, then 100:0 for 2.5 min at a temperature of 50° C.; or (3) Agilent 1100 HPLC and G1367A system on X-Bridge C18 (100×3 mm, 3.5 μM) and a gradient system of 20 mM $NH_4OH$ in $H_2O/CH_3CN$ 90:10 over 2 min, then 0:100 for 1 min at a flow rate of 2.4 mL/min at a temperature of 45° C. All compounds tested were of a minimum of 95% purity as determined by HPLC.

Rat Whole Blood Assay-Anti-rat IgD was purchased from Bio-Rad AbD Serotec, Ltd. (Oxford, United Kingdom). Rat B220-PE and rat CD86-FITC were purchased from eBioscience (San Diego, CA). Lysing buffer was purchased from BD Biosciences (San Diego, CA). To determine the potency of each compound, inhibition of anti-IgD-induced activation of B cells in rat whole blood was assessed by flow cytometry. Heparinized blood was collected from Wistar rats, supplemented with penicillin (100 U/mL) and streptomycin (100 μg/mL), and incubated for 1 hour with a titration of compound in DMSO (0.3% final concentration). The blood was then stimulated and incubated overnight at 37° C. with anti-IgD (10 μg/mL). The samples were then stained with fluorescent antibodies against CD86 and B220 for 30 minutes, red blood cells removed with lysing buffer, washed, fixed, and acquired on FACSCalibur. Each sample was gated on forward and side scatter for lymphocytes and on B220+ for B cells. The percentage of activated B cells was defined as the proportion of B220+CD86+ cells over total B220+ cells.

Inhibition percentage was determined by the following equation: Inhibition $\%=(ActB_{stim}-ActB_{compound})\times100/(ActB_{stim}-ActB_{unstim})$, where $ActB_{high}$, $ActB_{unstim}$, and $ActB_{compound}$ refer to the percentage of activated B cells of the stimulated (no compound), unstimulated (no antibody), and compound treated wells, respectively. The $IC_{50}$ for each compound was then calculated from the inhibition % of the titrations using a 4-PL fit. BTK Occupancy—Animal Studies—Rat studies were conducted using female Wistar rats (110-140 g for target engagement and PKPD studies, 144-175 g (6-8 weeks of age) for efficacy studies). These rats were supplied by Shanghai SLAC Laboratory Animal Co. Ltd (Shanghai, China) and acclimated at least 4 days following arrival at the animal facility. Rats were multiple housed (3-4 rats/cage). The holding and study rooms were maintained on a 12-hour light/dark cycle (light/dark cycle may be interrupted for study-related activities), within a temperature range of 24±1° C. and a relative humidity of 30-70%. Rats had free access to food (irradiated, Shanghai SLAC Laboratory Animal Co. Ltd., China) and water (filtered by Molanimal ultrapure water machine from the municipal water supply).

Test article preparation—The compound of Formula (III) was formulated in 20% HPβCD, pH adjusted to 2.1 using 6 M HCl. YiSaiPu was prepared by dissolving the lyophilized powder into normal saline to a working concentration of 1.5 mg/mL.

BTK Occupancy PK/PD Model—Rat in vivo target engagement—Two studies were conducted in which the compound of Formula (III) formulated in 20% HPCD, was administered orally to female Wistar rats. In study 1, compound of Formula (III) was evaluated at oral doses of 0.3, 1, 3 and 10 mg/kg; in study 2, compound of Formula (III) was evaluated at oral doses of 0.1, 0.3, 1, 2 and 3 mg/kg. (n=4/group for both studies). In both experiments, at assigned time points postdose (0.5, 4, 8 and 24 hr), animals were anesthetized and approximately 140 μL of blood was obtained by retro-orbital bleeding into heparinized tubes. These samples were split into two aliquots, with one aliquot used to measure compound levels by liquid chromatography mass spectrophotometry method and the other aliquot to assess BTK occupancy by a target-site occupancy ELISA.

Cell lysates were prepared from the blood samples using cell lysis buffer (BD Pharmingen™, BD Biosciences). Free BTK protein in each sample is tagged by the addition a biotinylated probe (1 μL of a 25 μM working solution per sample, final concentration 250 nM), which is then captured on the surface of a streptavidin coated microtiter plate and detected by ELISA using an antibody specific for BTK (BD Transduction). Samples from rats that were dosed with vehicle alone were used to define the level of total free BTK in the cell lysates and samples from compound of Formula (III) dosed animals were used to define the fraction of total BTK occupied via covalent modification.

Rat collagen-induced arthritis—An emulsion was prepared on ice from equal volumes of type II collagen (CII; Chondrex) (2 mg/mL in 100 mM acetic acid (Sinopharm Chemical Reagent Co. Ltd)) and Incomplete Freund's Adjuvant (IFA) (Sigma-Aldrich) by high speed homogenization (28,000 rpm) for 3 min (FLUKO Equipment Shanghai Co. Ltd). Eighty-two rats were used in the study. Before immunization, 6 rats were randomly selected as a naïve group. The other 76 rats were anesthetized with inhalational isoflurane, and injected intradermally at the base of the tail with 0.2 mL of the emulsion (1 mg/mL CII/IFA), 2 to 3 cm from the body on day 0 and day 7. On day 10, the 56 rats with the most developed arthritis based on paw volume measurements out of the 76 rats that were immunized were divided into 7 groups (n=8) with a stratified random block design according to average hind paw volume of each rat. Each group with similar starting paw inflammation was administered with vehicle or different doses of the compound of Formula (III) (0.3, 1, 2, 3, 10 mg/kg, PO, QD, days 10-17) or YiSaiPu (biosimilar etarnacept) (15 mg/kg, IP, QOD, days 10-16).

Hind paws volume and body weight were monitored daily for 7 consecutive days (days 10-16) after initiation of test article dosing. Left and right paw volumes in each rat were measured by a Plethysmometer (Catalog No. 7140, Ugo Basile. Italy). Blood (about 300 μL) in the groups treated with the compound of Formula (III) was collected into heparinized tubes via retro-orbital bleeding under isoflurane anesthesia on day 17-18. For groups treated with the compound of Formula (III), the composite collection time points were 0, 0.5, 1, 2, 4, 8, 12 and 24 hrs after last administration of the compound of Formula (III). After collection, blood samples were centrifuged (5,000 rpm for 10 min), plasma collected, and the concentrations of the compound of Formula (III) were determined using liquid chromatography mass spectrophotometry.

Additional Data on Preclinical PK Profile—Protein binding of the compound of Formula (III) was studied using an equilibrium dialysis method in plasma from human, cynomolgus monkey, beagle dog, Sprague Dawley rat, CD-1 mouse, and guinea pig at 0.25, 2.5, and 25 μM. Within the quantification limits of the assay, the compound of Formula (III) demonstrated high plasma protein binding across species with the unbound fraction ranging from 1.69% to 6.88% (Table 16). In human and monkey, the plasma protein binding was concentration dependent. Plasma protein binding was also determined by an equilibrium dialysis method in female Wistar rats used for both the PD and efficacy in vivo model; at a concentration of 1 μM, the free fraction in plasma was 7.54%. In addition, protein binding was examined in RPMI culture media containing 10% FBS used for BTK occupancy studies in Ramos human B cells in order to provide inputs for PK/PD modeling; the compound of Formula (III) was determined to be 31.7% free at an incubated concentration of 1 μM. Liver microsomal binding of the compound of Formula (III) (1 μM) was determined at a microsomal protein concentration of 0.25 and 1.0 mg/mL to provide inputs for human PK predictions. Free fraction of the compound of Formula (III) in liver microsomes from various species ranged from 75.1% to 87.9% at 0.25 mg/mL and from 58.9% to 86.5% at 1.0 mg/mL (Table 17). The blood-to-plasma concentration ratio of the compound of Formula (III) determined in fresh blood at a concentration of 1 μM was 0.67 in human, 0.69 in monkey, 0.75 in dog, 0.84 in mouse, and 1.37 in rat, suggesting a slightly preferential distribution into plasma (except for rat). In vitro metabolic stability of the compound of Formula (III) was investigated in liver microsomes (1.0 mg/mL; in presence of 1 mM NADPH) and hepatocytes ($0.5\times10^6$ cells/mL) from multiple species. In liver microsomes, the compound of formula (III) demonstrated moderate-to-high turnover with $T_{1/2}$ ranging from 4.9 minutes in mouse to 22.3 minutes in human (Table 18). In hepatocytes, the compound of Formula (III) turnover followed a similar trend, with $T_{1/2}$ ranging from 75.3 minutes in monkey to 278.1 minutes in human.

To assess the potential of the compound of Formula (III) to be a time-dependent inhibitor of CYP3A, human liver microsomes were preincubated for 30 minutes at 37° C. with the compound of Formula (III) at concentrations up to 10 μM, and CYP3A activity was measured using testosterone as a probe substrate. The results showed that the compound of Formula (III) did not inhibit CYP3A4 in a time-dependent manner at up to concentrations of 10 μM, with $IC_{50}$ values of 9.81 μM and >10 μM with and without preincubation, respectively. The potential of the compound of Formula (III) to induce CYPs at the transcriptional level was assessed using Puracyp™ DPX2 (CYP3A4, PXR) and DRE (CYP1A2, AhR) luciferase-reporter cell lines; rifampicin and omeprazole were used as positive controls for CYP3A and CYP1A induction, respectively. The activation by the compound of Formula (III) was <20% of positive control values for PXR (6.6% and 14.1% at 1 and 10 μM change, respectively) or AhR (0.1% and 0.3% change, respectively). Similarly, studies using plated human hepatocytes coincubated for 48 hours with the compound of Formula (III) at 1 and 10 μM followed by probe reactions with midazolam and phenacetin showed no increase in CYP3A (−0.8% and 0.8% change at 1 and 10 μM, respectively) or CYP1A (0.2% and 1.0% change, respectively) enzyme activities. Potential involvement of various CYP isoforms in the metabolism of the compound of Formula (III) was investigated by measuring the parent compound remaining after 1-hour incubation with the compound of Formula (III) (1 μM) with recombinant CYPs (rCYPs) at 100 pmol P450/mL in the presence of 1 mM NADPH at 37° C. The only isozyme that produced notable the compound of Formula (III) turnover with <1% parent remaining after 1-hour incubation was CYP3A4 (FIG. 24). To confirm CYP3A4 as a major contributor to the compound of Formula (III) metabolism, chemical inhibition studies were conducted; the compound of Formula (III) at 1 μM was incubated with pooled human liver microsomes (0.5 mg/mL) in the absence or presence of ketoconazole (CYP3A4 inhibitor, 1 μM). The turnover of the compound of Formula (III) was completely (>97%) inhibited by ketoconazole, suggesting that CYP3A4 is a main contributor to its CYP-mediated metabolism (FIG. 25).

The extent of the compound of Formula (III) covalent binding to hepatic proteins was determined in human hepatocytes at 1 and 10 μM (Table 19). A $^{14}C$ label was introduced at the acrylamide carbonyl carbon of the compound of Formula (III). The 1 μM incubations were carried out with $0.5\times10^6$ cells/mL for 4.5 h to correspond with the compound of Formula (III) half-life in test system; The 10 μM incubations were conducted with $0.75\times10^6$ cells/mL for 3 h. Troglitazone and pioglitazone served as positive and negative controls, respectively.

TABLE 16

Protein Binding of The Compound of Formula (III) in Plasma From Various Species

| Species<br>Concentration, μM | % Free | % Recovery |
|---|---|---|
| Human | | |
| 0.25 | 1.69 | 104.8 |
| 2.5 | 3.12 | 99.1 |
| 25 | 4.63 | 88.9 |
| Monkey | | |
| 0.25 | <0.4[a] | 102.9 |
| 2.5 | 3.21 | 95.6 |
| 25 | 5.32 | 87.6 |
| Dog | | |
| 0.25 | 6.88 | 91.8 |
| 2.5 | 6.33 | 87.5 |
| 25 | 6.85 | 91.9 |
| Rat | | |
| 0.25 | 3.73 | 90.0 |
| 2.5 | 3.65 | 94.0 |
| 25 | 4.05 | 92.6 |
| Mouse | | |
| 0.25 | 1.92 | 101.8 |
| 2.5 | 2.35 | 97.9 |
| 25 | 3.35 | 99.1 |
| Guinea Pig | | |
| 0.25 | 3.26 | 88.9 |
| 2.5 | 3.23 | 86.1 |
| 25 | 3.72 | 81.6 |

[a]Value was below 1 nM, the lower limit of quantification in assay. At 1 nM, the calculated % free is 0.4%.

TABLE 17

Liver Microsomal Binding of the Compound of Formula (III) at 1 μM in Various Species

| | % Free | |
|---|---|---|
| Species | 0.25 mg/mL | 1.0 mg/mL |
| Human | 75.8 | 64.1 |
| Monkey | 75.1 | 58.9 |
| Dog | 87.9 | 69.4 |
| Rat | 84.0 | 86.5 |
| Mouse | ND | 82.0 |

ND, not determined.

TABLE 18

Metabolic Stability of the compound of formula (III) in Liver Microsomes and Hepatocytes of Various Species

| | Liver Microsomes | | | Hepatocytes | | |
|---|---|---|---|---|---|---|
| Species | $T_{1/2}$, min | $CL_{int}$, μL/min/mg | Extraction Ratio | $T_{1/2}$, min | $CL_{int}$, μL/min/$10^6$ cells | Extraction Ratio |
| Human | 22.3 | 31.1 | 0.63 | 278.1 | 15.4 | 0.52 |
| Monkey | 11.4 | 61.0 | 0.65 | 75.3 | 66.3 | 0.78 |
| Dog | 17.1 | 40.6 | 0.65 | 277.4 | 19.2 | 0.46 |
| Rat | 12.9 | 53.8 | 0.58 | 127.1 | 52.3 | 0.53 |
| Mouse | 4.9 | 142.3 | 0.79 | NT | NT | NT |

$CL_{int}$, intrinsic clearance; NT, not tested; $T_{1/2}$, half-life.

TABLE 19

| [$^{14}$C]-Compound of Formula (III) Human Hepatocyte [Covalent Binding | | | |
|---|---|---|---|
| Test Compound | Net Covalent Binding, pmol eq/mg protein | Compound Turnover, % | Fraction Covalently Bound ($f_{cvb}$) |
| 1 μM study | | | |
| Compound of Formula (III) | 46.8 ± 5.1 | 49.1 | 0.07 ± 0.01 |
| Pioglitazone | 20.1 ± 1.8 | 57.2 | 0.0285 ± 0.0026 |
| Troglitazone | 83.7 ± 6.7 | 59.4 | 0.1071 ± 0.0086 |
| 10 μM study | | | |
| Compound of Formula (III) | 50.0 ± 0.8 | 70.1 | 0.00564 ± 0.0001 |
| Pioglitazone | 29.5 ± 2.1 | 52.9 | 0.00429 ± 0.00031 |
| Troglitazone | 98.6 ± 6.4 | 55.2 | 0.01393 ± 0.00090 |

Example 3—Predicted Cmax and BTK Occupancy Values for the Compound of Formula (III)

TABLE 20

| Cmax and AUC values for the compound of Formula (III) | | | | |
|---|---|---|---|---|
| | $C_{max,day1}$ [a] (ng/mL) | $C_{max,ss}$ [a] (ng/mL) | $AUC_{day1}$ [a] (ng · hr/mL) | $AUC_{ss}$ [a] (ng · hr/mL) |
| 140 mg QD Capsule Fasting | 429.75 (186.87, 950.72) [59.992, 2377.2] | 435.1 (190.24, 966.35) [66.855, 2395.4] | 2157.5 (1002, 4641.3) [312.1, 11517] | 2249.7 (1030.7, 4919.4) [312.27, 13015] |
| 560 mg QD Capsule Fasting | 1719 (747.47, 3802.9) [239.97, 9509] | 1740.4(760.97, 3865.4) [267.42, 9581.5] | 8629.9 (4007.9, 18565) [1248.4, 46068] | 8998.9 (4122.7, 19678) [1249.1, 52061] |

Simulations were conducted using the final population PK model (n = 5,000) developed from one Phase 1 study in healthy subjects
[a]Data shown as median ($5^{th}$-$95^{th}$) [min, max]

Key:

$C_{max,day1}$ = max concentration at day 1;

$C_{max,ss}$ = max concentration at steady state;

$AUC_{day1}$ = Area under the curve at day 1;

$AUC_{ss}$ = Area under the curve at steady state

TABLE 21

| BTO % occupancy for the compound of Formula (III) | | | | |
|---|---|---|---|---|
| | $BTKO_{max,day1}$ [a] (%) | $BTKO_{max,ss}$ [a] (%) | $BTKO_{trough, day1}$ [a] (%) | $BTKO_{trough,ss}$ [a] (%) |
| 140 mg QD Capsule Fasting | 90.4 (58.8, 99.2) [30.9, 99.8] | 95.9 (83.5, 99.5) [59.4, 99.9] | 77.4 (50.9, 86.2) [23.3, 91.3] | 80.7 (70.9, 87.8) [50.2, 95.4] |
| 560 mg QD Capsule Fasting | 99.8 (98.0, 99.9) [87.1, 100] | 99.8 (98.8, 99.9) [90.2, 100] | 85.4(81.4, 92.8) [63.9, 97.3] | 86.0 (81.8, 94.4) [75.5, 99.3] |

Simulations were conducted using the final population PK model (n = 1,000) developed from one Phase 1 study in healthy subjects
[a]Data shown as median ($5^{th}$-$95^{th}$) [min, max]

Key:

$BTKO_{max,day1}$= max BTKO at day 1;

$BTKO_{max,ss}$ = max BTKO at steady state;

$BTKO_{trough,day1}$ = trough BTKO at day 1;

$BTKO_{trough,ss}$ = trough BTKO at steady state

ASPECTS

The disclosure is also directed to the following aspects:

Aspect 1. A compound of formula (III):

(III)

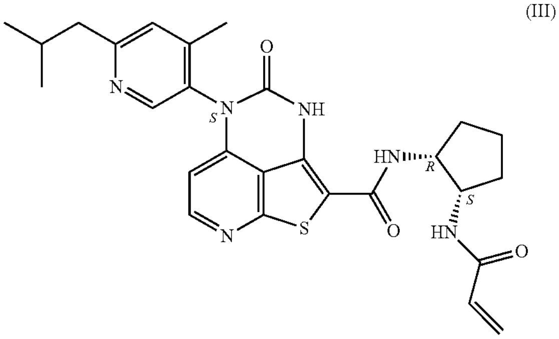

Aspect 2. The compound of formula (III) of the preceding aspect that is a pharmaceutically acceptable salt, hydrate, polymorph or solvate thereof.

Aspect 3. A pharmaceutical composition comprising a compound of formula (III), or a pharmaceutically acceptable salt, hydrate, polymorph or solvate thereof, and a pharmaceutically acceptable excipient.

Aspect 4. A method of inhibiting Bruton's tyrosine kinase comprising contacting the kinase with a compound of formula (III).

Aspect 5. A method of treating a malignancy in a patient comprising administering to the patient a therapeutically effective amount of a compound of formula (III), or a pharmaceutically acceptable salt, hydrate, polymorph or solvate thereof.

Aspect 6. The method of aspect 5, wherein the malignancy is is selected from the group consisting of a lymphoma, a leukemia, a carcinoma, and a sarcoma.

Aspect 7. The method of aspect 6, wherein the lymphoma is selected from the group consisting of non-Hodgkin's lymphoma (NHL (including B-cell NHL)), diffuse large B-cell lymphoma (DLBCL), mantle cell lymphoma (MCL), follicular lymphoma (FL), mucosa-associated lymphoid tissue (MALT) lymphoma, marginal zone lymphoma (MZL), T-cell lymphoma, Hodgkin's lymphoma, small lymphocytic lymphoma (SLL), Waldenstrom macroglobulinemia, and Burkitt's lymphoma.

Aspect 8. The method of aspect 6, wherein the leukemia is selected from the group consisting of chronic lymphocytic leukemia (CLL), lymphoblastic T cell leukemia, chronic myelogenous leukemia (CML), hairy-cell leukemia, acute lymphoblastic T cell leukemia, plasmacytoma, immunoblastic large cell leukemia, megakaryoblastic leukemia, acute megakaryocyte leukemia, promyelocytic leukemia, erythroleukemia and multiple myeloma.

Aspect 9. The method of aspect 6, wherein the malignancy is selected from the group consisting of brain (gliomas), glioblastomas, breast cancer, colorectal/colon cancer, prostate cancer, lung cancer, non-small-cell lung cancer, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head & neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, Chronic graft versus host disease, and gastrointestinal stromal tumor.

Aspect 10. A method of treating a diffuse large B-cell lymphoma (DLBCL) in a patient comprising administering to the patient a therapeutically effective amount of a compound of formula (III), or a pharmaceutically acceptable salt, hydrate, polymorph or solvate thereof.

Aspect 11. The method of aspect 10, wherein the method comprises further administering a Bcl2 inhibitor.

Aspect 12. A method of treating mantle cell lymphoma (MCL) in a patient comprising administering to the patient a therapeutically effective amount of a compound of formula (III), or a pharmaceutically acceptable salt, hydrate, polymorph or solvate thereof.

Aspect 13. A method of treating follicular lymphoma (FL) in a patient comprising administering to the patient a therapeutically effective amount of a compound of formula (III), or a pharmaceutically acceptable salt, hydrate, polymorph or solvate thereof.

Aspect 14. A method of treating marginal zone lymphoma (MZL) in a patient comprising administering to the patient a therapeutically effective amount of a compound of formula (III), or a pharmaceutically acceptable salt, hydrate, polymorph or solvate thereof.

Aspect 15. A method of treating chronic lymphocytic leukemia (CLL) in a patient comprising administering to the patient a therapeutically effective amount of a compound of formula (III), or a pharmaceutically acceptable salt, hydrate, polymorph or solvate thereof.

Aspect 16. A method of treating small lymphocytic lymphoma (SLL) in a patient comprising administering to the patient a therapeutically effective amount of a compound of formula (III), or a pharmaceutically acceptable salt, hydrate, polymorph or solvate thereof.

Aspect 17. A method of treating Waldenstrom macroglobulinemia in a patient comprising administering to the patient a therapeutically effective amount of a compound of formula (III), or a pharmaceutically acceptable salt, hydrate, polymorph or solvate thereof.

Aspect 18. A method of treating chronic graft versus host disease in a patient comprising administering to the patient a therapeutically effective amount of a compound of formula (III), or a pharmaceutically acceptable salt, hydrate, polymorph or solvate thereof.

Aspect 19. The method of aspects 5 to 18, wherein the therapeutically effective amount of the compound of Formula (III)is about 140 mg.

Aspect 20. The method of aspects 5 to 18, wherein the therapeutically effective amount of the compound of Formula (III) is about 280 mg.

Aspect 21. The method of aspects 5 to 18, wherein the therapeutically effective amount of the compound of Formula (III) is about 560 mg.

Aspect 22. The method of aspects 5 to 18, wherein the therapeutically effective amount of the compound of Formula (III) is an amount that results in a $C_{(max,day1)}$ of about 59.992 ng/ml to about 2,377.2 ng/ml.

Aspect 23. The method of aspects 5 to 18, wherein the therapeutically effective amount of the compound of Formula (III) is an amount that results in a $C_{(max,day1)}$ of about 239.97 ng/ml to about 9,509 ng/ml.

Aspect 24. The method of aspects 5 to 18, wherein the therapeutically effective amount of the compound of Formula (III) is an amount that results in a $C_{(max,day1)}$ of about 429.75 ng/ml.

Aspect 25. The method of aspects 5 to 18, wherein the therapeutically effective amount of the compound of Formula (III) is an amount that results in a $C_{(max,day1)}$ of about 1,719 ng/ml.

Aspect 26. The method of aspects 5 to 18, wherein the therapeutically effective amount of the compound of Formula (III) is an amount that results in a $C_{(max,ss)}$ of about 66.855 ng/ml to about 2,395.4 ng/ml.

Aspect 27. The method of aspects 5 to 18, wherein the therapeutically effective amount of the compound of Formula (III) is an amount that results in a $C_{(max,ss)}$ of about 267.42 ng/ml to about 9,581.5 ng/ml.

Aspect 28. The method of aspects 5 to 18, wherein the therapeutically effective amount of the compound of Formula (III) is an amount that results in a $C_{(max,ss)}$ of about 435.1 ng/ml.

Aspect 29. The method of aspects 5 to 18, wherein the therapeutically effective amount of the compound of Formula (III) is an amount that results in a $C_{(max,ss)}$ of about 1,740.4 ng/ml.

Aspect 30. The method of aspects 5 to 18, wherein the therapeutically effective amount of the compound of Formula (III) is an amount that results in a $AUC_{(day\ 1)}$ of about 312.1 ng·hr/ml to about 11,517 ng·hr/ml.

Aspect 31. The method of aspects 5 to 18, wherein the therapeutically effective amount of the compound of Formula (III) is an amount that results in a $AUC_{(day\ 1)}$ of about 1,248.4 ng·hr/ml to about 46,068 ng·hr/ml.

Aspect 32. The method of aspects 5 to 18, wherein the therapeutically effective amount of the compound of Formula (III) is an amount that results in a $AUC_{(day\ 1)}$ of about 2,157.5 ng·hr/ml.

Aspect 33. The method of aspects 5 to 18, wherein the therapeutically effective amount of the compound of Formula (III) is an amount that results in a $AUC_{(day\ 1)}$ of about 8,629.9 ng·hr/ml.

Aspect 34. The method of aspects 5 to 18, wherein the therapeutically effective amount of the compound of Formula (III) is an amount that results in a $AUC_{(ss)}$ of about 312.27 ng·hr/ml to about 13015 ng·hr/ml.

Aspect 35. The method of aspects 5 to 18, wherein the therapeutically effective amount of the compound of Formula (III) is an amount that results in a $AUC_{(ss)}$ of about 1,249.1 to about 52,061 ng·hr/ml.

Aspect 36. The method of aspects 5 to 18, wherein the therapeutically effective amount of the compound of Formula (III) is an amount that results in a $AUC_{(ss)}$ of about 2,249.7 ng·hr/ml.

Aspect 37. The method of aspects 5 to 18, wherein the therapeutically effective amount of the compound of Formula (III) is an amount that results in a $AUC_{(ss)}$ of about 8,998.9 ng·hr/ml.

Aspect 38. The method of aspects 5 to 18, wherein the therapeutically effective amount of the compound of Formula (III) is an amount that results in a BT-$KO_{(max/day1)}$ of about 30.9% occupancy to about 99.8% occupancy.

Aspect 39. The method of aspects 5 to 18, wherein the therapeutically effective amount of the compound of Formula (III) is an amount that results in a BT-$KO_{(max/day1)}$ of about 87.1% occupancy to about 100% occupancy.

Aspect 40. The method of aspects 5 to 18, wherein the therapeutically effective amount of the compound of Formula (III) is an amount that results in a BT-$KO_{(max/day1)}$ of about 90.4% occupancy.

Aspect 41. The method of aspects 5 to 18, wherein the therapeutically effective amount of the compound of Formula (III) is an amount that results in a BT-$KO_{(max/day1)}$ of about 95.9% occupancy.

Aspect 42. The method of aspects 5 to 18, wherein the therapeutically effective amount of the compound of Formula (III) is an amount that results in a BT-$KO_{(max/ss)}$ of about 59.4 to about 99.9% occupancy.

Aspect 43. The method of aspects 5 to 18, wherein the therapeutically effective amount of the compound of Formula (III) is an amount that results in a BT-$KO_{(max/ss)}$ of about 90.2 to about 100% occupancy.

Aspect 44. The method of aspects 5 to 18, wherein the therapeutically effective amount of the compound of Formula (III) is an amount that results in a BT-$KO_{(max/ss)}$ of about 99.8% occupancy.

Aspect 45. The method of aspects 5 to 18, wherein the therapeutically effective amount of the compound of Formula (III) is an amount that results in a BT-$KO_{(max/ss)}$ of about 99.8% occupancy.

Aspect 46. The method of aspects 5 to 18, wherein the therapeutically effective amount of the compound of Formula (III) is an amount that results in a BT-$KO_{(trough/day1)}$ of about 23.3% occupancy to about 91.3% occupancy.

Aspect 47. The method of aspects 5 to 18, wherein the therapeutically effective amount of the compound of Formula (III) is an amount that results in a BT-$KO_{(trough/day1)}$ of about 63.9% occupancy to about 97.3% occupancy.

Aspect 48. The method of aspects 5 to 18, wherein the therapeutically effective amount of the compound of Formula (III) is an amount that results in a $BTKO_{(trough/day1)}$ of about 77.4% occupancy.

Aspect 49. The method of aspects 5 to 18, wherein the therapeutically effective amount of the compound of Formula (III) is an amount that results in a $BTKO_{(trough/day1)}$ of about 85.4% occupancy.

Aspect 50. The method of aspects 5 to 18, wherein the therapeutically effective amount of the compound of Formula (III) is an amount that results in a $BTKO_{(trough/ss)}$ of about 50.2% occupancy to about 95.4% occupancy.

Aspect 51. The method of aspects 5 to 18, wherein the therapeutically effective amount of the compound of Formula (III) is an amount that results in a $BTKO_{(trough/ss)}$ of about 75.5% occupancy to about 99.3% occupancy.

Aspect 52. The method of aspects 5 to 18, wherein the therapeutically effective amount of the compound of Formula (III) is an amount that results in a $BTKO_{(trough/ss)}$ of about 80.7% occupancy.

Aspect 53. The method of aspects 5 to 18, wherein the therapeutically effective amount of the compound of Formula (III) is an amount that results in a $BTKO_{(trough/ss)}$ of about 86.0% occupancy.

Aspect 54. The method of aspects 5 to 18, wherein the therapeutically effective amount of the compound of Formula (III) is administered once a day.

Aspect 55. The method of aspects 5 to 18, wherein the therapeutically effective amount of the compound of Formula (III) is administered twice a day.

Aspect 56. The method of aspects 5 to 18, wherein the therapeutically effective amount of the compound of Formula (III) is administered three times a day.

Aspect 57. The method of aspects 5, wherein the compound of formula (III) is administered orally.

Aspect 58. The method of aspects 5 to 18, further comprising administering 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl) amino]phenyl}sulfonyl)-2-(1H-pyrrolo[2,3-b] pyridin5-yloxy)benzamide).

Aspect 59. The method of aspects 5 to 18, further comprising administering cyclophosphamide, doxorubicin, vincristine, prednisone and rituximab.

All aspects described herein for methods of treating a malignancy, are also applicable for use in treating said malignancy.

All aspects described herein for methods of treating a malignancy, are also applicable for use in a method of treating said malignancy.

What is claimed:

1. A method of treating a B-cell malignancy selected from the group consisting of diffuse large B-cell lymphoma (DLBCL), mantle cell lymphoma (MCL), follicular lymphoma (FL), marginal zone lymphoma (MZL), chronic lymphocytic leukemia (CLL), small lymphocytic lymphoma (SLL), and Waldenstrom macroglobulinemia in an individual in need thereof, comprising administering twice daily a therapeutically effective amount of a compound of Formula (III):

(III)

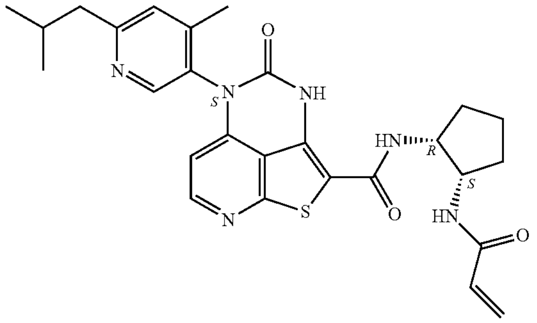

or a pharmaceutically acceptable salt, or hydrate thereof, wherein the therapeutically effective amount of the compound of Formula (III) is about 140 mg.

2. The method of claim 1, further comprising administering 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo [2,3-b]pyridin5-yloxy)benzamide).

3. A method of treating a B-cell malignancy selected from the group consisting of diffuse large B-cell lymphoma (DLBCL), mantle cell lymphoma (MCL), follicular lymphoma (FL), marginal zone lymphoma (MZL), chronic lymphocytic leukemia (CLL), small lymphocytic lymphoma (SLL), and Waldenstrom macroglobulinemia in an individual in need thereof, comprising administering twice daily a therapeutically effective amount of a compound of Formula (III):

(III)

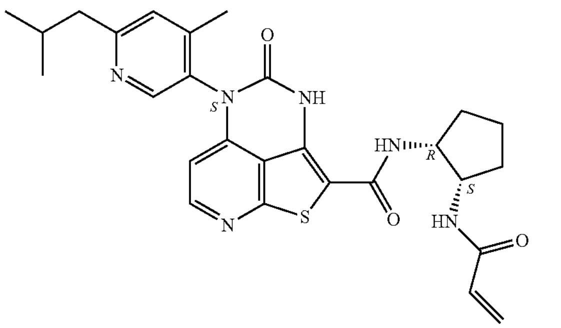

or a pharmaceutically acceptable salt, or hydrate thereof, wherein the therapeutically effective amount of the compound of Formula (III) is about 280 mg.

4. The method of claim 3, further comprising administering 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo [2,3-b]pyridin5-yloxy)benzamide).

5. A method of treating a B-cell malignancy selected from the group consisting of diffuse large B-cell lymphoma (DLBCL), mantle cell lymphoma (MCL), follicular lymphoma (FL), marginal zone lymphoma (MZL), chronic lymphocytic leukemia (CLL), small lymphocytic lymphoma (SLL), and Waldenstrom macroglobulinemia in an individual in need thereof, comprising administering twice daily a therapeutically effective amount of a compound of Formula (III):

(III)

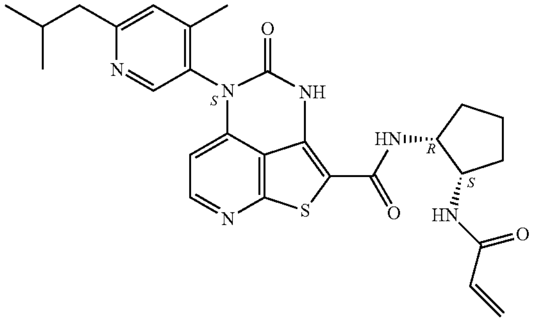

or a pharmaceutically acceptable salt, or hydrate thereof, wherein the therapeutically effective amount of the compound of Formula (III) is about 560 mg.

6. The method of claim 5, further comprising administering 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo [2,3-b]pyridin5-yloxy)benzamide).

* * * * *